United States Patent
Epshtein

(10) Patent No.: US 9,273,117 B2
(45) Date of Patent: Mar. 1, 2016

(54) METHOD FOR ADMINISTERING HOMEOPATHICALLY POTENTIZED ANTIBODY

(75) Inventor: Oleg Iliich Epshtein, Moscow (RU)

(73) Assignee: Oleg Iliich Epshtein, Moscow (RU)

( * ) Notice: Subject to any disclaimer, the term of this patent is extended or adjusted under 35 U.S.C. 154(b) by 0 days.

(21) Appl. No.: 12/701,197

(22) Filed: Feb. 5, 2010

(65) Prior Publication Data

US 2010/0166762 A1 Jul. 1, 2010

Related U.S. Application Data

(60) Continuation-in-part of application No. 11/656,225, filed on Jan. 22, 2007, now abandoned, which is a division of application No. 10/311,666, filed as application No. PCT/RU01/00239 on Jun. 19, 2001, now abandoned.

(51) Int. Cl.

| | |
|---|---|
| C07K 16/00 | (2006.01) |
| C07K 16/24 | (2006.01) |
| C07K 16/26 | (2006.01) |
| A61K 41/00 | (2006.01) |
| C07K 16/28 | (2006.01) |
| C07K 16/44 | (2006.01) |
| A61K 39/00 | (2006.01) |

(52) U.S. Cl.
CPC .............. *C07K 16/00* (2013.01); *A61K 41/0004* (2013.01); *C07K 16/24* (2013.01); *C07K 16/26* (2013.01); *C07K 16/28* (2013.01); *C07K 16/44* (2013.01); *A61K 2039/505* (2013.01); *A61K 2039/545* (2013.01); *C07K 2317/73* (2013.01); *C07K 2317/77* (2013.01)

(58) Field of Classification Search
CPC ................................................. A61K 41/0004
See application file for complete search history.

(56) References Cited

U.S. PATENT DOCUMENTS

| | | | |
|---|---|---|---|
| 4,963,367 A | 10/1990 | Ecanow | |
| 5,629,286 A | 5/1997 | Brewitt | |
| 5,683,712 A | 11/1997 | Cavazza | |
| 5,741,488 A | 4/1998 | Feldman et al. | |
| 5,879,677 A | 3/1999 | del Zoppo | |
| 7,572,441 B2 * | 8/2009 | Epshtein et al. | 424/130.1 |
| 7,582,294 B2 * | 9/2009 | Epshtein et al. | 424/130.1 |
| 8,178,498 B1 * | 5/2012 | Ephstein | 514/24 |
| 2003/0099636 A1 | 5/2003 | Epshtein et al. | |
| 2007/0224187 A1 * | 9/2007 | Epshtein et al. | 424/131.1 |
| 2010/0221258 A1 * | 9/2010 | Epshtein | 424/158.1 |

FOREIGN PATENT DOCUMENTS

| | | |
|---|---|---|
| EP | 0687466 A1 | 12/1995 |
| RU | 2007989 C1 | 2/1994 |
| RU | 2033784 | 4/1995 |
| RU | 2104032 C1 | 2/1998 |
| RU | 2122858 C1 | 12/1998 |
| RU | 98109384 A1 | 3/2000 |
| WO | 9412213 A1 | 6/1994 |

OTHER PUBLICATIONS

Pillemer et al., J. Rheumatol. (2003) 30: 41-43.*
Yoshinari et al., Eur J Paediatr Neurol., 2006, 10: 124-128.*
Thorsell (Exp. Biol. Med., 2010, 235: 1163-1167).*
Ebner et al. (Amino Acids, 2006, 31: 251-272).*
Post et al., American Family Physician, 2012, 85: 890-896.*
Declaration filed in USSN 10/522653 on Jan. 9, 2008.*
Office Action of May 4, 2009 in 10/522653.*
Declaration filed in USSN 10/522652 on Dec. 10, 2008.*
Decision by BPAI rendered on Nov. 18, 2011 in USSN 09/117838.*
Alexandrova et al., "An Experience of Application of Potentiated Compounds for Jugulation of Alcohol Abstinent Syndrome and Opiate Abstinent Syndrome," Bull of Siberian Branch of RAMS, No. 1 (91), 1999.
Beregovoy et al., On influence of various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.
Davenas et al., Nature, 1988, 333: 816-818.
Epshtein et al. May 1999, Bulletin of Experimental Biology and Medicine,vol. 5: 493-495.
Epshtein et al. Mar. 1999, Bulletin of Experimental Biology and Medicine,vol. 127, No. 3, pp. 286-289.
Frimel, G., ed., "Immunological Methods," Medicina Publishing House, 1987, pp. 9-33.
Gaevy, M.D. et al., "Osnovy klinicheskoi farmakologii I farmakoterapii," Moscow, Aliyans-B, 2002, pp. 42-44.
GOLDACRE (2007) Lancet 370: 1672-1673.
Grigoriev M. Yu. et al., "K probleme ispolzovaniya potentsirovannykh organnykh preparatov," Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.
International Search Report from International Application No. PCT/RU01/00239, filed Jun. 19, 2001, mailed on Sep. 20, 2001.
Ivaniushkin, A. Ja., "Gomeopatiya i sovremennaya meditsina," Vestnik Akademii Meditsinskikh Nauk SSSR, 4, 1988, izd. "Meditsina" (Moscow), pp. 76-82.
Janeway et al. Immunobiology, 1997, 3rd edition, Garland Publishing Inc., pp. 3:1-3:11.

(Continued)

*Primary Examiner* — Ilia Ouspenski

(74) *Attorney, Agent, or Firm* — Pergament & Cepeda LLP; Milagros A. Cepeda; Edward D. Pergament

(57) ABSTRACT

The invention provides for a method of treating neuropsychiatric disorders in a patient. The method comprises the step of administering to the patient a homeopathically potentized form of at least one antibody to an antigen capable of treating the neuropsychiatric disorders.

6 Claims, No Drawings

(56) References Cited

OTHER PUBLICATIONS

Linde et al., 1997, Lancet, vol. 350: 834-43.
Register of Pharmaceuticals of Russia, Encyclopedia of Pharmaceuticals (in Russian), Moscow, 2000, pp. 358-359.
Register of Pharmaceuticals of Russia, Encyclopedia of Pharmaceuticals (in Russian), Moscow, 2001, pp. 788-789.
Schwab, V., "Homeopathic Pharmaceutical Agents. A manual on description and preparation," Moscow, 1967, pp. 12-38.
Schwabe, W., "German Homeopathic pharmacopoeia (Homeopathisches Arzneibuch)," Stuttgart, Translation of the 5th Supplement (1991) to the 1978 edition.
Shang et al., 2005, Lancet, vol. 366: 726-32.
Skurkovich, et al. Multiple Sclerosis 7:277-284, 2001 "Randomized study of antibodies to IFN-g and TNF-a in secondary progressive multiple sclerosis.".
Stefani, D. V. et al., "Immunologiya i immunopatologiya detskogo vozrasta," Moscow, Meditsina, 1996, pp. 28, 29, 358-359.
Vasiliev, Yu, V. et al., "Gomeopatiya: vozrozhdenie traditsionnioy meditsinskoj shkoly," Vestnik Rossijkoj Akademii Nauk, 10, 1992, izd. "Nauka" (Moscow), pp. 145-148.
Vyazov, O.L., Laboratory Methods of Studies in Non-Infection Immunology (in Russian)m Moscow, Meditsina, 1968.

* cited by examiner

METHOD FOR ADMINISTERING HOMEOPATHICALLY POTENTIZED ANTIBODY

This application is a Continuation-in-Part of U.S. patent application Ser. No. 11/656,225 filed Jan. 22, 2007, which is a Divisional of U.S. patent application Ser. No. 10/311,666 filed Dec. 17, 2002 which claims the befit of International Application No. PCT/RU2001/000239, filed Jun. 19, 2001, all of which are hereby incorporate herein by reference in their entireties.

FIELD

The present application relates to medicine and can be employed for treating various diseases and for producing pharmaceutical preparations possessing no side effects.

BACKGROUND ART

The use of antibodies for treating pathological syndromes is well known (SU 1331508 A, A 61 K 39/00, 1984; SU 1730144 A1, C 12 N 7/00, 1992).

Also known are pharmaceutical preparations based on antibodies (serums, immunoglobulins) applied in therapeutic doses. (See, for example, Register of Pharmaceutical Agents of Russia, Encyclopedia of Drugs, 7.sup.th edition, 2000, pp. 358-359).

However, the range of application of these preparations is for the most part limited to etiological treatment of infectious diseases, and their use may be associated with undesirable side effects.

BRIEF DESCRIPTION

The present application is aimed at enhancing the efficacy of treatment of pathological syndromes by the use of antibodies in activated forms for fundamentally new indications, such as to control a pathological syndrome; it is also intended for producing pharmaceutical substances without marked side effects.

For solution of the given problem, the method for treating a pathological syndrome includes administration of activated forms of ultra-low doses (homeopathically potentized forms) of antibodies to an antigen, wherein said activated forms are obtained by repeated consecutive dilution combined with external treatment, and said antigen is a substance or a pharmaceutical agent implicated in or exerting influence upon the mechanisms of formation of the pathological syndrome; said antigen can also represent a substance (or drug) that is, upon its introduction into the body, with non-medical purposes included, can act as direct cause of the pathological syndrome.

To this end it is expedient to use ultra-low doses of antibodies in activated forms prepared by homeopathic technology of potentiation (dynamization).

Activated forms of ultra-low doses of antibodies to a substance or a pharmaceutical agent can be also introduced together with this very substance or pharmaceutical agent implicated in or exerting influence upon the mechanisms of the pathological syndrome or directly causing the pathological syndrome.

Besides, the objective is also accomplished by a pharmaceutical agent containing activated forms of ultra-low doses of monoclonal, polyclonal or natural antibodies to an antigen, wherein said activated forms are produced by repeated consecutive dilution and external treatment predominantly based on homeopathic technology, and said antigen is a substance or a pharmaceutical agent exerting influence upon regulation of the impaired function.

At that, antibodies used in activated (potentiated) forms of ultra-low doses are raised against antigens of exogenous or endogenous origin, against autologous antigens, fetal antigens; anti-idiotypic antibodies are used too.

The drugs (pharmaceutical agents) obtained in accordance with the present application constitute a novel class of pharmacological preparations, distinctive in combination of specific pharmacological activity, stable therapeutic action free from side effects, ecological purity and low prime cost. Said pharmaceutical agents are utilized in methods of treating a number of disorders or conditions including a number of neuropsychiatric disorders such as schizophrenia, Alzheimer's disease, depression and attention deficit disorder. The method of treating these disorders comprises administering to a patient suffering from the disorder a homeopathically potentized form of at least one antibody to an antigen, which antigen is a molecule capable of treating said disorder.

DETAILED DESCRIPTION

The pharmaceutical preparation can be prepared in the following way.

1. Obtaining of Antibodies.

Polyclonal antibodies specifically binding to compounds of various classes: proteins, polynucleotides, oligosaccharides, glycolipids, etc. and interacting with low-molecular substances (haptens) are obtained through active immunization of animals. For this purpose, animals are given a series of antigen injections according to a specially designed pattern, the antigen being either an individually isolated high-molecular substance, or a synthetic conjugate (for haptens). This procedure results in obtaining a monospecific antiserum with high content of antibodies apt for further processing. If necessary the antibodies present in the antiserum are purified. Fractionating by salt precipitation or ion exchange chromatography is used for this purpose.

Monoclonal antibodies of different specificity interacting both with low-molecular haptens and with epitopes of high-molecular substances are obtained by means of hybridome technology. At that, the initial stage of the process includes immunization based on the principles already developed for preparation of polyclonal antiserums. Further stages of work envisage yielding antibody-producing clones of hybrid cells, produced antibodies being of identical specificity. Their isolation is carried out with the same methods as for polyclonal antiserums.

Natural antibodies to exogenous antigens and biological regulators of various origins are isolated from human blood serum by the method of affinity chromatography. To this end, a carrier with a covalently bound antigen, either a hapten or a high-molecular compound is used as an immunosorbent. Chromatography yields antibodies with narrow specificity and affinity.

Methods of obtaining antibodies are described, for example, in Immunological Methods, under the editorship of G. Frimel, Moscow, Medicina Publishing House, 1987, p. 9-33).

Isolated antibodies to a substance or a pharmaceutical agent are consecutively repeatedly diluted and exposed to external treatment until ultra-low or low doses (homeopathically potentized form) are obtained, for example, in accordance with homeopathic technology of potentiation (dynamization) (see V. Shvabe, Homeopathic Pharmaceutical Agents. A Manual on Description and Preparation, Moscow, 1967, p. 12-38). At that, the concentration is proportionally reduced through consecutive dilution of 1 volumetric part of the initial substance (antibodies) in 9 volumetric parts (for decimal dilutions, D) or in 99 volumetric parts (for centesimal dilutions, C) of a neutral solvent until the required dose (potency) is obtained; each dilution is followed by multiple vertical mechanical shaking; for each dilution separate vessel is preferable.

External treatment in the process of dilution can also be performed by sound generator or other mechanical or electromagnetic action.

The pharmaceutical preparation thus yielded is used for the most part in dosage forms and dilutions common for homeopathic practice, such as alcoholic or aqueous solutions or tablets (granules) obtained by saturating the excipient of the formulation with potentiated solution or by direct introduction of the latter into liquid dosage form of the preparation.

An example of obtaining a pharmaceutical preparation in form of activated polyclonal antibodies (antiserum) to morphine is given below.

2. Obtaining Morphine-Ovalbumin Conjugate.

Solution of 50 mg (0.001 mmol) ovalbumin in 5.0 ml of distilled water was mixed with 2.0 ml dimethylformamide containing 15.0 mg (0.039 mmol) of morphine 6-hemisuccinate and while the mixture was cooling the solution of 15 mg (0.055 mmol) of water-soluble carbodiimide in 3 ml of distilled water was added to it by drops. The reaction mixture was incubated for 5 hours at 4.degree. C. The yielded conjugate was isolated by gel chromatography on Sephadex G25 column and exposed to lyophilization.

The quantity of conjugated morphine was calculated from UV-spectra of the original protein and the yielded conjugate by changes in absorption at 280 nm. According to UV-spectra, the synthesized conjugate contained 12-15 moles of hapten per mole of protein.

3. Obtaining a Monospecific Antiserum to Morphine-Ovalbumin Conjugate

Immunization of Viennese Blue rabbits weighing not more than 2 kg was performed in cycles with a 10-day interval between them. The maximal number of injections was four. The conjugate was injected into the area of periarticular lymph nodes of front and hind paws in the dose of 1 mg per immunization. To this end the antigen was previously diluted in 1 ml of complete Freund's adjuvant. The total volume of immunization mixture was 2 ml.

Subsequent immunizations were performed using incomplete Freund's adjuvant, adhering to the above-mentioned proportions of antigen and adjuvant. A test blood sample was drawn from marginal ear vein of the animal 10 days after immunization.

The rabbit blood serum was obtained by centrifugation at 1000 g for 10 minutes at room temperature; after that chloroform was added as a preservative its final concentration reaching 13%.

The antiserum obtained was tested for specific antibodies to morphine by means of enzyme immunoassay, the antibodies being detected with conjugate of enzyme-labeled antispecies (anti-rabbit) antibodies.

The obtained antiserum contained specific antibodies active in the dilution 1:1000-1:25000.

Further on, γ-globulin fraction was isolated from the yielded antiserum. To this end the protein was precipitated with 50% ammonium sulfate with subsequent rinsing of the precipitate with 30% saline solution, centrifugation and dialysis against phosphate buffer. The fraction thus prepared contained specific antibodies to morphine and was then used for producing the pharmaceutical preparation.

4. Obtaining the Activated Form (Ultra-Low Dose) of the Antibodies to Morphine.

Antiserum γ-globulins (0.5 ml) was placed into $E-6_1$ vessel and mixed with 4.5 ml of distilled water; the mixture was shaken 10 times yielding 5 ml of the first centesimal dilution. The first centesimal dilution (0.05 ml) was placed into $E-6_2$ vessel with 4.95 ml of distilled water; the mixture was shaken 10 times yielding 5 ml of the second centesimal dilution. The centesimal dilutions from the third to the twenty-ninth were prepared in a similar fashion. The thirtieth centesimal dilution was prepared by solving the twenty ninth one in 20% solution of ethanol. The yielded alcoholic solution was used for treatment purposes.

Examples of use of activated forms of ultra-low doses of antibodies conventionally designated as potentiated (dynamized) antibodies (by analogy with terminology used in homeopathic literature) for treatment of various pathological syndromes are given below.

EXAMPLE 1

Potentiated Antibodies to Hypnotic Medications

1A. Patient I., aged 46, a high school instructor, had long been suffering from insomnia manifested by difficulties in falling asleep. The patient had a history of hepatitis (hepatitis and impaired metabolism of xenobiotics in the liver resulting from it probably accounted for the aftereffects of the preparation). For the last six months the patient had been taking 7.5 mg of IMOVAN at bedtime 2-3 times a week; in the morning he suffered from drowsiness and dizziness. The dose reduced to ½ tablet did not produce-the-desirable somniferous effect. The treatment with antibodies to IMOVAN C200 in tablets was started after discontinuation of IMOVAN intake. Two weeks later dizziness and morning drowsiness disappeared. The patient's sleep became normal.

1B. Patient P., aged 62, complained of a sleeping disorder: awakening at 2-3 a.m. The patient had been using barbiturate derivatives as somniferous medications but abandoned these drugs because of their decreasing efficiency. The patient was recommended to take 10 drops of a 25% alcohol solution of potentiated monospecific antiserum to MIDAZOLAM (dormicum, flormidal, 8-chloro-6-(2-fluorophenyl)-1-methyl-4H-imidazo[1,5-a][1,4]benzodiazepine hydrochloride) at bedtime. Three days after the beginning of the treatment the patient stated that he was easier falling asleep; the sleep duration extended to 7. A continued intake of the preparation was recommended.

1C. Patient Ch., aged 42, was admitted to hospital in the condition of moderate alcohol intoxication. Next morning the patient complained of tremor and disorders in coordination of movements. After a single dose of 15 ml of an aqueous solution of potentiated monoclonal antibodies to NITRAZEPAM (radedorm, 1,3-dihydro-7-nitro-5-phenyl-2H-1,4-benzodiazepine-2-one) C30 the patient fell asleep. This suggested a conclusion that the preparation was efficient in restoration of sleep in the process of arresting alcohol abstinence syndrome.

1D. Patient R., aged 48, a-driver by profession, presented complaints of sleeping disorders due to overfatigue. An intranasal administration of 0.5 ml of a potentiated aqueous solution C20 of antibodies to ZOLPIDEM (N,N,6-trimethyl-2-(4-methylphenyl)imidazolo[1,2-a]pyridine acetamide) at bedtime was suggested for controlling his insomnia: At a new visit 5 days later the patient stated normalization of his sleep. Examination did not reveal any depression of reflexes or muscle tone. This suggested a conclusion that this preparation can be prescribed to the patients whose professional activities require precise coordination of movements.

1E. Patient M., aged 54, complained of drowsiness and disorders in coordination of movements and presented a long-time history of the use of somniferous medications. After a 7-day course of treatment with potentiated solution of monoclonal antibodies to ZOPICLON (imovan) (6-(5-chloro-2-pyridinyl)-6,7-dihydro-7-oxo-5H-pyrrolo-[3,4-b]-pyrazine-5-ylic ester of 4-methyl-1-piperazine carboxylic acid) C50 in a dose of 1 tablet twice a day the enhancement of motor activity and sleep normalization were observed.

EXAMPLE 2

Potentiated Antibodies to Anesthetic Drugs

2A. Patient M., aged 36, complained of nausea after the operation (appendectomy). For anesthesia THIOPENTAL SODIUM (monosodium salt of 5-ethyldihydro-5-(1-methylbutyl)-2-thioxo-4,6-(1H,5H)-pyrimidinedione) had been used. An oral intake of 20 ml of a C30 homeopathic dilution of the antiserum to thiopental 3 times a day was prescribed, which made it possible to attenuate nausea.

2B. Patient P., aged 28, complained of cramps in his lower extremities and hypertonicity of the gastrocnemius muscles. An oral intake of 15 ml of a C200 dilution of potentiated antiserum to SODIUM OXYBUTIRATE (sodium salt of 4-hydroxybenzoic acid) at bedtime was prescribed. The examination conducted 5 days later showed diminution of muscular tonicity.

2C. Patient M., aged 6, was admitted to the otorhinolaryngologic unit for a postoperative check-up after tonsillectomy. An oral administration of a C30 solution of potentiated antibodies to KETAMINE [(+−)-2-(2-chlorophenyl)-2-(methylamino)cyclohexanone hydrochloride] made it possible to reduce the sensitivity of the child's mucosa and to perform an examination.

2D. Patient A., aged 47, complained of hiccup and tachycardia after administration of ETHOMIDATE (ethyl ester of (R)-1-(1-phenylethyl)-1H-imidazole-5-carboxylic acid). A single oral dose of 50 ml of a homeopathic C30 solution of monoclonal antibodies to ethomidate was administered. Thirty minutes later hiccup disappeared and the cardiac rhythm was back to normal.

2E. Patient D., aged 68, was admitted to a surgical hospital for a scheduled operation on benign prostatic hyperplasia. Three years earlier he had undergone an operation for urolithiasis under HALOTHANE (1,1,1-trifluoro-2-chloro-2-bromoethane) anesthesia. The postoperative period was complicated by liver function disorders manifested by dyspepsia, hyperbilirubinemia, and positive liver function tests. The patient presented a history of poor tolerance of other anesthetics. Therefore, slow intravenous infusion of 3 ml of potentiated antibodies to HALOTHANE dissolved in a 5% glucose solution was used for anesthetic purposes. The operation and the postoperative period showed no complications.

EXAMPLE 3

Potentiated Antibodies to Anticonvulsant Drugs

3A. Patient B., aged 19, has been suffering from generalized epilepsy (grand mal seizures combined with psychomotor symptoms) since the age of 5. TEGRETOL (5-carbamoyl-5H-dibenz(b,f)azepine) chosen by the trial-and-error method had proved to be the most efficient anticonvulsant drug for the patient; she had been receiving a dose of 0.2 mg (1 tablet) 3 times a day for 2-years. The patient's mother consulted the attending doctor at to multiple bruises having appeared on the patient's body in the course of the last 10 days without any preceding mechanical trauma. Total blood test revealed a depressed white blood ($2.9 \times 10^3/\mu l$) and platelet count ($100 \times 10^3/\mu l$). The treatment with C30 potentiated monoclonal antibodies to the dibenzoazepine group forming the basis of the drug molecule was started whereas TEGRETOL was discontinued. Two weeks later the blood pattern was back to normal, no epileptic seizures were registered.

EXAMPLE 4

Potentiated Antibodies to Antiparkinsonian Drugs

4A. Patient Z., aged 37, developed parkinsonian symptoms after vernal encephalitis. The patient had been taking daily 10 mg (4 tablets) of BROMOKRYPTINE (2-bromo-α-ergokryptine) with good effect but complained of excessive fatigue, headaches, and constipation. The treatment with potentiated antibodies to 2-bromo-α-ergokryptine (a C1000 dilution) in a daily dose of 1 tablet taken in the morning was started. Three weeks later the bowel function was back to normal and headaches subsided; however, complaints of excessive fatigue persisted.

4B. Patient E., aged 72, was on LEVODOPA (3-hydroxy-1-tyrosine) for Parkinson's disease. He complained of nausea and vomiting. Antiemetic drugs of the phenothiazine group with smaller doses of LEVODOPA lead to the exacerbation of his main disease. The use of a C200 dilution of polyclonal potentiated antibodies to LEVODOPA in a dose of 1 tablet twice a day improved the patient's tolerance to the preparation.

EXAMPLE 5

Potentiated Antibodies to Neuroleptics

5A. Patient E., aged 42, was admitted to a psycho-neurological dispensary in a condition of psychomotor agitation due to alcohol intoxication. Fifteen minutes after intravenous administration of 1 ml of a C30 aqueous solution of potentiated antiserum to HALOPERIDOL (4-[4-(4-chlorophenyl)-4-hydroxy-1-piperidinyl]-1-(4-fluorophenyl)-1-butanone decanoate) in a 5% glucose solution the agitation arrested and the patient went to sleep.

5B. Patient L., aged 50, consulted her physician for disordered coordination of movements. The examination revealed inhibited reflexes in her low extremities, namely the knee-jerk and the Achilles tendon reflexes. She presented a long-time (1.5 months) history of FLUPHENAZINE (moditene) intake. The discontinued use of the preparation was combined with an intranasal administration of a C30 aqueous solution of monoclonal antibodies to fluphenazine (4-[3-[2-(trifluoromethyl)-10H-phenothiazine-10-yl]propyl]-1-piperazinylethanol) and a once-a-day slow intravenous administration of a dose of 1 ml. Four days later the patient's gait was back to normal and the muscle tone of her low extremities increased.

5C. Patient R., aged 62, complained of restlessness and groundless night fears. Earlier she sought for physician's advice for insomnia and used to take radedorm for it. Oral administration at bedtime of the antiserum to AZALEPTINE (clozapine, leponex) (8-chloro-11-(4-methyl-1-piperazinyl)-5H-dibenzo[b,e][1,4]diazepine) in a form of 10 ml of a C200 homeopathic solution was prescribed. Seven days later phobias disappeared and the sleep became normal.

5D. Patient Ch., aged 45, complained of tremor and disordered coordination of movements. He had a long-time history of neuroleptic drugs intake (haloperidol, aminazine) for schizophrenia. Oral administration of 5 ml of a C30 dilution of homeopathic solution of monoclonal antibodies to RISPERIDONE (3-[2-[4-(6-fluoro-1,2-benzisoxazol-3-yl)piperidino]ethyl]-6,7,8,9-tetrahydro-2-methyl-4H-pyrido[1,2-a]pyrimidin-4-one) twice a day by intramuscular injections was prescribed. Repeated examination 7 days later revealed absence of tremor and a tendency to normalization of the patient's gait. No psychotic disorders were observed.

5E. Patient S., aged 29, suffered from depressive-paranoid form of schizophrenia. He had been taking neuroleptic drugs of the phenothiazine series for some years; the best clinical effect was noted with TISERCINE (2-methoxy-10-(3-dimethylamino-2-methylpropyl)-phenothiazine hydrochloride). During last 4 months the patient himself and his relatives drew their attention to the aggravation of extrapyramidal disorders and impaired bowel function (constipation). Total blood rest revealed depressed white blood count reaching the lower bound of normal ($3.8 \times 10^3/\mu l$). The use of a C1000 dilution of potentiated monoclonal antibodies to PHENOTHIAZINE in a dose of 1 tablet 3 times a day for 20 days (with discontinued tisercine intake) resulted in a marked relaxation of extrapyramidal disorders and normalization of the bowel function; the patient's white blood count increased to $4.7 \times 10^3$ µl. No psychotic disorders were present. The patient's sleep, appetite and mood were within normal limits.

5F. Patient F., aged 19, suffered from oligophrenia in the form of idiocy; aggressive behavior. She received a maintaining dose of HALOPERIDOL (4-[4-(4-chlorophenyl)-4-hydroxy-1-piperidinyl]-1-(4-fluorophenyl)-1-butanone decanoate) (20 mg daily) and displayed marked extrapyramidal disorders. The lowering of the dose resulted in the enhancement of the patient's aggressiveness. The use of a C30 dilution of polyclonal potentiated antibodies to butyrophenone in a dose of 1 tablet twice a day improved the tolerance of HALOPERIDOL and made it possible to reduce the dose to 5 mg a day and subsequently to maintain the patient in a satisfactory condition by administering the potentiated preparation alone.

EXAMPLE 6

Potentiated Antibodies to Minor Tranquilizers

6A. Patient V., aged 50, a research worker, has been receiving a daytime tranquilizer, MEZAPAM, for his obsessive-compulsive neurosis. He complained of drowsiness (probably caused by impaired detoxifying function of his liver). The use of a C30 dilution of potentiated polyclonal antibodies to the benzodiazepine nucleus made it possible to replace the tranquilizer. The patient's condition became satisfactory; no neurotic disorders were noted.

6B. Patient E., aged 71, complained of restlessness and insomnia. Oral administration of a C200 preparation of potentiated polyclonal antibodies to DIAZEPAM (7-chloro-1,3-dihydro-1-methyl-5-phenyl-2H-1,4-benzodiazepine-2-one) in a dose of 1 tablet 3 times a day was prescribed. Four days later the district physician noted normalization of sleep along with fewer complaints of restlessness.

6C. Patient S., aged 30, registered in a psycho-neurological dispensary, complained of the onset of restlessness, anxiety, and insomnia after the withdrawal of PHENAZEPAM. Oral intake of the homeopathic solution of antiserum to 2H-1,4-benzodiazepine twice a day was prescribed. After two days of treatment the normalization of sleep and mood were noticed. The general state of health was satisfactory and no anxiety was observed.

6D. Patient I., aged 39, complained of fatigability, disorders in coordination of movements, and restlessness. Examination revealed no organic disorders of the central nervous system. After the diagnosis of neurasthenia was established a course of treatment with a C12 homeopathic solution of polyclonal anti-bodies to PHENIBUT (γ-amino-β-phenylbutyric acid hydrochloride) was suggested. After 2 days of oral intake (1 tablet twice a day) of the preparation tremor subsided and sleep became normal.

EXAMPLE 7

Potentiated Antibodies to Antidepressants

7A. Patient V., aged 36, complained of the worsening of mood and sleeping disorders in form of early awakening along with difficulties in falling asleep. The patient also stated irritability and tremor without objective reason. An intranasal administration of 5 drops of a C30 homeopathic solution of antiserum to FLUOXETIN (PROZAC) (+−)-N-methyl-γ-[4-(trifluormethyl)phenoxy]benzolpropanamine) 3 times a day was recommended. Upon a new examination 5 days later the patient stated the betterment of his mood along with a tendency to normalization of sleep. The physician's recommendation was to continue the course of treatment.

7B. Patient K., aged 39, complained of insomnia, tremor, restlessness, and impaired ability to work. He received a course of treatment with a C1000 dilution of potentiated polyclonal antibodies to FLUVOXAMINE ((E)-5-methoxy-1-[4-(trifluormethyl)phenyl]-1-pentanone-O-(2-aminoethyl) oxime) in an oral dose of 1 tablet 4 times a day. After 3 days of regular drug intake the normalization of sleep was observed along with the improvement of mood and control of restlessness.

7C. Patient Sh., aged 56, complained of restlessness, feeling of fear, and sleep disorders. An intranasal administration of 1 ml of a 2% C30 solution of antiserum to AMITRIPTYLINE (3-(10,11-dihydro-5H-dibenz[a,d]-cyclohepten-5-ylidene)-N,N-dimethyl-1-propanamine) 3 times a day was recommended. Upon a new examination 3 days later the patient stated the normalization of sleep along with the reduction in the frequency and intensity of his fits of phobia. He was advised to continue this treatment; high efficacy of the drug in this particular case was noted.

7D. A young man aged 18 had been suffering from enuresis since his childhood. AMITRIPTYLINE was found to have a good effect upon him. After three weeks of treatment the patient's relatives noticed his drowsiness; the patient himself complained of visual disorders (impaired accommodation) and bouts of arrhythmia from time to time. A C50 dilution of potentiated monoclonal anti-bodies to the tricyclic group, constituting the nucleus of tricyclic antidepressants was prescribed in a dose of 1 tablet twice a day. The symptoms of side effects disappeared whereas the curative action persisted.

7E. Patient Ch., aged 32, a manager, presented a vast number of complaints among which the dominating were constant tiredness, poor sleep with no refreshing effect, reduced ability to work, depression, constipation along with joint and muscle aches. This condition had been lasting for more than half a year. A thorough clinical and laboratory examination revealed no psycho-neurological or somatic lesions that would account for such syndromes. The diagnosis of a chronic fatigue syndrome was established. A month of combined therapy including physiotherapy, vitamin therapy, and antidepressant IMIPRAMINE intake resulted in a mild positive effect. The treatment with a C200 dilution of potentiated antibodies to IMIPRAMINE in a dose of 1 tablet 3 times a day was begun. A week later a marked improvement in the patient's condition was noted; his ability to work increased and the number of complaints declined.

7F. Patient K., aged 29, was admitted to a psycho-neurological hospital with an established diagnosis of manic-depressive psychosis in the phase of exacerbation. During examination the patient complained of the lack of motivations and tearfulness; the patient was not active physically. He used to take amitriptyline and diazepam for a long time. An oral intake of a C1000 solution of the antiserum to MOCLOBEMIDE (aurorix) (p-chloro-N-(2-morpholinoethyl)-benzamide) in the form of 5 ml of the aqueous solution 2 times a day was prescribed. A new examination 4 days later showed that the patient became more compliant; improved mood and enhanced liveliness were reported. A conclusion was drawn that the therapy was efficient.

7G. Patient C., aged 49, suffered from depression and sociophobia; he had been receiving daily 225 mg of MOCLOBEMIDE (aurorix) (1.5 tablets in three doses). Despite his attending-physician's warnings the patient sometimes broke his diet. Twice after eating a cheese sandwich and a pizza with cheese he had episodes of hypertension, his blood pressure reaching 190/110 mm Hg. With moclobemide discontinued, a C30 dilution of potentiated polyclonal antibodies to moclobemide was administered in a dose of 1 tablet once a day. Further on, the treatment was well tolerated and depression symptoms subsided rapidly.

7H. Patient S., aged 44, developed fluctuations of mood, tearfulness, and low vital activity caused by the climacteric period. Her psychiatrist estimated these symptoms as manifestations of a depressive syndrome. The use of traditional antidepressants caused somnolence and lethargy interfering with her professional duties. The prescription of a C12 dilution of potentiated antiserum to CERTRALINE purified by affinity chromatography in a dose of 1 tablet twice a day resulted in a rapid improvement of the patient's general state and stabilization of her mood.

EXAMPLE 8

Potentiated Antibodies to Antiemetic Drugs of Central Action

8A. Patient Zh., aged 64, developed nausea and vomiting during the course of radio- and chemotherapy for peripheral lung cancer. The prescription of MOTILIUM controlled manifestations of dyspepsia but caused weakness, somnolence and intestinal cramps. With MOTILIUM discontinued, the administration of 1 ml of a C6 dilution of potentiated antibodies to MOTILIUM in the form of intramuscular injections twice a day resulted in the disappearance of neurotoxic and spastic reactions. The use of the preparation was continued with a positive clinical effect.

EXAMPLE 9

Potentiated Antibodies to Central-Action Muscle Relaxants

9A. Patient B., aged 25, developed contractures of his lower extremities after a spinal trauma. MYDOCALM (1-piperidino-2-methyl-3-para-tolylpropanone-3 hydrochloride) in a dose of 300 mg a day was prescribed. After a favorable initial effect the patient noticed a gradual increase in the muscular tension in his lower extremities along with systemic arterial hypotension (105/60 mm Hg) after 2 months of the treatment. The prescription of a C200 dilution of potentiated anti-bodies to MYDOCALM in a dose of 1 tablet twice a day resulted in the normalization of arterial blood pressure (120/70) as well as in the reduction of muscular tension. The antibody therapy made it possible to reduce the dose of MYDOCALM by 25%.

EXAMPLE 10

Potentiated Antibodies to Choline Esterase Inhibitors

10A. Patient P., aged 20, with an established diagnosis of congenital myasthenia took UBRETIDE (3-oxy-1-methylpyridinium-hexamethylene-bis-(N-methylcarbamate) dibromide) (the maintaining dose was 1 tablet every other day). She started complaining of excessive salivation and abdominal cramps. The use of a D6 dilution of potentiated antibodies to UBRETIDE in a daily morning dose of 1 tablet improved the patient's tolerance of UBRETIDE without reducing its efficacy and later made it possible to switch to therapy with the potentiated preparation only.

EXAMPLE 11

Potentiated Antibodies to Psychostimulants and Nootropic Drugs

11A. Patient M., aged 58, complained of memory disorders and insomnia. An oral intake of 20 drops of an alcohol solution of antibodies to NOOTROPIL (pyracetam) (2-oxo-1-pyrrolidinylacetamide) in a potency of C200 at bedtime was prescribed. During her second visit 7 days later the patient reported of an extended duration of sleep along with less difficulties in falling asleep. The recommendation was to continue the course of treatment.

11B. Patient M., aged 43, was admitted to hospital in the state of alcohol withdrawal. The next day he started complaining of restlessness and tremor. A C30 dilution of potentiated antiserum to AMINALON (gammalon) (4-aminobutyric acid) in a dose of 1 tablet 6 times a day was prescribed. The reduction of tremor and the improvement of mood were noted. After 2 days of therapy the patient was discharged in a satisfactory condition.

11C. Patient S., aged 72, complained of tachycardia and sleeping disorders; she presented a long-time (3 weeks) history of SYDNOCARB (3-(α-methylphenyl)-N-phenyl-carbamoylsydnonimine) intake. The intranasal administration of 10 drops of a C15 solution of monoclonal antibodies to SYDNOCARB 3 times a day was prescribed. An examination after 5 days of treatment revealed the absence of tachycardia; the patient reported of less difficulties in falling asleep.

11D. Patient V., aged 65, with an established diagnosis of asthenic syndrome as a remote consequence of a craniocerebral trauma had been taking MOLSIDOMINE (ethylester of N-carboxy-3-morpholino-sydnonimine) in a dose of 1 tablet 3 times a day (6 mg per diem) to prevent fits. She sought her physician's advice for headaches and worsening of sleep. After MOLSIDOMINE withdrawal the treatment with C30 dilution of potentiated monoclonal antibodies to the sydnonimine group in a dose of 1 tablet in the morning was started. The favorable effect of the treatment has been lasting for 6 months.

11E. Patient D., aged 38, complained of fatigability, weakness, and headaches. The oral intake of 10 ml of a C40 dilution of potentiated polyclonal antibodies to CAFFEINE (1,3,7-trimethylxanthine) 3 times a day was prescribed. At his second visit to the physician 7 days later the patient pointed to easier awakening and the disappearance of headaches. He was recommended to continue the course of treatment.

11F. Patient P., aged 35, a journalist by profession, presented symptoms of caffeine addiction: he had to drink up to 12-15 cups of strong coffee to keep himself active. The patient was emotionally labile, inclined to overestimating his own personality, and complained of poor sleep. He also had a pronounced tremor of his hands. The use of a C200 dilution of potentiated antibodies to CAFFEINE (1,3,7-trimethylxanthine) in a dose of 1 tablet 3 times a day resulted in the reduction of the amount of consumed coffee to 4-5 cups, the improvement of sleep, the disappearance of tremor, and better mood. Now the patient is active and manifests high working efficiency.

11G. Patient R., aged 78, is on regular treatment with PYRACETAM (nootropil) (2-oxo-1-pyrrolidinylacetamide) in a daily dose of 1.6 g for Alzheimer's disease. The general effect of the treatment being favorable, the patient's relatives noticed enhancement of the patient's sexual activity manifested by his inappropriate behavior. The substitution of pyracetam by a C200 dilution of potentiated antibodies to PYRACETAM made it possible to get rid of sexual disinhibition while preserving the nootropic effect.

11H. Patient G., aged 4, suffered from mental retardation due to a birth trauma. A 4-week course of everyday injections of CEREBROLYSINE (a complex of peptides isolated from pig brain) resulted in some improvement of the child's cognitive activity. During repeated courses of treatment cerebrolysin was substituted by a C50 dilution of potentiated polyclonal antibodies to it (in a dose of 1 tablet 2 times a day). The patient's memory became much better as well as her abilities to develop and maintain skills.

EXAMPLE 12

Potentiated Antibodies to Preparations Improving Cerebral Circulation

12A. Patient L., aged 54, presented a history of cerebral atherosclerosis and an ischemic stroke a month ago. He was treated with HALIDOR (1-benzyl-1-(3-dimethylaminopropoxy)-cycloheptane fumarate) in tablets (100 mg twice a day). The patient complained of sleeping disorders and tachycardia (92 beats/min). The use of a C30 dilution of potentiated antibodies to HALIDOR (in a daily dose of 1 tablet within a month) improved his sleep; his heart rate went down to 76-80 beats/min.

EXAMPLE 13

Potentiated Antibodies to Analeptic Drugs

13A. Patient T. aged 15, was admitted in the state of alcohol intoxication. Examination revealed hypotension (90/60 mm Hg), bradycardia, and nausea. The intranasal administration of 1 ml per hour of a C200 dilution of antiserum to CORDIAMINE (N,N-diethyl-3-pyridinecarboxamide) was prescribed. After 6 hours of the treatment nausea disappeared and the patient's blood pressure was back to normal.

EXAMPLE 14

Potentiated Antibodies to Anticonvulsant (Antiepileptic) Drugs

14A. Patient D., aged 58, complained of tonic cramps in her lower extremities. The oral intake of calcium gluconate in combination with 10 ml of a D12 homeopathic solution of antibodies to DEPAKIN (SODIUM VALPROATE) (sodium 2-propylvalerate) at bedtime was recommended. The reduction of convulsive reactions was stated after 2 days of the therapy.

14B. Patient E., aged 47, was admitted to the in-patient unit of the hospital because of the exacerbation of lumbosacral radiculitis. Within the framework of combined therapy he received, along with conventional anti-inflammatory therapy, a 25% intranasal alcohol solution (a C30 dilution) of monoclonal antiserum to FINLEPSIN (TEGRETOL) (5H-dibenz [b,f]azepin-5-carboxamide) in the form of 10 drops per dose. The next day the pain subsided and the excessive tension of back muscles reduced.

14C. Patient T., aged 64, complained of insomnia and night cramps in his extremities. Within the framework of combined therapy he was receiving orally at bedtime 20 ml of a C30 dilution of potentiated antiserum to PHENOBARBITAL (5-ethyl-5-phenyl-2,4,6(1H, 3H, 5H)-pyrimidinetrione). At his new visit to the physician 10 days later the normalization of sleep was noted along with a reliable reduction in the frequency of convulsive reactions.

14D. Patient I., aged 45, with an established diagnosis of generalized form of epilepsy had to give up taking LAMOTRIGINE (6-(2,3-dichlorophenyl)-1,2,4-triazine-3,5-diamine) because of nausea. The prescription of a C30 homeopathic solution of monoclonal antibodies to LAMOTRIGINE in the form of 10 intranasal drops 3 times a day instead of LAMOTRIGINE made it possible to eliminate nausea and proceed with the course of treatment. There have been no generalized epileptic fits in the course of 3-months' observation.

14E. Patient U., aged 39, with an established diagnosis of epilepsy with rare absences was on PHENYTOINE (5,5-diphenyl-2,4-imidazolidinedione) treatment. She complained of dizziness and tremor for which reason and the use of the preparation was discontinued. Instead the oral intake of 20 ml of a D6 dilution of a potentiated antiserum to phenytoine 3 times a day was prescribed. Two days later the patient felt better and her tremor disappeared. No absences were registered within 8 weeks of observation.

14F. Patient P., aged 49, complained of pain and tension in her gastrocnemius muscles. She gave a history of sciatic neuralgia. In order to reduce the patient's muscular tension the physician prescribed an oral intake of 20 ml of a C30 homeopathized solution of monoclonal antibodies to BACLOPHEN (β(aminomethyl)-4-chlorobenzenepropanoic acid) 3 times a day in combination with anti-inflammatory therapy. At the new visit 7 days later she stated that her muscular rigidity and pain subsided.

EXAMPLE 15

Potentiated Antibodies to Antiparkinsonian Drugs

15A. Patient D., aged 76, with an established diagnosis of Parkinson's syndrome was taking a course of treatment with LEVODOPA (3-hydroxy-L-tyrosine). As the treatment was not very efficient, the additional oral intake of a C15 dilution of monoclonal antibodies to LEVODOPA was prescribed in a dose of 1 tablet 3 times a day. The elimination of tremor was registered 3 days later, which made it possible to conclude that the therapy became more efficient. Three months later the patient was completely switched to therapy with antibodies. The tremor is insignificant. The general condition of the patient is satisfactory.

15B. Patient K., aged 69, with an established diagnosis of Parkinson's syndrome due to atherosclerosis of cerebral vessels complained of nausea after the intake of SELEGILINE (DEPRENYL) ((R)—N,α-dimethyl-N-2-propenylbenzene ethanamine). The intranasal administration of 10 drops of a D24 dilution of homeopathic solution of antibodies to (R)—N-α-dimethyl-N-2-propenylbenzene ethanamine 3 times a day made it possible to eliminate nausea and to continue the course of treatment with antibodies as monotherapy.

EXAMPLE 16

Potentiated Antibodies to Preparations Used Predominantly for the Treatment of the State of Dependence 16A. Patient B., aged 41, had been taking a course of treatment in order to get rid of his habit of smoking. The intranasal administration of 20 drops of a C1000 dilution of the antiserum to NICOTINE (S)-3-(1-Methyl-2-pyrrolidinyl) pyridine) 2 times a day was prescribed. The patient stated the lessening of his attraction to smoking after 4 days of the treatment with the preparation.

16B. Patient D., aged 19, was admitted to hospital on a suspicion of drug addiction. Two hours after the oral administration of 3 ml of a C50 homeopathic solution of antibodies to NALOXONE (5-α)-4,5-epoxy-3,14-dihydroxy-17-(2-propenyl)morphinan-6-one hydrochloride) the development of the withdrawal syndrome was registered, which was regarded as the naloxone-like effect. The further treatment with potentiated antibodies within the framework of combined disintoxication therapy made it possible to arrest the state of abstinence within 4 days.

Potentiated antibodies to DISULFIRAM (antabuse, (tetraethylthio-peroxydicarbodiamide).

16C. Patient E., aged 56, was admitted to the in-patient unit of a hospital with low blood pressure (80/50 mm Hg), suffering from nausea. He presented a history of alcohol intake against the background of ESPERAL (DISULFIRAM) treatment. Five hours after the intranasal administration of 2 ml of a C30 solution of potentiated antibodies to DISULFIRAM the normalization of the patient's blood pressure and the control of nausea were achieved; however, vegetative disorders reappeared when the alcohol test was performed.

EXAMPLE 17

Potentiated Antibodies to Narcotic Analgesics

17A. Patient Ch., aged 22, was admitted to the in-patient unit with signs of heroin withdrawal. In order to control his pain syndrome intramuscular injections of 1 ml of a C50 dilution of polyclonal antiserum to TRAMAL (trans-(+−)-2-[(dimethylamino)methyl]-1-3(-metoxyphenyl)cyclohexanol hydrochloride) were given twice in the course of the first hour as monotherapy. The arrest of the pain syndrome was virtually achieved. Conventional disintoxication therapy was prescribed.

Potentiated antibodies to BUTORPHANOL (MORADOL) (17-cyclobuthylmethyl)morphinan-3,14-diol).

17B. Patient R., aged 24, was admitted to a narcological in-patient unit with an opiate withdrawal syndrome; the patient had been taking various opiates for long time (6 months). The oral intake of 30 ml of a C200 homeopathized solution of monoclonal antibodies to MORADOL 3 times a day lessened the intensity of the pain syndrome and the attraction to drugs.

Potentiated antibodies to PROMEDOL.

17C. Patient S., aged 24, whose diagnosis was "heroin drug addiction, remission of a 7 months' duration" applied for medical advice complaining of pain in her right temporomandibular joint. No organic lesions were found after examination A D24 dilution of potentiated antiserum to PROMEDOL, (1,2,5-trimethyl-4-phenyl-4-piperidinol propanoate) was prescribed. After a single dose of the preparation the pain disappeared with background transitory manifestations of the so-called dry abstinence. When questioned, the patient reported the easing of her attraction to heroin that had increased 10 days earlier.

Potentiated antibodies to MORPHINE (5α,6α)-7,8-didehydro-4,5-epoxy-17-methylmorphinan-3,6-diol.

17D. Patient Z., aged 29, underwent appendectomy. In order to control the postoperative pain he received a single 30 ml oral dose of a C30 solution of potentiated antiserum to MORPHINE at bedtime. The patient went to sleep. When questioned, he reported no feeling of euphoria upon the intake of the preparation.

Potentiated antibodies to PHENTANYL (N-Phenyl-N-[1-(2-phenylethyl)-4-piperidinyl]propanamide).

17E. Patient T., aged 68, complained upon admittance of pain in her spine. She had a history of metastases of stomach cancer into the vertebral bodies and of a long-time intake of narcotic analgesics. A slow intravenous infusion of 2 ml of a D12 solution of potentiated antibodies to PHENTANYL twice a day was prescribed. After 4 days of the treatment the patient reported that the pain syndrome subsided.

EXAMPLE 18

Potentiated Antibodies to Anticholinesterase Drugs

Potentiated antibodies to PHYSOSTIGMINE ((3aS-cis)-1,2,3a,8,8a-hexahydro-1,3a,8-trimethylpyrrolo[2,3-b]indole-5-olmethylcarbamate).

18A. Patient F., aged 63, was under medical observation after a stroke. Objective findings: the muscular tension in the left arm was lowered. The intranasal administration of 0.5 ml of a C50 solution of potentiated monoclonal antibodies to PHYSOSTIGMINE 3 times a day was prescribed within the framework of combined therapy. After 3 weeks of the treatment normalization of the muscular tension and reflexes was observed.

Potentiated antibodies to PROSERINE (3-[[dimethylamino)carbonyl]-oxy]-N,N,N-trimethylbenzolaminium bromide).

18B. Patient Ch., aged 60, after appendectomy suffered from the onset of intestinal paresis in the postoperative period. The oral intake of a C200 dilution of the antiserum to PROSERINE in a dose of 1 tablet 3 times a day was prescribed. After 4 days of the treatment the patient's gastrointestinal tract motility was back to normal.

EXAMPLE 19

Potentiated Antibodies to Anti-Glaucoma Drugs

19A. Patient Ya., aged 70, had had a long-time history of glaucoma. The patient had been taking ACETAZOLAMIDE (5-day courses of 250 mg every 6 hours) to good effect. The preparation's mechanism of action involves carbonic anhydrase blocking; on a prolonged use its efficacy is reduced due to compensatory mechanisms. Therefore, it was found necessary to discontinue the use of the preparation from time to time. During these interruptions of the treatment the attacks of glaucoma became more frequent but the patient did not tolerate any other anti-glaucoma drugs. The prescription of a C6 dilution of potentiated antibodies to ACETAZOLAMIDE in a dose of 1 tablet a day resulted in the restoration of the patient's sensitivity to the preparation; his intraocular pressure did not go beyond the upper bound of normal; the frequency of attacks of glaucoma was markedly reduced. ACETAZOLAMIDE intake was discontinued. The term of follow-up was 4 months.

EXAMPLE 20

Potentiated Antibodies to Drugs Used for Migraine

Antibodies to DIHYDROERGOTAMINE.

20A. Patient N., aged 41, complained of cramping pain in the left part of her head. The diagnosis of migraine was established; the intranasal administration of a. C200 dilution of potentiated monoclonal antibodies to DIHYDROERGOTAMINE (5α,10α)-9,10-dihydro-12-hydroxy-2-methyl-5-(phenylmethyl)ergotamine-3,6,18-trione mesilate) 4 times a day was prescribed. At her next visit to the physician 7 days later the patient reported the lessening of both frequency and intensity of pain. It was recommended to continue the course of treatment.

Antibodies to SUMATRIPTANE (3-[2-(dimethylamino) ethyl-]-N-methylindole-5-methanesulfonamide).

20B. Patient K., aged 42, addressed herself to an outpatient clinic complaining of attacks of headache localized in the left part of her head and accompanied with nausea. The prescription was to take orally 1 ml of a D24 solution of potentiated monoclonal antibodies to SUMATRIPTANE at the time of the attack of headache together with conventional analgesics. At her next visit to the physician the patient reported the disappearance of nausea and the lessening of the intensity of pain.

EXAMPLE 21

Potentiated Antibodies to Local Anesthetics

Antibodies to LIDOCAINE ((2-diethylamino)-N-(2,6-dimethylphenyl)acetamide).

21A. Patient R. aged 32, complained of heart palpitation. The diagnosis of ventricular tachyarrhythmia was established on examination. The recommendation was to take orally 1 tablet of a C12 dilution of potentiated antibodies to LIDOCAINE every hour during the attack. Using this drug, the patient reported normalization of the heart rhythm.

EXAMPLE 22

Potentiated Antibodies to Non-Steroid Antiinflammatory Drugs

Potentiated antibodies to DICLOFENAC (2-[(2,6-dichlorophenyl)amino]benzeneacetic acid).

22A. Patient M., aged 52, complained of pain in his knees. The diagnosis of arthritis in the phase of exacerbation was established on examination. The prescription was: compresses with a C6 homeopathic solution of antibodies to DICLOFENAC. After four procedures the lessening of hyperemia and soreness of the joints was noticed.

Potentiated antibodies to INDOMETHACINE.

22B. Patient D., aged 48, complained of pain in the epigastric area. He presented a long-time (1.5 month) history of the intake of INDOMETHACINE (1-(4-chlorobenzoyl)-5-methoxy-2-methyl-1H-indole-3-acetic acid). Gastroscopy revealed erosive gastritis. The homeopathized solution of an antiserum to indomethacine (a. C30 potency) in the form of 1 tablet 3 times a day was prescribed. At a new examination 7 days later the patient noted that the pain had disappeared.

Potentiated Antibodies to CYCLOOXYGENASE.

22C. Patient F., aged 49, had been suffering from rheumatoid polyarthritis for 12 years. The use of NSAIDs of all groups including MOVALIS (a preparation with a relatively selective effect upon cyclooxygenase-2) was extremely problematic due to concomitant hyperacidic gastritis. With the background treatment with a D12 dilution of a potentiated form of antibodies to cyclooxygenase-1 in a oral dose of 1 tablet 2 times a day the patient tolerated MOVALIS well. The pain in his joints subsided and the joint motility regained. The endoscopic examination showed the remission of hyperacidic gastritis.

Potentiated Antibodies To IBUPROFEN (α-methyl-4-(2-methylpropyl) benzeneacetic acid).

22D. Patient L., aged 56, complained of pain and limited motility of her ankle joint. The oral intake of IBUPROFEN in combination with the intranasal administration of 0.5 ml of a C12 dilution of potentiated antibodies to α-methyl-4-(2-methylpropyl)benzolacetic acid twice a day was prescribed. Five days later the normalization of joint motility and the absence of pain were noted. Ibuprofen was discontinued. The patient started receiving potentiated antibodies as monotherapy. No inflammatory symptoms or pain in her joints were found.

Potentiated Antibodies To ASPIRIN (2-(acetyloxy)benzoic acid).

22E. Patient T., aged 48, complained of headaches. The examination revealed a temperature rise to 37.1° C. A C30 preparation of potentiated antibodies to ASPIRIN in a dose of 1 tablet 4 times a day was recommended. Twenty-four hours later her body temperature was back to normal and the headache subsided completely.

22F. Patient T., aged 48, with an established diagnosis of ischemic heart disease developed instable angina attacks at minimal physical strain. ACETYLSALICYLIC ACID (325 mg once a day) was among the preparations the patient regularly took within the framework of combined therapy. The patient complained of stomach discomfort; a laboratory examination revealed the growth of the blood coagulation time from 5 to 12 minutes. The prescription was: 1 ml of a C12 dilution of potentiated antibodies to ASPIRIN in the form of intramuscular injections once a day. The stomach discomfort disappeared and the blood coagulation time shortened to 8 minutes.

Potentiated Antibodies to PARACETAMOL (N-(4-hydroxyphenyl) acetamide.

22G. Patient N., aged 11, was admitted to the hospital with an acute respiratory tract infection. The examination revealed a temperature rise to 38.2° C. and rhinitis. In addition to halazolin, the patient started receiving orally 10 ml of an aqueous solution of potentiated antibodies to PARACETAMOL 4 times a day. Twelve hours later his body temperature was back to normal and rhinitis subsided.

EXAMPLE 23

Potentiated Antibodies to Pharmaceutical Agents Influencing the Function of Respiratory Organs Potentiated Antibodies to PHENOTEROL (1-(3,5-dioxyphenyl)-2-(para-oxy-α-methyl-phenetylamino)-ethanol).

23A. Patient K., aged 22, suffering from asthmatic bronchitis used PHENOTEROL (berotec) in an aerosol form as his main therapeutic agent. The patient stated the reliability and efficiency of the preparation but complained of hand tremor and heart palpitations associated with the medication. The use of a C30 dilution of potentiated antibodies to phenoterol in a dose of 1 tablet 2 times a day improved the patient's tolerance for the preparation without affecting its-efficacy. Gradually the patient was switched to the potentiated preparation as monotherapy. No asthmatic episodes were registered within 5 weeks of observation.

Potentiated Antibodies to ATROVENT.

23B. Patient A., aged 26, suffered from polyvalent allergy including intolerance to soybeans and peanuts. He had been successfully receiving ATROVENT (in the form of an inhalation solution) for frequent attacks of bronchial asthma. After a single attempt to use ATROVENT in the form of an inhalation aerosol the patient developed a severe anaphylactic reaction. The latter was arrested by means of three intranasal administrations of 0.5 ml of a D24 dilution of antibodies to atrovent with 20-minutes intervals. Later on the patient started receiving 1 tablet a day of a D12 dilution of antibodies to atrovent every morning as monotherapy. He was feeling well and had no attacks of bronchial asthma in the course of three months.

23C. Patient A., aged 45, had been taking THEOPHYLLINE for a long time for the attacks of bronchial asthma until he noted the loss of efficiency of the preparation. The oral intake of a C30 dilution of a potentiated solution of antibodies to THEOPHYLLINE (1,3-dimethylxanthine) in a dose of 1 tablet 2 times a day enhanced the efficacy of the therapy, which allowed the dose of theophylline to be reduced.

23D. Patient D., aged 36, had been suffering from bronchial asthma since the age of 19. As his attacks occurred at night, he split his daily dose of 600 mg of THEOPECK into ⅔ in the evening and ⅓ in the morning. The patient complained of excessive irritability and the worsening of sleep. An attempt to reduce the dose of the preparation did not result in better sleep but nocturnal asthmatic fits became more frequent. Once the treatment with a C30 dilution of homeopathized antibodies to theophylline in a dose of 1 tablet 2 times a day had been started, the patient's sleep returned to normal within 3 weeks. The dose of theophylline was reduced to 300 mg, the asthmatic fits became rare.

Potentiated Antibodies to MENTHOL (2-isopropyl 5-methylcyclohexanol-1).

23E. Patient Ch., aged 39, complained of cough and dryness in his throat. The recommendation was to take a tablet of potentiated antibodies to MENTHOL (a C12 dilution) at the onset of a coughing fit. At the next visit the patient reported the efficiency of the preparation for controlling the cough. It was recommended to continue the course of treatment.

Potentiated Antibodies to Adrenomimetic Drugs

Potentiated antibodies to NAPHTHIZINE, (NAPHAZOLINE) (4,5-dihydro-2-(1-naphthalinemethyl)-1H-imidazole).

23F. Patient V., aged 49, complained of tachycardia after administration of naphthizine for rhinitis. Naphtizine was replaced by a homeopathic solution (a C6 dilution) of monoclonal antibodies to 4,5-dihydro-2-(1-naphthalinemethyl)-1H-imidazole in a dose of 1 tablet 3 times a day. The patient reported normalization of his cardiac rhythm, which made it possible to continue taking the preparation. Twenty-four hours after the beginning of the treatment rhinorrhea virtually disappeared.

Potentiated antibodies to SALBUTAMOL ($\alpha$1-[[(1,1-dimethylethyl) amino]methyl]-4-hydroxy-1,3-benzenedimethanol).

23G. Patient I., aged 54, complained of hard breathing fits. The intranasal instillations of a C50 homeopathic solution of antibodies to SALBUTAMOL in the form of 5 drops of an aqueous solution 3 times a day were prescribed. The use of the preparation made it possible to shorten the duration of hard breathing fits.

EXAMPLE 24

Potentiated Antibodies to Histamine and Antihistamine Drugs

Potentiated antibodies to CROMOLYN (5,5-[(2-hydroxy-1,3-propanediyl)bis-(oxy)]-biz-[4-oxo-4H-1-benzopyrane-2-carboxylic acid).

24A. Patient M., aged 57, had been suffering from seasonal pollinosis. The prescription of 1 ml of a C30 dilution of potentiated antibodies to CROMOLYN in the form of nasal drops 2 times a day made it possible to control the symptoms of rhinitis.

Potentiated antibodies to ZADITEN (KETOTIFEN) (4,9-dihydro-4-(1-methyl-4-piperidinylidene-10H-benzo[4,5]cyclohepta[1,2-b]-thiophen-10-one hydrofumarate).

24B. Patient M., aged 29, a software programmer by profession has been suffering from pollinosis with symptoms of kerato-conjunctivitis during spring and summer. He used to control exacerbations of his condition with 1 mg of ZADITEN (1 tablet) 2 times a day. The positive therapeutic effect of ZADITEN intake was accompanied by a depressed intensity of emotional and physical reactions, somnolence and listlessness. The administration of a C30 dilution of potentiated antibodies to ZADITEN in a dose of 1 tablet 2 times a day resulted in the elimination of ZADITEN's side effects. The ZADITEN intake was discontinued; the patient continued to receive the potentiated preparation as monotherapy. No manifestations of hay fever were noted afterwards.

Potentiated antibodies to TAVEGYL (1-methyl-2[2-($\alpha$-methyl-para-chlorbenzhydryl-oxy)-ethyl]-pyrrolidine).

24C. Patient Ch., aged 35, used to take TAVEGYL to good effect for chronic urticaria. The parenteral administration of TAVEGYL (in a dose of 2 ml intramuscularly) in the case of the next exacerbation accompanied by a pronounced allergic skin syndrome and a high eosinophile count (18%) in the peripheral blood resulted in a rapid clinical and laboratory improvement (eosinophile count going down to 7%); however, headache, nausea, and mouth dryness were noted. The administration of a C12 dilution of potentiated polyclonal antibodies to TAVEGYL in a dose of 1 tablet 2 times a day resulted in the elimination of the side effects of TAVEGIL use. Further on, the patient has been receiving TAVEGIL in combination with potentiated antibodies to TAVEGIL; a month later she was put on a maintaining dose of antibodies (once in three days) as monotherapy.

24D. Patient S., aged 48, was admitted to the pulmonology unit for pneumonia. The patient had an anaphylactic shock in response to the intravenous injection of calcium chloride. The intramuscular injection of 1 ml of C50 dilution of potentiated antibodies to HISTAMINE made it possible to arrest the symptoms of shock within 5 minutes.

Potentiated Antibodies to KETOTIFEN (4,9-dihydro-4-(1-methyl-4-piperidinylidene)-10H-benzo[4,5]cyclohepta[1,2-b]thiophen-10-one hydrofumarate).

24E. Patient D., aged 12, was hospitalized because of his complaint of heavy breathing during the season of poplar blossoming. The oral intake of 10 ml of a C24 dilution of homeopathic solution of antiserum to KETOTIFEN 3 times a day restored the patient's respiratory function to the normal level.

Potentiated antibodies to inhibitors of H1-histamine receptors.

Potentiated antibodies to LORATIDINE (CLARITINE) (ethyl ester of 4-(8-chloro-5,6-dihydro-11H-benzo-[5,6]cyclohepta[1,2-b]pyridin-1-ylidene-)-1-piperidine carboxylic acid).

24F. Patient K., aged 45, complained of an itching sensation in her nasopharynx after working with paintwork materials. After the administration of a C200 dilution of potentiated monoclonal antibodies to LORATIDINE (in a dose of 1 tablet 2 times a day) itching subsided. It was concluded that the preparation had proved its efficiency.

Potentiated antibodies to TAVEGYL (CLEMASTINE) ([R—(R*,R*)]-2-[2-[1-(4-chlorophenyl)-1-phenylethoxy]ethyl]-1-methylpyrrolidine fumarate or 1-methyl-2 [2-(α-methyl-para-chlorbenzhydryl-oxy)-ethyl]-pyrrolidine fumarate).

24G. Patient P., aged 34, complained of somnolence after the intake of TAVEGIL for the itching of her elbows. The oral intake of a D6 dilution of potentiated antibodies to [R—(R*,R*)]-2-[2-[1-(4-chlorophenyl)-1-phenylethoxy]ethyl]-1-methylpyrrolidine fumarate in a dose of 1 tablet 2 times a day was recommended. At her next visit to the physician the patient reported that her drowsiness had subsided and her mood improved. She was put on the potentiated preparation as monotherapy. At her visit to the physician 2 months later the patient reported that her itching had virtually disappeared.

EXAMPLE 25

Potentiated Antibodies to Medications Used for Treatment of Erosive Lesions of Gastrointestinal Tract Potentiated Antibodies to inhibitors of H2-histamine receptors.

Potentiated Antibodies to RANITIDINE (N-[2]-[[[5-[(Dimethylamino)methyl]-2-furanyl]methyl]thio]ethyl]-N-methyl-2-nitro-1,1-ethendiamine).

25A. Patient N., aged 56, complained of epigastric pain. The prescription was: 1 tablet of a C12 dilution of a potentiated polyclonal antiserum to RANITIDINE (N-[2]-[[[5-(dimethylamino)methyl]-2-furanyl]-methyl]-thio]-ethyl]-N-methyl-2-nitro-1,1-ethendiamine) to be taken after meals. After 3 days of the treatment the pain disappeared.

Potentiated antibodies to FAMOTIDINE (3-[[[2-[(aminoiminomethyl)-amino]-4-thiazolyl]-methyl]-thio]-N-(aminosulfonyl)-propaneimidamide).

25B. Patient G., aged 45, complained of nausea after meals. Gastroscopy revealed gastritis in an exacerbation phase. The recommendations involved diet and the oral intake of 10 ml of a C30 solution of potentiated polyclonal antibodies to FAMOTIDINE before meals. After 5 days of the treatment the patient's general condition and the gastroscopic pattern of his gastric mucosa were back to normal.

Potentiated Antibodies to Proton Pump Inhibitors

Potentiated antibodies to OMEPRAZOLE (5-metoxy-2-[[(4-metoxy-3,5-dimethyl-2-pyridinyl)methyl sulfonyl]1H-benzimidazole).

25C. Patient U., aged 33, felt a pronounced pain in the pit of the stomach from time to time. Gastroscopy revealed erosive gastritis. After the administration of a C12 homeopathic dilution of the preparation of polyclonal antibodies to OMEPRAZOLE in a dose of 1 tablet-3 times a day along with a diet the gastric mucosa was back to normal 6 days: later and both frequency and intensity of pain diminished.

25D. Patient A., aged 44, with an established diagnosis of ulcerative disease of stomach and duodenum in the phase of exacerbation had been taking OMEZ (20 mg daily, a proton pump inhibitor) for 4 weeks. Against the background of an improvement of the course of the disease the patient complained of dizziness and headache. The treatment with a D12 dilution of potentiated antibodies to OMEZ in a dose of 1 tablet 3 times a day resulted in the elimination of side effects on the part of the central nervous system and in the improvement of the patient's general condition within 3 days. Later on, the remission was maintained solely by the intake of potentiated antibodies to OMEZ.

Potentiated antibodies to M-cholinolytic drugs.

Potentiated antibodies to PIRENZEPINE (GASRTOZEPINE) (5,11-dihydro-11-[(4-methyl-1-piperazinyl)acetyl]-6H-pyrido[2,3-b][1,4]benzodiazepine-6-one).

25E. Patient P., aged 57, complained of tremor and pain in the pit of his stomach after meals. Gastroscopy revealed no organic lesions of stomach mucosa. The oral intake of a D8 homeopathic solution of antiserum to GASRTOZEPINE in a dose of 1 tablet before meals was recommended. A new examination 10 days later showed an improvement of the patient's mood; no epigastric pain was noted. It was concluded that the preparation was efficient.

Potentiated antibodies to ATROPINE (8-methyl-8-azabicyclo[3.2.1]oct-3-yl ester of endo-(+−)-α-(hydroxymethyl)benzolacetic acid).

25F. Patient M., aged 41, suffered of cramps in his right subcostal area 2 hours after meals rich in fat. The prescription was: a diet and the oral intake of a C200 aqueous solution of potentiated polyclonal antibodies to ATROPINE in a dose of 10 ml (after meals). The pain syndrome subsided 2 days later. It was recommended to continue the course of treatment.

25G. Patient F., aged 42, suffered from sinus bradycardia; his pulse rate was 48 beats/min. He had been taking the Belladonna Extract in tablets; the positive therapeutic effect of the extract (the pulse rate increased to 64 beats/min) was accompanied by general weakness and dryness of skin and mucosae. (ATROPINE, the active principle of the extract, is the tropinic ester of d,l-tropic acid; the L isomer is active whereas the D isomer manifests low activity). The recommendation was to take alternately potentiated antibodies (a C15 dilution) to both isomers. The patient's pulse rate stabilized at 64 beats/min; no cholinolytic side effects were observed.

Antibodies to NO-SPA (drotaverine) ([(3,4-diethoxyphenyl)methylene]-6,7-diethoxy-1,2,3,4-tetrahydroisoquinoline).

25H. Patient L., aged 38, complained of epigastric pain and belching. His examination revealed no organic lesions. The prescription was: the oral intake (before meals) of an aqueous solution (a C6 dilution) of monoclonal antibodies to NO-SPA (drotaverine) in a dose of 15 ml. After 2 days of the treatment the patient stated the lessening of dyspeptic manifestations.

EXAMPLE 26

Potentiated Antibodies to Antiemetic Drugs

Potentiated antibodies to DOMPERIDONE (MOTILIUM) (5-Chloro-1-[1-[3-(2,3-dihydro-2-oxo-1H-benzimidazol-1-yl)propyl]-4-piperidinyl]-1,3-dihydro-2H-benzimidazol-2-one).

26A. Patient N., aged 71, had been treated with levodopa for parkinsonism and had to stop the therapy because of nausea and vomiting. The oral intake of levodopa in combination with 30 ml of a C30 dilution of an aqueous solution of potentiated monoclonal antibodies to MOTILIUM was prescribed, which made it possible to eliminate vomiting and continue antiparkinsonic therapy.

26B. Patient Zh., aged 64, developed nausea and vomiting in response to radio- and chemotherapy he had been getting for peripheral lung cancer. The prescription of MOTILIUM controlled symptoms of dyspepsia but the patient developed weakness, drowsiness, and intestinal cramps. MOTILIUM was discontinued and a C6 dilution of potentiated antibodies to MOTILIUM was administered in a dose of 1 ml intramuscularly 2 times a day, which resulted in the elimination of neurotoxic and spastic reactions. The treatment was continued with a positive clinical effect.

26C. Patient Yu., aged 55, suffered from chronic gastritis and esophagitis. He had been taking MOTILIUM (the active principle is DOMPERIDONE, an antagonist of dopamine receptors) for 3 months in a dose of 10 mg 15-20 minutes before meals on his own initiative under the influence of commercial advertising. He sought for medical advice because of gynecomastia he had noticed. Motilium was discontinued and a C1000 dilution of potentiated antiidiopathic antibodies to DOMPERIDONE was prescribed for 2 months in a dose of 1 tablet a day. The symptoms of gynecomastia disappeared and dyspeptic problems never resumed.

Potentiated antibodies to METOCLOPRAMIDE (REGLAN, CERUCAL) (4-amino-5-chloro-N-[2-(diethylamino)ethyl]-2-metoxybenzamide).

26D. Patient D., aged 38, complained of nausea and belching after meals. A course of treatment with an oral preparation containing a C30 dilution of potentiated antibodies to METOCLOPRAMIDE (REGLAN, CERUCAL) in a dose of 2 tablets before meals was prescribed. Four days later the patient reported the disappearance of nausea. A conclusion about the efficiency of the preparation was drawn.

EXAMPLE 27

Potentiated Antibodies to Antitussive Drugs

Potentiated antibodies to CODEINE ((5α,6α)-7,8-didehydro-4,5-epoxy-3-methoxy-17-methylmorphinan-6-ol).

27A. Patient B., aged 47, complained of fits of dry cough. The diagnosis was: chronic bronchitis; the intranasal administration of a C200 dilution of an aqueous solution of potentiated monoclonal antibodies to CODEINE in a dose of 5 drops during a fit was recommended. Twenty-four hours after the beginning of the treatment the elimination of cough was registered.

Potentiated antibodies to LIBEXIN (PRENOXDIAZINE) (1-[2-[3-(2,2-diphenylethyl)-1,2,4-oxydiazol-5-yl]ethyl]piperidine).

27B. Patient T., aged 41, had been taking LIBEXIN tablets for her cough. She complained of dryness in her mouth and throat. LIBEXIN was discontinued. The suggestion was to take orally a C50 dilution of a potentiated antiserum to 1-[2-[3-(2,2-diphenylethyl)-1,2,4-oxydiazol-5-yl]ethyl]piperidine in a dose of 1 tablet 3 times a day. The administration of the homeopathic preparation eliminated the undesired symptoms within 2 hours. The examination two days later showed a satisfactory general condition of the patient and the absence of cough.

EXAMPLE 28

Potentiated Antibodies to Various Groups of Antihypertensive Drugs

Potentiated antibodies to sympatholythics.
Potentiated antibodies to RESERPINE

28A. Patient B., aged 36, had been taking a course of treatment with ADELPHAN for arterial hypertension. After 3 weeks of the treatment she started complaining of dizziness. The examination revealed that her blood pressure had dropped to 105/60 mm Hg. ADELPHAN was discontinued. The oral intake of a C12 dilution of potentiated antiserum to RESERPINE in a dose of 1 tablet 2 times a day was prescribed. Two days later her dizziness subsided and the blood pressure rose to 115/70 mm Hg.

28B. Patient P., aged 72, suffered from hypertensive disease, Stage II b. She had been taking RAUNATINE (1 tablet 2 times a day) for a long time to good effect. The patient complained of dizziness and stuffiness in her nose not associated with a common cold. A C50 dilution of potentiated antibodies to RESERPINE was prescribed; this agent lessened her dizziness and completely eliminated stuffiness in her nose. Later on, she had been taking the preparation for 3 months in a dose of 1 tablet 2 times a day. Her blood pressure stabilized at a level of 140/90 mm Hg.

Potentiated antibodies to α-adrenolytic drugs.
Potentiated antibodies to PRAZOSIN (MINIPRESS) (1-(4-amino-6,7-dimethoxy-2-quinazolinyl)-(2-furanylcarbonyl)piperazine).

28C. Patient Ch., aged 53, complained of headaches after the intake of PRAZOSIN for hypertensive disease. The prescription of a C30 dilution of a potentiated antiserum to (1-(4-amino-6,7-dimethoxy-2-quinazolinyl)-(2-furanylcarbonyl)piperazine) in a dose of 1 tablet together with the intake of the PRAZOSIN resulted in the lowering of the patient's blood pressure. Later on, he started the administration of the antibodies as monotherapy; the blood pressure did not rise above his optimal level of 150/90 mm Hg.

28D. Patient I., aged 64, with an established diagnosis of arterial atherosclerosis (predominantly of the vessels of his lower extremities) and hypertensive disease, Stage IIb, had been taking PRAZOSIN in a dose of 8 mg a day (16 tablets). The patient complained of nausea and constant drowsiness. An attempt to reduce the dose on his own initiative resulted in a rise of the blood pressure and reappearance of the pain in his legs. The administration of a C12 dilution of potentiated antibodies to PRAZOSIN in a dose of 1 tablet 3 times a day made it possible to eliminate the undesirable manifestations and to reduce the dose of PRAZOSIN to 10 mg a day. Two months later the patient switched to the maintaining dose of 1 tablet a day of a C50 dilution of potentiated antibodies to PRAZOSIN.

28E. Patient Shch., aged 69, has been receiving 1 tablet of OMNIC (400 mg after breakfast) for benign hyperplasia of the prostate. The patient developed symptoms of orthostatic hypotension. The treatment with a C30 dilution of potentiated antibodies to OMNIC in a dose of 1 tablet 3 times a day was begun. Orthostatic symptoms disappeared 2 days later whereas the therapeutic effect of the preparation was preserved: the patient felt better, the volume of the residual urine diminished and the frequency of urinations reduced.

Potentiated antibodies to CLOFELINE (2,6-dichloro-N-2-imidazolidinylidenbenzamine).

28F. Patient E., aged 58, complained of drowsiness after the administration of CLOFELINE she had been taking for hypertensive disease. The recommendation was to combine the intake of CLOFELINE and a C12 solution of monoclonal antibodies to 2,6-dichloro-N-2-imidazolidinylidenbenzamine in a dose of 1 tablet 3 times a day. After two days of the treatment the patient stated the improvement of her mood and an enhanced motor activity. CLOFELINE was gradually discontinued. Now the patient receives only the potentiated drug; the arterial blood is stable.

28G. Patient Yu., aged 59, had a 10-years' history of essential hypertension. A regular intake of CLOFELINE in a dose of 0.6 mg a day produced a favorable effect on the course of his illness. He sought for medical advice at his district outpatient clinic because of dryness in the mouth. Several weeks of the administration of a C200 dilution of potentiated antibodies to CLOFELINE in a dose of 15 drops of an aqueous solution 4 times a day resulted in the elimination of the undesirable manifestations. The patient was switched to the potentiated preparation alone as the maintaining therapy.

Potentiated antibodies to isomers of NEBILET.

28H. Patient R., aged 63, with an established diagnosis of hypertensive disease, Stage IIa, was on NEBILET treatment (the drug contains two isomers; both are biologically active but their metabolization rate varies in different people). The patient complained of nightmares, which had not been experienced before the NEBILET administration. Pharmacokinetic studies showed that the patient belonged to the group with a slow type of metabolism (high difference in the concentrations of L- and D-enantiomers in the plasma). The administration of a D24 dilution of potentiated antibodies to L-isomer in a dose of 1 tablet 3 times a day resulted in the normalization of sleep along with the conservation of a good hypotensive effect.

28I. Patient P., aged 67, has been taking LABETALOL (400 mg a day) for hypertensive disease. The patient complained of heavy breathing. A C15 dilution of potentiated antibodies to RR-isomer in an oral dose of 10 ml two times a day was prescribed. After two days of treatment the patient's condition improved and functional tests showed the improvement of bronchial conduction.

Potentiated antibodies to inactive isomers of LABETALOL.

28J. Patient A., aged 57, with an established diagnosis of hypertensive disease and ischemic heart disease took LABETALOL and complains of heavy breathing and dizziness. The prescription was: a mixture of a C30 dilution of potentiated antibodies to inactive isomers in a dose of 1 sachet of powder a day. The patient's condition improved and the dose of the drug was reduced from 400 mg to 50 mg a day.

28K. Patient Ya., aged 61, with an established diagnosis of hypertensive disease and ischemic heart disease took APRESSIN (HYDRALAZINE) (1-hydrazinophthalazine hydrochloride) 250 mg a day in 4 doses. She complained of headaches, hot flashes, and nausea. An attempt to reduce the dose did not result in the desired effect. The recommendation was start taking a D8 dilution of potentiated monoclonal antibodies to the hydrazine group of the APRESSIN molecule; this group is capable of inhibiting the inactivation of endogenous vasodilating factors (NO in particular). After two days of treatment with this preparation in a dose of 1 tablet before meals the patient noticed the improvement of her condition. The treatment with APRESSIN was continued; its dose was reduced without any attenuation of its pronounced therapeutic effect and two months later APRESSIN was discontinued. The patient was put on monotherapy with the antibodies.

Potentiated antibodies to calcium channel blockers.

Potentiated antibodies to NORVASK (AMPLODIPINE) (3-ethyl-5-methyl ester of 2-[(2-aminoethoxy)methyl]-4-(2-chlorophenyl)-1,4-dihydro-6-methyl-1-3,5-pyridine dicarboxylic acid).

28L. Patient Ch., aged 59, took NORVASK for hypertensive disease. He complained of headache after the intake of the preparation. The prescription was: the intranasal administration of 1 ml of a C1000 dilution of potentiated antiserum to 3-ethyl-5-methyl ester of 2-[(2-aminoethoxy)methyl]-4-(2-chlorophenyl)-1,4-dihydro-6-methyl-3,5-pyridine dicarboxylic acid once a day in the form of 10 drops to be taken 3 times a day. The next day his headache disappeared. The patient kept taking the two medications together. Six months later the patient was put on monotherapy with the potentiated preparation.

Potentiated antibodies to the antagonists of Angiotensin Converting Enzyme (ACE) and of angiotensin-2 receptors.

Potentiated antibodies to CAPTOPRIL ((S)-1-(3-mercapto-2-methyl-1-oxopropyl)-L-proline):

28M. Patient L., aged 40, complained of periodical headaches and episodes of hypertension. The oral intake of a C50 homeopathic solution of potentiated anti-bodies to CAPTOPRYL in a dose of 5 ml 2 times a day was recommended. Within 10 days of the treatment a decrease in the frequency of headaches was noticed.

Potentiated antibodies to LOSARTAN (COZAAR) (2-butyl-4-chloro-1-[[2-(1H-tetrazol-5-yl)[1,1'-biphenyl]-4-yl]methyl]-1H-imidazole-5-methanol).

28N. Patient G., aged 46, complained of tremor. He had a history of LOSARTAN intake for his hypertensive disease. The recommendation was to take a D24 dilution of potentiated antibodies to 2-butyl-4-chloro-1-[[2-(1H-tetrazol-5-yl)[1,1'-biphenyl]-4-yl]methyl]-1H-imidazole-5-methanol in a dose of 1 tablet 2 times a day. After three days of the treatment the tremor disappeared. Later on, in order to keep his blood pressure stable the patient received only potentiated antibodies.

28O. Patient E., aged 42, with an established diagnosis of essential arterial hypertension had been taking MOXONIDINE in a dose of 300 mg a day. The patient complains of dryness in his mouth and drowsiness. The treatment with a C30 dilution of potentiated antibodies to MOXONIDINE produced a positive effect. Later on, the patient was put on preventive treatment with antibodies to MOXONIDINE in a dose of 1 tablet a day.

28P. Patient M., aged 58, with an established diagnosis of essential arterial hypertension, Stage 11b had been taking ENALAPRIL (1-[N—[S]-1-carboxy-3-phenylpropylR-ala-nyl]-L-proline-1'-ethyl ester), an angiotensin-converting enzyme inhibitor) on her physician's advice in a dose of 20 mg once a day. She complains of cough and dyspepsia. The patient used to take medications for the treatment of the intestinal microflora disorder on her own initiative with no positive results. The bacteriological testing of her intestinal microflora yielded no pathological findings: ENALAPRIL was discontinued. The new therapy scheme included the addition of a C200 dilution of potentiated antibodies to ENALAPRIL in a dose of 1 tablet once a day. The patient's bowel function normalized and the cough ceased.

28Q. Patient Z., aged 47; with an established diagnosis of hypertensive disease had been taking VALSARTAN in a dose of 80 mg a day. She complained of incessant cough and pharyngitis. Neither X-ray examination nor phthisiologist's and otolaryngologist's consultations revealed any pathology. The administration of C30 potentiated antibodies to VALSARTAN in a dose of 1 tablet 2 times a day eliminated the side effects of the preparation. After that the dose of VALSARTAN was reduced first to 40 mg a day and later to 20 mg a day with a stable hypotensive effect.

Potentiated antibodies to DILTIAZEM.

28R. Patient C., aged 54, with an established diagnosis of hypertensive disease, ischemic heart disease, angina decubitus had been taking DILTIAZEM in a dose of 40 mg 4 times a day with good clinical effect. Rare attacks of angina: about once a week. After 1.5 month of treatment the patient noticed the slowing of the pulse rate (from 72 to 48-52 beats/min); the ECG indicated the extension of the P-Q interval from 0.12 to 0.20 s. The treatment with a D24 dilution of potentiated polyclonal antibodies to DILTIAZEM in a dose of 1 tablet 3 times a day was prescribed. The patient's pulse rate reached 60 beats/min, the P-Q interval shortened to 0.15 s, without angina attacks becoming more frequent. The dosage of DILTIAZEM was reduced to 20 mg 2 times a day.

Potentiated antibodies to spasmolytic drugs.

Potentiated antibodies to DIBAZOLE (2-(phenylmethyl)-1H-benzimidazole).

28S. Patient Z., aged 41, complained of headache and nausea. The diagnosis of hypertensive disease was established and the oral intake of a C12 homeopathic solution of polyclonal antibodies to DIBAZOLE in a dose of 1 tablet 2 times a day was recommended. Ten days later the patient reported feeling better and not suffering from headaches.

EXAMPLE 29

Potentiated Antibodies to Substances Taking Part in Natural Regulation of the Blood Pressure 29A. Patient S., aged 46, had been sent to hospital within several years because of hypertension crises. Once a crisis had been arrested the patient was put on the maintaining therapy with captopril. In order to enhance the hypotensive effect a C12 dilution of potentiated antibodies to RENIN in a dose of 1 tablet 2 times a day was added to the treatment. Combined therapy made it possible for the first time in many years to lower the patient's blood pressure to 140/100 mm Hg. The patient's condition is satisfactory.

29B. Patient H., aged 38, suffered from therapy-resistant essential hypertension. The closest to optimal drug for the patient was ENALAPRIL, which made it possible to stabilize the blood pressure at 160/110 mm Hg. The treatment protocol with an added intake of a D24 dilution of potentiated polyclonal antibodies to angiotensin-converting enzyme (in a dose of 15 drops of alcohol solution 3 times a day) made it possible to lower the patient's systolic pressure to 120-130 mm Hg. The patient had not presented any complaints for 2 months.

29C. Patient D., aged 19, had been suffering from therapy-resistant arterial hypertension for 6 months. The use of a C12 dilution of potentiated antibodies to ANGIOTENSIN II in a dose of 1 tablet 2 times a day made it possible to stabilize the patient's condition: no complaints, the blood pressure reached 120/75 mm Hg.

EXAMPLE 30

Potentiated Antibodies to Diuretic Drugs

Potentiated antibodies to FUROSEMIDE (5-(aminosulfonyl)-4-chloro-2-[(2-furanylmethyl)]aminobenzoic acid).

30A. Patient D., aged 67, had been taking a course of treatment with FUROSEMIDE for edemata caused by cardiac failure. She complained of nausea and the lack of appetite. Furosemide was discontinued. The recommendation was to start the oral intake of a C30 aqueous solution of potentiated monoclonal antibodies to 5-(aminosulfonyl)-4-chloro-2-[(2-furanylmethyl)]aminobenzoic acid 2 times a day in a dose of 20 ml. A new examination 7 days later revealed the improved appetite, the absence of nausea and edemata.

Potentiated antibodies to HYPOTHIAZIDE (6-chloro-3,4-dihydro-2H-1,2,4-benzothiadiazine-7-sulfonamide-1,1-dioxide).

30B. Patient N., aged 64, with established diagnosis of hypertensive disease had been taking HYPOTHIAZIDE. The patient noticed a decrease in the efficacy of the preparation; hence, HYPOTHIAZIDE was discontinued. The recommendation was to start the oral intake of a C200 dilution of a potentiated antiserum to HYPOTHIAZIDE in a dose of 1 tablet 3 times a day, which made it possible to pre-serve the diuretic effect after HYPOTHIAZIDE had been discontinued.

EXAMPLE 31

Potentiated Antibodies to Cardiotropic Drugs

Potentiated antibodies to nitrates.

Potentiated antibodies to NITROSORBIDE (1,4,3,6-dianghydrido-D-glucitol dinitrate).

31A. Patient Sh., aged 52, suffering from hypertensive disease complained of headache after the first intake of NITROSORBIDE. In addition to the conventional treatment, the oral intake of a C20 dilution of potentiated antiserum to NITROSORBIDE was prescribed in a dose of 10 ml 3 times a day. Seven days later the patient reported an improved tolerance to NITROSORBIDE and the lessening of pain.

Potentiated antibodies to NITROGLYCEROL.

31B. Patient U., aged 71, had been taking NITROSORBIDE (40 mg a day, 4 tablets) for 5 weeks for ischemic heart disease and angina of effort along with NITROGLYCEROL as needed (up to 8-10 tablets a day). Within the last week the dose of NITROSORBIDE was increased to 6 tablets, and that of NITROGLYCEROL, to 15-16 tablets as the angina attacks grew more frequent. The prescription was to take a C6 dilution of potentiated antibodies to NITROGLYCEROL in a dose of 1 tablet 2 times a day. After 5 days of treatment a marked reduction in the frequency of attacks was achieved, which made it possible to reduce the dose of NITROSORBIDE to 4 tablets and that of NITROGLYCEROL to 1-2 tablets a day.

Potentiated antibodies to Cytochromes aa3.

31C. Patient G., aged 39, was admitted to hospital with the diagnosis of hypertensive disease, ischemic heart disease, cardiac failure due to myocardial infarction; he had been treated with intravenous infusions of SODIUM NITROPRUSSIDE (sodium nitrozylpentacyanoferrate) in a dose of 100 mg a day for 4 days. By the $5^{th}$ day the hypotensive effect of the preparation had significantly decreased as sodium cyanide accumulating as a result of SODIUM NITROPRUSSIDE metabolism played an important part in the pharmacological effect of the preparation. (Cyanides act as blockers of the mitochondria respiratory chain at the level of Cytochrome aa3). The administration of a C200 dilution of potentiated polyclonal antibodies to CYTOCHROMES aa3 in a dose of 1 tablet 3 times a day restored the efficacy of SODIUM NITROPRUSSIDE.

Potentiated antibodies to β-adrenoblockers.

Potentiated antibodies to ATENOLOL (4-[2-hydroxy-3-[(1-methylethyl)amino]propoxy]benzeneacetamide).

31D. Patient E., aged 32, complained of episodes of tachycardia caused by overfatigue. Electrocardiography revealed no organic lesions. ATENOLOL was discontinued. The oral intake of a C12 dilution of a potentiated antiserum to ATENOLOL was prescribed. The intake of the preparation in a dose of 1 tablet 2 times a day resulted in a decrease both in the intensity and duration of episodes of tachycardia 5 days after the beginning of treatment.

Potentiated antibodies to ANAPRILIN (PROPRANOLOL) (1-[(1-methylethyl)amino]-3-(1-naphthalenyloxy)-2-propanol).

31E. Patient I., aged 54, sought for medical advice for periodic heavy breathing. She presented a history of a regular intake of ANAPRILIN (PROPRANOLOL). The intranasal administration of a C12 dilution of a potentiated solution of monoclonal antibodies to 1-[(1-methylethyl)amino]-3-(1-naphthalenyloxy)-2-propanol in a dose of 0.5 ml 2 times a day was prescribed as monotherapy. A new examination 7 days later showed an improvement of the respiratory function. A conclusion about the efficacy of the homeopathic preparation was drawn.

31F. Patient A., aged 57, developed bradyarrhythmia with Morgagni-Adams-Stokes attacks after myocardial infarction. To prevent attacks she took ORCIPRENALINE (½ tablet 6 times a day) and complained of nausea, dryness in her mouth, and the tremor of her hands. The treatment with a D3 dilution of potentiated monoclonal antibodies to ORCIPRENALINE (in a dose of 1 tablet 3 times a day) made it possible to eliminate the unpleasant sensations; the attacks of arrhythmia stopped recurring.

Potentiated antibodies to cardiac glycosides.

Potentiated antibodies to DIGITOXIN ((3β,5β.)-3-[(O-2,6-dideoxy-β-D-ribo-hexapyranosyl-(1-4)-O-2,6-dideoxy-β-D-ribo-hexopyranosyl)-(1-4)-2,6-didesoxy-β-D-ribo-hexapyranosyl)oxy]-14-hydroxycard-20(22)-enolide).

31G. Patient B., aged 68, had been taking a course of treatment with DIGITOXIN for cardiac failure complained of nausea associated with the intake of the preparation. The additional prescription was the oral intake of a C200 dilution of a potentiated preparation of polyclonal antibodies to ((3β,5β.)-3-[(O-2,6-dideoxy-β-D-ribo-hexopyranosyl-(1-4)-O-2,6-dideoxy-β-D-ribo-hexopyranosyl)-(1-4)-2,6-dideoxy-β-D-ribo-hexapyranosyl)oxy]-14-hydroxycard-20(22)-enolide) in a dose of 1 tablet 2 times a day. After two days of the treatment the patient noticed the disappearance of nausea. The intake of the homeopathic preparation made it possible to improve the patient's tolerance of DIGITOXIN and to reduce gradually its dose to ¼ of a tablet 2 times a day.

31H. Patient Ch., aged 31, with an established diagnosis of chronic cardiac failure caused by rheumatic heart disease had been taking the maintaining dose of DIGITOXIN 0.75 mg a day (3 tablets). She suffered from permanent nausea and periodical vomiting. An attempt to reduce the dose of DIGITOXIN resulted in the enhancement of manifestations of cardiac failure, edema in the first place. With DIGITOXIN discontinued, the patient started receiving a D6 dilution of potentiated antiidiotypic antibodies to DIGITOXIN (in a dose of 1 tablet 3 times a day). Two weeks later the patient's condition was satisfactory: the blood pressure became stable and no manifestations of cardiac failure were observed Potentiated antibodies to antiarrhythmic drugs.

Potentiated antibodies to DISOPYRAMIDE (α-[2-[bis(1-methylethyl)amino]ethyl]-α-phenyl-2-pyridine acetamide).

31I. Patient S., aged 35, complained of restlessness and tachycardia. The oral intake of a C200 dilution of potentiated monoclonal antibodies to RYTHMILEN (DISOPYRAMIDE) (α-[2-[bis(1-methylethyl)amino]ethyl]-α-phenyl-2-pyridine acetamide) in a dose of 1 tablet 2 times a day was prescribed. At the new examination the patient presented no complaints for tachycardia.

Potentiated antibodies to RHYTHMONORM.

31J. Patient Zh., aged 45, has been taking RHYTHMONORM (Propaphenone) (2[2-hydroxy-3-(propylamino) propoxy]-3-phenyl-propiophenone), an antiarrhythmic drug of the IC class) in a dose of 150 mg 3 times a day for ventricular extrasystoles. The planned blood test revealed leukopenia ($3.8 \times 10^3/\mu l$) and thrombocytopenia ($170 \times 10^3/\mu l$). Rhythmonorm was discontinued. The administration of a C50 dilution of potentiated antibodies to PROPAPHENONE in a dose of 1 tablet in the morning within 10 days resulted in the normalization of the patient's blood picture with preserved antiarrhythmic effect.

Potentiated antibodies to SOTALOL (N-[4-[1-hydroxy-2-[(1-methylethyl)amino]ethyl]phenyl]methane sulfonamide)

31K. Patient D., aged 28, complained of night episodes of pulse intermittence, mild pain in the left part of her thorax. Electrocardiography revealed no organic lesions of the myocardium. After the preceding therapy had been cancelled, the patient started the oral intake of a C30 dilution of potentiated antibodies to SOTALOL (N-[4-[1-hydroxy-2-[(1-methylethyl)amino]ethyl]phenyl]methane sulfonamide) in a dose of 1 tablet at bedtime. During the following 10 days there were no attacks of arrhythmia or pain.

Potentiated antibodies to VERAPAMIL (α-[3-[[2-(3,4-dimetoxyphenyl)ethyl]methylamino]propyl]-3,4-dimetoxy-α-(1-methylethyl)benzeneacetonitryl).

31L. Patient K., aged 34, complained of headache, tachycardia, and overfatigue. The examination revealed elevated blood pressure (140/90). The recommendation was to take nasal drops of a C200 aqueous solution of potentiated antibodies to VERAPAMIL (α-[3-[[2-(3,4-dimetoxyphenyl) ethyl]methylamino]propyl]-3,4-dimetoxy-α-(1-methylethyl)benzeneacetonitryl) in a dose of 0.5 ml at bedtime. The patient reported feeling better, his blood pressure dropped to the normal level after two days of the treatment. It was recommended to continue the course of treatment.

31M. Patient Z., aged 55, with an established diagnosis of ischemic heart disease, angina of effort, atrial extrasystoles, and tachycardia (90 beats/min) had been taking 240 mg of ISOPTIN daily in a dose of 1 tablet 3 times a day. The patient complained of constipation not associated with the regimen faults or diet changes. The intake of potentiated antibodies to ISOPTIN LM 50 in a-dose of 1 tablet 2 times a day resulted in the normalization of the bowel function without interfering with the basic therapeutic effect of ISOPTIN. Later on, the dose of ISOPTIN was gradually reduced and finally ISOPTIN was discontinued. The patient's condition remained satisfactory for two months against the background of therapy with antibodies.

31N. Patient D., aged 63, with the diagnosis of progressive chronic cardiac failure was treated at the cardiology unit of a clinical hospital (intravenous infusion of 30 mg of MILRINONE daily in a dose of 10 ml 3 times a day). As the patient's myocardial contractive capacity and hemodynamic indices were gradually improving, there appeared complaints of heartache. ECG revealed signs of myocardial ischemia. The treatment with a C12 dilution of potentiated antibodies to MILRINONE in a-dose of 1 tablet 3 times a day was started. Heartache disappeared, the ECG pattern returned to normal, and the treatment with MILRINONE was continued. Gradually the preparation was discontinued and the patient was switched to the treatment with antibodies alone in a dose of 1 tablet a day. The patient's condition is satisfactory.

31O. Patient S., aged 58, had been taking MILRINONE for 1.5 years for chronic cardiac failure. In the course of the period of treatment the daily dose had to be increased from 10 to 30 mg because of the developing resistance to the preparation. After the prescription of a C30 dilution of potentiated antibodies to the enzyme PHOSPHODIESTERASE in a dose of 1 sublingual tablet once a day to be taken in the morning the patient's condition markedly improved: the ECG signs of myocardial overload and ischemia became less pronounced and peripheral edema disappeared. Three months of a regular intake of potentiated antibodies made it possible to reduce the daily dose of MILRINONE to 10 mg.

Potentiated antibodies to CORDARON.

31P. Patient S., aged 50, had been suffering from stable angina of effort with paroxysms of ciliary arrhythmia for 2 years. From the onset of his illness the patient had been taking CORDARON in a dose of 600 mg a day (3 tablets). After a year of the treatment an increase in the frequency of paroxysms of ciliary arrhythmia was registered. Paroxysms occurred every day; an increase in the dose of CORDARON as well as the administration of other antiarrhythmic drugs was inefficient. No physical or emotional strain accounted for the paroxysms; the paroxysms cease spontaneously. This condition seemed indicative of a thyroid function disorder; the patient was examined by an endocrinologist who established the diagnosis of thyrotoxicosis of a moderate severity. The patient's thyroid profile looked as follows: TTH 1.29 mlU/l (the normal range is 0.45-6.2), total T4 180.3 nmol/l (the normal range is 39-155), T3 3.2 nmol/l (the normal range is 1.2-3.1). The treatment with a C24 dilution of potentiated antibodies to CORDARON in a dose of 1 tablet 3 times a day was started. Within a month the euthyroid state was achieved. Now the patient takes CORDARON in a dose of 100 mg a day (¼ of a tablet 2 times a day), paroxysms of ciliary arrhythmia are rare (about once a week).

EXAMPLE 32

Potentiated Antibodies to Hypocholesterolemic Drugs

Potentiated antibodies to PROBUCOL.

32A. Patient K., aged 62, with the diagnosis of-coronary sclerosis, angina of effort, and hypercholesterolemia had been taking PROBUCOL for 2 months along with antianginal drugs (in a dose of 500 mg 2 times a-day at mealtime). The patient complained of dyspepsia, meteorism in the first place, the onset of which dated back to one month after he had started taking the preparation. The administration of a C30 dilution of potentiated antibodies to PROBUCOL in a dose of 1 tablet a day controlled the patient's intestinal disorders. The daily dose of PROBUCOL was reduced by 50%.

Potentiated antibodies to NICOTINIC ACID.

32B. Patient L., aged 58, had been taking NICOTINIC ACID in a dose of 4.0 g a day for atherosclerosis of peripheral vessels (especially pronounced in the lower extremities). The patient complains of hot flashes and redness of the face. The intake of a C12 dilution of potentiated antibodies to nicotinic acid in a-dose of 1 tablet 3 times a day improved the patient's tolerance of the preparation and made it possible to reduce its dose to 1.0 g a day.

Potentiated antibodies to PRAVASTATIN.

32C. Patient F., aged 57, suffered from ischemic heart disease and primary hypercholesterolemia. He had been taking PRAVASTATIN for 3 months in a dose of 20 mg at bedtime along with NITROGLYCEROL (up to 5-6 tablets a day for angina attacks). In the course of the last 10-15 days he noticed the development of muscular weakness. The biochemical analysis of the patient's blood revealed transaminase levels elevated to the upper bound (ALT 50 IU/l, AST 45 IU/l). The administration of a C200 dilution of potentiated antibodies to PRAVASTATIN in a dose of 1 tablet once a day resulted in the improvement of the patient's condition of health, his blood transaminase level lowered (ALT 26 IU/l, AST 21 IU/l). Angina attacks became less frequent and the patient's intake of nitroglycerol tablets reduced to 1-2 tablets a day.

Potentiated antibodies to ETOFIBRATE.

32D. Patient P., aged 55, with an established diagnosis of ischemic heart disease and hypercholestrolemia had been taking ETOFIBRATE (in a dose of 500 mg once a day) following his physician's advice. The patient stated that after a month of the treatment with this preparation he began to suffer from abdominal pain and meteorism. The intake of a C30 dilution of potentiated antibodies to ETOFIBRATE in a dose of 1 tablet a day resulted in the normalization of the patient's condition. The dose of ETOFIBRATE was reduced by 50%. The patient's lipid metabolism indices remained within normal limits.

Potentiated antibodies to ORLISTATE.

32E. Patient O., aged 59, suffered from diabetes mellitus, Type 2, and obesity (height 160 cm, body weight 100 kg) and had been taking 120 mg of ORLISTATE (the inhibitor of gastric lipases) 3 times a day at meals. Within several months of the treatment combined with low-calorie diet the patient body weight decreased by 7 kg; however, the patient complained of poor feeling, which was manifested by meteorism and imperative rectal tenesmus. The prescription of a C200 dilution of potentiated polyclonal antibodies to ORLISTATE in a dose of 1 tablet a day improved the patient's tolerance of the preparation, decreased her blood sugar level, and made it possible to reduce the dose of insulin.

EXAMPLE 33

Potentiated Antibodies to Antitumor Drugs

Potentiated antibodies to DOXORUBICIN [(8S-cis)-10-[(3-amino-2,3,6-trideoxy-α-L-lyxo-hexopyranosyl)oxy]-7, 8,9,10-tetrahydro-6,8,11-trihydroxy-8-(hydroxyacetyl)-1-methoxy-5,12-naphtacenedione].

33A. Patient P., aged 61, had been receiving a course of chemotherapy with DOXORUBICIN [(8S-cis)-10-[(3-amino-2,3,6-trideoxy-α-L-lyxo-hexopyranosyl)oxy]-7,8,9, 10-tetrahydro-6,8,11-trihydroxy-8-(hydroxyacetyl)-1-methoxy-5,12-naphtacenedione] for lung cancer but had to stop taking the medication because of nausea and vomiting. The prescription was to combine the administration of the cytostatic drug with the oral intake of a C6 solution of potentiated monoclonal antibodies to DOXORUBICIN. As a result the nausea subsided, which made it possible to continue chemotherapy. Later on, DOXORUBICIN was discontinued and the patient was put on potentiated anti-bodies alone. The patient is feeling well and X-ray findings show the arrest of tumor growth.

Potentiated antibodies to CISPLATIN (cis-diaminodichloroplatinum).

33B. Patient D., aged 57, complained of cramps in her lower extremities during the process of chemotherapy with CISPLATIN for ovarian cancer. A C12 dilution of potentiated monoclonal antibodies to cis-diaminodichloroplatinum in a dose of 2 ml intramuscularly once a day was prescribed. This drug made it possible not only to control cramps and improve the patient's tolerance of cisplatin but also to reduce the dose of the latter by 50%.

Potentiated antibodies to METHOTREXATE (N-[4-[[(2, 4-diamino-6-pteridinyl)methyl]methylamino]benzoyl]-L-glutamic acid).

33C. Patient P., aged 9, was admitted to hospital for acute lymphoblastic leucosis. In the course of chemotherapy with METHOTREXATE the patient started complaining of severe headaches and nausea. The treatment with a D12 dilution of a potentiated antiserum to METHOTREXATE in a dose of 1 tablet 2 times a day was begun. Two days later, with continued chemotherapy, the patient reported that his headaches disappeared and nausea subsided. He kept taking the potentiated preparation. Two months later the patient's condition was satisfactory and METHOTREXATE was discontinued. Four months later, against the background of continued monotherapy with antibodies, the patient's lymphogram was close to normal.

Potentiated antibodies to THALIDOMIDE.

33D. Patient U., aged 42, suffered from multiple myeloma. Two bone marrow transplantations resulted in short remissions. The third transplantation did not lead to a remission; the blood MIG (myeloma immunoglobulin, a protein marker of tumor cells) level was rising. The treatment with THALIDOMIDE made it possible to achieve stable remission and the depression of the blood MIG level; however the patient started complaining of weakness, drowsiness constipation, and numbness sensation in his extremities. It was suggested to use the intranasal administration of a C30 dilution of potentiated antibodies to THALIDOMIDE in a dose of 1 ml 3 times a day as additional treatment. After a week of treatment with antibodies the patient started feeling better, no signs of the progressive course of his myeloma were observed, and the blood MIG level kept falling dramatically.

Potentiated antibodies to VERAPAMIL.

33E. Patient Sh., aged 29, with an established diagnosis of small-cell carcinoma of his left lung was going through a course of chemotherapy with cisplatin and methotrexate. The patient was also taking VERAPAMIL (a calcium channel blocker) in order to enhance the tumor cell sensitivity to the treatment. After a month of treatment, there appeared symptoms of cancer progression. Added to the treatment protocol was the intake of a C200 dilution of potentiated anti-bodies to VERAPAMIL in a dose of 1 tablet-a day. The patient started feeling better and his X-ray image showed the arrest of tumor progression.

Potentiated Antibodies to TOPOISOMERASE II

33F. Patient T., aged 40, with an established diagnosis of lung carcinoma underwent two courses of treatment with CISPLATIN and ETOPOSIDE, after which clinical and X-ray findings revealed the tumor's primary resistance to antitumor drugs. The third course of the treatment with cytostatic drugs was combined with the administration of a C30 dilution of potentiated antibodies to topoisomerase II in a dose of 1 sublingual tablet once a day. The patient started feeling better and X-ray patterns revealed the arrest of tumor progression.

Potentiated antibodies to PROSPIDINE.

33G. Patient R. aged 37 was undergoing hospital treatment with PROSPIDINE (300 mg in the form of intramuscular injections 3 times a week) as monochemotherapy for T lymphoma of the skin. A decrease in the area of skin lesions (by 30%) along with improved laboratory test data allowed the treatment to be regarded as efficient; however, there was no further progress in the patient's condition. The treatment was supplemented with a C200 dilution of potentiated anti-bodies to PROSPIDINE in a dose of 1 tablet a day. The area of skin lesions reduced by another 40%.

Potentiated Antibodies to Hormone Antagonists

TAMOXIFEN ((Z)-2-[4-(1,2-diphenyl-1-butenyl)phenoxy]-N,N-dimethylethanamine).

33H. Patient I., aged 47, was taking a course of chemotherapy with TAMOXIFEN ((Z)-2-[4-(1,2-diphenyl-1-butenyl)phenoxy]-N,N-dimethylethanamine) for breast cancer; she complained of dizziness and nausea. The intranasal administration of 0.5 ml of a C30 aqueous solution of potentiated monoclonal antibodies to TAMOXIFEN 3 times a day was prescribed. The patient's nausea subsided to a bearable level.

Potentiated antibodies to FLUTAMIDE (2-methyl-N[4-nitro-3-(trifluormethyl)phenyl]propanamide).

33I. Patient U., aged 41, complained of fatigue and the loss of libido and potency. The administration (in the form of intranasal drops at bedtime) of 0.5 ml of a C12 solution of a potentiated antiserum to FLUTAMIDE (2-methyl-N[4-nitro-3-(trifluormethyl)phenyl]propanamide). After 10 days of the treatment the patient stated the improvement of his ability to work and sexual activity. It was recommended to continue the course of treatment.

EXAMPLE 34

Potentiated Antibodies to Regulators of the Blood Coagulation Process

Potentiated antibodies to HEPARIN (mucopolysaccharide of a polysulfuric acid ester).

34A. Patient M., aged 59, complained of superficial pains in her lower extremities. The diagnosis of trombophlebitis was established; aqueous compresses with a D6 solution of a potentiated antiserum to heparin at bedtime were recommended. After 5 procedures the pain and local redness subsided.

Potentiated antibodies to TICLOPIDINE (5-[2-chlorophenyl)methyl]-4,5,6,7-tetrahydrothieno[3,2-c]pyridine).

34B. Patient K., aged 63, complained of moderate heartaches. The diagnosis of ischemic heart disease was made. The oral intake (at bedtime) of 20 ml of a C30 potentiated solution of polyclonal antibodies to TICLOPIDINE (5-[2-chlorophenyl)methyl]-4,5,6,7-tetrahydrothieno[3,2-c]pyridine) C30 in a dose of 1 tablet 3 times a day was prescribed. After 3 months of the treatment no worsening of the disease was observed. The conclusion was drawn about the efficiency of the potentiated preparation for the prevention of ischemic heart disease.

EXAMPLE 35

Potentiated Antibodies to Hormonal Agents

Potentiated antibodies to INSULIN.

35A. Patient R., aged 45, with an established diagnosis of diabetes mellitus Type 1 complained of ulcer of the skin integument of his lower extremities. Local rubbing with a C30 dilution of a 30% alcoholic solution of an antiserum to insulin was included into the scheme of combined therapy. Epithelization of skin integument lesions was achieved.

35B. Patient D., aged 52, with an established diagnosis of diabetes mellitus Type 2 had an excessive body weight. His fasting blood glucose level was 10 mmol/l. The glucose level correction could not be achieved by diet and synthetic antihyperglycemic agents. Within 3 months the daily dose of insulin increased from 5 to 25 units. The treatment with a C200 dilation of potentiated monoclonal antiidiotypic antibodies to insulin in a dose of 1 tablet a day was started. Two weeks later the patient's sensitivity to insulin increased; the dose of insulin was reduced to 5 units, the fasting blood glucose level reached 5 mmol/l. After 2 months of the treatment insulin was discontinued and the patient was switched to therapy with antibodies alone.

35C. Patient I., aged 48, suffered from a severe form of diabetes mellitus with a high degree of insulin resistance (the patient needed up to 128 units a day). The treatment with a C30 dilution of a potentiated antiserum to the insulin-like growth factor in a dose of 1 tablet 3 times a day resulted in a marked improvement of the patient's condition. His blood-glucose level dropped to 16 mmol/l. The daily dose of insulin was reduced by 50%.

Potentiated antibodies to ESTRADIOL.

35D. Patient B., aged 34, was admitted to the neurology department of a clinical hospital with complaints of rapid uncontrollable movements in her right extremities. These symptoms developed after a common cold. The patient gave no history of rheumatic fever. At the time of admission the patient was pregnant for the second time (the $21^{st}$-$22^{nd}$ week); she suffered from early gestosis; there had been no complications in the course of her first pregnancy. Before deciding to have another baby the patient had been taking oral contraceptives. The patient was slightly euphoric. The memory and intellect were unimpaired. Her arterial blood pressure was 120/80 mm Hg. Hyperkinesias of her right extremities, predominantly in her arm and hand were found. Gynecological examination did not reveal any indication for the termination of pregnancy. The treatment with a C200-dilution of a potentiated form of antibodies to ESTRADIOL in a dose of 1 tablet a day was started; a week later the symptoms of hyperkinesia disappeared. The patient had an uncomplicated delivery at term; her baby was in good health.

Potentiated antibodies to GLUCAGON.

35E. Patient T., aged 64, complained of bradycardia and arterial hypotension upon admission; she had been taking ATENOLOL. The oral administration of a C12 dilution of potentiated polyclonal antibodies to GLUCAGON in a dose of 1 tablet 3 times a day was prescribed. Within 24 hours the normalization of the cardiac rhythm and arterial pressure was achieved.

Potentiated antibodies to TRIIODOTHYRONINE (LIO-THYRONINE) (O-(4-hydroxy-3-iodophenyl)-3,5-diiodo-L-thyrosine).

35F. Patient D., aged 36, complained of tachycardia and heartaches. The examination revealed no organic disorders. The oral intake of a C12 dilution of potentiated polyclonal antibodies to TRIIODOTHYRONINE (O-(4-hydroxy-3-iodophenyl)-3,5-diiodo-L-thyrosine) in a dose of 1 tablet 3 times a day was prescribed. After 5 days of the treatment the normalization of cardiac rhythm and the disappearance of pain were achieved.

Potentiated antibodies to CALCITONIN.

35G. Patient I., aged 58, complained of pain in her tubular bones and soft tissues of her extremities. The examination confirmed the diagnosis of osteoporosis. The intranasal administration of 0.5 ml a C24 dilution of a potentiated monospecific antiserum to CALCITONIN twice a day was prescribed within the framework of combined therapy. Three days later the patient started feeling better and reported the lessening of pain.

Potentiated antibodies to the SOMATOTROPIC HORMONE.

35H. Patient Ch., aged 56, had been taking a course of treatment for obesity. Because of the oral administration of a C15 dilution of potentiated monoclonal antibodies to the somatotropic hormone in a dose of 1 tablet 3 times a day together with a diet the patient had lost 4 kilograms within 10 days; the dieting became easier.

Potentiated antibodies to STEROID HORMONES.

Potentiated antibodies to HYDROCORTISONE (11β)-11,17,21-trihydroxypregn-4-ene-3,20-dione).

35I. Patient Ts., aged 29, a welder by profession complained of sharp pain in his eyes. Twice doses of eye drops containing a C12 aqueous solution of a potentiated antiserum to HYDROCORTISONE (11β)-11,17,21-trihydroxypregn-4-ene-3,20-dione) made it possible to eliminate painful sensations within 24 hours.

Potentiated antibodies to DEXAMETHASONE (11β,16α)-9-fluoro-11,17,21-trihydroxy-16-methylpregna-1,4-diene-3,20-dione).

35J. Patient D., aged 39, complained of itching in his nasopharynx. After intranasal administration of 1 ml of a C12 dilution of a potentiated solution of monoclonal antibodies to DEXAMETHASONE (11α,16α)-9-fluoro-11,17,21-trihydroxy-16-methylpregna-1,4-diene-3,20-dione) itching disappeared.

Potentiated antibodies to TESTOSTERONE ((17β)-17-hydroxyandrost-4-en-3-one).

35K. Patient A., aged 41, complained of the lowering of potency. The examination revealed a moderate degree of obesity and no organic lesions of the central nervous system. A course of treatment with a C6 dilution of potentiated monoclonal antibodies to TESTOSTERONE to be taken by mouth in a dose of 1 tablet 3 times a day was proposed. At his next visit to the physician four weeks later the patient stated that his sexual performance improved and sexual activity enhanced. The patient had lost 5 kg; he tolerated well his food regimen under the conditions of the preparation intake. It was recommended to continue the course of treatment.

EXAMPLE 36

Potentiated Antibodies to Nervous System Mediators

Potentiated antibodies to ACETYLCHOLINE (2-(acetyloxy)-N,N,N-trimethyl-ethaneaminium).

36A. Patient Yu., aged 58, complained of constipation. The intranasal administration of 0.5 ml of a C50 dilution of a potentiated solution of antibodies to ACETYLCHOLINE (2-(acetyloxy)-N,N,N-trimethylethaneaminium) 4 times a day was recommended. The stool was back to normal 24 hours after the intake of the preparation.

Potentiated antibodies to NORADERNALINE.

36B. Patient D., aged 71, complained of dizziness and bradycardia. The examination revealed hypotension (100/65 mm Hg). The oral intake of 10 ml of an antiserum to noradrenaline in a potency of C14, 3 times a day was prescribed. At his next visit to the physician 6 days later the patient reported feeling better and not suffering from dizziness anymore; his blood pressure was 110/75 mm Hg. It was recommended to continue the course of treatment.

Potentiated antibodies to DOPAMINE.

36C. Patient L., aged 69, complained of tremor and gait disorders. The patient had had a long-time history of treatment with neuroleptics for schizophrenia. The treatment was supplemented with a C15 dilution of potentiated polyclonal antibodies to dopamine (oral intake, 1 tablet 3 times a day). Within 4 days the tremor disappeared and no neuroleptic manifestations were observed.

Potentiated antibodies to SEROTONIN (5-hydroxytriptamine).

36D. Patient G., aged 41, complained of the worsening of mood and apathy. The intake of a C1000 dilution of a potentiated solution of monoclonal antibodies to (serotonin) in the form of drops in a dose of 1 ml twice a day was proposed. Seven days later the patient reported the improvement of mood and the enhanced motivation to labor. It was recommended to continue the course of treatment.

Potentiated antibodies to ASPARTIC ACID (L-aspartic acid).

36E. Patient N., aged 75, complained of tremor of extremities. The examination revealed no organic lesions of the nervous system. The oral intake of a C200 dilution of a potentiated solution of antibodies to aspartic acid in a dose of 1 tablet 3 times a day was recommended. A new examination two days later showed the absence of tremor.

Potentiated antibodies to GLUTAMIC ACID (L-glutamic acid).

36F. Patient M., aged 29, complained of cramps in the lower extremities during sleep. The administration of potentiated polyclonal antibodies to L-glutamic acid in a dose of 1 tablet by mouth at bedtime resulted in a decrease in the frequency and intensity of convulsions.

Potentiated antibodies to GLYCINE.

36G. Patient P., aged 58, complained of restlessness and sleeping disorders. The oral intake of a C1000 dilution of potentiated antibodies to GLYCINE in a dose of 1 tablet at bedtime was recommended; within two days the patient's sleep became normal.

EXAMPLE 37

Potentiated Antibodies to Mediators of Inflammation and Allergy

Potentiated antibodies to PROSTAGLANDINS.

Potentiated antibodies to MISOPROSTOL (methyl ester of (11α,13E)-(+−)-11,16-dihydroxy-methyl-9-oxoprost-13-en-1-oic acid).

37A. Patient K., aged 41, complained of pain in the epigastric area after meals. The oral intake of a C50 dilution of a potentiated solution of polyclonal antibodies to MISOPROSTOL (methyl ester of (11α,13E)-(+−)-11,16-dihydroxy-methyl-9-oxoprost-13-en-1-oic acid) in a dose of 1 tablet before meals was recommended. At his new visit to the physician seven days later the patient reported the elimination of pain.

Potentiated antibodies to KININS.

Potentiated antibodies to BRADYKININ.

37B. Patient N., aged 15, complained of dry cough. The administration of potentiated monoclonal antibodies to bradykinin in the form of nasal drops in a dose of 0.5 ml 3 times a day resulted in the disappearance of cough within 2 days.

Potentiated antibodies to HISTAMINE (1H-imidazole-4-ethanamine).

37C. Patient Ts., aged 27, complained of severe itching of insect bites. Within the framework of combined therapy compresses with a C30 solution of potentiated antibodies to histamine were applied to the sites of lesions. The next day the redness subsided and the itching disappeared.

EXAMPLE 38

Potentiated Antibodies to Vitamins, Substances with Vitamin-Like Action, and Bioflavonoids 38A. Patient A., aged 51, had been taking rather large doses of ascorbic acid (5-6 g daily) with health-improvement purposes following his friends' advice. He was admitted to hospital with an attack of renal colic. The pain was controlled with spasmolytic drugs and alkaline solutions. Laboratory blood tests showed high glucose content (9 mmol/l, the normal range being from 3.3 to 5.5 mmol/l). The patient had never consulted endocrinologist and had no family history of diabetes; therefore, the toxic effect of high doses of ascorbic acid upon the pancreas was suggested as the cause of the patient's elevated blood sugar content. The treatment with potentiated antibodies to ascorbic acid in a dose of 1 tablet 3 times a day was started. Within two weeks the fasting blood glucose content dropped to 6 mmol/1.

Potentiated antibodies to THIAMINE (3-[(4-amino-2-methyl-5-pyrimidinyl)methyl]-5-(2-hydroxyethyl)-4-methylthiazolium chloride).

38B. Patient V., aged 57, complained of pain in her left thigh. The examination confirmed the diagnosis of neuralgia. A C200 dilution of a potentiated solution of monoclonal antibodies to THIAMINE (3-[(4-amino-2-methyl-5-pyrimidinyl)methyl]-5-(2-hydroxyethyl)-4-methylthiazolium chloride) in a dose of 1 tablet twice a day was recommended. After 6 days of the treatment the lessening of the pain intensity was achieved. A conclusion about the efficiency of such therapy was drawn.

Potentiated antibodies to NICOTINIC ACID (3-pyridinecarboxylic acid).

38C. Patient R., aged 48, complained of hot flashes and tachycardia after the intake of nicotinic acid she had been receiving for atherosclerosis. The oral intake of a C30 dilution of a potentiated solution of monoclonal antibodies to 3-pyridinecarboxylic acid in a dose of 1 tablet twice a day was recommended. The patient noticed the subsidence of her tachycardia, which allowed the antihypercholesterolemic therapy to be continued.

Potentiated antibodies to TROXERUTIN (2-[3,4-(bis(2-hydroxyethoxy)phenyl]-3-[[6-O-(6-deoxy-α-L-mannosopyranoz-yl)-β-D-glucopyranozyl]oxy]-5-hydroxy-7-(2-hydroxyethoxy)-4H-1-benzopyranone-4).

38D. Patient U., aged 42, complained of pain after she had bruised her thigh. The examination revealed a large hematoma. Compresses with a C6 dilution of an aqueous solution of a potentiated antiserum to TROXERUTIN were recommended. A new examination two days later showed the shrinking of the hematoma; the patient felt no pain.

Potentiated antibodies to DIHYDROERGOCRISTINE.

38E. Patient K., aged 29, had been taking 1 lozenge of ANAVENOL (the preparation composed of an α-adrenolytic agent DIHYDROERGOCRISTINE, ESCULINE, and RUTOZIDE) 3 times a day for varicose veins in her legs developed during pregnancy and the postpartum period. The edema and heavy feeling in the legs were lessening but the patient started complaining of headaches and dizziness. Anavenol was discontinued. The treatment with a C30 dilution of potentiated antibodies to dihydroergocristine in a dose of 1 tablet twice a day was begun. The patient's condition of health kept improving, headaches and dizziness disappeared. Two months later a marked regression of varicosity was registered.

Potentiated antibodies to DETRALEX bioflavonoid (contains a combination of diosmine and hesperedin).

38F. Patient V., aged 42, an operation nurse, had been suffering from varicose veins in her legs for 5 years. Following her doctor's recommendations, she started taking DETRALEX (1 tablet twice a day). She complained of dyspepsia not associated with diet faults. The treatment with a C30 dilution of potentiated antibodies to each component alternately (every other day) in a dose of 1 tablet daily was initiated. The patient started feeling much better after one week of the intake of the antibodies. Six weeks later no symptoms of varicose veins were seen.

Potentiated antibodies to VITAMIN A. (trans-9,13-dimethyl-7-(1,1,5-trimethylcyclohexen-5-yl-6)-nonatetraen-7,9,11,13-ol).

38G. Patient K., aged 26, complained of headache, running nose and artralgia. In order to raise the patient's immunity, the oral intake of a C200 dilution of a potentiated antiserum to VITAMIN A (trans-9,13-dimethyl-7-(1,1,5-trimethylcyclohexen-5-yl-6)-nonatetraen-7,9,11,13-ol) in a dose of 1 tablet a day was prescribed. At his next visit three days later the patient reported feeling well.

Potentiated antibodies to VITAMIN D (ERGOCALCIFEROL) (5Z,7E,22E)-9,10-secoergosta-5,7,10(19),22-tetraen-3-ol).

38H. Patient N., aged 55, complained of pain in his hands not associated with physical strain and cramps in his lower extremities. The recommendation was: the intake of a C200 dilution of potentiated solution of an antiserum to VITAMIN D (ERGOCALCIFEROL) (5Z,7E,22E)-9,10-secoergosta-5,7,10(19),22-tetraen-3-ol) in a dose of 1 tablet 2 times a day in combination with preparations of calcium. After three weeks of the therapy the lessening of pain and the disappearance of convulsive reactions were observed. It was recommended to continue the course of treatment.

Potentiated antibodies to VITAMIN E (3,4-dihydro-2,5,7,8,-tetramethyl-2-(4,8,12,trimethyltridecyl)-2H-1-benzopyranol acetate).

38I. Patient A., aged 43, complained of fatigability and muscle weakness. After a weeklong course of treatment with a C30 dilution of potentiated monoclonal antibodies to VITAMIN E (3,4-dihydro-2,5,7,8,-tetramethyl-2-(4,8,12,-trimethyltridecyl)-2H-1-benzopyranol acetate) in a dose of 1 tablet 3 times a day the patient stated an increase in his ability to work and the improvement of mood.

EXAMPLE 39

Potentiated Antibodies to Immunomodulators and Cytokines

Potentiated antibodies to interferon.

39A. Patient P., aged 34, complained of rhinitis and pain in his nasopharynx. The diagnosis of acute respiratory viral infection was established. A double administration of intranasal drops of a potentiated C12 aqueous solution of monoclonal antibodies to γ-interferon resulted in the normalization of the patient's condition of health within two days. A conclusion was made that the antibodies featured the antiviral effect.

Potentiated antibodies to interleukins.

Potentiated antibodies to aldesleukin (interleukin 2).

39B. Patient M., aged 42, had been running course of treatment for the exacerbation of chronic bronchitis. The oral intake of a C30 dilution of potentiated monoclonal antibodies to interleukin 2 in a dose of 1 tablet 3 times a day resulted in the normalization of the body temperature three days after the beginning of the treatment with the homeopathic preparation. The recommendation was to take the preparation in a dose of 1 tablet once a day for three months. Catamnesis: no exacerbations of chronic bronchitis occurred during 8 months of medical observation. A conclusion was made that the antibodies possessed an immunity boosting effect.

Potentiated antibodies to colony-stimulating factors.

39C. Patient L., aged 23, complained of dizziness. He had a long (20 days) history of the intake of baralgin containing a pyrazolone derivative with a hemopoiesis-suppressing effect. The oral intake of a C200 dilution of potentiated polyclonal antibodies to filgrastim (colony-stimulating factor) in a dose of 1 tablet 3 times a day was recommended; this made it possible to achieve normal counts of neutrophiles and erythrocytes within 6 days after the beginning of treatment. Conclusion: the antibodies possessed a hemopoietic effect.

Potentiated antibodies to LEVAMIZOL. ((S)-2,3,5,6-tetrahydro-5-phenylmidazo[2,1-b]thiazole).

39D. Patient K., aged 41, was hospitalized with an established diagnosis of maxillary sinusitis. The administration of a C12 dilution of potentiated monoclonal antibodies to LEVAMIZOL ((S)-2,3,5,6-tetrahydro-5-phenylmidazo[2,1-b]thiazole) in the form of nasal drops in a dose of 0.5 ml twice a day made it possible to control headache and to return the body temperature to the normal level within three days. It was the immunostimulating effect of potentiated antibodies that accounted for such results.

39E. Patient P., aged 53, suffered from the exacerbation of her hypertensive disease; the blood pressure reached 180/100 mm Hg. As she used to take DIBAZOL as part of her antihypertension treatment, there was made a suggestion to start treatment with a C30 dilution of potentiated polyclonal antibodies to DIBAZOL in a dose of 1 tablet twice a day. Within three days her blood pressure dropped to 150/80 mm Hg. The treatment with antibodies was continued. Despite the fact that there was an epidemic of flu in the city, to which all the members of the patient's family succumbed, the patient never developed any symptoms of viral respiratory infection. A conclusion was drawn about the hypotensive and immunostimulating effects of the antibodies.

Potentiated antibodies to immunodepressant drugs.

39F. Patient D., aged 27, complained of redness and itching of her hands after a contact with a synthetic detergent. Her condition was diagnosed as allergic dermatitis. The oral intake of a C200 dilution of a homeopathic solution of monoclonal antibodies to CYCLOSPORIN in a dose of 1 tablet twice a day lessened the severity of the allergic reaction within 24 hours.

39G. Patient A., aged 28, had been staying at hospital for basic antirheumatic therapy-resistant rheumatoid arthritis. The patient had been treated with CYCLOSPORIN A (CsA) (2.5 mg/kg per diem) for 4 months with good therapeutic effect. A routine blood test showed an elevated creatinine level; the patient's blood pressure was raising in the course of the last week (160/90 mm Hg). The danger of the exacerbation of arthritis and the inefficiency of other medications precluded cancellation of treatment with CsA. The dose of CsA was reduced to 1.5 mg/kg per diem and a C200 dilution of potentiated antibodies to CsA was prescribed in a dose of 1 tablet twice a day. After a week of the treatment the creatinine content went back to normal, the blood pressure dropped to 120/75 mm Hg. The stable antirheumatic effect of CsA persisted along with the patient's good tolerance of it. Later CsA was discontinued. The intake of potentiated anti-bodies was continued in a dose of 1 tablet every day. Catamnesis 6 months later: rheumatoid arthritis in the phase of remission.

39H. Patient L., aged 47, complained of lumbar pain. After the diagnosis of lumbosacral radiculitis had been established, a recommendation was made: the oral intake of a C12 dilution of polyclonal antibodies to CHONDROITIN SULFATE in a dose of 1 tablet 3 times a day along with conventional anti-inflammatory drugs. After two days of the treatment the pain syndrome subsided. Monotherapy with antibodies made it possible to begin to control the manifestations of radiculopathy within 7 days.

39I. Patient O., aged 40, had been participating in the elimination of the consequences of the Chernobyl catastrophe; he suffered from radiation cataract of both eyes. The patient used to take AZAPENTACENE (2 drops into both eyes 5 times a day) to good effect; however he complained to the attending oculist of an itching and burning sensation in his eyelids. The suggestion was to discontinue the administration of the preparation temporarily and to use a D12 dilution of anti-bodies to AZAPENTACENE in a dose of 1 tablet twice a day. When the irritation of the patient's eyelids had subsided, the treatment with potentiated antibodies was successfully continued.

EXAMPLE 40

Potentiated Antibodies to Antibiotics and Antiparasite Drugs

Potentiated antibodies to CIPROFLOXACIN (1-cyclopropyl-6-fluoro-1,4-dihydro-4-oxo-7-(1-piperazinyl)-3-quinolinecarboxylic acid).

40A. Patient Ts., aged 26, complained of cough and pain in his nasopharynx. Physical examination showed a rise in the body temperature to 37.1° C. After two days of the intake of a solution of potentiated antibodies to CIPROFLOXACIN (1-cyclopropyl-6-fluoro-1,4-dihydro-4-oxo-7-(1-piperazinyl)-3-quinolinecarboxylic acid) in a dose of 10 drops 3 times a day the patient's condition normalized and the body temperature dropped to 36.7° C.

Potentiated antibodies to METRONIDAZOLE (2-methyl-5-nitro-1H-imidazole-1-ethanol).

40B. Patient A., aged 32, complained of nausea after metronidazol intake. The additional administration a of C12 dilution of potentiated monoclonal antibodies to 2-methyl-5-nitro-1H-imidazole-1-ethanol in a dose of 1 tablet 3 times a day made it possible to eliminate nausea and continue the treatment.

Potentiated antibodies to CEFEPIM ([[7-[[(2-amino-4-thiazolyl)(metoxyimino)acetyl]amino]-2-carboxy-8-oxo-5-thia-1-azabicyclo[4.2.0]oct-2-en-3-yl]methyl]-1-methylpyrrolidinium hydroxide).

40C. Patient E., aged 36, complained of pain in his knee joints and tonsillitis. The diagnosis of rheumatoid arthritis was established earlier; however, concomitant duodenal ulcer precluded the administration of anti-inflammatory drugs. The recommendation was to take drops of a solution (a D24 dilution) of an antiserum to the antibiotic CEFEPIM ([[7-[[(2-amino-4-thiazolyl)(metoxyimino)acetyl]amino]-2-carboxy-8-oxo-5-thia-1-azabicyclo[4.2.0]oct-2-en-3-yl]methyl]-1-methylpyrrolidinium hydroxide) 3 times a day. Five days later the inflammatory reaction subsided and tonsillitis disappeared.

40D. Patient Zh., aged 33, was directed to the proctology unit of a clinical hospital with an established diagnosis of perianal abscess. Within the framework of therapy the patient was receiving AMOXYCLAV (a combination of semisynthetic penicillin amoxycillin and clavulonic acid, an inhibitor of β-lactamases), 1 tablet 3 times a day. The patient used to take various antibiotics on his own initiative and without system, including phenoxymethylpenicillin. Along with the amelioration of his general condition (the lowering of the body temperature, the lessening of pain, and the reduction of the white blood count), the patient started complaining of nausea. Following his doctor's advice, the patient began to take AMOXYCLAV at meals; however, nausea persisted. A 7-days' course of the treatment with a C6 dilution of potentiated antibodies to 6-aminopenicillanic acid (common for all penicillins) in a dose of 1 tablet 3 times a day was carried out. The tolerance of the preparation improved; the patient presented no complaints, no indications for surgical treatment were seen; as the blood count and the body temperature were back to normal, the patient was discharged from hospital under local polyclinic observation. Recommendations for the regimen and further treatment were given.

40E. Patient V., aged 34, suffered from severe bilateral polysegmentary pneumonia with a II-III degree of respiratory failure, chronic alcoholism, chronic hepatitis, secondary immunodeficiency. The patient started receiving MAXINIM (cephalosporin of the IV generation) in a dose of 1.0 gram intramuscularly every 12 hours. At the $3^{rd}$ day of the treatment the patient's condition ameliorated, dyspnea and cough subsided, and the body temperature went down. However, the paint started complaining of nausea, his functional liver tests showed elevated values of ALT and AST. The treatment protocol was completed with a C50 dilution of potentiated antibodies to MAXINIM in a dose of 1 tablet 3 times a day. The patient's condition kept improving, the nausea disappeared, and the ALT and AST values dropped to the upper bound of normal.

40F. Patient K., aged 46, was taking RULIDE for acute prostatitis in a dose of 150 mg twice a day. After three days of the treatment the symptoms of prostatitis subsided but the patient started complaining of dizziness and distorted smell and taste of food. The treatment with a C30 dilution of potentiated antibodies to RULIDE in a dose of 1 tablet 3 times a day was started and within three days the taste and odor perception was back to normal and dizziness disappeared.

40G. Patient G., aged 25, suffered from the exacerbation of chronic adnexitis after criminal abortion, polynarcomania, and secondary immunodeficiency. She was treated with CIPROBAY (125 mg 2 times a day). After 6 days of the treatment the patient felt better; however, she started having fainting spells and hot flashes. A C200 dilution of potentiated antibodies to CIPROBAY in a dose of 1 tablet twice a day was prescribed. Within the days the patient's complaints disappeared, her condition became satisfactory.

40H. Patient Sh., aged 44, had been treated with CIPROFLOXACIN for the exacerbation of chronic suppurative obstructive bronchitis. The choice of the drug had been based on the results provided by the antibioticogram; the repeated use if this medication had been giving clinical success. However, in this case no positive bronchological dynamics was achieved after 2 weeks of treatment. The antibiotic was discontinued and the treatment with a C6 dilution of potentiated monoclonal antibodies to CIPROFLOXACIN in a dose of 1 tablet twice a day began. Within ten days all symptoms of bronchial obstruction disappeared, no suppurative mucus was seen during bronchoscopy. A conclusion was drawn on the anti-bacterial and anti-inflammatory effects of potentiated antibodies.

40I. Patient I., aged 42, was staying in a phthisiologic hospital with an established diagnosis of infiltrative tuberculosis of the upper lobe of the right lung in the phase of disintegration and dissemination, with bacterioexcretion. After three months of the treatment with isoniazid, rifampicin, and streptomycin positive clinical and X-ray dynamics was achieved. However, the subsequent two months of the treatment with the antibacterial drugs did not bring any significant improvement of the patient's condition: infiltration and a cavern in the upper lobe of the right lung persisted and showed no tendency for a further reduction; the release of bacteria persisted as well. The in vitro resistance to antibiotics was not found at the initial stage of examinations or five months later. The treatment with a C200 dilution of potentiated antibodies to ISONIAZID, RIFAMPICIN, and STREPTOMYCIN in a dose of 1 tablet of each preparation daily made it possible to achieve positive X-ray dynamics within two months; the release of bacteria stopped.

40J. Patient Ch., aged 36, was staying at the infectious hospital for amebic dysentery. After four days of the administration of ORNIDAZOLE (1.0 g per diem) the patient started complaining of somnolence and dizziness. The additional treatment with a C12 dilution of potentiated antibodies to ORNIDAZOLE in a dose of 1 tablet twice a day resulted in the elimination of the undesirable effects within subsequent four days.

EXAMPLE 41

Potentiated Antibodies to Chelating Agents

41A. Patient D., aged 44, was undergoing a course of treatment with DOXORUBICIN (75 mg administrated intravenously once in 3 weeks) at the in-patient unit of an oncological dispensary for III degree breast cancer. For the prevention of myocardiopathy the patient was receiving CARDIOXANE intravenously 30 minutes before the injection of the cytostatic drug. The patient tolerated DOXORUBICIN well enough with a background treatment with CARDIOXANE; however, her hemoglobin level dropped to 70 g/l. It was suggested to include the administration of a C30 dilution of potentiated antibodies to CARDIOXANE in a dose of 1 tablet twice a day in the treatment protocol. Within subsequent three months the remission of the main disease was achieved and maintained; no signs of cardiac failure were observed and the hemoglobin level was 95-100 g/l.

EXAMPLE 42

Potentiated Antibodies to Anti-Gout Drugs

42A. Patient Kh., aged 49, with the diagnosis of hypertensive disease and chronic gout had been taking 1.5 g of PROBENECIDE daily for the prevention of gout exacerbation caused by a diuretic (hypothiazide) he was receiving for his hypertension. The patient complained of nausea, weakness and painful sensation in his gums. The treatment with a C12 dilution of potentiated antibodies to PROBENECIDE in a dose of 1 tablet twice a day was started and three days later the patient started feeling better. The treatment with hypothiazide and PROBENECIDE was continued; the PROBENECIDE dose was reduced by 50% with no negative effect on the therapeutic action.

42B. Patient V., aged 51, had been taking (on his physician's advice) IMODIUM (LOPERAMIDE) for chronic-diarrhea caused not by infection (presumably by heavy metal salts). The patient stated that the overall effect of the drug was positive but complained of dizziness. The treatment with a C50 dilution of potentiated antibodies to the piperidine group of IMODIUM in a dose of 1 tablet twice a day was started and after five days of the therapy with antibodies the unpleasant sensations ceased (with a persisting therapeutic effect of the drug).

EXAMPLE 43

Potentiated Antibodies to Autologous Antigens

Potentiated antibodies to DNA antigens.

43A. Patient P., aged 24, with clinical diagnosis of systemic lupus erythematosus accompanied by kidney affection (nephrotic type glomerulonephritis) and heart injury (myocarditis), subacute course, III degree of activity had been taking prednisolone (50 mg daily) and curantyl (200 mg daily). Because of the lessening of the effect of prednisolone she was began to receive potentiated polyclonal antibodies to native DNA isolated from lymphocytes of the patient's peripheral blood. Antibodies were obtained by immunization of a rabbit with subsequent purification of the antiserum and its potentiation based on homeopathic technology. The intake of a C1000 dilution of potentiated antibodies to autoantigens of DNA in a dose of 1 tablet twice a day resulted in a marked inhibition of the activity of the autoimmune process within two weeks. The laboratory findings were as follows: ESR decreased from 50 to 16 mm/h, the titer of the antinuclear factor lowered. Catamnesis: 6 months of the intake of potentiated antibodies gave clinical and laboratory remission.

EXAMPLE 44

Potentiated Antibodies to Rhesus (Rh) Factor

44A. Patient S., aged 28, Rh$^-$ (her husband was Rh$^+$) was admitted to hospital with the diagnosis of an 8-weeks pregnancy. This was her fourth pregnancy. She had a history of normal first pregnancy ending with normal delivery, the second pregnancy was interrupted by medical abortion at the term of 10 weeks, and the third pregnancy ended with antenatal death of the fetus because of the Rh conflict at the term of 38 weeks. In order to prevent the Rh conflict and to maintain the current pregnancy she started to take a C200 dilution of polyclonal potentiated antibodies to Rh factor beginning with the 8$^{th}$ week in a dose of 1 tablet twice a week. Catamnesis: the therapy favored uncomplicated pregnancy, which ended with labor at term. The baby (Rh$^+$) was healthy without symptoms of hemolytic disease.

EXAMPLE 45

Potentiated Antibodies to Substances Causing Intoxication and/or Dependence

Potentiated antibodies to opiates.

45A. Patient S., aged 28, had an almost uninterrupted 5-year history of intravenous self-injections of crude homemade acetylated opium (sultyga). He was admitted to a narcological unit 24 hours after the last injection. The patient was irritated and gloomy and complained of intense pains in his extremities, chills, and insomnia. The oral intake of 10 drops of a C200 dilution of a potentiated aqueous solution of natural antibodies to MORPHINE HYDROCHLORIDE every 15-30 minutes was prescribed. The antibodies had been isolated by affinity chromatography from the serum of a patient with chronic morphine dependency. The therapy resulted in a quick disappearance of vegetative disorders and the lessening of the intensity of the myalgia. Six hours after the beginning of the therapy the patient went to sleep. Two days later the withdrawal symptoms virtually disappeared. A conclusion was drawn on the sufficiency of monotherapy with antibodies to morphine in the case of the opiate withdrawal syndrome.

45B. Patient K., aged 21, was admitted to a narcology unit with typical manifestations of the opiate withdrawal syndrome. Questioning revealed that she had been abusing crude homemade extract of poppy seed straw (koknar) in the form of intravenous self-injections in the course of two years. A combined therapy with a C1000 dilution of potentiated monoclonal antibodies to MORPHINE in a dose of 1 tablet once in 2 hours and a C200 dilution of potentiated antibodies to codeine in a dose of 1 tablet in the morning and 1 at bedtime was prescribed. Within 48 hours all manifestations of the withdrawal syndrome were completely arrested.

45C. Patient I., aged 42, was emergently admitted to a narcology unit with the diagnosis of codeine overdosage. The patient was somnolent and had periodic bouts of nausea. The examination revealed depressed reflexes, bradycardia, and moderate hypotension. The patient was put on a slow intravenous infusion of 200 ml of an isotonic solution containing polyclonal potentiated antibodies to opiates of the phenotrene group mixed in the following proportions: 1 ml of a C200 dilution of antibodies to MORPHINE; 1 ml of a C1000 dilution to CODEINE; 1 ml of a C50 dilution to THEBAINE; 1 ml of a C3.0 dilution to PSEUDOMORPHINE; 1 ml of a C12 dilution of antibodies to NEOPINE. Within two hours after the beginning of the treatment the symptoms of intoxication completely disappeared.

45D. Patient D., aged 16, had been inhaling heroin at least three times a week in the course of the last 1.5 months. On his parents' accord he was hospitalized in a restricted admission unit for 24 days. Two days after admission he became irritable, developed sleeping disorders, and complained of attraction to the drug when talking to his physician. The prescription was: a C1000 dilution of potentiated polyclonal antibodies to HEROIN in a dose of 1 tablet 6 times a day. Three weeks later the patient reported even mood and satisfactory sleep and appetite. During individual talks with a psychologist he denied having attraction to the drug. It was recommended to keep taking antibodies to heroin in a dose of 1 tablet a day. Two months after his discharge from hospital he (according to his mother's information) has never been noticed taking drugs.

45E. Patient Kh., aged 24, had been injecting intravenously some crude homemade heroin preparations for three years. He was admitted to a narcology unit in a state of sopor. In view of the inefficiency of potentiated antibodies to heroin during his previous treatment, it was recommended to start the oral administration of a mixture of aqueous solutions of monoclonal antibodies to the following synthetic and semisynthetic opiates: a C50 dilution of antibodies to DIONINE (ethylmorphine); a C1000 dilution to PROMEDOL: a C30 dilution to PHENTANYL. Thirty minutes later the patient became fully conscious and oriented in time. His reflexes were moderately depressed. He told the physicians that he had self-injected a dose of an unknown drug at the discotheque.

Potentiated antibodies to barbiturates and other soporific drugs.

45F. Patient B., aged 32, was admitted to an intensive care unit in the status epilepticus. According to his relatives, he had been taking various drugs of the barbiturate group both orally and intravenously in the course of the last years. The intravenous infusion of the following mixture of potentiated monoclonal antibodies to barbiturates was prescribed: a C50 dilution of antibodies to BARBAMYL (amytal sodium); a C200 dilution to NEMBUTAL (ethaminal sodium); a C1000 dilution to FANODORM (cyclobarbital) in a dose of 1 ml each. Within 15 minutes after the beginning of the therapy the status epilepticus was controlled, the patient lapsed into a stunned condition. During further observation at the hospital the patient was irritated and suffered from insomnia and dysphoria from time to time. He tried to get hold of soporific drugs. An interview revealed that he had also been taking drugs of the ureide group (bromural) and noxyron besides barbiturates. In view of this the patient was advised to take a C50 dilution of potentiated monoclonal antibodies to BROMURAL in combination with a C200 dilution of potentiated polyclonal antibodies to NOXYRON 1 tablet alternately every two hours. The patient's condition seriously improved: there was no dysphoria, he became less torpid, and his sleep was back to normal. He stopped searching for soporific drugs and was discharged in a satisfactory condition.

Potentiated antibodies to cannabinoids.

45G. Patient S., aged 24, was admitted to a psychiatric unit with pronounced depressive disorders. He had had a long history of hashish use (up to 5-8 joints a day). As the treatment with antidepressants proved inefficient, the oral intake of 10 ml of an aqueous solution containing the following mixture of potentiated polyclonal antibodies to CANNABINOIDS: a C50 dilution of antibodies to canabidiol; a C30 dilution to cannabinol; a C200 dilution to (−)-trans-$\Delta^9$-tetrahydrocannabinol. After 10 days of the treatment the patient's mood became even and his sleep was back to normal. Two weeks after the beginning of the treatment with anti-bodies the patient was discharged in a satisfactory condition.

45H. Patient D., aged 14, had been using drugs for 6 months. She used to chew the so-called bang (hashish tar). She was willing to be treated and his district narcologist prescribed potentiated monoclonal antibodies to CANNABINOIDS in a dose of 1 tablet every morning according to the following scheme: a C50 dilution of potentiated monoclonal antibodies to $\Delta^8$-tetrahydrocannabinol during the first two weeks of the month and potentiated monoclonal antibodies to $\Delta^9$-tetrahydrocannabinolic acid during the last two weeks. Six months of medical observation showed that the patient had given up drug abuse. The patient is socially adapted and continues her studies.

Potentiated antibodies to cocaine and its metabolites.

45I. Patient S., aged 28, had been using crack (a mixture of cocaine with baking soda) for 1.5 years. He was admitted to a therapeutic unit with the diagnosis of cachexy caused by chronic hepatitis of an unknown origin. Two weeks of health-improving therapy and hepatotropic treatment did not produce any significant effect. In order to control asthenic symptoms the treatment was supplemented with tablets of a C50 dilution of monoclonal potentiated antibodies to COCAINE (in a dose of 1 tablet twice a day). After three weeks of the treatment the preparation was substituted by tablets containing polyclonal antibodies to cocaine metabolites: a C50 dilution of antibodies to benzoylecgonine and a C200 dilution of antibodies to ecgonine. The treatment resulted in the normalization of the patient's mood and sleep; he gained 18 kg of weight. Two months after the beginning of the therapy the patient was discharged in a satisfactory condition.

45J. Patient O., aged 17, was brought to the narcological restricted admission unit by her parents. In the course of the last two months she had been self-injecting cocaine solutions intravenously. An interview with a psychologist revealed signs of a psychic dependence on this drug. The prescription was: a C50 dilution of polyclonal antibodies to a cocaine metabolite, NORCOCAINE, in a dose of 1 tablet 3 times a day during the first 10 days of hospital stay. The same pattern was applied to her second 10 days of hospital stay (a C200 dilution of polyclonal antibodies to METHYLECGONINE) and to the third 10-days' period (a C1000 dilution of polyclonal antibodies to HYDROXYCOCAINE) in the third decade of her hospital stay. The treatment with homeopathic doses of antibodies to cocaine metabolites resulted in a considerable improvement of the patient's condition of health: her mood became even and her sleep was back to normal. A test before discharge one month later revealed no signs of psychic dependence. Catamnesis four months later: the patient is socially adapted and has not been noticed using drugs.

Potentiated antibodies to benzodiazepines.

45K. Patient S. aged 38, had a 20-year long history of the abuse of tranquilizers and psychotropic drugs of the benzodiazepine group. Against the background of the drug abuse the patient developed a psychoorganic syndrome with predominant astheno-apathic symptoms and the patient was granted the $2^{nd}$ degree of disability. The scheme of nootropic treatment prescribed by the district physician involved a long-term intake of polyclonal potentiated antibodies to a number of benzodiazepines, namely, a C50 dilution of antibodies to CHLOZEPID; a C50 dilution to diazepam; a C200 dilution to OXAZEPAM; a-C200 dilution to NITRAZEPAM; a C1000 dilution to LORAZEPAM. As a result a C1000 dilution of polyclonal potentiated antibodies to CLONAZEPAM proved to be the best choice for the patient. He had been taking them every day in a dose of 1 tablet twice a day for 14 months, which resulted in the improvement of his intellectual capacities and memory. Now his behavior is well ordered; the patient is capable of taking care of himself; his mother reports that he hasn't been using any sedatives during this period.

Potentiated antibodies to phenylalkylamines and other stimulants.

45L. Patient C., aged 26, was admitted to a psychiatry department with the diagnosis of psychosis caused by ephedron abuse. Among the symptoms anxiety, alertness, alarming expectations, and paranoid attitude prevailed. The intravenous administration of a C50 dilution of potentiated monoclonal antibodies to EPHEDRON in a dose of 1 ml twice within the first hour of treatment was prescribed. After 1.5 hours of the therapy psychotic disorders disappeared. The patient's attitude to his delusional episode is critical.

45M. Patient Kh., aged 41, engaged at diplomatic service was admitted to a intensive care unit because of a long period (about 18 hours) of somnolence. According to his wife's information, the patient used to indulge alone in an intravenous administration of some stimulants but definitely not cocaine. The prescription was: a slow intravenous infusion of physiological saline solution containing 1 ml of a C50 dilution of potentiated antibodies to AMPHETAMINE and 1 ml a C30 dilution of polyclonal potentiated antibodies to METHAMPHETAMINE. Within fifteen minutes the lethargic symptoms were arrested. The patient was fully conscious and well oriented. He told the physician that he had administered a single dose of amphetamine intravenously.

45N. Patient T., aged 17, administered himself ephedrine intravenously three times in the course of the last month for the first time in his life. On his own initiative he went to seek for narcologist's advice, as he was afraid of becoming an addict. The prescription was: the intake of a combined preparation containing polyclonal antibodies to EPHEDRINE and polyclonal antibodies to NOREPHEDRINE in a potentiated form (dilutions C50 and C200, respectively) in a dose of 1 tablet twice a day. For half a year the patient paid regular visits to his physician twice a month and reported no episodes of ephedrine use during this period.

45O. Patient L., aged 25, sought for narcologist's advice on his own initiative. After 1.5 years of imprisonment he had become addicted to chifir (an extra strong tea brew) and used it at least 1-2-times a day. C50 dilution of potentiated polyclonal antibodies to CAFFEINE (1,3,7-trimethylxanthine) in a dose of 1 tablet twice a day. During his subsequent visits the patient stated that he had been drinking chifir very rarely (not more often than once a week) but could not give it up altogether.

Potentiated antibodies to hallucinogens (psychedelic drugs).

45P. Patient K., aged 28, was brought to the psychiatric department from a hotel where he had attracted the hotel staffs attention by his inadequate behavior: he was contemplating something, used to freeze suddenly and stand motionless; he was poorly oriented in the situation around him. In response to physician's questions the patient answered that he used to take pieces of blotting paper impregnated with LSD, sublingually. A single dose (1 ml) of a C200 dilution of a solution containing potentiated polyclonal antibodies to lysergic acid diethylamide (LSD) was administered. Fifteen minutes after the administration of the preparation the psychotic disorders were arrested.

45Q. Two A. brothers, aged 16 and 19, with the diagnosis of poisoning with dried ink fungi were admitted to a psychiatric unit. As the quantity of potentiated preparation available at that moment at the unit was insufficient, one of the patients received intravenously 1 ml of a C200 dilution of potentiated polyclonal antibodies to PSILOCIN and the other, 1 ml of a C50 dilution of potentiated polyclonal antibodies to PSILOCYBIN. Within an hour the condition of both patients returned to normal, their excitement and unrestraint disappeared, and they both went to sleep. A conclusion was drawn on high efficiency of both preparations.

45R. Patient D., aged 19, was admitted to a neurology unit for manifestations of catalepsia. In view of the fact that the patient had been taking the drug phenycyclidine (PCP), she underwent hourly intramuscular administrations of 1 ml of a D3 dilution of the solution of potentiated antibodies to PHENYCYCLIDINE. Within three hours the cataleptic syndrome was completely arrested.

45S. Patient A., aged 38, has the 2.sup.nd degree of disability because of paranoid schizophrenia. For fifteen years he had been taking high daily doses of haloperidol in combination with parcopan or cyclodol for the prevention of narcolepsia and had already developed physical dependence on them. The attending physician started reducing gradually the dose of cyclodol ending up with replacing it completely with a C30 dilution of potentiated polyclonal antibodies to CYCLODOL in a dose of 1 tablet in the morning and 1 tablet at bedtime every day. The patient keeps taking haloperidol and doesn't have any neuroleptic symptoms; no requests for cyclodol prescription.

Potentiated antibodies to alkaloids of tobacco.

45T. Patient I., aged 29, consulted a narcologist for tobacco smoking Because the neuropharmacological preparations he used to take earlier had not succeeded to rid him of the bad habit, the physician prescribed a C200 dilution of a potentiated antiserum to NICOTINE in a dose of 1 tablet 3 times a day. Catamnesis 3 months later was as follows: in the course of the first weeks of the therapy with antibodies the patient's craving for tobacco was enhanced and he smoked more often. Later on, the situation changed, his craving receded, he was able to gradually reduce the number of smoked cigarettes and finally to give up smoking altogether.

Potentiated antibodies to alcohol.

45U. Patient B., aged 35, was admitted to a narcological hospital with pronounced symptoms of alcohol withdrawal. A C200 dilution of potentiated monoclonal antibodies to ETHANOL in a dose of 1 sublingual tablet every 15 minutes was prescribed. Within two hours of the therapy the patient's condition significantly improved: the tremor, hyperhydrosis, and weakness disappeared, the patient went to sleep. Twenty-four hours later he was discharged. Conclusion: potentiated antibodies to ethanol have a therapeutic effect in the case of the alcohol withdrawal syndrome.

EXAMPLE 46

Potentiated Antibodies to Antigens of Fetal and Primordial Tissues and Tissue Cultures 46A. Patient A. was a newborn baby 27 days old. He was born with symptoms of perinatal encephalopathy. As immunoenzyme diagnostic methods had revealed elevated levels of embryotropic neurospecific antigens in mother before this pregnancy, it was decided to administer to the baby a C200 dilution of a potentiated polyclonal antiserum to bovine fetal brain-specific non-species-specific protein (antigen), 14-3-2 (brain-specific enolase), in an oral dose of 5 drops of an aqueous solution to be administered 3 times a day. In the course of the treatment neurological symptoms subsided gradually; the reflexes of oral and spinal automatism restored and muscle hypertonus receded. The baby became calmer and started active breast sucking A conclusion was drawn on the efficiency of potentiated antibodies to the said fetal antigen controlling normal morphogenesis of the central nervous system in the treatment of perinatal encephalopathy.

46B. Patient D., aged 4, with an established diagnosis of mental retardation had been receiving a C1000 dilution of monoclonal potentiated antibodies to PRIMORDIAL ANTIGEN NESTIN, a protein marker of neuron stem cells, in a dose of 5 drops of an aqueous solution once a day in the morning for six months with the purpose of enhancing the child's intellectual capacities. After six months of the treatment a neuropyschological examination showed that D's intellect and memory were up to the standard age level; the child's kindergarten tutor reported that the boy comprehended and learned the material well in class.

46C. Patient I., aged 8, with an established diagnosis of Down's syndrome had been receiving a C200 dilution of potentiated polyclonal antibodies to A-FETOPROTEIN to be taken in a dose of 1 tablet a day for the first 12 months and in a dose of 1 tablet once in 3 days for subsequent 6 months. The neuropyschological examination by Bailey's method revealed a marked enhancement of the patient's intellect 1.5 years later. The patient's behavior is well ordered; he is adapted to being with other children.

46D. Patient S., aged 18, suffered from myasthenia of an unknown origin. In view of the inefficiency of conventional drugs the treatment was supplemented by the oral intake of a C30 dilution of potentiated polyclonal antibodies to the culture of neuronal stem cell of the tera-1 line enriched with the protein extract of the embryonic tissue in a dose of 1 ml 3 times a day for 6 months. The combined treatment resulted in an increased tolerance of physical strain, receded bulbar symptoms, diplopia, and ptosis, which made it possible to reduce the daily doses of corticosteroid drugs several times.

46E. Patient M., aged 42, suffered from the astheno-neurological syndrome accompanying the remote period of vernal encephalitis. As conventional therapy proved its inefficiency, it was decided to prescribe the oral intake of a C200 dilution of potentiated polyclonal antibodies to EMBRYONIC NEOCORTEX (the antiserum was obtained by immunization of rabbits with tissues from the occipital zone of the brain cortex of 15-day old embryos of Wistar line rats) in a dose of 1 ml twice a day, for 6 months. In the course of treatment the patient's asthenic symptoms became less pronounced, his ability to work was restored, though disseminated microsymptoms persisted in his neurological status.

46F. Patient K., aged 39, suffered from chronic alcoholism, grade II. He went to seek for narcologist's advice declaring his desire to start a sober life and asking for a new method of treatment because those he had already tried were of little effect. The prescription was: a regular intake of a C1000 dilution of polyclonal potentiated antibodies to homogenized hippocampi of embryos of Wistar line rats (hippocampi of several dozens of syngenic fetuses were used for immunization) in a dose of 1 tablet once a day. The remission had been lasting for 8 months, in the course of this period of medical observation no episodes of consuming alcoholic beverages have been registered, the patient states the absence of craving for alcohol.

46G. Patient A., aged 8, suffered from liver cirrhosis of an unknown etiology. As the conventional therapy had no significant effect, the oral intake of a C4 dilution of polyclonal potentiated antibodies to homogenized liver of the human fetus was prescribed in a dose of 1 ml 3 times a day. During four months of the therapy a clinical improvement of the patient's condition was observed, manifestations of general intoxication symptoms and liver failure subsided. The patient's emotional tone rose, the paleness of skin, the icteric hue of the scleras, and spider-like hemangiomas disappeared; the size of the liver diminished. A conclusion was drawn on high efficiency of this mode of treatment.

EXAMPLE 47

Potentiated Antibodies to Tissues or Tissue Cultures

47A. Patient O., aged 8, suffers from a malignant course of insulin-dependent diabetes mellitus. The intranasal administration of a C50 dilution of potentiated polyclonal antibodies to a culture of insular cells of the pancreas of newborn rabbits in a dose of 1 ml 3 times a day was prescribed with therapeutic purposes. After three months of the therapy the course of illness became stable, the blood glucose level went down, and the disposition to ketoacidosis receded. There were no comas or hypoglycemic episodes during the period of the treatment and the amount of insulin intake was reduced by 50%.

47B. Patient P., aged 35, suffered from insulin-dependent diabetes mellitus (mild course). As the patient was unwilling to take insulin, the recommendation was to start the oral intake of 1 ml of a C50 dilution of an aqueous solution of polyclonal potentiated antiserum to insular cells of the pancreas of a newborn calf once a day. As a result of the monotherapy with this preparation, the patient was feeling well. Her blood glucose level was within normal limits. The patient did not take insulin any more.

47C. Patient V. aged 56, suffered from obstructing atherosclerosis of coronary arteries and angina decubitus. In view the inefficiency of conventional therapy the prescription was to take intranasally a C30 dilution of potentiated polyclonal antibodies to the homogenized heart of a newborn rabbit in a dose of 3 drops of an aqueous solution 5 times a day. After six months of the therapy the intensity of pain was reduced, the patient had pain much more seldom and only after a sufficiently strong physical strain; his blood lipid formula became normal and the dose of nitrate drugs was reduced approximately by 50%.

Antibodies to Specific Lipids of Nervous System

EXAMPLE 48

Antibodies to Lipids of Nervous Cells of the Brain

48A. Antibodies to cholesterol. Experiments on biomembranes of nervous cells using neurochemical and physicochemical methods have shown that antibodies to cholesterol in C200 homeopathic dilution when added to the incubation medium in form of when added to the incubation medium in form of 1% solution imbed into phospholipid double layer and destroy quasi-crystal packing of the chains and diminish their mobility. The ability of antibodies to alter membrane fluidity and the processes associated with the latter, such as activation of ATP-ases, calcium-mediated release of mediators from synaptic terminals and the process of ligand binding to receptors, has been demonstrated. It has been found out that when antibodies to cholesterol are added to membranes of nervous cells the surface of lecithin molecule is reduced from 0.96 to 0.71 nm$^2$.

48B. Antibodies to cerebrosides. Experiments on biomembranes of nervous cells using neurochemical and physicochemical methods have shown the ability of the antibodies to cerebrosides in C200 homeopathic dilution to alter fluidity of the membrane of neurons of rat hippocampus when added to the incubation medium in form of 1% solution.

48C. Antibodies to sulfatides (sulfocerebrosides). It is well known that the sulfate group of sulfocerebroside belongs to the active center of the opiate receptors. It has been found out in experiments in vivo that antibodies to sulfocerebroside injected into the rat brain eliminate morphine's narcotic effect. The ability of the antibodies to sulfatides in C200 homeopathic dilution added to the incubation medium of rat neurons in form of 5% solution to alter membrane fluidity and the processes associated with the latter, such as activation of ATP-ases, calcium-mediated release of mediators from synaptic terminals and the process of ligand binding to receptors, has been demonstrated using neurochemical and physicochemical methods.

EXAMPLE 49

Antibodies to Phospholipids of Nervous Cells of the Brain

49A. Antibodies to citidine 5-diphosphocholine (citicholine, CDP-chorine). Antiamnesic activity of the antibodies to citidine 5-diphosphocholine has been shown in experiments on white mature rats. Administration of scopolamine to rats immediately prior to teaching them the conditioned reflex of passive avoidance in the dark-light chamber resulted in impaired process of reflex reproduction 24 hours after the training session. Oral administration of a single dose of 0.1 ml of the solution of the antibodies in C200 homeopathic dilution resulted in elimination of the amnesic effect of scopolamine, which was manifested by shortening (by a factor of 1.5) of the period of time spent in the dangerous dark chamber. Oral administration of a daily dose of 0.1 ml of the solution of the antibodies in C200 homeopathic dilution to old rats aged 24 months for 3 months resulted in restoration of impaired locomotor skills and improvement of training processes. Under the influence of the preparation the number of mistakes made by the animals dropped by 32% and the latency period of reflex formation in the T-shaped labyrinth shortened.

49B. Antibodies to phosphatidylcholine. The ability of the antibodies to phosphatidylcholine in C200 homeopathic dilution to cause activation of membrane enzymes Na+-, K+-ATPase and monoaminoxidase in the membranes of central nervous system of rats when added to the incubation medium in form of 1% solution was demonstrated in experiments in vitro using neurochemical methods.

49C. Antibodies to lisophosphatidylcholine. The ability of the antibodies to phosphatidylcholine in C200 homeopathic dilution to cause activation of membrane enzymes Na+-, K+-ATPase in biomembranes of animal brain by 20% when added to the incubation medium in form of 1% solution was demonstrated in experiments in vitro on biomembranes of nervous cells using neurochemical methods.

49D. Antibodies to sphingomyelin. The ability of the antibodies to phosphatidylcholine in C200 homeopathic dilution to cause activation of membrane enzymes Na+-, K+-ATPase in biomembranes of rat brain when added to the incubation medium in form of 1% solution was demonstrated in experiments in vitro on biomembranes of nervous cells using neurochemical methods.

49E. Antibodies to phosphatidyl serine. The ability of the antibodies to phosphatidyl serine in C400 homeopathic dilution to cause activation of membrane enzymes, such as protenkinase C, adenylate cyclase and Na+-, K+-ATPase in biomembranes of rat brain when added to the incubation medium in form of 5% solution was demonstrated in experiments in vitro on biomembranes of nervous cells using neurochemical methods.

49F. Antibodies to phosphoinositides (phosphatidyl inosite)-regulators of Ca2+ ion transport across the membrane. It has been shown in experiments in vitro on biomembranes of nervous cells using neurochemical methods that membrane depolarization leads to quick release of arachidonic acid out of phosphoinositides. Antibodies to phosphoinositides and their metabolites are also capable of regulating Ca2+ ion transport. Antibodies to 1,2-diacylglycerine in C200 homeopathic dilution when added to the incubation medium in form of 1% solution stimulate the activity of protenkinase C, which phosphorylates the protein of calcium channels and antibodies to triphosphoinositol are capable of binding divalent cations and thus stimulating Ca2+ ion transport.

49G. Antibodies to phosphatidyl ethanolamine. The ability of the antibodies to phosphatidyl ethanolamine in C200 homeopathic dilution to cause activation of membrane enzymes Na+-, K+-ATPase in biomembranes of rat brain when added to the incubation medium in form of 1% solution was demonstrated in experiments in vitro on biomembranes of nervous cells using neurochemical methods.

EXAMPLE 50

Antibodies to Gangliosides

50A. Antibodies to GM1 ganglioside. The affinity of antibodies to GM1 ganglioside to the dopamine ligand was demonstrated in experiments in vitro on nervous tissue of the cerebral cortex using methods of receptor binding. When the antibodies in C200 homeopathic dilution are added to the incubation medium of rat in form of 1% solution replacement of 20% of labeled dopamine in neurons is observed. Experiments in vivo have shown that antibodies to GM1 monosialoganglioside restore the neurochemical parameters of dopaminergic neurons after lesions of nigrostriate system, promote dopamine capture and enhance the activity of tyrosine hydroxylase. The substance normalizes the disbalance between the activity of dopaminergic and serotoninergic neurons induced in the experiment by administration of apomorphine. Under the influence of the substance reduction of cerebral edema and restoration of ion balance is observed after cerebral trauma in experiments on rats.

50B. Antibodies to monosialoganglioside GM1 and disialoganglioside GD1b having the affinity to the choleraic toxin ligand. It has been shown in experiments on tissue culture using neurochemical methods that the oligosacharride part of monosialoganglioside is bound to the recognizing molecule of the choleraic toxin—its protomer B, which causes increase in local density of gangliosides and their micelle formation. Ganglioside micelles interact with the regulatory unit of choleraic toxin—its protomer A possessing ADP-ribosylating activity. ADPribosylation of slow receptors results in adenylate cyclase activation. Antibodies to monosialoganglioside GM1 in C200 homeopathic dilution when added to the incubation medium in form of 1% solution start an analogous cascade of events resulting in adenylate cyclase activation by 30%.

50C. Antibodies to gangliosides GQ1b, GD1b and GT1b. Experiments in vitro on nervous tissue of the cerebral cortex using methods of receptor binding have revealed the affinity of antibodies. to gangliosides GQ1b, GD1b and GT1b to the tetanus toxin ligand, which was manifested by their ability to replace 3H-tetanus toxin in its binding sites in rat neurons and reduction of radioactivity of the samples by 30% when C200 homeopathic dilution of the antibodies is added to the incubation medium in form of 1% solution.

50D. Antibodies to GT1b ganglioside. Experiments in vitro on nervous tissue of the cerebral cortex using methods of receptor binding have revealed the affinity of antibodies to GT1b ganglioside to the botulinum toxin ligand, which was manifested by their ability to replace 3H-botulinum toxin in its binding sites in rat neurons and reduction of radioactivity of the samples by 30% when C200 homeopathic dilution of the antibodies is added to the incubation medium in form of 1% solution.

50E. Antibodies to GM1 ganglioside. Experiments in vitro on nervous tissue of the cerebral cortex using methods of receptor binding have revealed the affinity of antibodies to GM1 ganglioside to the *E. coli* toxin ligand, which was manifested by their ability to replace 3H-toxin in its binding sites in rat neurons and reduction of radioactivity of the samples by 20% when C200 homeopathic dilution of the antibodies is added to the incubation medium in form of 1% solution.

50F. Antibodies to GP1, GQ1b and GT1a gangliosides. Experiments in vitro on nervous tissue of the cerebral cortex using methods of receptor binding have revealed the affinity of antibodies to GP1, GQ1b and GT1a gangliosides to the Sendai virus ligand, which was manifested by their ability to replace the virus in its binding sites in rat neurons by 20% when C200 homeopathic dilution of the antibodies is added to the incubation medium in form of 1% solution.

50G. Antibodies to GD1b and GT1b gangliosides. Experiments in vitro on nervous tissue of the cerebral cortex using methods of receptor binding have revealed the affinity of antibodies to GD1b and GT1b gangliosides to the influenza virus ligand, which was manifested by their ability to replace the virus in its binding sites in rat neurons by 30% when C200 homeopathic dilution of the antibodies is added to the incubation medium in form of 1% solution.

50H. Antibodies to GD3 ganglioside. Experiments in vitro on nervous tissue of the cerebral cortex using methods of receptor binding have revealed the affinity of antibodies to GD3 ganglioside to serotonin ligand, which was manifested by their ability to replace labeled serotonin in its binding sites in rat neurons by 20% when C200 homeopathic dilution of the antibodies is added to the incubation medium in form of 1% solution.

50I. Antibodies to GM2 and GT1 gangliosides. Experiments in vitro on nervous tissue of the cerebral cortex using methods of receptor binding have revealed the affinity of antibodies to GM2 and GT1 gangliosides to interferon ligand, which was manifested by their ability to replace interferon in its binding sites in rat neurons by 20% when C200 homeopathic dilution of the antibodies is added to the incubation medium in form of 5% solution.

50J. Antibodies to GM1, GD1b and GT1b gangliosides. Experiments in vitro on nervous tissue of the cerebral cortex using methods of receptor binding have revealed the affinity of antibodies to GM1, GD1b and GT1b gangliosides to tyrotropine ligand, which was manifested by their ability to replace tyrotropine in its binding sites in rat neurons by 30% when C200 homeopathic dilution of the antibodies is added to the incubation medium in form of 1% solution.

50K. Antibodies to GD1b and GT1b gangliosides. Experiments in vitro on nervous tissue of the cerebral cortex using methods of receptor binding have revealed the affinity of antibodies to GD1b and GT1b gangliosides to luteotropine ligand, which was manifested by their ability to replace luteotropine in its binding sites in rat neurons by 20% when C200 homeopathic dilution of the antibodies is added to the incubation medium in form of 1% solution.

50L. Antibodies to GT1b ganglioside. Experiments in vitro using methods of receptor binding have revealed the affinity of antibodies to GD1b ganglioside to gonadotropine ligand, which was manifested by their ability to replace 3H-gonadotropine in its binding sites in rat neurons by 30% when C200 homeopathic dilution of the antibodies is added to the incubation medium in form of 2% solution.

50M. Antibodies to GD1a and GT1 GANGLIOSIDES. Experiments in vitro on nervous tissue of the cerebral cortex using methods of receptor binding have revealed the affinity of antibodies to GD1a and GT1 gangliosides to fibronectine ligand, which was manifested by their ability to replace fluorescent labeled fibronectine in its binding sites in rat neurons when C200 homeopathic dilution of the antibodies is added to the incubation medium in form of 1% solution.

Antibodies to Specific Amino Acids, Peptides and Proteins of Nervous Tissue

EXAMPLE 51

Antibodies to Free Amino Acids of Nervous System

51A. Antibodies to glutamic acid. Patient K. aged 48 years suffering from depression with symptoms of emaciation was administered antibodies to glutamic acid in C400 homeopathic dilution (a teaspoonful of the solution taken orally twice a day) in the course of a month. The patient's mood improved considerably, she started feeling better, developed a desire to work and her symptoms of nervous exhaustion disappeared.

51B. Antibodies to gamma-aminobutyric acid. Injection of 0.01 ml of the solution of antibodies to gamma-aminobutyric acid in C200 homeopathic dilution directly into brain ventricles in experiments on rats resulted in calming the animal down and reducing its motor activity registered in the open field test.

51C. Antibodies to proline. It has been shown in the experiments on rats that oral administration of 0.1 ml of the solution of antibodies to proline in C400 homeopathic dilution causes impairment of teaching the animals the conditioned reflex of avoidance in the shuttle-box type two-section chamber where light signal was used as conditioned stimulus and painful stimulation via electrode floor as unconditioned stimulus.

51D. Antibodies to methionine. It has been shown in experiments on nervous tissue culture using neurochemical methods that antibodies to methionine promote choline synthesis and restore impaired synthesis of phospholipids out of fats.

51E. Antibodies to cysteine. Patient S. aged 57 years with initial form of senile cataract was prescribed antibodies to cysteine as cysteine takes part in metabolism of crystalline lens and changes in the lens occurring with cataract development are associated abnormal content of this amino acid in the lens. Use of antibodies in C200 homeopathic dilution in the dose of one teaspoonful of the solution once a day for 7 months resulted in considerable therapeutic effect-retardation of cataract.

51F. Antibodies to histidine. A three-month course of antibodies to histidine in C400 homeopathic dilution in the daily dose of one teaspoonful of the solution once a day prescribed to the patient V. aged 62 years suffering from moderate form of atherosclerosis resulted in normalization of the indices of lipoprotein metabolism, improvement of memory, attention and general state of health.

51G. Antibodies to N-acetyl aspartic acid, glutamine, aspartic acid, cystothionine, alanine, glutathione, serine, phenylalanine, tyrosine, treonine, tryptophane, valine, lysine, asparagines, isoleucine and leucine. In vitro studies on rat nervous tissue culture using neurochemical methods have demonstrated the ability of antibodies to these amino acids in C200 homeopathic dilution to satisfy plastic and energy needs of a cell and increase acetylcholine and noradrenalin concentration in the synaptic slit when added to the incubation medium in form of 2% solution.

51H. Antibodies to TAURINE-2-aminoethansulfonic acid. It has been shown in experiments on mature rats that antibodies to taurine produce anticonvulsive effect. It has been found out that electric current applied to the electrode floor encourages a pair of rats to fight. Use of antibodies to taurine in C200 homeopathic dilution (administered orally in the dose of 0.1 ml of the solution reduces the number of fighting episodes by 30% and shortens the duration of a single episode (by 45%).

51I. Antibodies to glycine. It has been shown that oral administration of antibodies to glycine in C200 homeopathic dilution in the dose of 0.1 ml of the solution for 7 days improves the process of memory trace fixation during training of the reflex in a U-shaped complicated labyrinth. Under the influence of the substance improvement of orientation, reduction of the number of mistakes (by 30%) and more rapid reflex formation can be observed.

Antibodies to Neurospecific Proteins

Antibodies to β-amyloid peptide (APβ) and to substances affecting AP (AP plays the key role in etiopathogenesis of neurodegeneration, including that in Alzheimer's disease).

EXAMPLE 52

Antibodies to β-Amyloid Peptide and its Precursors

52A. Antibodies to β-amyloid peptide (APβ) playing the key role in etiopathogenesis of Alzheimer's disease. Antibodies to APβ are regarded as diagnostic markers for Alzheimer's disease. It has been found out in experiments on transgenous mice (PDAPP line) with increased production of APβ2 and excessive amyloid plaque depositing that oral administration of 0.1 ml of the solution of antibodies to amyloid APβ342 in C200 homeopathic dilution results in prevention of amyloid plaque depositing in young animals and significant reduction of both number and size of plaques in old animals and hampers memory deterioration.

52B. Antibodies to fragments of APP protein. It has been shown that antibodies to IgM508 to fragments of APP protein are capable of blocking formation of insoluble APβ aggregates and of dissolving already formed amyloid fibrils upon oral administration of 0.1 ml of the solution of the said antibodies in C200 homeopathic dilution to mice for 10 days.

52C. Antibodies to the synthetic form of AP432 (preparation AN-1792). It has been shown that oral administration of 0.1 ml of the solution of the antibodies in C200 homeopathic dilution to mice for 7 days results in preventing and, in some animals, even in reversing the process of amyloid patching.

EXAMPLE 53

Antibodies to Inhibitors of β-Amyloid Peptide Formation

Antibodies to inhibitors of β-amyloid peptide (APβ) formation out of its protein precursor APP, expression of which is stimulated by a number of endogenous factors, such, for instance, as cytokines, certain neurotrophic factors (BFGF, EGF), estrogens and stress conditions.

53A. Antibodies to calpain and catepsin D proteases— specific blockers of production of β-synthetase affecting APβ formation out of its protein precursor APP. It has been shown in experiments in vitro by means of neurochemical methods that these antibodies when added to the incubation medium in C200 homeopathic dilution in form of 2% solution exert influence upon the first phase of APβ formation, namely, they stimulate by 30% the intracellular proteolysis induced by β-secretases forming the amino-terminal APβ residue.

53B. Antibodies to presenilin I protein. It has been shown in experiments in vitro by means of neurochemical methods that antibodies to presenilin I in C200 homeopathic dilution when added to the incubation medium of rat neurons in form of 2% solution inhibit the activity of the enzyme calpain II producing neurotoxic effect on cell level.

53C. Antibodies to monensin. It has been shown by means of neurochemical methods in experiments in vitro on nervous cell culture that antibodies to monensin in C200 homeopathic dilution when added to the incubation medium in form of 2% solution hamper APβ formation by causing destabilization of pH-gradient and vesicular transport.

53D. Antibodies to brefeldin A. It has been found out by means of neurochemical methods in experiments in vitro on nervous cell culture that introduction of the antibodies in C200 homeopathic dilution to the incubation medium in form of 2% solution hamper APβ formation.

53E. Antibodies to baphilomycin A and its analogues. It has been found out by means of neurochemical methods in experiments on nervous cell culture that antibodies to baphilomycin A in C200 homeopathic dilution when added to the incubation medium in form of 1% solution selectively block APβ formation via indirect inhibition of β-secretase activity, prevent lysosomal acidation by inhibition of V-type ATP-ase. The EC50 of the blocking effect of these substances is 50 nM.

53F. Antibodies to the peptides leupeptin (MDL-28170) and E-64. It has been shown by means of neurochemical methods in experiments in vitro that antibodies to leupeptin in C200 homeopathic dilution when added to the incubation medium in form of 2% solution stabilize the C-terminal fragment of APβ and cause drop in brain APβ content by direct or indirect inhibition of γ-secretase activity.

53G. Antibodies to ethers of N-arylalanin. It has been found out by means of neurochemical methods in experiments in vivo on transgenous mice that oral administration of a single dose of 0.1 ml of antibodies to ethers of N-arylalanin in C200 homeopathic dilution results in inhibition of γ-secretase activity leading to a drop in APβ level in the animals' brain.

EXAMPLE 54

Antibodies to Substances Affecting the Processes of APβ Aggregation-disaggregation and to APβ-binding substances 54A. Antibodies to peptides, reduced or modified fragments of APβ, namely, the pentapeptide KLVFF, an APβ fragment with 16-20 sequence of amino acids, and its modified analogues: LPFFD, LPYFD and RDLPFYPVPID. It has been shown by means of neurochemical methods in experiments on nervous cell culture that antibodies to pentapeptide KLVFF in C200 homeopathic dilution when added to the incubation medium in form of 1% solution slow down the process of APβ transformation from its soluble form into aggregated i.e. prevent APβ from transforming into the form with neurodegenerative properties. The ability of these peptides to affect the process of APβ fibrilization via hampering formation of β-plicate aggregates has been demonstrated in experiments in vitro using morphohistochemical methods. The ability of APβ to form β-plicate oligomeric structures is reduced under the influence of the antibodies.

54B. Antibodies to endogenous proteoglycanes and glucosaminoglycanes. It has been found out in experiments in vitro on tissue culture using morphohistochemical methods that these antibodies in C200 homeopathic dilution when added to the incubation medium in form of 2% solution reduce both aggregation and depositing of APβ fibril structures in the brain. It has been shown in experiments on tissue culture that antibodies to glycoprotein laminin expressed in the brain after cerebral trauma block formation of β-fibrils and induce their desaggregation.

54C. Antibodies to apoJ protein. It has been shown using morphohistochemical methods antibodies to apoJ protein in C200 homeopathic dilution stimulate accumulation of the trophic form of amyloid sAPPα in the central nervous system of rats (when administered orally in the dose of 0.2 ml for 10 days) and thus influence the apoE/apoJ-controlled process of formation and depositing of amyloid fibrils in the brain.

54D. Antibodies to apolipoprotein E (E2, E3 and E4 isoforms). It has been shown by means of morphohistochemical and neurochemical methods on rat nervous tissue culture that antibodies to apolipoprotein E in C200 homeopathic dilution when added to the incubation medium in form of 1% solution possess neurodegenerative properties, which is experimentally proved by demonstrating their ability to enhance APβ fibril genesis and reduce evacuation. of APβ from the intercellular space.

EXAMPLE 55

Antibodies to Non-Enzyme Neurospecific Calcium-Binding Proteins

55A. Antibodies to S-100 protein, a geterogenous acid calcium-binding protein contained mostly in glia. Injection of 0.01 ml of the solution of antibodies to S-100 protein in C200 homeopathic dilution into cerebral ventricles of a rat affects the process of formation of the active avoidance reflex in two-section chamber. A correlation has been found between the S-100 protein content in the brain of inbred mice and their training abilities: the higher is the protein content the more efficient the training process is. Enhancement of S-100 protein biosynthesis occurs in the course of training aimed at conditioned reflex formation. Administration of antibodies to S-100 protein improves the training process. Under the influence of the substance the number of mistakes made during reflex performing decreases by 37% along with decrease in the number of combinations required to meet the criterion of trained animal.

55B. Antibodies to calmodulin—the main regulator and mediator of calcium effects. Experiments using neurochemical methods have shown that antibodies to calmodulin in the form of 2% solution when added to the incubation medium of rat neurons in form of 2% solution in C200 homeopathic dilution activate calcium-dependent proteinkinases.

55C. Antibodies to calcineurin, a protein controlling functions. Experiments using neurochemical methods have shown that antibodies to calcineurin in C200 homeopathic dilution when added to the incubation medium in form of 1% solution are capable of inhibiting calmodulin activity by 30% and possess protein phosphatase activity.

55D. Antibodies to phosphomyristin, a protein capable of binding and reserving calmodulin. Experiments on rat nervous tissue culture using neurochemical methods have shown that antibodies to phosphomyristin in C200 homeopathic dilution are capable of binding and reserving dephosphorylated calmodulin when added to the incubation medium in form of 2% solution and to release calmodulin after its phosphorylation.

55E. Antibodies to GP-350 sialoglicoprotein (with high content of glutamic and asparaginic acids). Experiments using neurochemical methods have demonstrated the ability of the antibodies to GP-350 sialoglicoprotein in C200 homeopathic dilution to bind calcium when added to the incubation medium of neurons in form of 5% solution.

55F. Antibodies to B-50 protein, one of the basic synaptic (mostly presynaptic) membrane proteins that can be phosphorylated. It has been found out using neurochemical methods that antibodies to B-50 protein in C200 homeopathic dilution when added to the incubation medium in form of 2% solution enhance interneuron transmission, affect calcium-dependent proteinkinase C and stimulate phosphorylation of B-50 protein, which results in protracted change of the charge and the state of postsynaptic membrane channel thus keeping synaptic track beaten.

55G. Antibodies to fodrin, a structural protein of postsynaptic membranes of glutamate synapses serving as a substrate to neuronal calpein. It has been found out in experiments using methods of radioligand binding that antibodies to fodrin in C200 homeopathic dilution block glutamate receptors when added to the incubation medium in form of 2% solution, which leads to drop in binding of labeled glutamate to rat neurons by 20%.

55H. Antibodies to calpein, a membrane calcium-dependent proteinase that activates in response to increase in concentration of calcium ions in the vicinity of postsynaptic membrane and cleaves fodrin. It has been shown using methods of neurochemical analysis that antibodies to calpein in C200 homeopathic dilution when added to the incubation medium in form of 1% solution cleave fodrin and release active glutamate receptors previously closed and blocked by fodrin and thus enhance conductibility of the synapse.

55I. Antibodies to phosphoprotein F 1-20. It has been shown using methods of neurochemical analysis that antibodies to phosphoprotein F 1-20 in C200 homeopathic dilution when added to the incubation medium of rat neurons in form of 2% solution activate glutamate neurons and serve, like fodrin, as substrate for neuronal calpein.

EXAMPLE 56

Antibodies to Non-Enzyme Neurospecific Proteins Conjugated with Functions of Vesicules in Nervous Terminals 56A. Antibodies to synapsines (the family of phosphoproteins) conjugated with functions of vesicules in nervous terminals. It has been shown that dephosphorylated synapsin when binding to membranes of vesicules promotes their ligation with actinic philaments (actin), which results in formation of a reserve inactive pool. It has been shown using methods of neurochemical analysis that antibodies to synapsins in C200 homeopathic dilution when added to the incubation medium of rat neurons in form of 2% solution promote phosphorylation of synapsins in response to increased concentration of calcium in the terminal, which reduces synapsins' affinity to membranes of vesicles, releases them from their bond with actinic filaments resulting in "melting" of vesicules and their passing from the reserve into active state securing noradrenalin release into the medium.

56B. Antibodies to synaptic proteins synaptobrevine, synaptophisine, syntexine and synaptogamine. It has been shown using methods of neurochemical analysis that antibodies to these synaptic proteins in C200 homeopathic dilution when added to the incubation medium in form of 2% solution regulate the process of vesicule melting and modulate dopamine release from neurons in cell culture.

56C. Antibodies to synaptoporine. It has been shown using methods of neurochemical analysis that antibodies to synaptoporine in C200 homeopathic dilution when added to the incubation medium of rat neurons in form of 1% solution promote formation of the pore, a channel through which the content of vesicule (neuromediator) is released. The dopamine concentration in the medium increases by 30%.

EXAMPLE 57

Antibodies to Non-Enzyme Neurospecific Proteins Responsible for the Processes of Adhesion and Intercellular Recognition 57A. Antibodies to glycoproteins consisting of peptide and carbohydrate parts. It has been shown using methods of neurochemical analysis that antibodies to glycoproteins in C200 homeopathic dilution when added to the incubation medium in form of 2% solution stimulate formation of specific contacts between neurons and their mutual recognition and facilitate synaptic transmission and memory formation.

57B. Antibodies to superficial glycoproteins taking part in cell adhesion. It has been shown using methods of neurochemical analysis that antibodies to D2, N-CAM, K4 and BSP-2 in C200 homeopathic dilution when added to the incubation medium in form of 1% solution stimulate homotypic adhesion between neurons in cell culture by 20%.

57C. Antibodies to glycoproteins Ng-CAM and L-1. It has been shown using methods of neurochemical analysis that antibodies to glycoproteins Ng-CAM and L-1 in C200 homeopathic dilution when added to the incubation medium in form of 2% solution stimulate heterotype calcium-independent adhesion between neurons and glial cells in cell culture.

57D. Antibodies to glycoproteins located in postsynaptic densifications and in the sites of synaptic junctions. It has been shown using methods of neurochemical analysis that antibodies to glycoproteins NSA-3, MBA-2 and Thy-1 in C200 homeopathic dilution when added to the incubation medium of rat neurons in form of 1% solution serve as substrate to proteinases and sialidases and cause local modifications of glycoprotein structure in response to changes in the functional state of the synapse.

EXAMPLE 58

Antibodies to Cytoskeletal and Contractile Proteins of Nervous Tissue

58A. Antibodies to neurotubulin forming part of neurotubules, specific contractile proteins taking part in self-assembly and depletion of nucleinic acids, proteins and lipids and also in their transport along axon from neuron body to synaptic terminals. Experiments in vitro using methods of neurochemical analysis have shown that antibodies to neurotubulin in C200 homeopathic dilution when added to the incubation medium in form of 1% solution possess phosphokinase and proteinkinase activity.

58B. Antibodies to neurosterin, an actomiosin-like protein (one of the family of contractile proteins of nervous tissue) forming part of neurofilaments. It has been shown using methods of neurochemical analysis in tissue culture that antibodies to neurosterin in C200 homeopathic dilution when added to the incubation medium in form of 2% solution possess ATPase activity and stimulate opening of vesicules, which promotes release of neuromediator into cytoplasm and synaptic slit.

58C. Antibodies to kinesine (a contractile neuronal protein)—a cytoplasm translocator providing anterograde axonal current. It has been shown using methods of neurochemical analysis that antibodies to kinesine in C200 homeopathic dilution perform ATP hydrolysis and the energy released in this process is sufficient for the movement of intracellular organelles along neurotubules (in axons).

58D. Antibodies to dineine. It has been found out using methods of neurochemical analysis that antibodies to dineine in C200 homeopathic dilution secure retrograde axonal talk in cell culture of rat hippocampus neurons.

58E. Antibodies to spectrine and ankirine, components of nervous cells that reduce protein mobility in the plane of membrane via interaction with other cytoskeletal proteins. It has been shown in experiments on cerebral tissue culture using methods of neurochemical analysis that antibodies to spectrine in C200 homeopathic dilution alter the distribution of sodium and potassium ions on the surface of membranes of excitable cells.

58F. Antibodies to clatrine, a protein forming multicellular claritine sheath in form of a basket-like net on the surface of vesicules and providing rapid intracellular transport of substances. It has been shown using methods of neurochemical analysis in the culture of rat neurons that antibodies to clatrine in C200 homeopathic dilution secure internalization i.e. ingress of large groups of peptide receptors having bound each with its ligand, thus realizing a specific way of introducing information into cytoplasm across the membrane.

EXAMPLE 59

Neurospecific Proteins—Enzymes

59A. Antibodies to 14-3-2 protein (enzyme enolase) located in neurons. Protein 14-3-2, aldolase, arylsulfatase, BB-isozyme creatinkinase are cerebral isomers of known enzymes. It has been shown using methods of neurochemical analysis that antibodies to these cerebral isomers of known enzymes in C200 homeopathic dilution stimulate noradrenalin synthesis and inhibit its degradation in rat nervous cell culture.

EXAMPLE 60

Secreted Regulatory and Transport Neurospecific Proteins

60A. Antibodies to neurofisine (NFI, NFII, NFIII) proteins—carriers of peptide regulators located in the posterior lobe of hypophysis and hypothalamus. In intact state the NF form stable complexes with oxytocin or vasopressine and secure their protection. It has been shown by means of nuclear magnetic resonance method that antibodies to NF in C200 homeopathic dilution enhance rapid (5.10-8 sec.) exchange between NF-oxytocin or NF-vasopressine complexes and free hormone in homogenate of rat brain tissues.

60B. Antibodies to secreted proteins ependymins. It has been shown in experiments on goldfishes that oral administration of a single dose of 0.1 ml of the solution of the antibodies to ependymins in C200 homeopathic dilution enhance adaptation of fishes to new conditions of swimming, which indicates that these antibodies take part in mechanisms of long-term memory formation.

EXAMPLE 61

Antibodies to Neurospecific Glial Proteins

61A. Antibodies to α2-glycoprotein and glial fibrilar acid protein (GFA). Stimulating effect of these antibodies in C200 homeopathic dilution on building up of myelin in rat nervous tissue culture has been demonstrated using methods of neurochemical analysis.

Antibodies to Regulators of Growth and Proliferation of Nervous Tissue

EXAMPLE 62

Antibodies to Neurotrophins—Growth and Trophic Factors

62A. Antibodies to nerves growth factor (NGF) located on cholinergic neurons. It has been shown in experiments on outbred white rats that oral administration of 0.1 ml of the solution of antibodies to NGF in C200 homeopathic dilution results in improvement of the training process during formation of the conditioned reflex of active avoidance of electric painful stimulation in double-section chamber. Under the influence of the substance shortening of latency periods of the reflex and decrease in the number of combinations required to meet the criterion of trained animal are observed.

62B. Antibodies to brain-specific neurotrophic factor (BDNF) located on cholinergic neurons. It has been shown in experiments in vivo that single-dose oral administration of 0.1 ml of the solution of antibodies to BDNF in C200 homeopathic dilution stimulates neuronal transmission in the cortex, namely, responses from the II/III to the IY layer of visual cortex and this effect is blocked by κ252a—a specific blocker of TrkB receptor, the agonist of which BDNF is. Use of antibodies of BDNF modulates elevation of the level of proteins of the AMPA receptors, which evidences the influence of this substance upon the process of transformation of silent neurons into functional ones.

62C. Antibodies to neurotrophine 3 (NT-3) located on the neurons of the hippocampus. It has been shown in experiments in vivo and in vitro using morphochemical methods that antibodies to NT-3 support neuron survival and neuron growth, take part in restoration of communications between neurons during the period of development and maturation of nervous tissue and after trauma upon single-dose oral administration of 0.1 ml of the solution of antibodies in C200 homeopathic dilution.

62D. Antibodies to neurotrophine 4/5 (NT4/5). It has been shown in experiments in vivo and in vitro that antibodies to NT-4/5 support neuron survival and take part in restoration of communications between neurons after trauma upon single-dose oral administration of 0.1 ml of the solution of antibodies in C200 homeopathic dilution. It has been shown using electrophysiological methods that these antibodies are involved in the process of synaptic plasticity following the pattern of long-term potentiation.

62E. Antibodies to erythropoietin. Patient T. aged 36 years complained of fatigability and weakness. The diagnosis of iron-deficient anemia was established based on depressed hemoglobin level. Oral administration of antibodies to erythropoietin in the dose of 10 ml of the solution of the antibodies in C400 homeopathic dilution twice a day for 3 weeks resulted in significant alleviation of such symptoms as vertigo and fatigability along with elevation of hemoglobin level.

62F. Antibodies to vascular growth factor. Patient A. aged 59 years suffering from ischemic heart disease and arrhythmia was prescribed oral intake of antibodies to vascular growth factor in C400 homeopathic dilution in the dose of one teaspoonful 3 times a day for 2 weeks. As a result of treatment the patient started feeling much better, his angina and arrhythmia became less severe.

62G. Antibodies to platelet growth factor. Patient S. aged 71 years with multiple petechias had been receiving antibodies to platelet growth factor for two weeks. The course of treatment (oral administration of 5 ml of the solution of antibodies in C400 homeopathic dilution twice a day for 7 days) hampered formation of petechial hematomas.

62H. Antibodies to endothelial growth factor. It has been found out in experiments on tissue culture that antibodies to endothelium in C200 homeopathic dilution when added to the incubation medium in form of 2% solution stimulate cell proliferation by 18%, which indicates activation of endothelial growth.

EXAMPLE 63

Antibodies to Cytokines and Interleukins

63A. Antibodies to IL-1. It has been shown that this cytokine is synthesized in the brain in response to cerebral tissue lesion or infection. It has been shown in experiments on rats using morphohistochemical methods that under the influence of oral administration of 0.1 ml of the solution of antibodies to IL-1 in C200 homeopathic dilution for 7 days synthesis of nerve growth factors is enhanced and neurovascularization of the brain is improved.

63B. Antibodies to IL-2-cytokine, synthesized in the brain in response to cerebral tissue lesion or infection. It has been shown on the model of cerebral trauma in rats that oral administration of 0.1 ml of the solution of antibodies to IL-2 in C200 homeopathic dilution prior to the trauma improved brain circulation and prevented neurodegeneration after the trauma as the results of morphohistochemical studies have demonstrated.

63C. Antibodies to IL-6-cytokine synthesized in the brain in response to cerebral tissue lesion or infection. It has been shown using morphohistochemical methods that antibodies to IL-6 in C200 homeopathic dilution when added to the incubation medium in form of 2% solution inhibit exotoxic lesions of the cells.

63D. Antibodies to TNF-α-cytokine synthesized in the brain in response to cerebral tissue lesion or infection. It has been shown on the model of cerebral trauma in rats that oral administration of 0.1 ml of the solution of antibodies to IL-2 in C200 homeopathic dilution improved brain circulation and prevented neurodegeneration after the trauma as the results of morphohistochemical studies have demonstrated.

EXAMPLE 64

Antibodies to Neuroinnunitrophins

64A. Antibodies to cerebrolysine. It has been found out in experiments on nervous cell culture using neurochemical methods that antibodies to cerebrolysine in C200 homeopathic dilution when added to the incubation medium in form of 2% solution produce inhibitory effect upon calpain II an enzyme with neurotoxic properties on the cell level in pathological processing of APβ precursor-APP protein.

EXAMPLE 65

Antibodies to Neurotrophins

65A. Antibodies to leteprinin. Enhancement of neurotrophic effects and improvement of brain metabolism and energy metabolism under the influence of single-dose oral administration of 0.1 ml of the solution of antibodies leteprinin in C200 homeopathic dilution has been demonstrated using neurochemical methods in experiments on rats.

65B. Antibodies to CEP-1347. Enhancement of neurotrophic effects and improvement of brain metabolism and energy metabolism under the influence of single-dose oral. administration of 0.1 ml of the solution of antibodies to CEP-1347 in C200 homeopathic dilution has been demonstrated using neurochemical methods in experiments on rats.

65C. Antibodies to NDD-094. Enhancement of neurotrophic effects and improvement of brain metabolism and energy metabolism under the influence of single-dose oral administration of 0.1 ml of the solution of antibodies to NDD-094 in C200 homeopathic dilution has been demonstrated using neurochemical methods in experiments on rats.

Antibodies to Neuropeptides

EXAMPLE 66

Antibodies to Liberins

66A. Antibodies to thyroliberin. Experiments were carried out on outbred white rats using the method of forced swimming in a vessel with freely revolving wheels, which is a modification of Porsolt method and is used with the original one for investigation of substances with antidepressant properties. According to this method, the rats having been put into water try in vain to get out rotating the wheels. The number of revolutions of the wheels serves as a measure of antidepressant activity. It has been found out that oral administration of 0.1 ml of the solution of antibodies to thyroliberin in C200 homeopathic dilution for three days significantly increases the number of revolutions of the wheels just like in case of administration of stimulants or antidepressants but unlike stimulants and similarly to antidepressants antibodies to thyroliberin elevate the correlation quotient between the number of revolutions of the wheels during the first and the second 5-minute interval. Thus, antibodies to thyroliberin produce an antidepressant effect.

66B. Antibodies to thyroliberin produce a moderate activating effect. Experiments were carried out on outbred white rats that were placed by groups consisting of 5 animals each into the chamber of Opto Varimex (Columbus Instr., USA) device. Oral administration of a single dose of 0.1 ml of the solution of antibodies to thyroliberin in C200 homeopathic dilution increased (by a factor of 1.4) the number of animals' migrations over the chamber of the device.

66C. Antibodies to thyroliberin have properties of an opioid antagonist. Experiments were carried out on outbred white male rats with morphine-induced analgesia, the symptom of which was elevation of the threshold of vocalization in response to electric stimulation of the animal's tail base. Oral administration of 0.1 ml of the solution of antibodies to thyroliberin in C200 homeopathic dilution weakens the analgesic effect of morphine, which is indicated by lowering of threshold of reaction to pain elevated until then due to morphine.

66D. Antibodies to corticoliberin. Experiments were carried out on outbred white rats that were placed by groups consisting of 5 animals each into the chamber of Opto Varimex (Columbus Instr., USA) device. Oral administration of a single dose of 0.1 ml of the solution of antibodies to thyroliberin in C400 homeopathic dilution increased (by a factor of 1.3) the number of animals' migrations over the camber of the device via enhancing their spontaneous motor activity.

66E. Antibodies to gonadotropin. Experiments were carried out on outbred white rats that were placed together with females in the phase of estrus or proestrus. It has been found out that oral administration of 0.1 ml of the solution of antibodies to gonadotropin in C200 homeopathic dilution for 5 days significantly increased erectile function of the males, which was manifested by significant and statistically reliable increase of the main indices of this process, namely, the number of settings with cuddling and especially that of settings with intromission. In comparison with control animals, in which there were few settings with intromission, if at all, antibodies to gonadotropin caused not only their onset but also appearance of significant number of them the majority of which ended up with intromission of penis into vagina.

EXAMPLE 67

Antibodies to Statins

67A. Antibodies to somatostatin. Experiments were carried out on outbred white male rats that were placed by groups consisting of 5 animals each into the chamber of Opto Varimex (Columbus Instr., USA) device. It has been found out that oral administration of 0.1 ml of the solution of antibodies to somatostatin in C200 homeopathic dilution significantly (by a factor of 1.8) suppress spontaneous motor activity of outbred white male rats thus manifesting sedative properties.

67B. Antibodies to melanostatin. Experiments were carried out on outbred white rats using the method of forced swimming in a vessel with freely revolving wheels, which is a modification of Porsolt method and is used with the original one for investigation of substances with antidepressant properties. According to this method, the rats having been put into water try in vain to get out rotating the wheels. The number of revolutions of the wheels serves as a measure of antidepressant activity. It has been found out that oral administration of 0.1 ml of the solution of antibodies to melanostatin in C200 homeopathic dilution for 5 days significantly increases the number of revolutions of the wheels just like in case of administration of stimulants or antidepressants but unlike stimulants and similarly to antidepressants antibodies to melanostatin elevate the correlation quotient between the number of revolutions of the wheels during the first and the second 5-minute interval. Thus, antibodies to melanostatin produce an antidepressant effect.

67C. Antibodies to melanostatin. Experiments were carried out on outbred white male rats that were placed by groups consisting of 5 animals each into the chamber of Opto Varimex (Columbus Instr., USA) device. Oral administration of a single dose of 0.1 ml of the solution of antibodies to melanostatin in C200 homeopathic dilution makes the animals' behavior more active (by a factor of 1.4) by increasing their spontaneous motor activity.

Opioid Peptides

EXAMPLE 68

Antibodies to Enkephalins

68A. Antibodies to met-enkephalin. Experiments were carried out on outbred white male rats in circumstances of evaluation of pain threshold by appearance of vocalization in response to electric stimulation of the base of the animal's tail. The rats were orally administered a single dose of 0.1 ml of the solution of the antibodies in C200 homeopathic dilution prior to electric stimulation. It has been found out that antibodies to met-enkephalin elevate (by 30%) the threshold of pain reaction thus producing an analgesic effect.

68B. Antibodies to leu-enkephalin. Experiments were carried out on outbred white male rats in circumstances of evaluation of pain threshold by appearance of vocalization in response to electric stimulation of the base of the animal's tail. The rats were orally administered a single dose of 0.1 ml of the solution of the antibodies in C400 homeopathic dilution prior to electric stimulation. It has been found out that antibodies to met-enkephalin elevate (by 35%) the threshold of pain reaction thus producing an analgesic effect.

68C. Antibodies to leu-enkephalin. Experiments were carried out on outbred white male rats with electrodes implanted in hypothalamic zones of positive reinforcement in conditions of the method of self-stimulation by pressing the lever for obtaining positive reinforcement. The rats were orally administered a daily dose of 0.1 ml of the solution of the antibodies in C200 homeopathic dilution for 7 days. It has been found out that antibodies to leuenkephalin facilitate the reaction of self-stimulation increasing the number of pressings on the lever by a factor of 2.1, which can be regarded as an evidence of activation of systems of positive reinforcement under their influence.

68D. Antibodies to β-endorphin. Experiments were carried out on outbred white male rats in circumstances of evaluation of pain threshold by appearance of vocalization in response to electric stimulation of the base of the animal's tail. The rats were orally administered a single dose of 0.1 ml of the solution of the antibodies in C200 homeopathic dilution prior to electric stimulation. It has been found out that antibodies to β-endorphin produce an analgesic effect elevating (by a factor of 1.4) the threshold of vocalization in response to electric stimulation of the base of the animal's tail.

68E. Antibodies to β-endorphin. Experiments were carried out on outbred white male rats with electrodes implanted in hypothalamic zones of positive reinforcement in conditions of the method of self-stimulation by pressing the lever for obtaining positive reinforcement. The rats were orally administered a single dose of 0.1 ml of the solution of the antibodies in C200 homeopathic dilution for 5 days. It has been found out that antibodies to β-endorphin facilitate the reaction of self-stimulation increasing the number of pressings on the lever by a factor of 1.7, which can be regarded as an evidence of activation of systems of positive reinforcement under their influence.

68F. Antibodies to Iβ-endorphin. Experiments were carried out on outbred white male rats in conditions of training the conditioned reflex of passive avoidance. It has been found out that antibodies to β-endorphin produce amnestic effect. The rats of the control group remember that the usually preferred dark compartment has become dangerous and don't enter it during testing, which is manifested by long latency period and little time spent there. On the contrary, the rats having been orally administered a daily dose of 0.1 ml of the solution of antibodies to β-endorphin in C400 homeopathic dilution after the reflex had been formed on the first day of the experiment enter the dark compartment with a short latency period and spend much time there. It indicates that retrograde amnesia is formed under the influence of antibodies to β-endorphin.

68G. Antibodies to γ-endorphin. Experiments were carried out on outbred white male rats using the method of evaluation of the cataleptogenic effect of the preparation—the ability of antibodies to γ-endorphin to make the animals stiffen in uncomfortable positions, a typical neuroleptic effect. The rats were orally administered 0.1 ml of the solution of antibodies to γ-endorphin in C200 homeopathic dilution. It has been found out that antibodies to γ-endorphin produce moderate cataleptic effect: the animals stiffened in position when their anterior and posterior extremities were fixed 5 cm above the surface of the experimental table.

68H. Antibodies to α-endorphin. Experiments were carried out on outbred white male rats that were placed by groups consisting of 5 animals each into the chamber of Opto Varimex (Columbus Instr., USA) device for estimation of the influence of the substance upon the animals' spontaneous motor activity. Oral administration of 0.1 ml of the solution of antibodies to α-endorphin in C400 homeopathic dilution makes the animals' behavior more active (by a factor of 1.5) by increasing the number of migrations in the chamber of the device.

68I. Antibodies to α-neoendorphin. Experiments were carried out on outbred white male rats in circumstances of evaluation of pain threshold by appearance of vocalization in response to electric stimulation of the base of the animal's tail. The rats were orally administered a single dose of 0.1 ml of the solution of the antibodies in C200 homeopathic dilution prior to electric stimulation. It has been found out that antibodies to α-neoendorphin produce pronounced analgesic effect elevating (by a factor of 1.3) the threshold of pain reaction.

68J. Antibodies to α-neoendorphin. Experiments were carried out on outbred white male rats in circumstances of open field test. The rats were orally administered a single dose of 0.1 ml of the solution of the antibodies in C200 homeopathic dilution. It has been found out that antibodies to α-neoendorphin suppress the animals' activities in the open field, especially the vertical activity (by a factor of 1.5) and investigation of orifices, which indicates suppression of exploratory behavior.

68K. Antibodies to dinorphin. Experiments were carried out on outbred white male rats that were placed by groups consisting of 5 animals each into the chamber of Opto Varimex (Columbus Instr., USA) device. The rats were orally administered a single dose of 0.1 ml of the solution of antibodies to dinorphin in C200 homeopathic dilution. It has been shown that antibodies to dinorphin suppress the locomotor activity of the animals (by a factor of 1.4), which is an evidence of the presence of sedative component in the mechanism of its action.

68L. Antibodies to dinorphin. Experiments were carried out on outbred white male rats in circumstances of open field test. The rats were orally administered a daily dose of 0.1 ml of the solution of the antibodies in C200 homeopathic dilution for 4 days. It has been found out that antibodies to dinorphin significantly suppress all types of the animals' activities in the open field. This indicates that antibodies to dinorphin possess a sedative effect.

68M. Antibodies to met-enkephalin-RGL and met-enkephalin-RF. Experiments were carried out on outbred white male rats in circumstances of evaluation of analgesic effect of morphine. The appearance of vocalization in response to electric stimulation of the base of the animal's tail served as a criterion of pain reaction. The rats were orally administered a single dose of 0.1 ml of the solution of the antibodies in C200 homeopathic dilution prior to electric stimulation. It has been found out that antibodies to both met-enkephalins lower (by a factor of 1.7) the threshold of pain reaction elevated until the under the influence of morphine i.e. they demonstrate properties of opiate antagonists.

Melanocortins

EXAMPLE 69

Antibodies Corticotropins

69A. Antibodies to adrenocorticotropin. Experiments were carried out on outbred white male rats in conditions of training the conditioned reflex of passive avoidance. It has been found out that the rats of the control group remember that they had been punished in the dark chamber the day before. Therefore, they enter it with long latency period and spend little time there. The rats having been orally administered a daily dose of 0.1 ml of the solution of antibodies to adrenocorticotropin in C200 homeopathic dilution for 5 days enter the dark compartment with a still longer latency period and spend even less time there. It is an evidence of activation of memorization process under the influence of this substance.

EXAMPLE 70

Antibodies to Melanotropins

70A. Antibodies to α-melanotropin. Experiments were carried out on outbred white male rats that were placed by groups consisting of 5 animals each into the chamber of Opto Varimex (Columbus Instr., USA) device. The rats were orally administered a single dose of 0.1 ml of the solution of antibodies to α-melanotropin in C200 homeopathic dilution. It has been found out that antibodies to α-melanotropin increase the number of animals' migrations (by 30%), which indicates possible existence of an activating component in the spectrum of their pharmacological" activity.

70B. Antibodies to α-melanotropin. Experiments were carried out on outbred white male rats in circumstances of open field test. The rats were orally administered a daily dose of 0.1 ml of the solution of antibodies to α-melanotropin in C200 homeopathic dilution for 10 days. It has been found out that the preparation of the antibodies enhances motor activity, vertical motor activity included (by 40%). This is an evidence of activation of emotional behavior under its influence.

70C. Antibodies to α-melanotropin. Experiments were carried out on outbred white male rats in circumstances of training of the conditioned reflex of passive avoidance. The rats were orally administered a daily dose of 0.1 ml of the solution of antibodies to α-melanotropin in C200 homeopathic dilution for 7 days. It has been found out that antibodies to α-melanotropin improve memory processes. As it has been mentioned already, the rats of the control group memorize that the usually preferred dark compartment has become dangerous. Therefore, they enter it with as long latency period and spend little time there. Antibodies to α-melanotropin prolong the latency period of the first entry even further and shorten the time of stay there. Consequently, they stimulate the memorization process.

Vasopressin-tocins

EXAMPLE 71

Antibodies to Vasopressins

71A. Antibodies to vasopressin. Experiments were carried out on outbred white male rats in circumstances of training of the conditioned reflex of passive avoidance. Amnesia was by caused by convulsions induced by maximal electric shock immediately after the reflex formation. The rats were orally administered a single dose of 0.1 ml of the solution of antibodies to vasopressin in C200 homeopathic dilution prior to electric stimulation. It has been found out that antibodies to vasopressin produce an antiamnesic effect. The rats of the control group memorize that the usually preferred dark compartment has become dangerous and don't enter it during testing which is manifested by long latency period and little time spent there. On the contrary, the rats having received maximal electric shock on the first day of the experiment enter the dark compartment with a short latency period and spend much time there. The rats having received antibodies to vasopressin along with maximal electric shock remembered the punishment they had received in the dark chamber the day before entered it with long latency period and spent little time there. It indicates that memory consolidation impaired by maximal electric shock activates under the influence of antibodies to vasopressin.

EXAMPLE 72

Antibodies to Tocins

72A. Antibodies to oxitocin. Experiments were carried out on outbred white male rats in circumstances of training of the conditioned reflex of passive avoidance. The rats were orally administered a daily dose of 0.1 ml of the solution of antibodies to oxitocin in C200 homeopathic dilution for 7 days. It has been found out that antibodies to oxitocin produce a proamnesic effect interfering with formation of the conditioned reflex of passive avoidance. This is indicated by shortening of latency period of entering the dark compartment of the chamber and extended duration of stay there in animals having received antibodies to oxitocin in comparison with the control group.

EXAMPLE 73

Antibodies to Pancreatic Peptides

73A. Antibodies to neuropeptide Y. Experiments were carried out on outbred white male rats using the method of conflict situation method when rats submitted to drinking deprivation are punished by electric current when trying to quench their thirst. The rats were orally administered a single dose of 0.1 ml of the solution of antibodies to neuropeptide Y in C200 homeopathic dilution prior to electric stimulation. It has been found out that oral administration of antibodies to neuropeptide Y increases (by a factor of 2.3) the number of drinks from the water bowl despite the painful stimulus (punished water intakes), which indicates anxiolytic action of the antibodies to the substance.

EXAMPLE 74

Antibodies to Gastrin-Like Peptides

74A. Antibodies to cholecystokinin-8 Experiments were carried out on outbred white male rats using the method of evaluation of the cataleptogenic effect of the preparation—its ability to make the animals stiffen in an uncomfortable position. The rats were orally administered 0.1 ml of the solution of antibodies to cholecystokinin-8 in C200 homeopathic dilution. It has been found out that antibodies to cholecystokinin-8 produce moderate cataleptic effect: the animals stiffened in position when their anterior and posterior extremities were fixed 5 cm above the surface of the experimental table. Thus, antibodies to cholecystokinin-8 demonstrate neuroleptic properties.

74B. Antibodies to cholecystokinin-4 Experiments were carried out on outbred white male rats using the method of conflict situation method when rats submitted to drinking deprivation are punished by electric current when trying to quench their thirst. The rats were orally administered a single dose of 0.1 ml of the solution of antibodies to cholecystokinin-4 in C200 homeopathic dilution prior to electric stimulation. It has been found out that oral administration of antibodies to cholecystokinin-4 increases (by 75%) the number of drinks from the water bowl despite the painful stimulus (punished water intakes), which indicates anxiolytic action of the antibodies to the substance.

EXAMPLE 75

Antibodies to Tachykinins

75A. Antibodies to the substance P. Experiments were carried out on outbred white male rats using electrophysiological method in conditions of acute experiment for registering evoked potentials (primary responses) in sensomotor cortex of white rats after peripheral stimulation. The rats were orally administered a single dose of 0.1 ml of the solution of antibodies to the substance P in C400 homeopathic dilution prior to electric stimulation. It has been found out that antibodies to the substance P lower the amplitude of evoked potentials. Thus they affect transmission of sensor impulses.

EXAMPLE 76

Antibodies to Neurotensins

76A. Antibodies to neurotensin. Experiments were carried out on outbred white male rats with electrodes implanted in hypothalamic zones of positive reinforcement in conditions of the method of self-stimulation by pressing the lever for obtaining positive reinforcement. The rats were orally administered a daily dose of 0.1 ml of the solution of the antibodies in C200 homeopathic dilution for 5 days. It has been found out that antibodies to neurotensin facilitate the reaction of self-stimulation increasing the number of pressings on the lever by a factor of 2.5, which can be regarded as an evidence of activation of systems of positive reinforcement under their influence.

EXAMPLE 77

Antibodies to Bombesin

77A. Antibodies to bombesin. Experiments were carried out on outbred white male rats in conditions of registration of rectal temperature. The rats were orally administered a single dose of 0.1 ml of the solution of the antibodies in C200 homeopathic dilution. It has been found out that antibodies to bombesin produce a marked hypothermic effect significantly (by 20%) lowering body temperature 1 hour after administration.

EXAMPLE 78

Antibodies to Kinins

78A. Antibodies to bradykinin. Experiments were carried out on outbred white male rats, in which registration of spontaneous activity of sensory neurons of the spinal cord was performed using electrophysiological methods in acute experiment. The rats were orally administered a single dose of 0.1 ml of the solution of antibodies to bradykinin in C200 homeopathic dilution prior to insertion of electrodes. It was found out that antibodies to bradykinin cause marked enhancement of spontaneous activity of sensory neurons of the spinal cord, which is an evidence of influence of the antibodies to this substance upon modulation of pain sensitivity.

78B. Patient N. aged 15 years complained of dry cough. Administration of potentiated monoclonal antibodies to bradykinin in form of nasal drops in the dose of 0.5 ml 3 times a day resulted in disappearance of cough within 2 days.

EXAMPLE 79

Antibodies to Angiotensins

79A. Antibodies to angiotensin II. Experiments were carried out on outbred white male rats, in which measurement of blood pressure in the tail artery was carried out using implanted catheter. The rats were orally administered a single dose of 0.1 ml of the solution of the antibodies in C200 homeopathic dilution prior to pressure taking. It has been found out that antibodies to angiotensin II cause marked (by 15%) hypertension.

79B. Antibodies to angiotensin II. Experiments were carried out on outbred white male rats, that were kept in cages with free access to water bowls. The rats were orally administered a daily dose of 0.1 ml of the solution of the antibodies in C200 homeopathic dilution for 3 days. It has been found out that antibodies to angiotensin II cause thirst, which is indicated by activation of drinking behavior and increase in water intake under their influence.

EXAMPLE 80

Antibodies to Enclosepins

80A. Antibodies to enclosepin. Experiments were carried out on outbred white male rats using the method of electric shock-induced conflict situation method. The rats were orally administered a single dose of 0.1 ml of the solution of antibodies to enclosepin in C200 homeopathic dilution prior to electric stimulation. It has been found out that oral administration of antibodies to enclosepin increases the number of punished water intakes in comparison with control group, which indicates anxiogenic conflict-promoting action of these antibodies.

80B. Antibodies to DBI (peptide diazepam binding inhibitor). Experiments aimed at studying the influence of the antibodies to DBI upon GABAA receptors were carried out on the culture of central cerebral neurons of mammals using intracellular microelectrodes. It has been found out that antibodies to DBI in C200 homeopathic dilution when added to the incubation medium in form of 2% solution cause reversible reduction of neuron answers to GABA application, demonstrating properties of its antagonist.

EXAMPLE 81

Antibodies to Galanin

81A. Antibodies to galanin. Experiments were carried out on outbred white male rats that were kept in cages with free access to food and water. The rats were orally administered a daily dose of 0.1 ml of the solution of the antibodies in C200 homeopathic dilution for 4 days. It has been found out that antibodies to galanin stimulate food behavior and cause an increase in food consumption by 20%.

EXAMPLE 82

Antibodies to Peptide-Inductor of Slow Wave (Deep) Sleep (DSIP)

82A. Antibodies to DSIP. Experiments were carried out on outbred white male rats with electrodes implanted in cerebral cortex, hippocampus and neck muscles using electro-physiological methods in conditions of free behavior. The rats were orally administered a daily dose of 0.1 ml of the solution of the antibodies in C200 homeopathic dilution for 5 days. Registration of the sleep-vigil cycles has shown that antibodies to DSIP shorten vigil periods and increase the share of slow wave sleep without affecting the quick (paradox) sleep.

EXAMPLE 83

Antibodies to Endogenous Antioxidant Factors

83A. Antibodies to α-tocopherol. Patient M. Suffering from muscular dystrophy was prescribed a 3-month of antibodies to α-tocopherol in C200 homeopathic dilution (by a teaspoonful twice a day). The patient's condition bettered, his muscle bulk grew and the indices of neuro-muscular transmission improved along with his mood and general state of health.

83B. Antibodies to urinic acid. The rats were orally administered a single dose of 0.1 ml of the solution of the antibodies in C200 homeopathic dilution prior to experimental cerebral hypoxia. Experiments on outbred white rats using the model of focal brain ischemia induced by cross-clamping of the median cerebral artery for 48 hours have shown that administration of antibodies to urinic acid shrinks the infarction zone by 50%.

83C. Antibodies to CP-traps PBN, DMPO. The rats were orally administered a single dose of 0.1 ml of the solution of the antibodies in C200 homeopathic dilution prior to inducing ischemia. Experiments on outbred white rats using the model of focal brain ischemia induced by cross-clamping of the median cerebral artery for 48 hours have shown that administration of antibodies to CP-traps PBN, DMPO shrinks the infarction zone by 45 and 55% respectively.

83D. Antibodies to catechin-flavinoid. The model of total brain ischemia induced by complete cross-clamping of brain vessels for 5 minutes, which led to death of 75% of the hippocampus cells and enhancement of free radical peroxidation was used in experiments on rats. Oral administration of 0.1 ml of the solution of antibodies to catechin-flavinoid in C200 homeopathic dilution prior to vessel clamping produced a neuroprotector effect manifested by 30% restoration of the hippocampus cells and antioxidant effect.

83E. Antibodies to recombinant superoxide dismutase. The model of total brain ischemia induced by complete cross-clamping of brain vessels for 5 minutes, which led to death of 80% of the Cl hippocampus cells was used in experiments on rats. Oral administration of 0.1 ml of the solution of antibodies to recombinant superoxide dismutase in C400 homeopathic dilution prior to ischemia produced a neuroprotector effect manifested by 25% restoration of the hippocampus cells.

83F. Antibodies to liposomal superoxide dismutase. The rats were orally administered a single dose of 0.1 ml of the solution of the antibodies in C200 homeopathic dilution prior to the experiment. Experiments on outbred white rats using the model of focal brain ischemia induced by cross-clamping of the median cerebral artery have shown that administration of antibodies to liposomal superoxide dismutase shrinks the infarction zone by 40%.

83G. Antibodies to MCI-186. The model of total brain ischemia induced by complete cross-clamping of brain vessels for 10 minutes, which led to death of 70% of pyramidal Cl hippocampus cells and enhancement of free radical peroxidation was used in experiments on rats. Oral administration of 0.1 ml of the solution of antibodies to MCI-186 in C200 homeopathic dilution prior to ischemia produced a neuroprotector effect manifested by 50% restoration of the hippocampus cells and reduction of free radical peroxidation.

83H. Antibodies to U-74006F (21 amino steroid). Experiments on outbred white rats using the model of focal brain ischemia induced by cross-clamping of the median cerebral artery have shown that administration of antibodies to U-74006F shrinks the infarction zone and reduces lesions of hippocampus cells by 30%. The rats were orally administered a single dose of 0.1 ml of the solution of the antibodies in C200 homeopathic dilution prior to inducing ischemia.

83I. Antibodies to desmethyldeprenyl. The rats were orally administered a single dose of 0.1 ml of the solution of the antibodies in C200 homeopathic dilution prior to clamping brain arteries. It has been found out using morphohistochemical methods that administration of antibodies to desmethyldeprenyl diminishes apoptosis of neurons induced by experimental brain ischemia and causes activation of new protein synthesis.

83J. Antibodies to N-acetylcystein. The rats were orally administered a single dose of 0.1 ml of the solution of the antibodies in C400 homeopathic dilution prior to inducing ischemia. It has been found out using morphohistochemical methods that administration of antibodies to N-acetylcystein diminishes apoptosis of neurons by 50% and causes activation of new protein synthesis in preapoptotic nervous cells after clamping of brain arteries.

Antibodies to Cytokines

EXAMPLE 84

Antibodies to Interleukins

84A. Patient K. aged 52 years after oncological chemotherapy was admitted to the hematology department after a course of chemotherapy for an oncological disease with the diagnosis of toxic pancytopenia. His peripheral erythrocyte count (E) was 2.5×10¹²/l, leucocyte count (L) was 1.8×10⁹/l and platelet count (P) was 72×10⁹/l. The patient was prescribed antibodies to interleukin 6—a mixture of homeopathic dilutions C200 and C1000 in the dose of 1 tablet twice a day. Peripheral blood cell counts after 7 and 14 days of treatment respectively were as follows: E—3.5 and 4.5×10¹²/l, L—3.8 and 5.6×10⁹/l and P—153 and 230×10⁹/n.

84B. Patient U. aged 34 years has been suffering from psoriasis of moderate degree of severity complicated with psoriatic arthritis for 10 years. In the phase of exacerbation of the disease accompanied with symptoms of arthritis the patient was prescribed polyclonal rabbit antibodies to interleukin 10-in homeopathic dilution LM 10 in the dose of 1 tablet twice a day. On the third day of treatment new plaques stopped appearing, the patient's general condition improved, symptoms of arthritis disappeared; within 10 days after the beginning of treatment remission of the disease manifested by marked regression of all psoriatic plaques was achieved. The patient was recommended to taking the preparation with preventive purpose.

84C. The model of anaphylactic bronchiospasm in sensibilized guinea pigs (GP) induced by exposure of aerosol form of antigen was used in experimental studies of the efficiency of ultra-low doses of antibodies to interleukin 13 (IL-13). To this end GP weighing 300 grams were sensibilized by intramuscular injection of 0.5 ml of saline solution containing 20 mcg of ovalbumin and 100 mg of aluminum hydrate. 3 weeks after sensibilization the anaphylactic reaction (AR) in animals was caused by the resolving dose of ovalbumin administered in aerosol form (0.5% in 0.9% NaCl solution) in the course of 60 minutes using ultrasound nebulizer. Polyclonal rabbit antibodies to polypeptide fragment of IL-13 (a mixture of homeopathic dilutions C12+C30+−C200) was administered orally every day in the dose of 0.5 ml per a GP starting 5 days prior to the AR, the last dose of antibodies was administered 30 minutes prior to inducing the AR. The control group was administered distillated water. Duration of the latency period starting from the beginning of inhalation to the appearance of the first symptoms of the AR (contraction of abdominal muscles) was assessed along with the degree of bronchial constriction. It has been found out that in-group having been administered the preparation the average duration of the latency period was 35 minutes as opposed to 7 minutes in the control group; the degree of bronchial constriction was 15% in the experimental group and 48%—in the control group.

84D. The ability of ultra-low doses of antibodies to interleukin 12 (IL-12) to stimulate resistance against intracellular pathogenic microorganisms was studied on the model of tuberculosis infection in mice. The model of generalized tuberculosis was created by intravenous administration of virulent culture of *M. tuberculosis* in the dose of 0.5 mg of culture in 0.5 ml of saline into the tail vein of the animal. Monoclonal antibodies to polypeptide fragments of IL-12 (a mixture of homeopathic dilutions C6, C1000) were administered per os in the dose of 0.2 ml of aqueous solution 2 times a day beginning with the day of infection. The control group was administered distilled water. The treatment was started on the 4-th day after the onset of the infection. The animals' general state of health (activity, breathing disorders, weight loss), life span and the lesion index based on microscopic evaluation of the state of the animals' internals after their death or after the end of the experiment (lasting 4 weeks) were assessed based on the four-point scale (according to G. N. Pershin and A. N. Togunova). The results of the experiment are presented in the table 1.

TABLE 1

| Index under investigation | Control group | Experimental group |
|---|---|---|
| Average internal lesion index | 3.2 | 1.3 (p < 0.05) |
| Lethality after 4 weeks | 92% | 6% (p < 0.05) |
| Average life span | 15 days | 25 days in dead mice |

The results obtained show that ultra-low doses of antibodies to IL-12 prepared by homeopathic technique significantly increase the experimental animals' resistance to tuberculosis.

84E. Experimental sepsis was caused in mice of both sexes belonging to the CBA line (18-22 gram) by intraperitoneal injection of the LD 100 of *Staph. aureus* in 0.1 ml of saline. After that mice of the experimental group received 0.2 ml of the mixture of monoclonal antibodies to interleukin 1 and polyclonal antibodies to tumor necrosis factor (TNFα) by mouth every 3 hours. Each type of antibodies was in form of a mixture of homeopathic dilutions C6+C30+C200. Mice of the control group received distilled water. Evaluation of the animals' life span showed that in the experimental group lethality was 36% as opposed to 100% in the control group. The death of animals in the experimental group occurred later than in the control group.

84F. Patient L. aged 49 years complained of excessive fatigability, drowsiness, pain and stiffness of both knee joints. He was established the diagnosis of bilateral acute gonarthritis and prescribed oral intake of the solution of monoclonal antibodies to interleukin 1 in homeopathic dilution C50 in the dose of 10 drops 3 times a day. Within a week the patient reported elimination of pain and enhancement of physical activity.

84G. Patient M. aged 56 years complained of exacerbation of chronic non-obstructive bronchitis manifested by cough and fever. Examination revealed rise in body temperature up to 37.5° C. The patient was prescribed potentiated solution of monoclonal antibodies to the antagonist of interleukin 1 receptor in homeopathic dilution C50 in the dose of 15 drops 3 times a day made it possible to achieve normalization of body temperature and elimination of cough within 4 days of treatment.

84H. Mice of the C57BL line were orally administered 0.1 ml of the solution of rabbit polyclonal antibodies to interleukin 2 in homeopathic dilution C100 Immunological test performed after 7 days of administration of the preparation revealed enhancement of FHA-stimulated proliferation of thymocytes by 30%.

84I. Patient Sh. aged 48 years complained of palpitations, weakness and vertigo. Examination revealed asiderotic anemia, drop in blood hemoglobin level to 70 g per l., he was prescribed diet and intake of the solution of monoclonal antibodies to interleukin 3 in C200 homeopathic dilution in the dose of 1 teaspoonful 3 times a day. Within 2 weeks of treatment the abovementioned complaints disappeared, hemoglobin level rose to 110 g per l.

84J. Experimental studies of biological activity of the preparation of activated ultra-low doses of antibodies to interleukin 4 were carried out on the culture of endothelium cells of human aorta. It has been found out that introduction of 1% of antibodies in homeopathic dilution C100 into incubation medium results in enhanced (by 20%) expression of VCAM-1 adhesion molecules on endothelium cells after 48 hours of incubation.

84K. Patient M. aged 7 years was consulted for complaints of nausea, lack of appetite, abdominal pains and hiccough. Examination revealed eosinophilia due to ascaridosis. Prescription of sheep polyclonal antibodies to interleukin 5 in a mixture of homeopathic dilutions C12+C30+C200 in the dose of 1 teaspoonful 3 times a day made it possible to eliminate the said complaints within 4 days of treatment; after 10 days of treatment absence of helminthosis and eosinophilia was confirmed by laboratory methods.

84L. Patient D. aged 65 years complained of lumbar pain. Examination revealed exacerbation of lumbosacral radiculitis. The patient was prescribed potentiated solution of monoclonal antibodies to interleukin 6 in C200 homeopathic dilution in the dose of 1 tablet 3 times a day. After 5 days of treatment the patient reported elimination of pain.

84M. Experiments on mice of the CBA line having been administered a single injection of maximal tolerated dose of cyclophosphamide showed that oral administration of 0.1 ml of potentiated solution of goat antibodies to interleukin 7 in C200 homeopathic dilution for 5 days resulted in restoration of up to 90% of the initial thymus mass. In the control group thymus mass of the cyclophosphamide-treated animals was 50% of that of the intact ones.

84N. The influence of ultra-low activated doses of antibodies to interleukin 8 upon development of inflammation in rats was assessed experimentally. The animals were injected formaldehyde solution under the plantar aponeurosis of one of their hind paws. Animals of the experimental group were orally administered 0.5 ml of the solution of monoclonal antibodies to IL-8 in C100 homeopathic dilution for 7 days. Assessment of the paw weight difference in the control and experimental groups by the $2^{nd}$-$7^{th}$ day revealed reduction of inflammatory reaction by 35% under the influence of the preparation.

84O. Patient S. aged 36 years complained of pollinosis. She was prescribed monoclonal antibodies to interleukin 9 in form of solution in C50 homeopathic dilution in the dose of 5 drops administered intranasally twice a day. Within 5 days of treatment disappearance of allergic symptoms was registered.

84P. Patient M. aged 58 years suffering from ischemic heart disease complained of heartache and insufficient efficacy of the antianginal medications he was taking. He was suggested intake of monoclonal antibodies to interleukin 10 in C100 homeopathic dilution in the dose of 1 tablet 3 times a day. Within 3 days the patient reported that his heartache had subsided. The course of treatment was recommended to be continued.

84Q. Patient D. aged 64 years complained of pain, cyanosis and puffing of her low extremities. She was established the diagnosis of thrombosis of deep crural veins associated with excessive platelet count in peripheral blood. She was recommended intake of antibodies to interleukin 11 in form of a mixture of homeopathic dilutions D6+C30+C1000 in the dose of 1 teaspoonful 3 times a day. Within 7 days disappearance of all the said complaints was reported along with normalization of platelet level.

84R. Rats with dinitrochlorbenzol-induced mammary gland tumors were orally administered 0.5 ml of the solution of polyclonal rat antibodies to interleukin 12 in homeopathic dilution C50. It has been found out that 30-day course of treatment with this preparation reduces both the size of tumors and the number of metastases by 40% and increases the animals' life span and antitumor activity of NK cells isolated from rats of the experimental group.

84S. Transplantation of skin graft to mice of the C57BL line showed that oral. administration of homeopathically potentiated antibodies to interleukin 13 extends the life interval by 30%. Conditions of the experiment: administration of the daily dose of 0.1 ml of the solution of antibodies in C200 homeopathic dilution for 7 days.

84T. Experimental assessment of biological activity of activated ultra-low doses of antibodies to interleukin 14 was performed. It has been found out that introduction of 1% of antibodies in C200 homeopathic dilution into the incubation medium of LPS-activated human B-lymphocytes results in stimulation of proliferative activity of B cells by 50% within 72 hours of incubation.

84U. Inhibition of interleukin 2-induced proliferation of thymocytes in mice of C57BL line was registered after introduction of 0.1% potentiated solution of antibodies to interleukin 15 in homeopathic dilution C50 into the incubation medium (medium RPMI1640 containing 20% embryonic calf serum and 10 ml n/ml thymocytes).

84V. Experimental assessment of biological activity of ultra-low doses of antibodies to interleukin 16 was performed. Mice with experimental immunosuppression induced by injection of maximal tolerated dose of cyclophosphamide were orally administered the daily dose of 0.2 ml of the solution of antibodies to IL 16 in homeopathic dilution C 1000 for three days. Administration of antibodies resulted in restoration of the content of T-helpers in peripheral blood (their level increased by a factor of 3 in comparison with the control group treated with placebo).

84W. Introduction of 0.5% solution monoclonal antibodies to interleukin 17 in C200 homeopathic dilution into the incubation medium 199 of fibroblasts of human skin results in inhibition of prostaglandin E production by 30% after 24 hours of incubation.

84X. Activated ultra-low doses of antibodies to interleukin 18 in vitro enhanced the antitumor activity of NK cells in relation to the cells of human melanoma by 40% within 24 hours after introduction of 1% of antibodies in homeopathic dilution C30 into the incubation medium.

EXAMPLE 85

Antibodies to Interferons

85A. In order to study the effect of antibodies to interferon upon humoral immune response immunization of mice with ram erythrocytes (thymus-dependent corpuscular antigen). After that the preparation containing homeopathically dynamized polyclonal sheep antibodies to murine α-interferon (α-IFN) in form of mixture of C12+C30 dilutions was administered to the mice for 5 days. On the first day of the 5-day course the mice were also administered a single dose of Cyclophosphamide (one half of the maximal tolerated dose) intraperitoneally. Evaluation of parameters of humoral and cellular immunity 5 days later revealed that administration of dynamized antibodies to α-IFN promote enhancement of functional activity of antibody-forming cells of the spleen along with elevation of hemagglutinin titers in blood serum, which is particularly important in the state of immune suppression. Thus the preparation pending produces a stimulating effect upon humoral immunity.

85B. In order to study the effect of activated forms of ultra-low doses of antibodies to interferon upon the intensity of the reaction of delayed-type hypersensitivity (DTH) mice were subcutaneously immunized with ram erythrocytes (RE). Resolving dose of RE was inoculated into the hinder paw-pad at the end of the 10-day course of oral administration of 0.2 ml of the preparation containing homeopathically dynamized monoclonal antibodies (AB) to murine β-interferon β-IFN) in form of the mixture of dilutions C12+C30+C200. Simultaneously the same amount of physiological solution was inoculated into the contralateral paw. The intensity of the reaction was evaluated 24 hours later by the reaction index (RI) that was individually calculated for each animal by the following formula:

$$RI(\%)=(Pe-Pc)/Pc\times100,$$

where Pe—is the weight of the experimental paw, Pc—is the weight of the control paw. The obtained data is presented in the table 2.

TABLE 2

Effect of dynamized AB to β-IFN upon the intensity of the reaction of DTH

| Indices | Experimental groups | |
|---|---|---|
| | RE | AB to β-IFN + RE |
| RI of DTH | 28.00 ± 2.34 | 36.60 ± 2.00 |

The data presented in the table 2 show that AB to β-IFN activate the function of Teffectors, which is manifested by enhanced intensity of the reaction of delayed-type hypersensitivity in response to sensibilization with ram erythrocytes.

85C. In order to study the effect of activated forms of ultra-low doses of antibodies to interferon upon phagocytic activity of neutrophiles of peritoneal exudation the phagocytic activity of neutrophiles was evaluated 24 hours after the end of 10-day course of subcutaneous inoculation of 0.1 ml of the preparation of natural antibodies (AB) to γ-interferon (γ-IFN) in form of homeopathic dilution D60. Phagocytic activity was evaluated based on the ability of these cells to absorb the daily culture of the *St. aureus*, strain 209 (the microbe suspension concentration was 100 million/ml). At that the percentage of neutrophiles having absorbed the bacteria (phagocytic index—PI) and the average number of staphylococci absorbed by one cell (phagocytic count—PC) were calculated.

TABLE 3

Effect of the AB to γ-IFN upon phagocytic activity of neutrophiles

| Indices | Experimental groups | |
|---|---|---|
| | RE | AB to γ-IFN |
| PI (%) | 8.80 ± 1.36 | 29.20 ± 3.20 |
| PC | 7.61 ± 1.24 | 8.78 ± 2.33 |

The results of these experiments presented in the table 3 indicate that AB to y-IFN produce a significant stimulating effect upon phagocytosis in comparison with the control group (immunization with RE) via increasing the share of neutrophiles capable of absorbing staphylococci.

85D. Patient K. aged 62 years, complained of recurring episodes of fever accompanied by eruption on her chest and pain along intercostal nerves. Her condition was diagnosed as recurrent herpes zoster. No stable results were achieved with conventional therapy (antiviral preparations and analgesics). Daily intake of dynamized monoclonal antibodies to human γ-interferon C 1000 in the dose of 1 tablet twice a day fever and pain subsided on the 3-rd day of treatment. The eruption practically disappeared on the 7-th day of treatment. The patient was recommended preventive intake of the preparation of 1 tablet once in two days. For a year there was no recurrence of herpes in this patient.

85E. Patient Sh. aged 5 years is under medical supervision for recurrent infections of his upper respiratory tract (suffers from rhinolaryngotracheitis for 10 days every two months). Evaluation of the patient's immune state revealed lowered count of CD4+ lymphocytes, neutrophilic leucocytes and γ-interferon in the peripheral blood. The patient was prescribed administration of dynamized polyclonal (immune) antibodies to recombinant human γ-interferon in form of the mixture of D24+C30+C200 dilutions in the dose of 1 tablet a day. No recurrence of acute respiratory tract infections has occurred in the child for 4 months, according to his parents he has become more active and made up for his body weight deficit. Repeated evaluation of his immune state 6 months after the beginning of the treatment revealed normalization of the cellular and humoral immunity indices.

85F. Patient P. aged 34 years complained of rhinitis, pain in his nasopharynx and subfebrile temperature. His condition was diagnosed as acute respiratory viral infection. Intranasal administration of drops of dynamized aqueous solution of monoclonal antibodies to recombinant human γ-interferon C12 3 times a day led to normalization of the patient's condition after two days of treatment. Repeated examination revealed no catarrhal symptoms.

85G. Patient C. aged 32 years, was admitted to the Department of Infections on the second day of illness with the diagnosis of severe form of influenza. Virological verification of the diagnosis was obtained later. Upon admission the patient's condition was grave, he was in the state of mental confusion, had heavy breathing, dry cough and was running fever up to 41.6° C. Auscultation findings: vesicular respiration. The patient was prescribed subcutaneous injections of 1 ml of aqueous solution of monoclonal antibodies to human γ-interferon in form of mixture of the C12+C30+C200 potencies every 2 hours. In the course of 6 hours the patient's body temperature fell down to 37.4° C. and his general condition became satisfactory. During the following three days the patient was administered the preparation in form of parenteral injections of 1 ml of aqueous solution twice a day. On the fourth day of treatment the patient was in satisfactory condition and complained of general weakness only, his body temperature was 36.4° C. He was discharged on the fifth day after admission in satisfactory condition.

85H. Patient U. aged 27 years consulted a urologist a month after the onset of such symptoms as urethral discomfort itching and pain, voiding frequency and mucous discharge from the urethra. Upon detailed history taking he also complained of pain in the ankle joints and mucous-purulent discharge from the eyes. Physical findings: labia of the urethra are swollen, hyperemic and sick together. Laboratory examination of the urethral discharge by immunofluorescent test discovered *Chlamidia trachomatis*. The patient was prescribed administration of the mixture of polyclonal antibodies to human α- and γ-interferon in homeopathic dilution C1000 in the dose of 1 tablet a day for 2 weeks. 5 days after the beginning of treatment the patient noticed significant subsidence of his subjective feeling of discomfort and of the discharge from the urethra and the eyes. After the end of the course of treatment repeated immunofluorescent testing of prostate secretion for *Chlamidia trachomatis* was performed. The result was negative. The patient was recommended oral intake of the preparation once in two days for two weeks. He presented no complaints upon repeated attendance and no symptoms of anterior urethritis or conjunctivitis were found.

85I. In order to study the effect of ultra-low doses of antibodies to interferon upon humoral immune response immunization of mice with ram erythrocytes (thymus-dependent corpuscular antigen). After that the preparation containing homeopathically dynamized natural antibodies to γ-interferon (γ-IFN) in form of mixture of C12+C30 dilutions was administered to the mice for 5 days. Natural antibodies were isolated from the pool of sera of the patients protractedly treated with to γ-interferon for viral infections using the method of affinity chromatography (immunosorption) on columns with synthetic fragments of endothelial NO synthase adsorbed on the solid phase (sefadex) as described, for instance, in the book Immunological Methods under the editorship of G. Frimel, Moscow, Medicine Publishing House, 1987, p. 427-432. On the first day of the 5-day course the mice were also administered a single dose of Cyclophosphamide (one half of the maximal tolerated dose) intraperitoneally. Evaluation of parameters of humoral and cellular immunity 5 days later revealed that administration of dynamized antibodies to γ-IFN promote enhancement of functional activity of antibody-forming cells of the spleen along with elevation of hemagglutinin titers in blood serum, which is particularly important in the state of immune suppression. Thus the preparation pending produces a stimulating effect upon humoral immunity.

85J. It has been found out in experiments on an isolated section of human aorta that monoclonal antibodies to murine γ-interferon stimulate transport of Ca ions by 15% when 1% preparation of antibodies in homeopathic dilution C200 is introduced into the incubation medium.

85K. The preparation of rabbit antibodies to human α-interferon resulted in rise of intracellular cAMP level in the culture of fibroblasts of mice after introduction of 1% of antibodies in homeopathic dilution C12 into the incubation medium.

85L. Patient K. aged 56 years complained of typical eruption on the lips and on the face accompanied by burning pain and elevated body temperature. The patient was established the diagnosis of herpetic infection and was recommended intake of the preparation of antibodies to interferon β. Oral administration of antibodies to interferon β in a mixture of homeopathic dilutions C6+C30+C1000 in the dose of 1 tablet 3 times a day made it possible to eliminate both general and local manifestations of the infection within 5 days.

85M. Patient U. aged 24 years was admitted to the hospital in her seventh month of pregnancy for late gestosis. Administration of potentiated solution of monoclonal antibodies to τ-interferon (IFN-Tau) in C200 homeopathic dilution made it possible to eliminate edema, hypertension and symptoms of feto-placentary insufficiency within 7 days of intake of the preparation in the dose of 10 drops 3 times a day.

EXAMPLE 86

Antibodies to Tumor Necrosis Factors

86A. In order to study anti-inflammatory effects of activated forms of ultra-low doses of antibodies to TNF-α in rats immune inflammation was induced in the animals by complete Freund's adjuvant. A single dose of the phlogogenic agent was administered to male rats by injection under the plantar aponeurosis of their paw-pad. The animals were administered polyclonal rabbit antibodies to rat TNF-α in form of homeopathic dilutions C12+C3O+C200. The solution of antibodies was administered once a day orally via a tube in the dose 0.5 ml per animal for 15 days starting on the day preceding the injection of the adjuvant and comprising the whole period of development of the inflammatory process. Dynamics of hyperemia and edema of the right and left paw monitored by oncometry every 2 days were used as evaluation criteria. Analysis of the findings on the progression of edema of the inflamed paw proved that the preparation reduced severity of the edema due to the secondary inflammatory reaction (appearing on the $10^{th}$ day) quite efficiently: by 50-80% in comparison with the control.

86B. In order to study analgesic effects of activated forms of ultra-low doses of antibodies to pro-inflammatory cytokines in rats immune inflammation was induced in the animals by complete Freund's adjuvant. A single dose of the phlogogenic agent was administered to male rats by injection under the plantar aponeurosis of their paw-pad. The solution of the mixture of polyclonal rabbit antibodies to rat TNF-α and rat interleukin-8 in form of homeopathic dilution C30 was administered once a day orally via a tube in the dose 0.5 ml per animal for 15 days starting on the day preceding the inoculation of the adjuvant and comprising the whole period of development of the inflammatory process. The analgesic effect of the preparation upon the threshold of pain sensitivity of the inflamed tissues to the painful stimulation was tested using the "hot plate" model. The animals were placed on the hot plate and the latency time of their stay on the plate before starting licking the inflamed paw was registered 3 hours, 1 day and 3 days after the phlogogenic agent injection. Administration of the mixture of activated antibodies to TNF-α and interleukin-8 prolonged the animals' stay on the hot plate by the factor of 1.7 and 3.0 on the 1-st and the 3-rd day respectively in comparison with control (administration of distilled water).

86C. Patient K. aged 57 years with a 5-year history of rheumatoid arthritis (RA), class III by the functional classification of the American Board of Rheumatologists was admitted to the hospital for exacerbation of the disease. Upon admission he complained of fever, marked enhancement of morning stiffness and pain in the afflicted joints and their swelling. Physical findings: body temperature 37.5° C., pronounced hyperemia, disfiguration and pain upon palpation of wrist, ankle and proximal interphalangeal joints. His blood tests showed ESR 35 mm per hour and ++ rheumatoid factor. As the patient showed poor tolerance for nonsteroid anti-inflammatory drugs he was prescribed administration of monoclonal antibodies to recombinant human tumor necrosis factor α in form of a mixture of homeopathic dilutions C50, C200 and C1000 in the dose of 1 tablet 3 times a day. 3 days after the beginning of treatment the patient stated marked reduction of pain, his body temperature reduced to normal. On the $7^{th}$ day of treatment the patient still complained of morning stiffness as prior to admission to the hospital. The patient was discharged on the $14^{th}$ day with clinical and laboratory remission. He was recommended to take the preparation in the dose of 1 tablet once in 2 days with preventive purpose. Two months after his discharge from the hospital the functional class III in patient's diagnosis was substituted for the functional class II of the RA classification.

86D. Patient U. aged 67 had been suffering from right-side coxarthrosis. She was seeking medical help for increased night pain and pain on movement along with reduced joint mobility. The patient was prescribed administration of rabbit antibodies to recombinant human tumor necrosis factor (TNF)-α in form of a mixture of homeopathic dilutions C12, C30 and C200 in the dose of 5 ml of aqueous solution 3 times a day. 3 days after the beginning of treatment the patient stated disappearance of night pain and pain on movement. On the $7^{th}$ day of treatment with the preparation mobility of her afflicted hip joint returned to its prior-to-exacerbation level. A 2-months course of treatment with antibodies to TNF-α resulted in regression of roentgenological symptoms of coxarthrosis along with increase in amplitude of passive and active movements of the joint. During the whole period of treatment the patient stated lack of joint pain.

86E. In order to study analgesic effects of activated forms of ultra-low doses of antibodies to pro-inflammatory cytokine TNF-α in rats immune inflammation was induced in the animals by complete Freund's adjuvant. A single dose of the phlogogenic agent was administered to male rats by injection under the plantar aponeurosis of their paw-pad. Solution of polyclonal rabbit antibodies to human TNF-α in form of homeopathic dilutions D6, C30+C200 and LM1 were administered to the three groups of animals (n=10) once a day orally via a tube in the dose 0.5 ml per animal for 15 days starting on the day preceding the inoculation of the adjuvant and comprising the whole period of development of the inflammatory process (administration of distilled water served as control). The analgesic effect of the preparation upon the threshold of pain sensitivity of the inflamed tissues to the painful stimulation was tested using the "hot plate" model. The animals were placed on the hot plate and the latency time of their stay on the plate before starting licking the inflamed paw was registered 3 hours, 1 day and 3 days after the phlogogenic agent injection. The results are presented in table 4.

TABLE 4

Effect of various dilutions upon latency time of the reaction (sec) in the "hot plate" model

|  | 3 hours | 1 day | 3 days |
| --- | --- | --- | --- |
| Control | 11.9 ± 2.6 | 10.2 ± 3.1 | 5.5 ± 2.4 |
| D6 | 17.9 ± 3.5 | 20.3 ± 6.2 | 13.4 ± 5.1 |
| C30 + C200 | 24.2 ± 8.9 | 36.6 ± 5.2 | 16.7 ± 6.1 |
| LM1 | 25.2 ± 7.2 | 34.5 ± 4.2 | 14.8 ± 7.3 |

Thus, centesimal dilutions of the activated form of antibodies to TNF-α showed the most pronounced analgesic effect manifested by prolongation of the latency time of the reaction in the "hot plate" model.

86F. In order to investigate the effect of ultra-low doses of antibodies to TNF-α upon the development of tumor process female mice of the C57B61 line were intramuscularly inoculated Lewis lung carcinoma (LLC) in the dose of 1×106 cells in 0.1 ml of saline. Administration of polyclonal rabbit antibodies to recombinant human TNF-α (a mixture of homeopathic dilutions C12+C30+C200) in the dose of 0.3 ml per mouse via gastric tube was performed 24 hours after transplantation of tumor cells and was continued for 16 days. The results of the treatment were assessed on the 19$^{th}$ day after tumor inoculation. At that the weight of the tumor and the total weight of the animal's lungs were measured along with the incidence of tumor dissemination, the number of metastases and their space. A course of treatment with antibodies to TNF in animals with experimental tumors resulted in reliable inhibition of growth of the primary tumor focus. Tumor mass in this group of mice was 1.3 times smaller than that in the control group. Besides, treatment of mice with antibodies to TNF cased significant (by a factor of 2.3) decrease in the number of metastatic foci in the lungs, metastasis inhibition index was 73%.

86G. Patient M. aged 58 years complained of pains, swelling and stiffness of his knee joints. Examination results led to the establishment of the diagnosis of reactive arthritis. Administration of the preparation of monoclonal antibodies to TNF-α in homeopathic dilution C30 in the dose of 1 tablet 3 times a day made it possible to eliminate symptoms of inflammation within 4 days.

86H. Patient B. aged 38 years complained of painful hard lumps in her breasts. Examination revealed mastopathy and the patient was recommended treatment with monoclonal antibodies to TNFβ in homeopathic dilution C200 in suppositories once a day. Repeated examination two weeks later showed disappearance of symptoms of mastopathy.

86I. Patient N. aged 28 years was undergoing a course of treatment for acquired immunodeficiency syndrome in form of Kaposi's sarcoma. Administration of the preparation of monoclonal antibodies to leucosis inhibiting factor (LIF) in a mixture of homeopathic dilutions C12+C200–1–C1000 in the dose of 1 tablet 3 times a day resulted in regression of the tumor, improvement of the patient's general state of health within 14 days after the beginning of treatment.

EXAMPLE 87

Antibodies to Colony-Stimulating Factors

87A. Patient V. aged 30 years was admitted to the hematology department with the diagnosis of autoimmune agranulocytosis, Her peripheral white blood count was 1×109/π. In view of intolerance for glucocorticoid hormones the patient was prescribed activated ultra-low doses of monoclonal antibodies to human granulocytes-macrophage colony-stimulating factor—a mixture of homeopathic dilutions D6, C30 and C1000 in the dose of 1 tablet every day. 7 days after the beginning of treatment the patient's peripheral white blood count was 4×109/l, after 14 days it reached 6×109/l, differential WBC was within normal limits.

87B. Patient L. aged 67 years complained of poor healing and purulent discharge in the site of a II degree burn of his lower extremity the patient had got two weeks prior to his visit to the doctor's. He was prescribed intake of the solution of antibodies to GM-CSF (granulocytes-macrophage colony-stimulating factor) in C200 homeopathic dilution in the dose of 1 tablet 3 times a day. Upon the patient's second visit 7 days later epithelization of the wound surface and disappearance of purulent discharge were registered.

87C. Biological activity of ultra-low doses of antibodies to G-CSF (granulocyte-macrophage colony-stimulating factor) was demonstrated using the experimental model of septic inflammation in rats induced by subcutaneous administration of the culture of St. aureus (LD 90). Solution of antibodies in homeopathic dilution C1000 was administered orally in the dose of 0.3 ml for 5 days. In the experimental group of animals decrease (by a factor of 3) of lethality rate was observed along with marked reduction of suppurative and septic manifestations in the site of inoculation of microorganisms and parenchymatose viscera of the animals.

87D. Rise of monocyte count in peripheral blood and in bone marrow (by 25% and 70% respectively) was registered in mice of the C57BL line in the state of myelosuppression induced by a single injection of maximal tolerated dose of cyclophosphamide after 5 days of oral administration of 0.1 ml of potentiated solution of polyclonal sheep antibodies to M-CSF (macrophage colony-stimulating factor) in homeopathic dilution C12.

EXAMPLE 88

Antibodies to Chemokines

88A. The influence of ultra-low doses of antibodies to chemokines upon the course of autoimmune pancreatitis (AP) and associated respiratory distress syndrome (RDS) in rats was studied on the model of AP induced by intraperitoneal injections of cerulin in the dose of 100 mkg/kg (three subsequent injections with a one hour-interval). Rats of the experimental group were administered (after cerulin injections) activated ultra-low doses of anti-CINC-polyclonal rabbit antibodies to chemokine CINC (cytokine-induced neutrophiles chemo attractant) as a mixture of homeopathic dilutions C12, C30, and C200 in aqueous solution. On the first day the animals could drink the aqueous solution ad libitum and further on they got 0.2 ml once a day. Rats of the control group got distilled water. Severity of AP was assessed based on the level of plasma amylase and on morphological lesions in the pancreas (degree of acinar cells necrosis, parenchymal edema and severity of inflammatory infiltration of the pancreas). Severity of RDS was assessed based on measurements of permeability of micro vascular network of the lungs and of myeloperoxidase activity. It has been found out that in the rats having been administered antibodies to CINC 24 hours after cerulin injection all the indices were reliably lower than in the animals of the control group, the level of serum amylase—by a factor of 1.8, the degree of acinar cells necrosis—by a factor of 3, the degree of parenchymal edema—by a factor of 2.3 and severity of inflammatory infiltration of the pancreas—by a factor of 2.5 in particular. Administration of the preparation also resulted in decrease in myeloperoxidase activity by a factor of 1.8 and decrease in permeability of micro vascular network of the lungs—by a factor of 3.

88B. Patient B. aged 22 years sought medical advice for severe allergic dermatitis (food allergy) refractory to conventional therapy. The patient was prescribed monoclonal antibodies to eotaxine—a mixture of homeopathic dilutions D12+C30+LM10, in the dose of 1 tablet twice a day. On the $3^{rd}$ day of treatment the patient noted considerable alleviation of skin itching and normalization of her sleep. 7 days after the beginning of treatment skin rash and itch subsided completely. Intake of the preparation with preventive purpose was recommended 6 month. Catamnesis: no recurrence of dermatitis occurred despite the fact that the patient was not keeping at strict diet.

88C. It has been shown in the experiments on the suspension of leucocytes isolated from human peripheral blood that monoclonal antibodies to MIF (migration inhibiting factor) in C200 homeopathic dilution reliably inhibit migration by 30%, $p<0.05$) after introduction of 1% preparation into incubation medium.

88D. Patient R. aged 45 years complained of small vesicular rash and itching of his skin after insolation. The diagnosis of urticaria was established and the patient was prescribed monoclonal antibodies to MCAF (monocyte chemotactic activating factor) in form of a mixture of homeopathic dilutions C6+C30+C200 in the dose of 1 tablet 3 times a day. After 2 days of treatment disappearance of rash and itching was registered.

EXAMPLE 89

Antibodies to CXC-Chemokines (a-Chemokines)

89A. Patient R. aged 43 years complained of multiple furuncles in her armpit. She was prescribed intake of potentiated solution of chimeric antibodies to CXC-chemokine IP10 in homeopathic dilution C30 in the dose of 1 teaspoonful 3 times a day. 3 days after the beginning of treatment reliable decrease in the number and size of furuncles.

89B. Patient N. aged 48 years complained of exacerbation of lumbosacral radiculitis. He was prescribed oral intake of monoclonal antibodies to chemokine GROα in C200 homeopathic dilution (obtained by means of treatment with sonic generator at 20 Hertz in the dose of 5 drops 3 times a day. 3 days after the beginning of treatment disappearance of pain was registered.

89C. Patient V. aged 32 years complained of pain in her low abdomen and rise in body temperature after a cold. She presented a history of adnexitis and adhesive process in her abdominal cavity. She was prescribed intake of the solution of monoclonal antibodies to CXC α-chemokine GRO in homeopathic dilution C6 in the dose of 10 drops 5 times a day. After 3 days of treatment disappearance of pain and normalization of body temperature were registered.

EXAMPLE 90

Antibodies to C-C-Chemokines 63-Chemokines

90A. Experimental assessment of the influence of ultra-low doses of antibodies to β-chemokine rantes upon histamine release by rat mast cells isolated from peritoneal exudate was performed. Histamine release was assessed microscopically by degranulation of cells. Introduction of 1% potentiated solution of monoclonal antibodies to chemokine in homeopathic dilution C24 into incubation medium resulted in significant (by 35%) stimulation of degranulation within 1 hour.

90B. Patient L. aged 15 years complained of dry itching eruptions in the area of her elbow folds and neck. The diagnosis of neurodermitis was established as a result of examination. She was prescribed intake of ultra-low doses of monoclonal antibodies to CC chemokine eotaxine in C200 homeopathic dilution in the dose of 1 tablet 2 times a day. Elimination of itching and skin eruptions was achieved within 5 days of treatment.

90C. Patient G. aged 28 years complained of piercing pain in her lower jaw having appeared acutely after a cold and rise of body temperature. The diagnosis established as a result of examination was trigeminal neuralgia. Prescription of the preparation of monoclonal antibodies to chemokine MIP-1 in homeopathic dilution C50 in the dose of 1 tablet 3 times a day made it possible to eliminate pain and normalize body temperature within 2 days of treatment.

EXAMPLE 91

Antibodies to C-Chemokines (γ-Chemokines)

91A. NK cells of mice of the C57BL line were incubated with 0.1% solution of monoclonal antibodies to γ-chemokine lymphotactine in homeopathic dilution C 100. Addition of NK cells preincubated with antibodies to the cells of B16 melanoma (at a ratio of 10:1) showed that the preparation stimulates natural killers' antitumor activity by 42%.

EXAMPLE 92

Antibodies to C-CXXXC-chemokines

92B. Protective effect of the preparation of monoclonal antibodies to chemokine fractalkine was demonstrated in experiments on rats with transplantable tumor (Erlich's hepatoma). The life span of animals that had been orally administered potentiated solution of antibodies in homeopathic dilution C100 in the dose of 0.1 ml for 30 days was extended by 30%.

EXAMPLE 93

Antibodies to Non-Classic (Lipid) Chemokines

93A. Patient L. aged 31 years complained of migraine resistant to conventional therapy. She was recommended a preparation of antibodies to platelet-activating factor (a mixture of homeopathic dilutions C12+C30+C200) in the dose of 1 tablet daily. In the course of 3 weeks of treatment with the preparation no migraine spells were registered. The course of treatment was recommended to be continued.

93B. Patient A. aged 47 years complained of periodic headache and sensation of heaviness in the area of the heart. Examination revealed elevation of blood pressure up to 160/90 mm of mercury column. The patient was established the diagnosis of II degree morbus hypertonicus and was recommended intake of potentiated solution of antibodies to chemokine 5HETE in C200 homeopathic dilution in the dose of 10 drops 3 times a day along with daily control of blood pressure. Repeated examination 2 weeks later showed stable normalization of blood pressure.

EXAMPLE 94

Antibodies to Growth Factors

94A. Experimental assessment of the influence of antibodies to transforming growth factor α (TGFα) upon proliferation of fibroblasts was performed. 0.1% potentiated solution of antibodies to TGF α in homeopathic dilution C200 was added to primary culture of fibroblasts. After 24 hours of incubation proliferative activity of the cells was measured by 3H-thymidine inclusion. It has been found out that the preparation of antibodies enhances proliferative activity of fibroblasts by 20%.

94B. Experimental model of autoimmune pancreatitis in mice of the C57B1 line was created by means of three subsequent intraperitoneal injections of cerulin in the dose of 100 mcg/kg with 1 hour interval between injections. Mice of the experimental group were administered (after cerulin injections) ultra-low doses of polyclonal rabbit antibodies to human transforming growth factor β1(anti-TGF-β1)—a mixture of homeopathic dilutions C12, C30 and C200 in aqueous solution. The first day the animals could drink the aqueous solution ad libitum and further on they got 0.2 ml once a day. Rats of the control group got distilled water. Part of the mice of both groups were decapitated 24 hours after administration of cerulin and their serum amylase level and pancreatic edema index (calculated as the pancreas weight/animal's weight ratio) were measured; histological study of their pancreas was performed with measurement of the degree of acinar cells necrosis, parenchymal edema and severity of inflammatory infiltration. On the 10-th day after cerulin administration the animals' blood samples were taken and the level of auto antibodies to pancreatic acinar cells was assessed using the method of indirect immunofluorescence on pancreatic cross sections of intact mice. It has been found out that in mice having been administered anti-TGF-β1 serum amylase level, pancreatic edema index, the degree of acinar cells necrosis, parenchymal edema and severity of inflammatory infiltration of the pancreas were reliably lower than in the animals of the control group 24 hours after cerulin administration. On the 10-th day the titre of auto antibodies in the control group was 1:64, whereas in the mice having been administered anti-TGF-β1—1:4.

94C. Patient A. aged 46 years was admitted to the department of surgery for repeated planned surgery for adhesive bowel obstruction. It was found out in the course of examination that the patient had a tendency to formation of keloid postoperative scars. In order to prevent adhesive disease and keloid tissue formation the patient was being administered activated ultra-low doses of polyclonal rabbit antibodies to human transforming growth factor β1 (anti-TGF-β1) in form of a mixture of homeopathic dilutions C12, C30, C200 in the dose of 1 tablet daily for 7 days as preparatory preoperative course and for 1 month after the operation with recurrence-prevention purpose. The patient was examined 30 days after the operation: no keloid tissue was found in the area of operation wound and the amount of keloid tissue in preexisting scars was found to have reduced. Catamnestic data: for 2 years the patient A. had no recurrences of adhesive disease.

94D. Patient Ts. aged 27 years complained of progressive circumscribed alopecia he has been suffering from for the last 3 month. The patient was prescribed activated ultra-low doses of monoclonal antibodies to human transforming growth factor TGF-β2 in form of a mixture of homeopathic dilutions D6, C30 and C1000 in the dose of 1 tablet daily. Repeated examination 2 weeks later revealed arrest of alopecia progressive worsening and beginning of restoration of hair. A month after the beginning of treatment no signs of alopecia were found.

94E. Patient G. aged 54 years complained of cough and subfebrile temperature he had been suffering from for 3 weeks after a flue. Examination revealed secondary immune deficiency (lymphopenia and decreased serum immunoglobulin level). The patient was prescribed intake of the solution of antibodies to transforming growth factor TGFβ in C200 homeopathic dilution in the dose of 10 drops 3 times a day. Within 5 days the patient's temperature was back to normal and cough disappeared, within 10 days laboratory indices were back to normal.

94F. It has been shown in the experiment on the culture of fibroblasts of human skinB that ultra-low doses antibodies to fibroblast growth factor obtained by homeopathic technology stimulate protein biosynthesis. 0.1% of antibodies in homeopathic dilution C30 were introduced into the holes of 96-hole pad containing cellular monolayer. 24 hours later 3H-leucine was added to the cells. The results were assessed by inclusion of radioactive label in the course of 4 hour-incubation. Stimulation of label inclusion under the influence of the preparation of antibodies by 35% was observed.

94G. Patient N. aged 59 years complained of decompensated insulin-independent diabetes mellitus. He was suggested intake of antibodies to insulin-mimetic growth factor (IGF 1) in C200 homeopathic dilution in the dose of 1 tablet 3 times a day. 2 days later marked reduction in severity of clinical symptoms of hyperglycemia was registered and 7 days later normalization of blood glucose level was achieved along with enhanced tolerance to physical strain.

94H. In order to investigate the influence of activated ultra-low doses of antibodies to insulin-mimetic growth factor (IGF1) upon the course of ischemic cerebral stroke local brain ischemia in rats was induced by unilateral ligation of median brain artery was performed under general anesthesia. Polyclonal antibodies to a fragment of IGF1 (a mixture of homeopathic dilutions C200+C1000) were administered orally in the dose of 0.4 ml of aqueous solution per rat once a day for 3 days prior to ischemia and later on—in the dose of 0.1 ml of aqueous solution every hour in the course of one day in the $1^{st}$ group and in the same dose once a day in the course of 30 days in the 2-group. In the $1^{st}$ group (short-term observation) the degree of locomotor ataxia was evaluated 24 hours after occlusion and then, after the animals were killed by neck dislocation, the size of the focus of ischemic necrosis in their brain was measured (2,3,5-triphenyltetrazolium chloride (TTCh) stain). In the 2-group of rats (long-term observation) the degree of locomotor ataxia was assessed every day for 30 days after the occlusion and then, after the animals were killed by neck dislocation, the size of the focus of postischemic necrosis focus in their cerebral hemisphere on the side of occlusion was measured (TTCh stain). It has been found out that in the groups of animals treated with the preparation the degree of locomotor ataxia was reliably lower than in control group. The size of the focus of ischemic necrosis 24 hours after the occlusion and the size of the focus of postischemic lesion 30 days after the occlusion also were significantly smaller in the groups of rats treated with potentiated antibodies to IGF 1.

94I. Patient L. aged 54 years complained of lumbar pain and reduced plantar sensitivity of his right foot. He presented a history of ostheochondrosis and radicular syndrome. Prescription of the preparation of antibodies to nerve growth factor in homeopathic dilution C1000 in the dose of 1 tablet 3 times a day made it possible to eliminate the algesic syndrome and restore sensitivity within 5 days of treatment.

94J. Patient R. aged 48 years complained of more frequent attacks of bronchial asthma and a drop in the efficacy of medical treatment. He was prescribed potentiated solution monoclonal antibodies to nerve growth factor in C200 homeopathic dilution in the dose of 1 tea-spoonful 3 times a day. Drop in intensity and frequency of attacks was registered after 3 days of treatment.

94K. Patient K. aged 71 years suffering from insulin-independent diabetes mellitus complained of an ulcer in the lower part of his leg that had not been healing in the course of 2 weeks. The patient was established the diagnosis of trophic ulcer and was prescribed a course of potentiated solution of antibodies to epidermal growth factor in homeopathic dilution C100 in the dose of 10 drops 3 times a day. The wound was healed within 1 week.

94L. Patient P. aged 62 years sought medical advice for recurrent bilateral corneal erosion due to type II diabetes mellitus. A 3-month course of treatment with regeneration-stimulating medications (solcoseryl, actovegin, derinat) was of no sufficient effect. The patient was prescribed goat polyclonal antibodies to human epidermal growth factor (a mixture of homeopathic dilutions C30+C200+C1000) in the dose of 1 tablet twice a day in combination with instillations of aqueous solution of the said preparation. Upon repeated examination 7 days after shrinking of the erosion surface by half was registered and 4 weeks after the beginning of treatment complete epithelization of the erosions was achieved.

94M. Application of 0.1 ml of the solution of monoclonal antibodies to vascular growth factor in homeopathic dilution C1000 upon bulbar conjunctiva of a rabbit every day results in enhanced vascularization of conjunctiva within 7 days of the experiment.

94N. Patient Zh. aged 61 years developed progressive worsening of retinopathy due to decompensated type II diabetes mellitus refractory to conventional therapy. The patient was consulted by an ophthalmologist, whose findings were as follows: Visus OD, OS=0.1, without correction; the patient's eye grounds showed proliferative retinopathy, a large number of newly-formed vessels and multiple foci of extravasations. The patient was prescribed monoclonal antibodies to vascular endothelium growth factor, VEGF 9a mixture of homeopathic dilutions C3, C30, C 1000) in the dose of 5 drops 3 times a day. Within 20 days after the beginning of treatment the patient reported subjective improvement of vision. Objective findings: visus OD=OS=0.3 (without correction), eye grounds: no fresh foci of extravasations and new vessels. The treatment was recommended to be continued.

94O. Patient U. aged 27 years complained of weakness, vertigo, nausea and buzzing in the ears. Examination revealed lowering of her blood pressure to 90/60 mm of mercury column. She was established the diagnosis of vegetal-vascular dystonia and prescribed intake of the solution of monoclonal antibodies to platelet-derived growth factor (PDGF) in C200 homeopathic dilution in the dose of 5 drops 3 times a day. After 2 days of treatment normalization of blood pressure was registered along with improvement of the patient's general state of health.

94P. Mice of the C57BL were orally administered solution of potentiated monoclonal antibodies to stem cell factor (SCF) in homeopathic dilution C30 in the dose of 0.1 ml for 5 days. Significant increase in the content of stem cells in the animals' bone marrow (by 20%) was registered along with increase of weight and cellularity of thymus parenchyma by 30%.

94Q. Patient M. aged 57 years with a long history of suffering from chronic hepatitis B was hospitalized in view of progressive hepato-renal failure. The patient was prescribed monoclonal antibodies to hepatocyte growth factor in form of a mixture of homeopathic dilutions C12+C30+C200 in the dose of 1 tablet 3 times a day. Within 5 days after the beginning of treatment the patient's general state of health improved, clinical and laboratory symptoms of hepatocellular insufficiency subsided and serum bilirubin level dropped. The course of treatment was recommended to be continued.

EXAMPLE 95

Antibodies to Lymphokines

95A. Patient D. aged 42 years suffering from chronic tonsillitis complained of acute pain in her throat and elevated body temperature. Prescription of polyclonal rabbit antibodies to interleukin 2 in C200 homeopathic dilution in the dose of 1 tablet once in 3 hours made it possible to the disease within 3 days of treatment.

95B. Experiment on suspension of spleen cells of mice of the C57B1 line has demonstrated that addition of 0.2% solution of monoclonal antibodies to low molecular weight B cell growth factor, (LMW-BCGF) in homeopathic dilution C12 to the incubation medium results in stimulation of proliferative activity of splenocytes by 20% after 24 hours of incubation.

95C. 1% of antibodies to lymphotoxin β in homeopathic potency C1000 were added to the incubation medium of human skin fibroblast culture. It has been found out that the solution of antibodies causes reduction of proliferation of fibroblast culture by 30% within 24 hours of incubation.

95D. It has been found out in the experiment on outbred white mice inoculated with B16 melanoma that oral administration of 0.1 ml of potentiated solution of antibodies to oncostatin M in C200 homeopathic dilution in the course of 30 days increases the animals' longevity by 20%.—

EXAMPLE 96

Antibodies to Monokines

96A. Experiment on fibroblast culture of the L line mice has demonstrated that addition of 0.1% solution of monoclonal antibodies heparin-binding epidermal growth factor HB-EGF in C200 homeopathic dilution results in stimulation of proliferative activity of by 25% within 24 hours of incubation.

96B. Patient Z. aged 51 years suffering from chronic prostatitis complained of exacerbation of the disease manifested by voiding problem and pain in his perineum that appeared after body cooling. He was prescribed intake of the solution of monoclonal antibodies to interleukin 1α in homeopathic dilution C300 in the dose of 10 drops twice a day. 2 days after the beginning of treatment pain and disuria disappeared.

96C. Patient N. aged 25 years complained of headache, cough and fever. Examination revealed that the patient was running temperature of 38° C. and the diagnosis of acute respiratory viral infection was established. He was prescribed monoclonal antibodies to interleukin 1β in C200 homeopathic dilution in the dose of 1 tablet every 2 hours. After 24 hours of treatment the patient's general state of health improved, his body temperature dropped to normal and his cough subsided.

EXAMPLE 97

Antibodies to Minicytokines

97A. Patient R. aged 46 years suffering from duodenal ulcer complicated with pyloric stenosis and duodenitis complained of nausea, burping and a feeling of heaviness in his epigastric area enhanced after meals. He was prescribed a course of treatment with the solution of monoclonal antibodies to BOMBEZIN in C200 homeopathic dilution in the dose of 1 tablet 30 minutes before meals. 3 days after the symptoms described above subsided.

97B. It has been shown in the experiment on thymusectomized mice of the C57BL line that oral administration of 0.1 ml solution of monoclonal antibodies to thymosin al in C200 homeopathic dilution for 4 days results in increase of the number of rosette-forming spleen cells by 30%.

97C. Rats suffering from experimental osteomyelitis of their upper jaw caused by inoculation of the culture of *St. aureus* were orally administered a daily dose of 0.1 ml of the solution of monoclonal antibodies to osteogenous growth factor (OGF) in homeopathic dilution C12. Ossification of the lesion focus occurred 2-3 days earlier in comparison with the control group of rats.

97D. Patient A. aged 11 years was consulted for everyday enuresis. He was prescribed a course of oral intake of the solution of monoclonal antibodies to vasopressin in C200 homeopathic dilution in the dose of 1 tablet at bedtime. No episodes of enuresis were registered during 3-week observation.

97E. Patient N. aged 54 years suffering from psoriasis complained of exacerbation of the disease. He was prescribed the preparation of monoclonal antibodies to epidermal inhibitory pentapeptide (EIP) in C200 homeopathic dilution to be taken orally in the dose of 1 tablet 3 times a day. Within 3 days exacerbation of the disease was arrested, within 7 days his skin was completely cleared of psoriatic plaques.

97F. Patient L. aged 34 years complained of nasal itching, sneezing and rhinorrhea with thin nasal discharge. The patient was established the diagnosis of vasomotor rhinitis and was recommended intake of the solution of monoclonal antibodies to bradykinin in homeopathic dilution C30 in the dose of 1 tablet 3 times a day. Within 2 days symptoms of vasomotor rhinitis disappeared.

EXAMPLE 98

Antibodies to Hemopoietic Factors

98A. In order to study the effect of activated forms of ultra-low doses of antibodies to erythropoietin (anti-EP) upon bone marrow erythropoiesis suppressed by maximal tolerated dose of Adriamycin the control and the experimental group of CBA/CaLac line mice were preliminarily administered a single intraperitoneal injection of Adriamycin in the dose 6 mg/kg. After that the animals of the experimental group were administered monoclonal antibodies to recombinant human erythropoietin in form of homeopathic dilutions C12+C30–1–C200. The solution of antibodies was administered once a day orally via a tube in the dose 0.2 ml per animal for 10 days beginning with the day of administration of the cytostatic drug. The animals of the control group received the corresponding solvent (distilled water) in equivalent volume and following the same pattern. The animals were then slain by cervical dislocation of their spine each day from the $3^{rd}$ to the $10^{th}$ and on the $12^{th}$ day of the experiment. Total cellularity of the bone marrow (TCBM), total leucocyte count (TLC) reticulocyte and erythrocyte count were determined in peripheral blood. Hemogram and myelogram indices were counted by blood and bone marrow smear respectively.

Table 5. Dynamics of bone marrow indices ($\times 10^6$/l) in CBA/CaLac line mice after oral administration of solvent (1) and ultra-low doses of antibodies to ERYTHROPOIETIN (2) in the dose 0.2 ml per animal for 10 days following single intraperitoneal administration of maximal tolerated dose of Adriamycin (6 mg/kg). X±m.

TABLE 5

| No | Index under study | $3^{rd}$ day | | $4^{th}$ day | |
|---|---|---|---|---|---|
| | | 1 | 2 | 1 | 2 |
| 1 | TCBM | 11 ± 0.96*** | 12.12 ± 0.52*** | 14.12 ± 0.75** | 13.15 ± 0.52*** |
| 2 | Immature neutrophiles | 2.20 ± 0.26 | 1.72 ± 0.09 | 2.03 ± 0.13* | 1.72 ± 0.18 |
| 3 | Mature neutrophiles | 6.54 ± 0.76 | 6.91 ± 0.52 | 8.66 ± 0.52 | 7.55 ± 0.60 |
| 4 | Eosinopliles | 0.20 ± 0.09 | 0.27 ± 0.06 | 0.17 ± 0.05* | 0.16 ± 0.04* |
| 5 | Myeloid mitoses | 0.21 ± 0.04** | 0.20 ± 0.05** | 0.08 ± 0.03 | 0.08 ± 0.02 |
| 6 | Lymphoid cells | 1.40 ± 0.15** | 2.20 ± 0.17**$$ | 1.79 ± 0.40** | 2.41 ± 0.40* |
| 7 | Monocytes | 0.19 ± 0.06** | 0.15 ± 0.03** | 0*** | *** |
| 8 | Plasma cells | 0.04 ± 0.02 | 0.09 ± 0.02*** | 0.09 ± 0.03** | 0.07 ± 0.03 |
| 9 | Macrophages | 0.02 ± 0.02 | 0.02 ± 0.01 | 0.01 ± 0.01 | 0.02 ± 0.01 |
| 10 | Megacariocytes | 0 | 0 | 0.01 ± 0.01 | |
| 11 | Erythroid cells | 0.19 ± 0.03*** | 0.72 ± 0.18**$ | 1.29 ± 0.26 | 2.11 ± 0.19$ |

TABLE 5-continued

| | 5$^{th}$ day | | Intact For the |
|---|---|---|---|
| No. | 1 | 2 | 3$^{rd}$-7$^{th}$ day |
| 1 | 18.81 ± 1.26 | 18.31 ± 0.95 | 19.8 ± 1.14 |
| 2 | 2.44 ± 0.24* | 1.50 ± 0.20$ | 1.63 ± 0.12 |
| 3 | 8.70 ± 0.65 | 8.65 ± 0.34 | 8.41 ± 0.86 |
| 4 | 0.57 ± 0.14 | 0.39 ± 0.10 | 0.46 ± 0.10 |
| 5 | 0.04 ± 0.03 | 0.09 ± 0.04 | 0.02 ± 0.02 |
| 6 | 3.52 ± 0.51 | 2.97 ± 0.46 | 4.69 ± 0.71 |
| 7 | 0.58 ± 0.09 | 0.47 ± 0.09 | 0.47 ± 0.05 |
| 8 | 0.01 ± 0.01 | 0 | 0 |
| 9 | 0.11 ± 0.05 | 0.03 ± 0.03 | 0.06 ± 0.03 |
| 10 | 0.11 ± 0.04 | 0.15 ± 0.04 | 0.08 ± 0.04 |
| 11 | 2.72 ± 0.29* | 4.07 ± 0.24***$$ | 1.82 ± 0.20 |

Note:
*differences from the intact mice are reliable;
$differences from the control mice are reliable.

Results of the study of the pharmacological effects of the preparation presented in the table 5 showed that its administration to mice suffering from cytostatic drug-induces erythropoiesis suppression led to acceleration of erythropoiesis restoration process in comparison with animals of the control group which were administered solvent only.

98B. Patient K. aged 40 years, after a course of chemotherapy for chronic myeloleucosis complained of marked general weakness, dizziness and dyspnea at mild exertion. Physical findings: pronounced paleness of the skin and visible mucosae. Blood analysis revealed severe hypoplastic anemia. The patient was prescribed administration of polyclonal antibodies to recombinant human erythropoietin α in form of a mixture of homeopathic dilutions D30+C30+C200 in the dose of 1 tablet a day. Repeated blood analysis 5 days later showed elevation of hemoglobin level as well as erythrocyte and reticulocyte count in peripheral blood. On the 10$^{th}$ day the patient's condition was back to normal and his blood analysis was as follows: hemoglobin 100 g/l, erythrocyte count—3.1×10$^6$ per ml, reticulocyte share—5% o.

98C. Patient U. aged 47 years, appealed for medical help for general weakness, dyspnea, dizziness and heartache. More detailed medical history taking unearthed such complaints as voiding urgency, perversion of appetite and taste and dryness of skin. Her O&G history included three deliveries, hypermenorrhea and repeated dysfunctional uterine bleeding. Physical findings: paleness of the skin and visible mucosae, pulse rate 80 beats/min, systolic murmur auscultated at the heart apex. General blood count showed hypochromic hyporegenerative anemia: hemoglobin level 60 g/l, erythrocyte count 2.5×106 per ml, reticulocyte share 1% o. The patient stated poor tolerance of all iron preparations she had ever been treated with for anemia. She was prescribed administration of polyclonal antibodies to recombinant human erythropoietin α in form of a mixture of homeopathic dilutions C30+C200+C 1000 in the dose of 1 tablet a day. 7 days after the beginning of treatment the patient stated feeling better, voiding urgency, dyspnea and heartache subsided. General blood analysis: hemoglobin level 85 g/l, erythrocyte count 3×106 per ml, reticulocyte share 6% o. The patient was discharged after 15 days of treatment in satisfactory condition with hemoglobin level 110 g/l and erythrocyte count 4×106 per ml in her general blood count.

98D. Patient R. aged 34 years complained of weakness, vertigo, fainting fits and dysgeusia. She had a history of 3 deliveries and frequent uterine flooding. Examination revealed drop of hemoglobin level to 80 g/l. Prescription of monoclonal antibodies to erythropoietin in homeopathic dilution C24 in the dose of 1 teaspoonful of aqueous solution 3 times a day made it possible to eliminate clinical manifestations of anemia within 7 days of treatment. 20 days after the beginning of treatment hemoglobin level rose to 120 g/l.

98E. Patient M. aged 54 years complained of multiple extravasations. Examination revealed a thrombocytopathy. The patient was prescribed a course of treatment with monoclonal antibodies to thrombopoietin (TPO) in C200 homeopathic dilution in the dose of 1 tablet 3 times a day. Within 7 days of treatment disappearance of hematomas was registered.

EXAMPLE 99

Antibodies to Ligands of CD Receptors

99A. Patient D. aged 26 years has been suffering from psoriasis for 15 years and as he sought medical advice for a periodical exacerbation he was prescribed monoclonal antibodies to CD2 molecule in combination with monoclonal antibodies to CD45RO molecule—a mixture of homeopathic dilutions C12, C30 and C200 in the dose of 1 tablet twice a day. On the 2 day of treatment new plaques stopped appearing, the patient's general condition improved; 12 days after the beginning of treatment clinical remission manifested by marked regression of psoriatic plaques was registered. Intake of the preparation with preventive purpose was recommended 99B. Patient U. aged 6 years has been suffering from myasthenia gravis since the age of 2 years. At the moment of consultation the patient presented marked retardation in motor skills development, generalized muscle weakness and moderate ptosis of eyelids. Antibodies to acetylcholine receptors were detected. In view of inefficiency of conventional therapy the patient was prescribed monoclonal antibodies to ligand of CD40 molecule in homeopathic dilution C1000 in the dose of 1 tablet a day. 2 weeks after the beginning of treatment increase in the patient's muscle strength and disappearance of ptosis was observed. 2 months after the beginning of treatment decrease in titers of antibodies to acetylcholine receptors, restoration of muscle strength and development of muscular skills were noticed. The patient was recommended to keep taking the preparation.

Antibodies to Cholinergic Receptors

EXAMPLE 100

M-Cholinergic Receptors

100A. Patient K. aged 65 years complained of pain in his eyes after administration of pylocarpine for glaucoma. He was recommended administration of potentiated solution of polyclonal antibodies to M-cholinergic receptors in homeopathic dilution C20 in form of eye drops. Upon repeated examination 7 days later the patient reported disappearance of pain. The course of treatment was recommended to be continued.

100B. Oral administration of 0.1 ml of the solution of potentiated antibodies to M1 cholinergic receptors in homeopathic dilution C50 caused reduction of acetylcholine-induced edema of conjunctiva and excretion of tear fluid.

100C. Incubation of isolated atriums with the solution of antibodies to M2 cholinergic receptors in homeopathic potency C20 results in increase of cells permeability for potassium ions by 25% in the average.

100D. Patient L. aged 58 years complained of dryness in his mouth after intake of pirylen. Administration of the solution of potentiated antibodies to M3 cholinergic receptor in homeopathic dilution C50 in the dose of 10 ml 3 times a day made it possible to reduce severity of side effects of the ganglion blocker.

100E. Patient K. aged 63 years complained of palpitations after instillation of scopolamine drops for examination of eye grounds. Oral administration of the solution of monoclonal antibodies to phospholipase C conjugated with M-cholinergic receptors, in homeopathic dilution C 100 made it possible to control tachycardia.

100F. It has been demonstrated in an experiment on isolated segment of rat ileum that the preparation of polyclonal antibodies to M-cholinergic receptor in form of combination of homeopathic dilutions C30 and C200 potentiated increase in intestinal wall permeability for potassium ions under the influence of acetylcholine.

100G. Oral administration of 0.1 ml of the solution of potentiated antibodies, toM5 cholinergic receptor in homeopathic dilution C40 to rats resulted in increase of the animals' heartbeat rate by 30%.

EXAMPLE 101

Antibodies to N-Cholinergic Receptors

101A. Patient A, aged 52 years complained of cramps in his lower extremities. Electrolyte disorders or diabetes mellitus were not found. The patient had a history of ischialgia. After 2 days of oral intake of the solution of potentiated polyclonal antibodies to N-cholinergic receptors in homeopathic dilution C30 in the dose of 5 ml 3 times a day lessening of severity of cramps and algesic syndrome was registered.

101B. Addition of the solution of antibodies to α1 subunit of N-cholinergic receptor in homeopathic dilution C30 to the incubation medium of isolated cortical neurons of rat brain potentiated acetylcholine-induced depolarization.

101C. Isolated myocytes reacted by change of membrane potential by 20% to introduction of potentiated antibodies to β-subunit of N-cholinergic receptor in homeopathic dilution C100 into the incubation medium.

101D. It has been found out in an experiment on isolated cortical neurons of rat brain that antibodies to α-subunit of N-cholinergic receptor in homeopathic potency C30 modulate transmembrane potential and stimulate response to acetylcholine.

101E. It has been found out in an experiment on isolated rat heart that introduction into the incubation medium of 1% of potentiated antibodies to γ-subunit of N-cholinergic receptor in homeopathic dilution C50 results in increase in concentration of sodium ions in atrial myocytes.

101F. Patient G. aged 47 years complained of back pain. Examination revealed rigidity of muscles of shoulder girdle and the diagnosis of cervical osteochondrosis and radiculopathy was established. In order to reduce muscle rigidity oral intake of the solution of antibodies to N-cholinergic receptor of skeletal muscles in homeopathic dilution C30 in the dose of 10 ml 3 times a day was prescribed as part of complex therapy. Repeated examination a week later revealed lessening of muscle hypertonus and disappearance of pain.

Antibodies to Receptors of Hormones - Amino Acid Derivatives

EXAMPLE 102

Antibodies to Adrenoreceptors

102A. Patient K. aged 48 years complained of headaches and heart palpitations associated with emotional stresses. Examination revealed elevation of blood pressure up to 175/90 mm of mercury column. The patient was suggested intake of potentiated solution of antibodies to α-adrenoreceptors in homeopathic dilution C30 in the dose of 1 teaspoonful at bedtime. Repeated examination 2 weeks later revealed a tendency to normalization of blood pressure (150/80 during examination). The course of treatment was recommended to be continued.

102B. Oral administration of the solution of antibodies to adrenoreceptors in homeopathic potency C24 in the dose of 1 ml in the course of 3 days resulted in elevation of glucose and free fatty acid level in Chinese hamsters, which is an evidence of stimulation of glycogenolyisis and lipolysis.

102C. Introduction of antibodies to calmodulin in homeopathic dilution C30 into the incubation medium of rat hepatocytes results in reduced intensity of adrenalin-induced glycogenolysis. Specific biological activity present in this homeopathic preparation was noted.

102D. Patient Z. aged 61 years, complained of periodical dyspnea occurring at night and productive cough. The patient had a history of bronchial asthma. Oral intake of potentiated solution of polyclonal antibodies to phosphodiestherase of cAMP in homeopathic dilution C100 in the dose of 1 tablespoonful at bedtime was recommended for arresting asthmatic fits. During his next visit 5 days later the patient reported subsidence of the severity of symptoms.

102E. It has been shown on the model of isolated rat enterocytes that incubation of cells with potentiated solution of polyclonal antibodies to adenylate cyclase in homeopathic dilution C24 results in enhancement of sodium ions transport and modulation of transmembrane potential.

EXAMPLE 103

Antibodies to α-Adrenoreceptors

103A. Patient M. aged 67 years was taking clonidine as antihypertensive medication. He complained of somnolence and coordination disorders. The patient was prescribed intake of antibodies to α2 adrenoreceptors in homeopathic potency C20 in the dose of 1 table spoonful at bedtime and the dose of clofelin was suggested to be reduced. After 4 days of treatment the patient reported elimination of side effects of clonidine with persisting hypotensive effect. Further on the patient was switched to monotheapy with the preparation of potentiated antibodies.

103B. Patient R. aged 56 years was taking prasosin as antihypertensive medication. She complained of persisting dizziness and nausea. The patient was prescribed intake of antibodies to α1 adrenoreceptors in homeopathic dilution C50 in the dose of 1 teaspoonful 3 times a day. During her next visit to the doctor the patient presented no complaints for dizziness.

103C. Patient D. aged 62 years was taking a course of treatment with the preparation omnic for is voiding problems. Within 2 weeks no significant effect was achieved and the patient was additionally prescribed oral intake of antibodies to α1A subtype of adrenoreceptors in homeopathic potency C30 in the dose of 5 drops 3 times a day. After a week of combined therapy the patient reported better voiding. The course of treatment was recommended to be continued.

103D. Patient V. aged 58 years suffering from benign prostate hypertrophy was taking a course of treatment with prasosin for the purpose of improving his voiding. He complained of dizziness and tinnitus. Hypotensive effect of prasosin accounted for these symptoms. The patient was additionally recommended intake of the solution of potentiated antibodies to α1B subtype of adrenoreceptors in homeopathic dilution C20 in the dose of 1 teaspoonful at bedtime. A week later the patient noted subsidence of symptoms of hypotension to the point of their tolerance along with enhancement of the therapeutic effect of the preparation, which made it possible to reduce the dose of prasosin.

103E. It has been shown in an experiment on an isolated rabbit ureter that introduction of monoclonal antibodies to α1L-adrenoreceptors in homeopathic potency C60 into the incubation medium lowered the tonus and widened the lumen of the organ. Conclusion was drawn on the prospects of the preparation for treatment of impaired passage of urine.

103F. Patient L. aged 45 years complained of impaired sexual function. He was prescribed combined intake of yohimbine and potentiated antibodies to α2 adrenoreceptors in homeopathic dilution C20. 2 weeks after the patient reported better erection. The course of treatment was recommended to be continued.

103G. It has been found out in an experiment on isolated rat uterus that combined introduction of adrenalin and potentiated solution of antibodies to α adrenoreceptor in homeopathic dilution C40 into the incubation medium results in 15-20% bigger increase in number of muscle contractions than addition of adrenalin alone.

103H. Introduction of antibodies to α2 adrenoreceptors in homeopathic potency C30 into the incubation medium of guinea pig synaptosomes resulted in inhibition of serotonin release by 20-30%.

103I. Increase of membrane potential of isolated rat hepatocytes was observed in response to introduction of antibodies to al adrenoreceptors in homeopathic potency C20 into the incubation medium.

103J. Incubation of suspension of human platelets with 1% solution of antibodies to α2 adrenoreceptor in homeopathic potency C40 resulted in stimulation of aggregation.

EXAMPLE 104

Antibodies to β-Adrenoreceptors

104A. Incubation of isolated guinea pig myocardiocytes with adrenalin resulted in stimulation of oxygen and glucose consumption. Introduction of 2% of monoclonal antibodies to β1 adrenoreceptor in homeopathic dilution C20 resulted in depression of metabolic indices.

104B. Patient F. aged 39 years suffering from bronchial asthma complained of decrease in efficacy of salbutamole and aggravation of attacks of bronchial asthma. The patient was prescribed intake of potentiated antibodies to β2 adrenoreceptors in homeopathic dilution C40 in the dose of 1 teaspoonful 3 times a day. Decrease in both frequency and severity of asthmatic fits was noted after a week of treatment. Conclusion was made on the efficacy of this therapy.

104C. Addition of 1% solution of potentiated antibodies to β1 adrenoreceptor in homeopathic dilution C40 in combination with mitogenic agent phytohemagglutinin to the suspension of human lymphocytes results in significant depression of indices of blast transformation reaction within 72 hours.

104D. Incubation of isolated myocytes of rat uterus with 5% of antibodies to β2 adrenoreceptor in homeopathic potency C50 results in diminution of transmembrane potential and decrease in contractile activity 10 minutes after the beginning of incubation.

104E. Patient Sh. aged 46 years complained of palpitation and retrosternal pain after physical strain. The patient was recommended intake of the solution of polyclonal antibodies to β1 adrenoreceptor in homeopathic dilution C30 in the dose of 1 teaspoonful 3 times a day. At his next visit the patient reported decrease in frequency and intensity of the attacks.

104F. Patient E. aged 54 years complained of respiratory disorders and dyspnea. The patient had a history of ischemic heart disease and long-term intake of anaprilin. Oral administration of the solution of polyclonal antibodies to β-adrenoreceptor in homeopathic potency C20 for 10 days made it possible to reduce respiratory symptoms and continue anaprilin therapy. Conclusion on the efficiency of this homeopathic preparation for eliminating side effects of anaprilin was drawn.

EXAMPLE 105

Antibodies to Dopamine Receptors

105A. Patient L. aged 29 years was taking a course of treatment with haloperidol for hallucinations. He started complaining of tremor and movement coordination disorders 5 days after the beginning of the treatment. He was prescribed the preparation of the solution of polyclonal antibodies to dopamine receptors in homeopathic dilution C40 in the dose of 1 teaspoonful twice a day. Repeated examination a week later revealed lessening of tremor and betterment of movement coordination. Intake of the preparation of antibodies made it possible to reduce doses of haloperidol.

105B. It has been demonstrated in the experiment on rat cerebral sections that incubation with the solution of monoclonal antibodies to D2-dopamine receptor in homeopathic potency C40 for 1 hour reduced noradrenalin release by 12%.

105C. Patient A. aged 56 years complained of nausea, heaviness in the epigastric area and foul-smelling eructation. Examination revealed impaired gastric motility due to chronic gastritis. Within the framework of complex therapy the patient was prescribed oral intake of the solution of polyclonal antibodies to D2a dopamine receptor in homeopathic potency C20 in the dose of 10 ml twice a day in combination with diet. Within 5 days the patient reported disappearance of the symptoms.

105D. Administration of monoclonal antibodies to D1a subtype of dopamine receptors in homeopathic dilution C40 to mice for 6 days results in increase in concentration of mRNA of dopamine receptors of the hypothalamus. Homeopathic preparation modulates the activity of dopaminergic structures on genome translation level.

105E. In order to investigate biological effects of the preparation of monoclonal antibodies to D1 dopamine receptor the solution of antibodies in homeopathic dilution C30 was orally administered to Wistar line rats. After euthanasia of the animals dopamine concentration in their central nervous system was measured. It has been shown that 30 minutes after administration of the preparation dopamine release in the nucleus caudatus increases. Conclusion on specific biological activity of the said homeopathic preparation was made.

105F. Oral administration of 200 mcl of the solution of monoclonal antibodies to D1d receptor to rats resulted in modulation of binding of 3H-dopamine in specimens of cerebral cortex. Conclusion on specific influence of the homeopathic preparation on receptor properties was drawn.

105G. Patient R. aged 63 years complained of inefficacy of clozapin prescribed to him for phobias. He was suggested to complete conventional therapy with intake of aqueous solution of antibodies to D3 dopamine receptor in form of a mixture of homeopathic dilutions C50 and C200 in the dose of 20 drops 3 times a day. After 2 days of treatment the patient reported disappearance of night phobias; he was recommended to continue combined therapy.

105H. The preparation of monoclonal antibodies to D4 receptor in form of a solution in C30 homeopathic dilution was administered orally to rats in the dose of 100 mcl. Within 20 minutes after administration 25% drop in cAMP level in cerebral cortex and cerebellum was registered, which is typical for activation of D4 receptor structures. Conclusion of specific dopamine-mimetic biological effect of the solution of antibodies was made.

105I. Sections of the rat hypothalamus were incubated in the medium containing 3% of monoclonal antibodies to D5 dopamine receptors in homeopathic dilution C40. Enhancement of hydrolysis of 3H-phosphositoldiphosphate was registered after 15 minutes of incubation. Conclusion on the ability of the preparation under study to affect the systems of intracellular signal transmission conjugated with D5 receptors.

105J. Patient R. aged 65 years complained of tremor. He had a history of Parkinson's disease and long-term intake of levodopa. The efficacy of the medication was found to have decreased. Administration of polyclonal antibodies to dopamine receptor in form of solution in homeopathic dilution C30 in the dose of 10 drops at bedtime in addition to levodopa made it possible to achieve subsidence of symptoms of parkinsonism.

105K. Oral administration of antibodies to D2b receptors in homeopathic dilution C50 to rats in the dose of 100 mcl of the solution resulted in stimulation of potassium ions transport in the intestinal wall. The homeopathic preparation is thus capable of modulating gastrointestinal motility.

EXAMPLE 106

Antibodies to Serotonin Receptors

106A. Patient M. aged 57 years complained of anxiety and unrest without obvious reasons. The patient was suggested intake of polyclonal antibodies to serotonin receptors in homeopathic potency C40 in the dose of 1 teaspoonful per intake. By repeated examination 5 days later the said complaints had disappeared. Conclusion on the efficiency of this therapeutic modality was drawn.

106B. Patient M. aged 39 years was treated with sumatriptan, an agonist of 5HT1D-serotonin receptors, for migraine. Administration of potentiated solution of monoclonal antibodies to 5HT1-receptor in form of a mixture of homeopathic dilutions C50 and C200 together with sumatriptan made it possible to reduce the dose of the medication as well as intensity and frequency of episodes of migraine.

106C. Patient R. aged 48 years complained of insomnia and tremor. The patient had a history of long psychic overstrain. Intake of the solution of monoclonal antibodies to 5HT2 serotonin receptor in C40 potency in the dose of 1 teaspoonful at bedtime for 7 days made it possible to normalize the patient's sleep.

106D. Patient S. aged 36 years complained of depressed mood and impaired working capacity without any obvious reasons for it. The patient was prescribed intake of potentiated solution of antibodies to 5HT4 serotonin receptor in homeopathic dilution C40 upon repeated visit to the doctor the patient reported betterment of mood and elimination of the feeling of depression.

106E. An experiment aimed at investigation of aggregation was performed. 1% solution of antibodies to 5HT2 serotonin receptor was introduced into platelet suspension. Change of ADP-stimulated aggregation in the presence of the preparation in homeopathic dilution C50 was observed.

106F. Patient L. aged 45 years complained of unbearable nausea during car rides. The patient was recommended oral intake of antibodies to 5HT1-serotonin receptor in homeopathic dilution C30 in the dose of 10 drops prior to a ride. Positive kinetosis-controlling effect of the preparation was registered.

106G. Introduction of 5% solution of monoclonal antibodies to 5HT4 serotonin receptors into the incubation medium of rat brain sections in homeopathic dilution C40 promoted enhancement of labeled serotonin release by 15%. Conclusion on the ability of the preparation to control serotonin recapture was made.

106H. The preparation of monoclonal antibodies to 5HT3-serotonin receptor in homeopathic potency C20 was applied to the surface of an isolated uterine horn of a rabbit. Significant enhancement of contractile activity of the isolated organ was registered.

106I. Patient L. aged 32 years complained of skin itching. Oral intake of the preparation of antibodies to 5HT1-serotonin receptor in form of a mixture of homeopathic dilutions C20 and C200 in the dose of 1 tablet 3 times a day reduced the unwanted symptoms. The course of treatment was recommended to be continued.

106J. Experimental assessment of biological activity of the homeopathic preparation of monoclonal antibodies to imipramin receptors was performed. A specimen in form of 2% solution in homeopathic dilution C30 was introduced into the incubation medium of rat brain sections. It has been found out that the preparation stimulates serotonin consumption from the incubation medium.

EXAMPLE 107

Antibodies to Imidazolin Receptors

107A. Patient P. aged 52 years complained of headache and fatigability. In the course of examination the diagnosis of I degree morbus hypertonicus was established. The patient was prescribed intake of homeopathic preparation of antibodies to imidazolin receptors in C40 potency in the dose of 1 tablespoonful at bedtime. Repeated examination 7 days later revealed disappearance of headaches and normalization of blood pressure. Conclusion on the efficiency of this therapeutic modality was drawn.

EXAMPLE 108

Antibodies to Histamine Receptors

108A. Patient I. aged 35 years complained of somnolence and depressed mood after intake of tavegyl for allergic rhinitis. The patient was prescribed intake of potentiated solution of polyclonal antibodies to histamine receptors in homeopathic dilution C24. At his next visit the patient reported enhancement of his psychic activity along with subsidence of symptoms of the main illness. The course of treatment was recommended to be continued.

108B. Patient O. aged 51 years complained of asthmatic fits and unproductive cough. The patient had a history of bronchial asthma. He was suggested intake of the solution of potentiated monoclonal antibodies to H1 histamine receptor in homeopathic dilution C40 in the dose of 10 drops 3 times a day. At his next visit the patient reported diminution of both frequency and intensity of fits. The course of treatment was recommended to be continued.

108C. Patient L. aged 46 years suffering from exacerbation of chronic gastritis was prescribed oral intake of the solution of monoclonal antibodies to H2 histamine receptor in homeopathic dilution C60 in the dose of 5 ml twice a day. 3 days after the beginning of the course of treatment disappearance of symptoms of exacerbation of the disease (pain, feeling of flatulence and nausea) was registered.

108D. The preparation of antibodies to H3 histamine receptor in homeopathic potency C30 modulated contractile activity of the isolated heart of a rabbit when introduced into the incubation medium in the amount of 1% Noradrenalin concentration in the incubation medium increased. Conclusion on the influence of the preparation on noradrenalin release was made.

108E. Patient Sh. aged 35 years was prescribed betaserk, a histamine receptor blocker, for vestibular disorders. She complained of nausea as a side effect of the preparation. The patient was recommended intake of the solution of potentiated polyclonal antibodies to H3 histamine receptors in homeopathic dilution C40 in the dose of 10 drops twice a day. Elimination of nausea after intake of the preparation of antibodies made it possible to continue therapy with betaserk.

EXAMPLE 109

Antibodies to Receptors of Purines

109A. Patient R. aged 47 years complained of dyspnea fits and wheezing. Based on examination findings the diagnosis of bronchial asthma was established. The patient was prescribed polyclonal rabbit antibodies to purine receptors in C200 homeopathic dilution in the dose of 1 tablet 3 times a day. 7 weeks after the beginning of treatment the patient noted diminution of both frequency and intensity of fits.

109B. Preparation of 1% antibodies to adenosine receptor in homeopathic dilution C50 was introduced into the incubation medium of murine thymocytes together with mitogenic agent phytohemagglutinin. 72 hours later parameters of the reaction of blast transformation were checked. It has been found out that the preparation of antibodies in C50 potency caused suppression of proliferative activity of thymocytes.

109C. Patient M. aged 57 years complained of dyspnea and edema of her lower extremities. She had a history of myocardial infarction and of IIB cardiac failure. The patient was treated with the preparation of cocarboxylase with no significant effect. In addition to conventional therapy the patient was prescribed the preparation of antibodies to A2 purine receptors in homeopathic dilution C50 during repeated examination 7 days later the patient noted amelioration of his general state of health and subsidence of dyspnea. The course of treatment was recommended to be continued.

EXAMPLE 110

Antibodies to GABA Receptors

110A. The preparation of monoclonal antibodies to GABA (C30 homeopathic dilution) modulated bioelectric activity of cerebral cortex of experimental rats after oral administration of 0.5 ml of aqueous solution. Conclusion on the influence of the preparation upon electrophysiological characteristics of neurons was made.

110B. Contractile response to acetylcholine of an isolated striated muscle of rat was lower when 1% of monoclonal antibodies to GABA-B receptors in homeopathic dilution C50 were introduced into the incubation medium.

110C. Patient G. aged 41 years, complained of sleeping disorders. The patient was prescribed intake of homeopathic preparation of antibodies to GABA-A receptor in form of aqueous solution in C20 potency in the dose of 10 drops at bedtime. The patient's sleep was back to normal within a week of treatment.

110D. In order to study anticonvulsant activity of antibodies to benzodiasepine receptor convulsive syndrome in mice was modeled in the test of maximal electric shock. 0.2 second-long electric stimuli were applied to the animals via corneal electrodes (50 Hz, 50 mA). Maximal tonic extension of the animal's hind paws appearing in 100% of the control animals was assessed. Mice of the experimental group were twice orally administered monoclonal antibodies to benzodiasepine receptor (a mixture of homeopathic dilutions C12+ C30) in the dose of 0.2 ml of the solution 30 and 10 prior to electric stimulation. The animals treated with the preparation developed convulsive syndrome in 55% of cases and its intensity was less pronounced by 30% in the average.

110E. The preparation of monoclonal antibodies to benzodiasepine receptor in C200 homeopathic dilution was introduced into the incubation medium of cortical sections of rat brain in the amount of 1%. Measurement of transmembrane potential of neurons revealed elevation of depolarization threshold after administration of the preparation. Conclusion on specific receptor activity of the preparation was made.

110F. Monoclonal antibodies to γ-subunit of GABA-A receptor in homeopathic dilution D12 enhanced transport of Cl ions in isolated cortical neurons of guinea pig brain.

110G. Polyclonal antibodies to components of chlorine channel in homeopathic potency C40 elevated the threshold of depolarization of neurons of Chinese hamsters upon oral administration of 0.1 ml.

EXAMPLE 111

Antibodies to Amino Acids Receptors

111A. Biological activity of the preparation of polyclonal antibodies to receptors of stimulating amino acids in form of solution in homeopathic dilution C70 was studied on the model of hypoxic hypoxia. The chamber where the animals were kept was blown through with nitrogen and the moment of animals' death was registered. It has been found out that oral administration of antibodies significantly enhances the animals' resistance to hypoxia—both survival rate and the animals' longevity increase.

111B. In order to study the influence of ultra-low doses of activated antibodies to NMDA receptor upon the course of ischemic stroke local cerebral ischemia in rats was caused by unilateral ligation of the median brain artery under general anesthesia. Antibodies to NR1 fragment of N-methyl-D-aspartate receptor (a mixture of homeopathic dilutions C200+C 1000) were administered orally (0.4 ml of aqueous solution per rat) once a day for 3 days prior to ischemia and further on—every hour in the dose of 0.1 ml of aqueous solution in the course of a day in the $1^{st}$ group and every day in the course of 30 days in the $2^{nd}$ group. In the $1^{st}$ group (short-term observation) the degree of locomotor ataxia was evaluated 24 hours after occlusion and then, after the animals were killed by neck dislocation, the size of the focus of ischemic necrosis in their brain was measured (2,3,5-triphenyltetrazolium chloride (TTCh) stain). In the $2^{nd}$ group of rats (long-term observation) the degree of locomotor ataxia was assessed every day for 30 days after the occlusion and then, after the animals were killed by neck dislocation, the size of the focus of postischemic necrosis focus in their cerebral hemisphere on the side of occlusion was measured (TTCh stain). It has been found out that in the groups of animals treated with the preparation the degree of locomotor ataxia was reliably lower than in control group. The size of the focus of ischemic necrosis 24 hours after the occlusion and the size of the focus of postischemic lesion 30 days after the occlusion also were significantly smaller in the groups of rats treated with potentiated antibodies to NMDA receptor.

111C. Antibodies to NMDA-receptor in homeopathic dilution C100 were introduced into the incubation medium of rat cerebral sections together with NMDA. Synergic effect of NMDA and the solution of antibodies upon the level of cGMP in cerebral sections were registered.

111D. Patient G. aged 26 years was taking a course of treatment for exacerbation of epilepsy. He was prescribed oral intake of the solution of polyclonal antibodies to cainate receptors in homeopathic dilution C200. The patient reported reduction of frequency and intensity of his fits, which was supported by electroencephalography results.

111E. Patient K. aged 43 years complained of tremor and cramps in his lower extremities having appeared after intellectual strain. The patient was recommended intake of the solution of monoclonal antibodies to quisqualate receptors in homeopathic dilution C50 in the dose of 10 drops at bedtime. During his repeated visit a week later the patient presented fewer complaints. The course of treatment was recommended to be continued.

111F. Antibodies to AMPA-receptors in homeopathic dilution C50 were introduced into the culture of rat embryo neurons. Within 10 minutes of incubation increase in concentration of calcium ions inside the cells was registered, which is an evidence of biological activity of ultra-low doses of antibodies.

111G. Monoclonal antibodies to glutamate receptors in homeopathic dilution C50 reduced the sensitivity of the cells of guinea pig cerebral sections to cyanide when added to the incubation medium. Intensity of glucose consumption in the experimental group dropped by 40% when sodium cyanide was introduced into the incubation medium in the final concentration 0.01M, whereas in the control group the corresponding value dropped by 70%. Conclusion on specific protector antihypoxic activity of the preparation was made.

111H. Patient Z. aged 57 years complained of pain and cramps in his lower extremities. Administration of antibodies to glycine receptors in homeopathic dilution C30 in the dose of 1 tablet 3 times a day made it possible to reduce intensity of convulsive reactions.

111I. Introduction into the incubation medium of rat cerebral sections 1% solution of antibodies to receptors of asparaginic acid in homeopathic dilution C 100 resulted in change of neuron transmembrane potential.

EXAMPLE 112

Antibodies to Receptors of Epiphysis Hormones

112A. Patient N. aged 45 years complained of sleeping disorders. The patient was prescribed oral intake of the solution of antibodies to melatonin receptor in the potency C40 in the dose of 10 ml at bedtime. 4 days later the patient reported that her sleep was back to normal. The course of treatment was recommended to be continued.

EXAMPLE 113

Antibodies to Receptors of Eicosanoids

113A. Patient L. aged 66 years complained of nausea and lack of appetite. Examination revealed exacerbation of chronic gastritis. The patient had a long history of ibuprofen intake for osteochondrosis with radiculopathy. The patient was prescribed the preparation of polyclonal antibodies to prostaglandin receptors in C200 homeopathic dilution in the dose of 10 ml 4 times a day. 4 days later the patient reported better appetite and subsidence of nausea, which made it possible to continue the course of therapy of her main illness.

113B. Anti-inflammatory activity of the preparation of monoclonal antibodies to prostaglandin E receptor was investigated. Oral administration of 01 ml of the solution in C50 homeopathic dilution reduced the intensity of inflammatory reaction in rats in the model of formaldehyde-induced swelling of the animal's hind paw. Conclusion on anti-inflammatory properties of this homeopathic medication was drawn.

113C. Biological activity of the preparation of antibodies to prostaglandin F receptor was investigated on the model of isolated rat uterus horn. It has been found out that introduction of antibodies in homeopathic dilution C50 (1 ml/100 ml of medium) into the incubation medium potentiates contractile activity of the isolated organ.

113D. Patient U. aged 51 years complained of pain in the joints of his lower extremities. He had a history of gout. Intake of monoclonal antibodies to cyclooxygenase in homeopathic dilutions C100 and C200 in the dose of 10 ml 3 times a day was prescribed. During repeated examination subsidence of soreness and swelling of knee joints was noted. Conclusion on the efficacy of the used therapy was made.

113E. Patient E. aged 62 years complained of pain in her hands. The diagnosis of metabolic polyarthritis was established based on examination findings. Conventional antiinflammatory therapy was impossible because of concomitant gastric ulcer. The patient was recommended oral intake of the preparation of antibodies to COG-2 (II type cyclooxygenase) in C50 potency. Within 5 days the patient reported betterment of her general condition, lessening of severity of pain in the joints of her hands.

113F. Patient R. aged 47 years was treated at the hospital for exacerbation of ischemic heart disease. The possibilities of conventional medical therapy were limited due to the patient's concomitant diseases, such as gastric ulcer and bronchial asthma. After his discharge from the hospital the patient was prescribed long-term intake of the preparation of antibodies to thromboxan receptors in homeopathic dilution C20 in the dose of 1 tablet at bedtime. There were no exacerbations of ischemic heart disease in the course of 6 months of medical supervision; both the patient and his doctor assessed the results of treatment as positive. The course of treatment was recommended to be continued.

113G. It has been demonstrated in the experiment on human platelets that introduction of 1% solution of antibodies to platelet receptor of thromboxan A2 in homeopathic dilution C20 into the incubation medium resulted in suppression of ADP-stimulated aggregation.

113H. Patient V. aged 54 years complained of fits of dyspnea and dry cough.

The diagnosis of mild degree of bronchial asthma was established. The patient was suggested intake of the solution of antibodies to leucotriene receptor in homeopathic potency C30. After 7 days of treatment disappearance of cough was noted. The course of treatment was recommended to be continued.

113I. Patient M. aged 38 years complained of urticaria and itching. The patient had a history of bronchial asthma; symptoms of urticaria developed after administration of a leucotriene receptor antagonist zafirlucast as additional therapy. Intake of homeopathic preparation of antibodies to CysLT leucotriene receptor in C50 potency in the dose of 20 drops 3 times a day was prescribed, which made it possible to eliminate the side effect and continue therapy.

113J. Patient T. aged 57 years complained of pain in her lower extremities. The diagnosis of thrombofiebitis was established based on examination findings. Within the framework of complex therapy the patient was prescribed intake of potentiated antibodies to prostacyclin receptor in homeopathic dilution C100 in the dose of 10 drops 3 times a day, which made it possible to reduce the severity of the process of clot formation. The results of the 14-day course of treatment were positively estimated by both the patient and her doctor.

113K. Patient E. aged 61 years, was taking a course of treatment with inhalation of a phytopreparation Gingko biloba for dry cough. In view of insufficient efficacy of therapy oral intake of the solution of antibodies to platelet activating factor (PAF) receptor in homeopathic dilution C100 in the dose of 10 drops 3 times a day was additionally prescribed, which made it possible to eliminate cough.

EXAMPLE 114

Antibodies to Lipoprotein Receptors

114A. Patient K. aged 58 years complained of palpitation fits. Examination revealed elevated serum cholesterol level; the patient was established the diagnosis of ischemic heart disease and paroxysmal form of complete arrhythmia. Within the framework of complex therapy the patient was prescribed intake of polyclonal antibodies to receptors of polyunsaturated lipoproteins in form of a mixture of homeopathic dilutions C30 and C200 in the dose of 10 drops 3 times a day. After 30 days of intake of the preparation a tendency to normalization of cholesterol level along with subsidence of the symptoms of arrhythmia was registered. The course of treatment was recommended to be continued.

EXAMPLE 115

Antibodies to Nitrogen Oxide (NO)-Binding Proteins

115A. It has been found out in an experiment on isolated myocytes of vessel wall that homeopathic preparation of antibodies to NO-binding section of guanylate cyclase in homeopathic dilution D6 promotes elevation of cGMP level when added to the incubation medium to 5% final concentration.

EXAMPLE 116

Antibodies to Steroid Receptors

116A. Administration of the solution of antibodies to glucocorticoid receptor to rats led to elevation of serum glucose level in experimental animals. The preparation was administered orally in form of C40 potency solution in the dose of 0.4 ml. The animals were killed by decapitation under ether anesthesia 30 minutes after injection.

116B. Patient M. aged 46 years complained of overfatigue. He was established the diagnosis of functional asthenia. 5 day-course of treatment with the solution of antibodies to glucocorticoid receptor in homeopathic potency C40 in the dose of 10 ml made it possible to enhance physical labor capacity and achieve normal sleep.

116C. Patient U. aged 42 years complained of dizziness and sexual dysfunction. Examination revealed hypotension with psycho-emotional overstrains in the background. The patient was suggested intake of homeopathic preparation of antibodies to androgen receptor in homeopathic dilution C30 in the dose of 10 drops at bedtime. The course of treatment led to normalization of sexual function within 5 days of treatment.

116D. Patient D. aged 51 years, complained of heart palpitations, hot flushes, unstable blood pressure and mood and fits of dyspnea. No organic disorders were revealed during examination. The patient was established the diagnosis of climacteric syndrome. Administration of the preparation of polyclonal antibodies to estrogen receptors in homeopathic dilution C100 in the dose of 1 tablet at bedtime made it possible to eliminate the said symptoms. The patient's personal opinion on the results of treatment is positive.

116E. Patient S. aged 27 years complained of pain in her lower abdomen, bloody vaginal discharge in between menstruations. She had a history of endometriosis and long use of oral contraceptives. She was additionally prescribed homeopathic preparation of antibodies to progesterone receptors in homeopathic dilution C200. Oral intake of the preparation in the dose of 5 ml 3 times a day resulted in subsidence of symptoms within 2 weeks of treatment.

116F. Patient N. aged 58 years complained of dyspnea and edema. Examination revealed cardiac insufficiency due to cardiosclerosis. The patient was prescribed the preparation of monoclonal antibodies to aldosterone receptor in homeopathic dilution C30 in form of aqueous solution. Intake of homeopathic medication 3 times a day in the dose of 10 drops made it possible to control symptoms of fluid retention.

116G. Patient S. aged 12 years complained upon admittance of cramps and excessive muscle tonus. Examination revealed symptoms of hypocalcaemia. The patient was recommended intake of calcium preparations and vitamin D3 in combination with monoclonal antibodies to ergocalciferol in homeopathic dilution C50 in the dose of 1 tablet twice a day. The treatment made it possible to eliminate symptoms of hypocalcaemia 116H. In an experiment on isolated segment of intestine it was found that introduction of 1% of antibodies to vitamin D3 receptor in homeopathic dilution C60 into incubation medium promotes enhancement of biotransport of calcium ions across the intestinal wall.

Antibodies to Receptors of Protein-Peptide Hormones

EXAMPLE 117

Antibodies to Kinin Receptors

117A. Patient I. aged 43 years complained of dry cough she had been suffering from for 3 weeks. Based on examination findings the diagnosis of exacerbation of chronic obstructive bronchitis was established. The patient was suggested intake of antibodies to bradykinin receptor in homeopathic dilution C100 in the dose of 10 drops 4 times a day. Repeated examination 5 days later revealed elimination of cough and lessening of obstructive symptoms in the patient's lungs.

117B. Patient V. aged 57 years with a long history of allergic dermatitis complained of skin itching. The patient was prescribed oral intake of the preparation of polyclonal antibodies to kinin receptors in homeopathic dilution C50 3 times a day in the dose of 5 ml. After 4 days of treatment itching subsided. The patient noted betterment of her condition. The course of treatment was recommended to be continued.

117C. It has been found out in an experiment on isolated segment of rat ileum that antibodies to kinin receptor in homeopathic dilution C50 when added to the medium (2%) stimulate contractile activity of iliac segment after 30-minute incubation.

EXAMPLE 118

Antibodies to B1 Kinin Receptors

118A. Antibodies to B1 kinin receptors in homeopathic dilution C40 when administered orally to rats in the dose of 0.1 ml were found to suppress hypotensive reaction to histamine administration. Conclusion on biological activity of the said antibodies in ultra-low doses was drawn.

EXAMPLE 119

Antibodies to B2 Kinin Receptors

119A. The preparation of monoclonal antibodies to B2 kinin receptors in homeopathic dilution C50 was introduced into the incubation medium of isolated myocytes of the vascular wall to achieve final 1% dilution. Stimulation of transmembrane flux of Ca ions was registered, which is an evidence of specific biological activity of the preparation.

EXAMPLE 120

Antibodies to Leptin Receptors

120A. Patient Sh. aged 29 years was under medical supervision for III degree alimentary obesity. The patient's body mass index (BMI) was 35 kg/m2. Repeated diet therapy and intake of anorexigenic medications proved ineffective. The patient was prescribed polyclonal rabbit antibodies to leptin receptor (a mixture of homeopathic dilutions C200+C1000) in the dose of 1 tablet twice a day in combination with appropriate doses of physical strain. One month after the beginning of treatment Sh. reported betterment of his general condition along with enhanced tolerance of physical strain; his BMI dropped from 35 to 32 units. 2 months after the beginning of treatment his BMI=29; along with weight loss the patient reported natural lessening of appetite and further enhancement tolerance of physical strain. The patient was recommended to keep taking the preparation in the dose of 1 tablet every other day.

EXAMPLE 121

Antibodies to Opiate Receptors

121A. Patient G. aged 23 years was taking a course of treatment for drug addiction. He had a history of addiction to opiate drugs he had been suffering from for years. Administration of antibodies to opiate receptors in homeopathic dilution C1000 in the dose of 10 ml 5 times a day within the framework of complex therapy made it possible to control depression and reduce the intensity of withdrawal syndrome.

EXAMPLE 122

Antibodies to Opiate $\mu_1$ Receptors

122A. Patient I. aged 68 years was taking tramal as symptomatic therapy of algesic syndrome due to cancer. She complained of insufficient efficacy of the preparation. The patient was suggested intake of antibodies to opiate $\mu_1$ receptors in homeopathic dilution C50 in the dose of 10 drops per intake together with tramal. The patient reported lessening of algesic syndrome. The course of treatment was recommended to be continued.

EXAMPLE 123

Antibodies to Opiate $\mu_2$ Receptors

123A. Patient G. aged 19 years was brought to the reception hall of the hospital with symptoms of severe alcohol intoxication, respiratory insufficiency and bradycardia. Administration of the solution of antibodies to $\mu_2$ opiate receptors in homeopathic dilution C40 in the dose of 10 ml 3 times a day made it possible to reduce the severity of respiratory distress and normalize the heart rhythm.

EXAMPLE 124

Antibodies to Opiate $\sigma$ Receptor

124A. Patient V. aged 21 years was brought to the hospital in the state of psychic and motor agitation due to intake of an unidentified drug. Examination revealed disorders of form and color perception and dysphoria. Intake of the solution of monoclonal antibodies to opiate $\sigma$-receptor in homeopathic dilution C60 in the dose of 10 ml 3 times a day made it possible to achieve subsidence of productive symptoms.

EXAMPLE 125

Antibodies to Opiate $\delta$-Receptors

125A. It has been found out in an experimental study performed on a segment of rat intestine that the preparation of monoclonal antibodies to opiate $\delta$-receptors in homeopathic dilution D24 modulated contractile activity of the isolated organ when introduced into the incubation medium in form of 1% aqueous solution.

EXAMPLE 126

Antibodies to Opiate $\kappa$-Receptors

126A. Patient A. aged 57 years complained of somnolence and dizziness after tramal intake, which was prescribed to the patient in view of posttraumatic algesic syndrome. Oral administration of the solution of antibodies to opiate $\kappa$-receptors in homeopathic dilution C40 in the dose of 10 drops 3 times a day made it possible to eliminate dizziness and unwanted sedative effect.

EXAMPLE 127

Antibodies to Opiate $\epsilon$-Receptors

127A. Antibodies to opiate $\epsilon$-receptors were orally administered to guinea pigs in form of aqueous solution in homeopathic dilution C40 in the dose of 0.1 ml once a day for 7 days. Control animals were administered a solvent. After decapitation of the animals performed under ether anesthesia serum level of hormones was measured. Significant changes in concentration of prolactin and gonadotropins were registered in the group of animals treated with the preparation.

Antibodies to Receptors of Hypothalamic Releasing Factors

EXAMPLE 128

Antibodies to Corticoliberin Receptors

128A. Patient K. aged 43 years complained of dizziness, headache and tinnitus. Examination revealed lowering of blood pressure to 100/60 mm of mercury column and preliminary diagnosis of hypothalamic crisis was established based on examination findings. Intake of monoclonal antibodies to corticoliberin receptor in form of the solution in homeopathic dilution C60 in the dose of 10 drops at bedtime was recommended as a tonic. Repeated examination 7 days later revealed betterment of the patient's condition along with stabilization of blood pressure.

EXAMPLE 129

Antibodies to Gonadoliberin Receptors

129A. Patient L. aged 45 years complained of impaired sexual function and irritability. Examination revealed no organic disorders. Administration of the preparation of polyclonal antibodies to gonadoliberin receptors in homeopathic dilution C40 in the dose of 10 ml 3 times a day contributed to betterment of mood and elimination of erectile dysfunction.

EXAMPLE 130

Antibodies to Prolactoliberin Receptors

130A. Patient R. aged 52 years complained of periodic redness of skin, hot flashes and heart palpitation, instability of blood pressure and of her moods. No organic lesions were revealed during examination. She was established the diagnosis of climacteric syndrome and recommended intake of monoclonal antibodies to prolactoliberin receptor in homeopathic dilution C50 in the dose of 15 drops at bedtime. Upon repeated visit 10 days later the patient noted subsidence of vegetative manifestations of climacteric syndrome. Her assessment of the results of treatment was positive.

EXAMPLE 131

Antibodies to Thyroliberin Receptors

131A. Patient A. aged 34 years complained of heart palpitation, heartache, anxiety and sleeping disorders. Based on the examination results the diagnosis of thyrotoxicosis was established. The patient was prescribed antibodies to thyroliberin receptor in homeopathic dilution C50 in the dose of 10 drops at bedtime within the framework of complex therapy. Repeated examination 7 days later revealed subsidence of the abovementioned symptoms. The course of treatment was recommended to be continued.

EXAMPLE 132

Antibodies to Somatoliberin Receptors

132A. Solution of antibodies to somatoliberin receptors in homeopathic dilution C50 was introduced into the incubation medium of adenohypophysis cells to achieve final 1% dilution in conversion to the volume of the medium. A tendency to stimulation of somatotropic hormone secretion was registered after 24 hours of incubation.

EXAMPLE 133

Antibodies to Somatostatin Receptors

133A. Incubation of primary monolayer culture of adenohypophysis with the solution of potentiated antibodies to somatostatin receptor in homeopathic dilution C40 results in significant change of intracellular Ca level after 15 minutes of incubation, which is an evidence of biological activity of the preparation.

Antibodies to Receptors of Hypophysal Hormones

EXAMPLE 134

Antibodies to Somatotropic Hormone Receptors

134A. Stimulation of proliferative activity of the culture of human fibroblasts upon introduction of the solution of polyclonal antibodies to somatotropic hormone receptor in homeopathic potency C50 into the incubation medium was demonstrated experimentally; term of incubation was 24 hours.

EXAMPLE 135

Antibodies to Thyrotropic Hormone Receptors

135A. Patient M. aged 23 years complained of somnolence, inertia and frequent infectious diseases. Examination revealed functional insufficiency of thyroid gland. Administration of preparation of antibodies to thyrotropic hormone receptor in homeopathic dilution C50 in the dose of 5 ml 3 times a day made it possible to reduce symptoms of hypothyrosis—the patient's general condition ameliorated and blood pressure was back to normal after 2 weeks of therapy.

EXAMPLE 136

Antibodies to Receptors of Luteinizing Hormone

136A. Patient P. aged 35 years complained of menstrual cycle disorders. Examination revealed anovulatory cycles. The patient was prescribed antibodies to receptor of luteinizing hormone in C200 homeopathic dilution in the dose of 1 tablet every other day. After 30 days of treatment with the preparation her menstrual cycle became normal.

EXAMPLE 137

Antibodies to Receptors of Follicle-Stimulating Hormone

137A. Patient G. aged 31 years, was taking a course of treatment for sterility. She was recommended intake of antibodies to receptors of stimulating-stimulating hormone in homeopathic potency LM5 in the dose of 1 tablet every other day. After two months of treatment the patient became pregnant.

EXAMPLE 138

Antibodies to Prolactin Receptors

138A. Patient D. aged 25 years complained of discontinuance of lactation 2 weeks after childbirth. She was suggested intake of monoclonal antibodies to prolactin receptor in homeopathic potency C60 in the dose of 10 ml 3 times a day. After 3 days of treatment the patient reported stimulation of lactation.

EXAMPLE 139

Antibodies to Receptors of Melanocyte-Stimulating Hormone

139A. Patient M. aged 28 years complained of fatigability and pain in her eyes. Examination revealed elevated intraocular pressure. She was recommended intake of antibodies to receptors of melanotropin (intermedin, melanocyte-stimulating hormone) in homeopathic potency C50 in the dose of 5 ml 3 times a day. Normalization of intraocular pressure was registered at repeated examination 4 days later.

EXAMPLE 140

Antibodies to ACTH Receptors

140A. Elevated cAMP level was registered in an experiment on adrenal cell culture after introduction of 1% of antibodies to adrenocorticotropic hormone (corticotrophin) receptor in homeopathic dilution C30 into the incubation medium.

EXAMPLE 141

Antibodies to Vasopressin Receptors

141A. Drop in blood pressure was registered in rats with hereditary hypertension after oral administration of 0.1 ml of antibodies to vasopressin receptor in homeopathic potency C40.

EXAMPLE 142

Antibodies to Oxytocin Receptors

142A. Concentration of calcium ions in rat uterus under the influence of the solution of antibodies to oxytocin receptor was investigated. Elevated level of intracellular calcium was registered in rat uterine tissue after oral administration of 0.05 ml of solution of potentiated antibodies to oxytocin receptor in homeopathic dilution D6.

EXAMPLE 143

Antibodies to Receptors of Neuropeptide Y

143A. Patient K. aged 64 years was taking a course of rehabilitation after ischemic stroke. Intake of monoclonal antibodies to receptor of neuropeptide Y in form of solution in homeopathic dilution C40 in the dose of 10 drops 3 times a day for 10 days made it possible to significantly speed up regression of aphasia as well as intellectual and memory disorders.

EXAMPLE 144

Antibodies to Neurotensin Receptors

144A. Patient D. aged 41 years, complained of headache and nausea. Examination revealed elevated blood pressure—up to 160/90 mm of mercury column. The diagnosis of essential hypertension was established. The patient was prescribed intake of antibodies to neurotensin receptor in homeopathic potency C50 in the dose of 5 ml 3 times a day. After 5 days of treatment the patient reported betterment of her general state of health. The course of treatment was recommended to be continued.

EXAMPLE 145

Antibodies to Receptors of ACTH 4-10 Peptide

145A. An experiment aimed at assessment of psychotropic activity of homeopathic. dilutions of the preparation of antibodies to receptor of ACTH 4-10 peptide was carried out. Rats were orally administered a mixture of homeopathic dilutions C12 and C30 in form of a solution, in the dose of 0.1 ml. It has been found out that the preparation accelerates formation and promotes fixation of conditional reflexes.

EXAMPLE 146

Antibodies to Receptors of the Substance P

146A. Patient L. aged 57 years complained of memory disorders and impaired concentration of attention. The patient was prescribed intake of monoclonal antibodies to receptor of the substance P in homeopathic potency C200 in the dose of 10 drops 3 times a day. After 7 days of treatment the patient reported amelioration of his memory. The course of treatment was recommended to be continued.

EXAMPLE 147

Antibodies to Receptors of Delta Sleep-Inducing Peptide

147A. Patient G. aged 48 years complained of insomnia. She was recommended intake of the C50 potency solution of antibodies to receptor of 6-sleep peptide in the dose of 20 drops at bedtime. 3 days later the patient reported easier falling asleep and increased duration of sleep.

Antibodies to Receptors of Thyroid Gland Hormones

EXAMPLE 148

Antibodies to Thyroxin Receptors

148A. Patient L. Aged 32 years complained of tachycardia, high blood pressure, drops of mood and sleeping disorders. Examination revealed thyrotoxicosis. The patient was prescribed the preparation of antibodies to thyroxin receptor in C200 homeopathic dilution in the dose of 10 drops 3 times a day. Within 7 days the patient reported betterment of her general state of health.

Antibodies to Receptors of Hormones of Parathyroid Glands

EXAMPLE 149

Antibodies to Receptors of Thyrocalcitonin

149A. Changes of concentration of calcium and phosphate were registered in rat blood serum after 7 days of oral administration in the dose of 0.1 ml of the solution of antibodies to receptor of thyrocalcitonin in homeopathic potency C40.

EXAMPLE 150

Antibodies to Parathormone Receptors

150A. Patient Sh. aged 46 years complained of cramps in the lower extremities. The patient was prescribed intake of calcium gluconate in combination with solution of antibodies to parathyroidin (parathormone) receptor in the dose of 10 ml in homeopathic potency C50. the course of treatment made it possible to eliminate cramps.

Antibodies to Receptors of Pancreatic Hormones

EXAMPLE 151

Antibodies to Insulin Receptors

151A. Biological activity of monoclonal antibodies to insulin receptor was assessed in the experiment on cell culture of fibroblasts. It has been found out that introduction of 1% of antibodies in homeopathic potency C30 into the incubation medium resulted in stimulation of proliferative cells after 4 hours of incubation.

151B. Patient V. aged 60 years is under endocrinologist's supervision for subcompensated II type diabetes mellitus with risk of microangiopathy and hypercholesterolemia. The patient suffers from obesity; his body weight index (BWI) is 30. Oral hyperglycemic medications and insulin preparations do not allow achieving sufficient control of glycemia level. The patient was prescribed monoclonal antibodies to a insulin receptor (a mixture of homeopathic dilutions D6+C12+C30) in the dose of 5 drops of alcohol solution twice a day. Round-the-clock monitoring of glycemia level carried out a week after the beginning of treatment revealed marked decrease in tolerance of insulin. 3 weeks after the beginning of treatment administration of insulin was discontinued as his glycemia level was sufficiently controlled by manninyl 5 weeks after the beginning of treatment the patient reported betterment of his general state of health and increased tolerance of physical strain; his BWI dropped to 27. Fasting glycemia level dropped to 6 mmole/l. Patient was switched to monotherapy with preparation of antibodies to insulin receptor in the dose of 1 tablet twice a day.

EXAMPLE 152

Antibodies to Glucose Carrier

152A. Patient M. aged 48 years suffering from insulin-dependent diabetes mellitus complained of insufficient efficacy of insulin therapy. The preparation of antibodies to glucose carrier in homeopathic dilution C 1000 in the dose of 1 tablet twice a day was prescribed along with the diet. 10-day course of treatment with the preparation of antibodies made it possible to reduce tolerance of insulin. The course of treatment was recommended to be continued.

EXAMPLE 153

Antibodies to Glucagon Receptors

153A. Patient R. aged 26 years complained of intolerance of hunger, dizziness nausea and weakness. Examination revealed hypotension, bradycardia and a tendency to hypoglycemia. The patient was recommended monoclonal antibodies to glucagon receptor. Oral intake of the antibodies in homeopathic potency C60 in the dose of 10 ml made it possible to normalize blood pressure and enhance tolerance of hunger within 7 days of therapy.

Antibodies to Receptors of Hormones of Gastrointestinal Tract

EXAMPLE 154

Antibodies to Receptors of Gastrin-Releasing Peptide

154A. Patient R. aged 46 years complained of heaviness in her stomach, nausea and heartburn. Examination revealed chronic gastritis in the phase of exacerbation. The patient was prescribed antibodies to receptor of gastrin-releasing peptide in C200 homeopathic dilution in the dose of 1 tablet twice a day. The patient's condition was back to normal within 3 days of treatment.

EXAMPLE 155

Antibodies to Gastrin Receptors

155A. Patient G. aged 52 years complained of nausea and lack of appetite. Examination findings revealed atrophic subacid gastritis. The patient was recommended intake of polyclonal antibodies to gastrin receptor in homeopathic dilution C80 in the dose of 10 ml 3 times a day. Repeated examination 5 days later revealed normalization of gastric secretion.

EXAMPLE 156

Antibodies to Enterogastrin Receptors

156A. Patient N. aged 42 years complained of burping, heartburn and meteorism. Examination revealed chronic gastritis in the phase of exacerbation. Intake of monoclonal antibodies to enterogastrin receptor in homeopathic dilution C50 in the dose of 20 drops 3 times a day made it possible to normalize the patient's condition within 2 days of treatment.

EXAMPLE 157

Antibodies to Secretin Receptors

157A. An experiment aimed at assessment of biological activity of ultra-low doses of antibodies to secretin receptor was carried out. After administration of 1 ml of the preparation in homeopathic dilution D100 to the dog the animal was tested for pancreatic secretion of enzymes and bicarbonate. Modulating effect of the homeopathic preparation was registered.

EXAMPLE 158

Antibodies to Cholecystokinine Receptors

158A. Patient M. aged 57 years complained of nausea and pain in her right infracostal area. Examination revealed cholelithiasis. Administration of the preparation of monoclonal antibodies to cholecystokinine receptor in homeopathic dilution C50 in the dose of 10 ml 3 times a day made it possible to control algesic syndrome.

EXAMPLE 159

Antibodies to Motilin Receptors

159A. Patient L. aged 56 years complained of atonic constipation. Examination revealed no organic intestinal lesions.

The patient was prescribed intake of antibodies to motilin receptor in homeopathic potency C40 in the dose of 5 ml 3 times a day. After 7 days of treatment the patient reported improvement of evacuation function of his bowels.

EXAMPLE 160

Antibodies to Receptors of Vasointestinal Peptide

160A. Introduction of 1% of antibodies to receptor of vasointestinal peptide in homeopathic dilution C30 into the incubation medium of the primary culture of pancreatic cells resulted in increase of cAMP level within 10 minutes of incubation.

EXAMPLE 161

Antibodies to Bombezin Receptors

161A. Oral administration of ultra-low doses of potentiated antibodies to born bezin receptor in homeopathic potency C50 to rats resulted in elevation of intracellular calcium in their cells of the pancreas. Conclusion was then made on specific activity of the said antibodies

EXAMPLE 162

Antibodies to Receptors of Pancreatic Peptide

162A. Patient 0. aged 39 years was taking a course of treatment for obesity. Within the framework of complex therapy she was prescribed ultra-low doses of antibodies to receptor of pancreatic peptide in homeopathic potency C1000 in the dose of 10 ml 3 times a day. Reduced appetite and enhanced tolerance of physical strain were noted after 7 days of treatment with the preparation.

Antibodies Receptors of Peptide Regulators of Vascular Wall

EXAMPLE 163

Antibodies to Endothelin Receptors

163A. Patient I. aged 57 years complained of heartache and irregular heartbeats. He was established the diagnosis of ischemic heart disease. Oral intake of monoclonal antibodies to endothelin receptor in homeopathic potency C40 in the dose of 10 drops 3 times a day was included into complex therapy. Repeated examination revealed subsidence of symptoms of arrhythmia and angina. The patient's estimation of the results is positive. The course of treatment was recommended to be continued.

EXAMPLE 164

Antibodies to Receptors of Hyperpolarizing Relaxation Factor

164A. Patient M. aged 37 years is under medical supervision for $1^{st}$ degree essential hypertension (blood pressure 150/90). Administration of ultra-low doses of potentiated antibodies to receptors of hyperpolarizing relaxation factor in homeopathic dilution C30 in the dose of 1 tablet 2 times a day made it possible to normalize blood pressure.

EXAMPLE 165

Antibodies to Receptors of Endothelial Sodium-Uretic Peptide

165A. Biological activity of the preparation of antibodies to receptor of endothelial sodium-uretic peptide was registered in an experiment on isolated myocytes of arteries. The solution of antibodies in homeopathic potency C50 caused change of membrane potential of myocytes when added to the incubation medium in 1% concentration.

Antibodies to Angiotensin Receptors

EXAMPLE 166

Antibodies to Receptors of Agiotensin II

166A. In the course of studies of the effect of activated forms of ultra-low doses of antibodies (AB) to AT1 receptor of angiotensin II upon blood pressure (BP) in rats of ISIAH strain with inherited arterial hypertension BP on the tail artery was measured 5 days after oral administration of potentiated polyclonal rabbit antibodies to C-terminal fragment of the receptor of human angiotensin II on form of a mixture of homeopathic dilutions C12+C30+C200 in the dose of 0.5 ml of aqueous solution. The results of BP values measured before and after administration of the preparation are presented in the table 6. The data given in the table indicate that the preparation possesses marked hypotensive effect.

TABLE 6

Influence of the preparation Anti-R-angiotensin-II upon (BP) of hypertensive rats of the ISIAH strain.

| No | No. of rat | Initial BP (arithmetic mean of 3 measurements) | BP after 5 days of treatment | Drop in BP (3) − (4) | BP after 7 days of discontinuance of treatment with the preparation | Drop in BP (6) − (4) | BP after the 2-nd 5 day course of treatment | Drop in BP (6) − (8) |
|---|---|---|---|---|---|---|---|---|
| 1 | 31 | 175 | 151 | 24 | 166 | 15 | 150 | 16 |
| 2 | 32 | 184 | 163 | 21 | 186 | 23 | 170 | 16 |
| 3 | 33 | 186 | 169 | 17 | 165 | −4 | 150 | 15 |
| 4 | 4 | 171 | 165 | 6 | 189 | 24 | 170 | 19 |
| 5 | 34 | 187 | 172 | 15 | 190 | 18 | 175 | 15 |
| 6 | 10 | 181 | 166 | 15 | 185 | 19 | 170 | 15 |
| 7 | 11 | 171 | 162 | 9 | 169 | 7 | 155 | 14 |
| 8 | 38 | 182 | 160 | 22 | 185 | 25 | 165 | 20 |
| 9 | 16 | 180 | 169 | 11 | 183 | 14 | 165 | 18 |
| 10 | 19 | 186 | 166 | 20 | 186 | 20 | 170 | 16 |
| | X ± M | 180 ± 1.91 | 164 ± 1.86 | 16 ± 1.88 | 180 ± 3.08 | 16.1 ± 2.81 | 164 ± 2.87 | 16.4 ± 0.62 |

166B. Patient D. aged 56 years treated with captopril for morbus hypertonicus complained of cough. It has been found out that cough is a side effect of captopril. The patient was recommended intake of monoclonal antibodies to angiotensin II receptor in homeopathic potency C50 in the dose of 1 tablet 3 times a day, which made it possible to reduce the dose of captopril without interfering with hypotensive effect of the latter.

EXAMPLE 167

Antibodies to Receptors of Vascular Permeability Factor

167A. The preparation of antibodies to receptor of vascular permeability factor in homeopathic dilution C30 was introduced together with noradrenalin into the incubation medium where a section of an artery was incubated. It has been found out that the solution of antibodies potentiated constrictor activity of noradrenalin.

EXAMPLE 168

Antibodies to Receptors of Atrial Sodium-Uretic Peptide

168A. Patient B. 46 years complained of heartache and dizziness. Examination revealed II degree morbus hypertonicus. The patient was recommended antibodies to receptors of atrial sodium-uretic peptide in homeopathic dilution C50 in the dose of 10 drops 3 times a day. Repeated examination revealed normalization of blood pressure along with overall betterment of the patient's condition.
Antibodies to Growth Factor Receptors

EXAMPLE 169

Antibodies to Erythropoietin Receptors

169A. Patient L. aged 34 years complained of dizziness, weakness and fatigability. She had a history of 3 childbirths. Examination revealed depressed hemoglobin level and the diagnosis of iron-deficiency anemia was established. The effect of iron preparations was insufficient. Administration of monoclonal antibodies to erythropoietin receptor in homeopathic potency C50 in the dose of 1 tablet 3 times a day made it possible to achieve subsidence of symptoms of anemia within 3 weeks of treatment.

EXAMPLE 170

Antibodies to Receptors of Platelet Growth Factor

170A. Patient G. aged 68 years complained of subcutaneous extravasations. Examination revealed multiple petechias. The patient was prescribed monoclonal antibodies to receptors of platelet growth factor in homeopathic potency C200 in the dose of 5 ml of aqueous solution 3 times a day. Repeated examination 10 days later revealed a tendency to reduction of the number of new extravasations.

EXAMPLE 171

Antibodies to Receptors of Vascular Growth Factors

171A. Patient M 56 years complained of heartache and arrhythmia. Based on the results of examination he was established the diagnosis of ischemic heart disease and exertional angina. Administration of ultra-low doses of potentiated antibodies to receptors of vascular growth factor in homeopathic potency C50 in the dose of 10 drops 3 times a day made it possible to achieve subsidence of symptoms of arrhythmia and angina. The course of treatment was recommended to be continued.

EXAMPLE 172

Antibodies to Receptors of Nerve Growth Factor

172A. Patient A. aged 61 years, was taking a rehabilitation course after an ischemic stroke. In view of paresis of lower extremities the patient was prescribed intake of C30 dilution of antibodies to nerve growth factor potentiated according to homeopathic technology in the dose of 1 tablet twice a day. After 14 days of therapy the range of voluntary movements broadened along with enhancement of strength and sensitivity of the patient's lower extremities.

EXAMPLE 173

Antibodies to Receptors of Endothelium Growth Factor

173A. It has been found out at cultivation of endothelium of human umbilical cord in the presence of antibodies to receptors of endothelium growth factor in homeopathic dilution C50 that antibodies stimulate proliferation of cells by 15%, which is an evidence of specific biological activity.

EXAMPLE 174

Antibodies to Receptors of Epidermal Growth Factor

174A. Patient O. aged 63 years complained of recurrent extensive trophic ulcers on medial surface of the lower third of both legs due to varicose veins of low extremities. Surgical treatment of varicose veins is impossible because of the actual state of the skin integument. Treatment with regeneration-stimulating preparations (solkoseryl, actovegin and derinate) had been going on for 3 months without any pronounced effect. The patient was prescribed rabbit polyclonal antibodies to receptor of epidermal growth factor (a mixture of homeopathic dilutions C30+C200+C1000) in the dose of 1 tablet twice a day. Repeated visit 2 weeks later revealed shrinking of the surface of trophic ulcers by half and 4 weeks after the beginning of treatment complete epithelization of trophic ulcers was achieved.
174B. Patient M. aged 67 years complained of a trophic ulcer of the lower extremity. Application of antibodies to receptors of epithelium growth factor in homeopathic dilution C50 (aqueous solution) made it possible to stimulate healing after 7 days of treatment.

EXAMPLE 175

Antibodies to Receptors of Hepatocyte Growth Factor

175A. Primary culture of human hepatocytes was grown in the presence of 2% aqueous solution of antibodies to receptor of hepatocyte growth factor in homeopathic dilution C40. Stimulating effect of the preparation on proliferation of the cells was discovered after 24 hours of incubation (by 20%).

EXAMPLE 176

Antibodies to Receptors of Insulin-Mimetic Growth Factors

176A. Biological activity of antibodies to somatomedin receptor (IGF-1) was assessed in the experiment on rats. The preparation was administered orally in the course of 7 days in form of C30 potency solution in the dose of 0.1 ml. Weight gain was registered in the animals of experimental group, which is an evidence of anabolic effect of ultra-low doses of antibodies.

EXAMPLE 177

Antibodies to Receptors of Mesenchimal Growth Factor

177A. Patient M. aged 51 years complained of pain in her back and joints. Examination revealed metabolic polyarthritis and ostheochondrosis. The patient was suggested oral intake of polyclonal antibodies to receptor of mesenchimal growth factor in homeopathic potency C50 in the dose of 5 ml of aqueous solution 3 times a day. 7-day course of treatment made it possible to reduce intensity of algesic syndrome.

EXAMPLE 178

Antibodies to Receptors of Fibroblast Growth Factors

178A. An experiment aimed at evaluation of the influence of ultra-low doses of antibodies to receptor of fibroblast growth factor upon the level of secondary messengers was carried out. It has been found out that introduction of 1% solution of homeopathic C50 dilution of antibodies into the incubation medium resulted in change of the level of cAMP within 10 minutes, which indicated presence of specific biological activity.

Antibodies to Receptors of Cytokines

EXAMPLE 179

Antibodies to Receptors of Interleukins

179A. Patient R. 51 years sought medical advice for cough he had been suffering from for 2 months after pneumonia with chronic bronchitis in the background. He was prescribed intake of polyclonal antibodies to receptors of interleukin 4 in form of C50 homeopathic dilution in the dose of 1 tablet 3 times a day. Upon repeated visit 7 days later the patient reported betterment of his state of health and subsidence of cough.

179B. Patient M. aged 46 years complained of skin itching. The diagnosis of atopic dermatitis was established. Administration of antibodies to interleukin 1 (IL-1) in homeopathic potency C30 in the dose of 5 ml 3 times a day made it possible to eliminate itching within 7 days of treatment.

179C. The intensity of the reaction of blast-transformation of proliferation of mice thymocytes in the presence of antibodies to receptors of IL-2 (interleukin 2) was assessed. It has been found out that introduction of 1% of antibodies in homeopathic potency C60 into the incubation medium modulates proliferative activity of thymus cells.

EXAMPLE 180

Antibodies to Interferon Receptors

180A. Patient L. aged 38 years complained of rash on his lips after acute respiratory infection. After examination the diagnosis of acute herpes was established. Polyclonal antibodies to α-interferon receptor were prescribed in form of a mixture of homeopathic dilutions C12, C50 and C200 in the dose of 1 tablet 4 times a day. 3 days later disappearance of symptoms of the disease was noted.

180B. Polyclonal antibodies to receptors of α- and β-interferon in C200 homeopathic dilution administered to experimental mice increased the animals' survival rate at low temperature. The preparation was administered orally in form of a solution in the dose of 0.1 ml. The animals were kept on the standard diet of the vivarium at 120 CO. After 5 days survival rate in the experimental group was 25% higher than in the control group.

EXAMPLE 181

Antibodies to γ-Interferon Receptors

181A. Patient D. aged 23 years was taking a course of chemotherapy for osteogenic sarcoma of his hip. Marked side effects (vomiting) resulted in discontinuance of chemotherapy. Administration of monoclonal antibodies to γ-interferon receptor in homeopathic potency C40 in the dose of 10 ml of aqueous solution 3 times a day made it possible to control nausea and proceed with the course of treatment. Reduction of the tumor size was also noted.

EXAMPLE 182

Antibodies to Receptors of Granulocyte and Granulocyte Macrophage Growth Factors 182A. Patient Yu. aged 54 years complained of subfebrile temperature and cough he had been suffering from 3 weeks. He was prescribed monoclonal antibodies to granulocyte colony-stimulating factor (CSF) and granulocyte-macrophage CSF in homeopathic dilution C70 in the dose of 10 drops 3 times a day. Upon repeated examination 7 days later normalization of body temperature and betterment of the patient's general state of health was noted. The course of treatment was recommended to be continued.

EXAMPLE 183

Antibodies to Receptors of GM-CSF

183A. Enhancement of the activity of rat peritoneal macrophages was registered after introduction of 1% solution of monoclonal antibodies to receptors of granulocyte-macrophage colony-stimulating factor in homeopathic dilution C50 into the incubation medium.

EXAMPLE 184

Antibodies to Receptors of G-CSF

184A. The preparation of antibodies to receptors of granulocyte colony-stimulating factor in homeopathic potency C60 was administered to mice orally 2 times a day in the dose of 0.1 ml for 7 days. Increase in the number of granulocytes was noted, which indicated specific biological activity of the preparation.

EXAMPLE 185

Antibodies to Receptors of Macrophage Colony-Stimulating Factor

185A. The preparation of antibodies to receptors of macrophage colony-stimulating factor increased macrophage count in mice when administered orally in the dose of 0.1 ml of solution in homeopathic potency C50 for 5 days. Conclusion on biological activity of the preparation was drawn.

EXAMPLE 186

Antibodies to Receptors of TNFα

186A. Increase in longevity of mice with induced breast cancer du to administration of monoclonal antibodies to tumor necrosis factor α in homeopathic potency C50 was registered. The preparation was administered orally in form of a solution in the dose of 0.1 ml once a day for 4 weeks.

186B. An experiment aimed at assessment of biological activity of the preparation of monoclonal antibodies to the receptor of tumor necrosis factor α was performed. Increased level of Ca was registered in the cells of HeLa culture within 5 minutes after introduction of 1% of antibodies in homeopathic dilution C70 into the incubation medium, which indicates high biological activity of the said homeopathic preparation.

EXAMPLE 187

Antibodies to Receptors of TNFβ

187A. Patient S. aged 78 years complained of enlargement of a pigment spot on his right leg. The patient was prescribed intake of monoclonal antibodies to tumor necrosis factor β in form of a solution in homeopathic potency C60 in the dose of 10 ml twice a day. In the course of 3-week observation no progression of the disease was observed. Conclusion on the efficiency of the antibodies was drawn.

EXAMPLE 188

Antibodies to Oncostatin Receptors

188A. Ultra-low doses of monoclonal antibodies to oncostatin receptor were introduced into the cell culture of skin sarcoma of mice. It has been found out that the preparation of antibodies in homeopathic potency C50 inhibits proliferative activity of tumor cells.

EXAMPLE 189

Antibodies to Receptors of Transforming Growth Factor β

189A. Patient P. 61 years complained of stomachache. Gastroscopy revealed an ulcer of the small curvature of the stomach 1 cm in diameter. In view of inefficiency of conventional therapy the patient was suggested additional intake of monoclonal antibodies to receptor of transforming growth factor β in homeopathic potency C20 in the dose of 1 tablet 3 times a day. Repeated examination 2 weeks after revealed epithelization of the mucosa lesion.

EXAMPLE 190

Antibodies to Activin Receptors

190A. The effect of monoclonal antibodies to activin receptor upon contractile activity of rat uterus was assessed experimentally. The animals were orally administered solution of antibodies in homeopathic potency C60 in the dose of 0.1 ml for 7 days. After euthanasia contractile activity of uterine tissue was assessed. It has been found out that potentiated antibodies modulate oxytocine-stimulated contractile activity of rat uterine horn.

EXAMPLE 191

Antibodies to Inhibin Receptors

191A. Patient P. aged 34 years complained of pain in her groin. She had a history of adnexitis and adhesions in her abdominal cavity. Administration of antibodies to inhibin receptor in homeopathic potency C30 in the dose of 10 drops 3 times a day made it possible to control algesic syndrome within 5 days of treatment.

EXAMPLE 192

Antibodies to Chemokine Receptors

192A. Patient V. aged 57 years complained of lumbar pain irradiating to the lower extremities. The patient was established the diagnosis of radicular syndrome and radiculitis. Within the framework of complex therapy the patient was prescribed oral intake of monoclonal antibodies to chemokine receptor RANTES in homeopathic potency C200 in the dose of 5 ml of aqueous solution 3 times a day. Within 3 days disappearance of algesic syndrome was registered.

192B. Patient V. aged 59 years suffering from rheumatoid arthritis complained of enhancement of pain in his knee joints. He was suggested intake of antibodies to receptor of interleukin 8 (chemokine) in homeopathic potency C70 in the dose of 5 ml 3 times a day. Subsidence of algesic syndrome was registered after 4 days of treatment with the preparation.

EXAMPLE 193

Antibodies Immunoglobulin Receptors

193A. Patient N. aged 47 years complained of pain in her spine. The diagnosis of osteochondrosis was established in the course of examination. Intake of the preparation of antibodies immunoglobulin receptors in form of a solution in homeopathic potency C50 made it possible to eliminate algesic syndrome.

193B. Patient U. aged 56 years complained of night asthmatic fits occurring at night. The diagnosis of bronchial asthma was established and intake of monoclonal antibodies to poly-Ig-receptor in form of solution in homeopathic potency C50 in the dose of 10 drops per diem. In the course of 3 weeks of treatment no asthmatic fits were registered.

EXAMPLE 194

Antibodies to Immunoglobulins Fc-Receptors

194A. Patient D. 57 years complained of rhinitis, sneezing and itching in his nose. He was established the diagnosis of allergic rhinitis. Administration of the preparation of monoclonal antibodies to Fc-receptor in form of a solution in homeopathic potency C50 made it possible to eliminate symptoms of the disease within 2 days of treatment in the dose of 1 tablet 3 times a day.

EXAMPLE 195

Antibodies to Receptors CD (Cluster of Differentiation)

195A. Patient Zh. aged 56 years was admitted to a TB dispensary after a long period of medical supervision for tuberculoma of the segments I and II of the left lung. Upon admission the patient's condition was grave, he was running fever 39.5° C., suffered from dyspnea (respiration rate 26 per minute), his ESR was 60 mm per hour, sputum positive for *Mycobacterium tuberculosi*, Mantoux test with 2 tuberculin units (TU) was 3 mm (hypoergic reaction). As the patient was resistant to antituberculous preparations of the first row, he was prescribed ultra-low doses of activated monoclonal antibodies to the peptide fragment of human molecule CD4 (a mixture of homeopathic dilutions C12+C3O+C200)—in the dose of 1 sublingual tablet 5 times a day. 7 days after the beginning of treatment the patient's general condition improved, his body temperature was back to normal, he was no longer suffering from dyspnea, his ESR dropped to 24 mm per hour, bacterioexcretion stopped, Mantoux test with 2 tuberculin units reached 7 mm (normoergic reaction). 2 weeks after the beginning of treatment the patient's chest X-ray showed distinct positive dynamics. The treatment was recommended to be continued.

195B. Patient III. aged 24 years was admitted to the department of infectious diseases with the diagnosis of HIV-infection, disseminated form of AIDS, mycobacteriosis of skin integument, chronic herpetic infection. Upon admission the number of CD4+ cells was 300 per mcl. The patient was prescribed ultra-low doses of activated polyclonal rabbit antibodies to recombinant molecule of human CD4 (a mixture of homeopathic dilutions C12+C30+LM10)—in the dose of 1 sublingual tablet 5 times a day. 7 days after the beginning of treatment the patient's body temperature became normal, his general condition improved and symptoms of asthenia subsided. 3 weeks after the beginning of treatment the number of CD4+ cells reached 420 per mcl, symptoms of mycobacteriosis and chronic herpetic infection subsided, body temperature was stable 36.8, and the patient had gained 3 kg. The treatment was recommended to be continued.

195C. Patient E. aged 32 years was admitted to the department of infectious diseases with the diagnosis of exacerbation of chronic active viral hepatitis B. Upon admission the patient was running fever up to 38.5° C. and suffered from pronounced arthralgic syndrome and hemorrhages. In view of her resistance to conventional therapy the patient was prescribed ultralow doses of activated monoclonal antibodies to recombinant molecule of human CD4 (a mixture of homeopathic dilutions C12+C30+C200 in the dose of 1 sublingual tablet 5 times a day. 3 days after the beginning of treatment fever and arthralgia subsided along with a drop in serum levels of bilirubin ALT and AST had been suffering from. 10 days after the beginning of treatment exacerbation of chronic hepatitis was arrested. Maintenance treatment was recommended to be continued.

195D. Patient V. aged 27 years had been suffering from systemic lupus erythematosus for 8 years and was admitted to the hospital for an exacerbation of her condition. Her exacted diagnosis upon admission was systemic lupus erythematosus with high degree of activity with involvement of skin (exsudative erythema), joints (acute polyarthritis), serosae (dry pleurisy) and kidneys (diffuse glomerulonephritis). Upon admission the patient's body temperature was 38° C., marked loss of weight and lupus erythema were observed; blood hemoglobin level was 95 g/l., ESR 50 mm per hour, LE-cell count was 5:1000 leucocytes, antinuclear factor 1:128. In view of poor tolerance of glucocorticoid medications, the patient was prescribed ultralow doses of activated polyclonal rabbit antibodies to recombinant molecule of human CD4 (a mixture of homeopathic dilutions C12+C30+LM10)—in the dose of 1 sublingual tablet every 2 hours. 5 days after the beginning of treatment decrease in the activity of autoimmune process was registered (body temperature dropped to subfebrile level, symptoms of arthritis and serositis subsided, proteinuria decreased). 14 days after the beginning of treatment exacerbation of the disease was arrested, the patient's blood hemoglobin level reached 110 g/l, ESR dropped to 20 mm per hour, LE-cell count—to 1:1000 leucocytes and antinuclear factor—to 1:64. Maintenance treatment was recommended to be continued.

195E. Patient T. aged 70 years had been suffering from Alzheimer's disease (Alzheimer-type dementia) for 5 years. In view of progressive dementia and inefficient conventional therapy, the patient was prescribed ultra-low doses of activated polyclonal rabbit antibodies to recombinant molecule of human CD4 (a mixture of homeopathic dilutions C12+C3O+C200)—in the dose of 1 sublingual tablet 2 times a day. 12 weeks after the beginning of treatment improvement of memory and attention was noted along with more adequate behavior. Positron emission tomography performed 4 months after the beginning of treatment revealed reliable regression of symptoms of degenerative and vascular cerebral lesions typical for Alzheimer's disease. The treatment was recommended to be continued.

195F. Studies of the effects of activated forms of ultra-low doses of antibodies to the molecule CD4 upon induction of immunological tolerance in male rats of Wistar line (weighing 180-200 g) were carried out using the model of experimental adjuvant arthritis. After the induction of arthritis the rats were orally administered ultra-low doses of activated polyclonal rabbit antibodies to recombinant molecule of human CD4 (a mixture of homeopathic dilutions D6+C200) in the daily dose of 1.5 ml of aqueous solution along with oral administration of 0.5 mg of II type collagen (in form of aqueous solution). The results of assessment of severity of edema on the inflamed extremity 7 days after the beginning of treatment are presented in table 7.

TABLE 7

| Experimental group | Regression of edema of the extremity after 7 days, % |
|---|---|
| Control 1 (distillated water) | 12% |
| Control 2 (II type collagen) | 52% |
| Experiment 1 (anti-CD4) | 46% |
| Experiment 2 (anti-CD4 + II type collagen) | 78%, p(4-2) < 0.05 |

Conclusion: potentiated antibodies to CD4 molecule produce marked anti-inflammatory effect in adjuvant arthritis enhanced via induction of immunological tolerance when administered in combination with collagen.

195G. Patient S. aged 46 years was taking a course of treatment for eczema. She complained of itching and insufficient efficacy of local therapy. Administration of the solution of antibodies to CD4 in homeopathic potency C70 in the dose of 10 drops 3 times a day made it possible to reduce intensity of clinical manifestations of the disease. The course of treatment was recommended to be continued.

195H. Biological activity of ultra-low potentiated doses of antibodies to CD20 (calcium channel of B-lymphocytes) was assessed experimentally. It has been found out that introduction of 1% preparation into the incubation medium of human lymphocytes in homeopathic dilution C50 increased intracellular concentration of Ca ions. Conclusion on the presence of biological activity in this preparation was drawn.

EXAMPLE 196

Antibodies to Receptors of Complement System Components

196A. Patient O. aged 67 years was taking a course of treatment for trophic ulcer on the foot on the background of diabetes mellitus. Oral administration of antibodies to C4 complement receptor in homeopathic dilution C50, in the dose of 1 tablet 3 times a day made it possible to speed up healing and reduce severity of inflammatory reaction.

196B. The ability of 1% solution of monoclonal antibodies to C3b complement receptor to reduce intensity of hemolysis of erythrocytes when added to incubation medium in homeopathic dilution in the D6 potency was demonstrated experimentally, which led to the conclusion of specific biological activity of the said homeopathic preparation.

EXAMPLE 197

Antibodies to Receptors of Components of Histocompatibility Complex

197A. Patient R. aged 48 years had been suffering from chronic glomerulonephritis complicated with glomerulosclerosis, chronic kidney failure (CKF) and nephrogenic arterial hypertension for 27 years. In view of progressive CKF (up to $3^{rd}$ degree, creatinine level reaching 1000 mcM), the patient underwent donor kidney transplantation (with preceding HLA-typing) and simultaneous nephrectomy of primarily contracted kidneys. In view of symptoms of acute graft rejection having appeared on the $5^{th}$ day after the operation and intolerance for cyclosporine A the patient was prescribed activated form of monoclonal antibodies to HLA-A, B and DR molecules corresponding to the HLA-phenotype of donor kidney (a mixture of homeopathic dilutions C12+C30+C200) in the dose of 10 drops of aqueous solution per os every hour. 24 hours after the beginning of treatment general symptoms of rejection crisis (headache, anorexia, hyperthermia, leucocytosis) subsided, 3 days after the beginning of treatment creatinine clearance increased and proteinuria diminished. Reliable suppression of the in vitro reaction of blastic transformation of recipient's leukocytes in mixed culture with donor's leukocytes was demonstrated using laboratory methods. Administration of the preparation continued 3-5 times a day. The function of the graft remained satisfactory 14, 30 and 60 days after the transplantation, no symptoms of rejection appeared.

197B. Patient U. aged 36 years suffering from dilated cardiomyopathy was consulted 4 weeks after heart transplantation in view of appearance of graft rejection symptoms despite antibacterial and cytostatic (immunosuppressive) therapy. The patient was prescribed activated (potentiated) form of ultra-low dose of monoclonal antibodies to the composition of peptide fragments of molecules of the major histocompatibility complex HLA-A, B, C, G and DR belonging to the corresponding molecules of HLA-phenotype of donor heart (in a mixture of homeopathic dilutions C30+C 1000) in the dose of 1 tablet 3 times a day. 7 days after the beginning of treatment symptoms of graft rejection (and concomitant heart failure) subsided significantly, the recipient's condition became satisfactory. The treatment was recommended to be continued.

197C. Patient V. aged 19 years had been suffering from insulin-dependent diabetes mellitus (IDDM) for 5 years. In view of decrease in efficacy of insulin therapy and persistent hyperglycemia having developed after a viral infection the patient was prescribed a composition of monoclonal antibodies to the molecules of HLA corresponding to the basic haplotypes associated with juvenile IDDM, namely, B8, B15, B18, Dw3, Dw4 and DR4. Antibodies were prescribed in form of activated (potentiated) ultra-low doses (a mixture of homeopathic dilutions C12+C3O+C200) in the dose of 1 tablet 3 times a day. 3 days after the beginning of treatment, the patient's after meal glycemia decreased and 7 days later normal fasting blood glucose level was achieved. Within 2 weeks doses of administrated insulin were reduced by half 197D. Patient L. aged 42 years has been suffering from rheumatoid arthritis (RA) for 5 years). She is a HLA B27 carrier. The patient was admitted to the hospital in view of exacerbation of her condition with the exacted clinical diagnosis of rheumatoid arthritis with high degree of activity, polyarthritis with febrile syndrome. In view of intolerance for glucocorticosteroid preparations, the patient was prescribed polyclonal antibodies to synthetic peptide fragment of the HLA B27 molecule associated with rheumatoid arthritis. Antibodies were prescribed in form of activated (potentiated) ultra-low doses (a mixture of homeopathic dilutions. C12+C3O+C200)—in the dose of 1 sublingual tablet every 2 hours. 3 days after the beginning of treatment decrease in activity of the inflammatory process was registered (drop in body temperature to subfebrile level, subsiding arthritis symptoms). 10 days after the beginning of treatment exacerbation of the disease was arrested; maintenance treatment was recommended to be continued (in the dose of 1 tablet 3 times a day). Upon repeated examination 3 weeks later clinical remission of RA was registered.

197E. Depressed expression of the molecules of the I class of the major histocompatibility complex (MHC I) on tumor cells followed by reduction in efficiency of cell mechanisms of antitumor cytotoxicity accounts to a great extent for tumor progression in oncological diseases. In order to investigate the influence of activated forms of ultra-low doses of antibodies to the molecules of the I class of the MHC upon the course of tumor progression mice of the C57B1/6 line were administered 4-6 106 melanoma B-16 cells in 0.1 ml of saline solution in form of intramuscular injections into the thigh of the animal's hind paw. Mice of the experimental group received ultra-low doses of activated antibodies to the composition of peptide fragments of the murine molecules of MHC of the I class (a mixture of homeopathic dilutions D12+C30+LM2) in the dose of 0.2 ml aqueous solution per os 2 times a day. It has been shown that average life span of the mice in the experimental group was 60-80 days (as opposed to 30-40 days in the control group); both tumor mass and the number of metastases in mice treated with activated antibodies were significantly lower than in the control group.

197F. Oral administration of polyclonal antibodies to T-cell receptor in homeopathic potency C50 in the dose of 0.1 ml for 7 days enhanced engraftment of a skin graft, which was demonstrated in an experimental on mice.

197G. Patient K. aged 64 years complained of inefficacy of treatment for ankylosing spondiloarthritis. The patient was prescribed oral administration of antibodies to receptors of immunoglobulins of B-lymphocytes in homeopathic dilution C50 in the dose of 5 ml of aqueous solution 3 times a day. Due to this therapy intensity of algesic syndrome subsided within 5 days after the beginning of treatment.

Antibodies to Receptors of Thymus Hormones

EXAMPLE 198

Antibodies to Thymosin a Receptors

198A. Antibodies to thymosin al in homeopathic potency C50 stimulated sensitivity of rosette forming cells of the spleen of thymectomized mice to inhibitory effect of azathioprine, which indicates the preparation possess specific differentiating activity.

EXAMPLE 199

Antibodies to Receptors Offactors of Adhesion and Intercellular Interactions

199A. Patient R. aged 65 years complained of poor healing of a burn on his hand. The patient was prescribed the preparation of antibodies to selectin receptors in homeopathic dilution C50 in the dose of 5 ml 3 times a day. Stimulation of epithelization of the wound surface was observed after 5 days of therapy.

199B. Stimulation of the reaction of blast-transformation of lymphocytes was registered in mice having been orally administered monoclonal antibodies to mannose phosphate receptor in form of aqueous solution in homeopathic dilution C60 in the dose of 0.1 ml per diem for 7 days.

199C. Increase in Ca ion concentration was registered in the cells of primary culture of human fibroblasts after addition of 1% solution of polyclonal antibodies to integrin receptors in homeopathic dilution C70.

199D. Monoclonal antibodies to occludine receptors caused change of membrane potential of keratinocytes in conditions of primary cell culture upon introduction of 1% solution of antibodies in homeopathic dilution C50 into the medium.

199E. Patient R aged 67 years complained of pain in his chest. Examination revealed ischemic heart disease due to atherosclerosis. Prescribed oral administration of ultra-low doses of antibodies to cadguerin receptor in homeopathic potency C200 in the dose of 1 tablet 3 times a day made it possible to control symptoms of stenocardia.

199F. Patient A. aged 46 years complained of nausea and pain in the epigastric area. Examination revealed gastric ulcer. Oral administration of the preparation of monoclonal antibodies to β-catenin receptor in homeopathic potency C50 in the dose of 10 ml 3 times a day was included into complex therapy in order to promote healing. Administration of the preparation made it possible to control symptoms of the disease within 5 days after the beginning of therapy.

EXAMPLE 200

Antibodies to ATP-ases

200A. Example. Patient R. aged 57 years complained of palpitation. Examination revealed complete cardiac arrhythmia due to ischemic heart disease. The patient was prescribed oral intake of antibodies to Ca-ATP-ase in homeopathic dilution C50 in the dose of 10 drops 3 times a day. 3 days later elimination of arrhythmia was registered.

EXAMPLE 201

Antibodies to Amino Acid Carriers

201A. Patient P. aged 54 years complained of pain in his right infracostal area and nausea. He had a history of chronic drug hepatitis. He was suggested oral intake of polyclonal antibodies to carriers of amino acids (glycine, glutamic acid, asparginic acid) in homeopathic dilution C100 in the dose of 5 ml twice a day. Within 5 days betterment of his condition was registered.

EXAMPLE 202

Antibodies to Glucose Carriers

202A. Patient L. aged 63 years suffering from type II diabetes mellitus complained of dryness of mouth, weakness, vertigo and inefficacy of hypoglycemic preparations. The patient was prescribed oral intake of monoclonal antibodies to lactose carrier in homeopathic dilution C50 in the dose of 5 ml 3 times a day. 2 days later disappearance of symptoms of hyperglycemia was noted.

EXAMPLE 203

Antibodies to Endogenous Factors Regulating or Involved in Carbohydrate or Lipid Metabolism 203A. Patient A. aged 23 years has been suffering from 1 type diabetes mellitus for 10 years. In view of decrease in efficiency of insulin therapy the patient was prescribed ultra-low doses of activated form of monoclonal antibodies to insulin (a mixture of homeopathic dilutions C12+C30+C200) in the dose of 1 sublingual tablet 2 times a day. 10 days after the beginning of treatment a significant increase in the efficiency of insulin therapy was registered, which made it possible to reduce the administered daily dose of insulin from 30 unit to 15 units. 5 weeks after the beginning of treatment the daily dose of insulin was reduced to 5 units with stable normoglycemia at that.

203B. Patient 0. aged 11 years suffered from I type diabetes mellitus. In view of progressive impairment of endocrine function of pancreas the patient was prescribed polyclonal rabbit antibodies to amylin (a mixture of homeopathic dilutions C12+C30+C200) in the dose of 1 sublingual tablet 2 times a day. 2 weeks after the beginning of treatment the efficiency of treatment with insulin increased, which made it possible to reduce the administered dose of insulin by half.

203C. Patient K aged 71 years suffering from insulin-independent diabetes mellitus complained of an ulcer on his foot that was not healing for 4 weeks. The diagnosis of diabetic foot was established and the patient was prescribed a complex preparation consisting of polyclonal rabbit antibodies to the receptor if insulin-mimetic growth factor 1 (a mixture of homeopathic dilutions C12+C30+C200) and monoclonal antibodies to insulin receptor (in homeopathic dilution C 100) in the dose of 1 tablet 3 times a day. 2 weeks after the beginning of treatment healing of the ulcer was registered along with decrease in tolerance for insulin and stabilization of glycemia.

203D. Patient T. aged 40 years had been suffering from rapidly progressing type I diabetes mellitus. In the course of the last year there have appeared symptoms of complications such as diabetic nephropathy (proteinuria up to 0.5 g/l), skin lesions (trophic ulcers on legs), neuropathy (skin itching, reduced sensitivity, pricking sensations and burning pain in the legs). In addition to insulin therapy the patient was prescribed ultra-low doses of activated form of monoclonal antibodies to C-peptide (a mixture of homeopathic dilutions C12+C30+C200) in the dose of 1 sublingual tablet 3 times a day. 3 weeks after the beginning of treatment enhancement of efficacy of insulin therapy was registered (which made it possible to reduce by half the doses of insulin prescribed to the patient) along with reduction of proteinuria to 0.1 g/l, healing of ulcers in the legs, subsiding of skin itching and other symptoms of neuropathy. The treatment was recommended to be continued.

203E. Patient G. aged 63 years sought medical advice for decompensated insulin-independent diabetes mellitus. He was suggested intake of monoclonal antibodies to insulin receptors in C200 homeopathic dilution in the dose of 1 tablet 3 times a day. 5 days after the beginning of treatment severity of clinical symptoms of hyperglycemia was reduced and within 20 days stable normalization of blood glucose level was achieved along with increased tolerance for physical strain and drop in body weight index from 37 to 36 kg/m2.

203F. Patient D. aged 32 years complaining of headache and palpitation underwent a preventive overall check-up, which revealed arterial hypertension (up to 160/85 mm of mercury column) and hyperglycemia (up to 7.5 mmole/l fasting) with elevated catecholamines blood level. The patient was prescribed a composition of activated ultra-low doses of goat polyclonal antibodies to adrenaline (a mixture of homeopathic dilutions C12+C30+C200) and activated ultra-low doses of monoclonal antibodies to noradrenalin (a mixture of homeopathic dilutions C12-1-C30+C200) in the dose of 10 drops of aqueous solution 3 times a day. 2 weeks after the beginning of treatment the patient's blood pressure was 125/80 mm of mercury column and fasting serum glucose level 5.5 mmole/l/l.

203G. Patient V. aged 34 years with a long history of diabetes mellitus was admitted to the hospital in view of insufficient efficacy of insulin therapy. In addition to the diet the patient was prescribed a preparation of antibodies to glucose-carrying protein in homeopathic dilution C1000 in the dose of 1 tablet twice a day. 10-day course of treatment with the preparation of antibodies made it possible to reduce tolerance for insulin, achieve stabilization of blood glucose on the level of 10-12 mmole/l and reduce daily dose of insulin to no more than 24 units.

203H. Patient B. aged 62 years suffering from decompensated insulin-independent diabetes mellitus and alimentary obesity, was established the diagnosis of obliterating atherosclerosis of femoral arteries and was prescribed potentiated ultra-low doses of polyclonal antibodies to glucokinase (a mixture of homeopathic dilutions C12+C30+C200) in the dose of 1 sublingual tablet 3 times a day, which made it possible to eliminate resistance to insulin within 4 weeks after the beginning of treatment and reduce clinical (intermittent claudicating) and angiographic symptoms of stenosis due to atherosclerosis of femoral arteries.

203I. Patient A. aged 27 years was found to have developed glucosuria and hyperglycemia in her $22^{nd}$ week of pregnancy (8.5 mmole/l fasting). The established diagnosis was gestational diabetes mellitus. The patient was prescribed potentiated (by exposure to acoustic generator—frequency 20 Hrz—in combination multiple consecutive dilution) ultra-low doses of monoclonal antibodies to α-glucosidase fragment (a mixture of dilutions C12+C30+C200) in the dose of 10 ml of aqueous solution 3 times a day. 7 days after the beginning of treatment the patient's blood glucose level was normal (5.2 mmole/l fasting), and glucosuria was absent.

203J. The parents of the patient I. aged 8 years have noticed their child develop enuresis, polyuria and polydipsia after acute respiratory viral infection. Examination revealed elevation of serum glucose level to 7.7 mmole/l. The patient was established the diagnosis of juvenile form of insulin-dependent diabetes mellitus and was prescribed ultra-low doses of monoclonal antibodies to glutamate decarboxylase (a mixture of homeopathic dilutions C12+C30+C200) in the dose of 3 sublingual grains 3 times a day. Repeated examination 14 days after the beginning of treatment revealed glycemia level 5.8 mmole/l fasting; the parents reported absence of enuresis, polyuria and polydipsia. Maintaining treatment was recommended.

203K. Patient M. aged 45 years developed hypothyrosis-associated hyperglycemia. In view of insufficient efficacy of the treatment with L-thyroxin the patient was prescribed ultra-low doses of polyclonal antibodies obtained by means of immunization of a composition of thyroxin and triiodothyronine (a mixture of homeopathic dilutions C12+C30+C200) in the dose of 1 tablet 3 times a day. 3 weeks after the beginning of treatment normalization of serum glucose level was registered along with subsidence of severity of hypothyrosis symptoms.

203L. Patient V. aged 60 years has been under supervision of an endocrinologist for subcompensated type II diabetes mellitus with manifestations of non-proliferative diabetic retinopathy and hypercholesterinemia associated with III degree of obesity (body weight index BWI=30). Hypoglycemic preparations and insulin preparations proved unable to control glycemia level efficiently enough. The patient was prescribed monoclonal antibodies to insulin a receptor (a mixture of homeopathic dilutions D6+C30+C200) in the dose of 5 drops of alcohol solution twice a day. Round-the-clock monitoring of glycemia level undertaken a week after the beginning of treatment revealed marked depression of tolerance of insulin. 3 weeks after the beginning of treatment administration of insulin was discontinued and the patient was put on manninyl alone. 5 weeks after the beginning of treatment the patient reported improvement of his general state of health and enhanced tolerance of physical strain, his BWI was reduced to 27 and fasting glycemia level—to 6 mmole/l. The patient was switched to monotherapy with the preparation of antibodies to insulin receptor in the dose of 5 drops twice a day.

203M. Patient K. aged 50 years suffers from alimentary obesity; his body weight index (BWI) is 39. A regular examination has revealed fasting glycemia level of 8.0 mmole/l. The patient was prescribed potentiated ultra-low doses of monoclonal antibodies to uncoupling protein 2 (a mixture of homeopathic dilutions C30+C200+LM2) in the dose of 1 tablet twice a day. 4 weeks after the beginning of treatment the patient's fasting glycemia level dropped to 6.5 mmole/l and his BWI—to 36 kg/m2. The treatment was recommended to be continued.

203N. Patient M. aged 44 years complained of dyspnea and tachycardia. Examination revealed II degree of obesity. The patient was recommended intake of potentiated solution of antibodies to neuropeptide Y in homeopathic dilution C30 in the dose of 10 drops before meals. Administration of the preparation made it possible to reduce the patient's weight by 5% within 4 weeks and enhance his tolerance of physical strain.

203O. Food behavior of rats in the conditions of zoosocial stress associated with lowering of body weight was investigated experimentally. Administration of the solution of potentiated antibodies to the fragment of receptor of neuropeptide Y in C200 homeopathic dilution in the dose of 0.1 ml to the animals of experimental group for 7 days resulted in restoration of the animals' body weight up to 90% of the level of intact control animals.

203P. Patient R. aged 37 years complained of dramatic increase of body weight (12 kg of weight gain within 2 months), excessive feeling of hunger, low mood and tearfulness. She was suggested intake of ultra-low doses of activated form of antibodies to serotonin receptors (a mixture of homeopathic dilutions C12+C30+C200) in the dose of 1 teaspoonful of aqueous solution 3 times a day. Repeated examination 1 week after revealed reduced food motivation, 2 kg loss of body weight and betterment of the mood. The course of treatment was recommended to be continued.

203Q. Patient T. aged 46 years complained of insomnia, excessive food consumption and dyspnea. Examination revealed III degree of obesity, body weight index 40 kg/m2. Intake of potentiated ultra-low doses of antibodies to bombezin (a mixture of homeopathic dilutions C12+C30+C200) in the dose of 5 drops of aqueous solution at bedtime made it possible to normalize the patient's demand of food and reduce her body weight to 36 kg/m2 within 4 weeks.

203R. Patient D. aged 36 years was taking a course of treatment for obesity and complained of inefficiency of diet therapy. Oral administration of the solution of polyclonal antibodies to leptin in C200 homeopathic dilution in the dose of 10 drops 3 times a day made it possible to reduce the patient's body weight by 10% within 6 weeks of treatment.

203S. Experimental study of the influence of ultra-low doses of activated form of antibodies to leptin receptor upon rats' food behavior was carried out. Oral administration of monoclonal antibodies to the fragment of leptin receptor in C200 homeopathic dilution to rats on fat-enriched diet in the dose of 0.5 ml of aqueous solution twice a day reduced the quotient of food consumption by 25% within 7 days and resulted in the animals' body weight loss by 15%.

203T. Patient N. aged 32 years complained of dramatic body weight loss, sleeping disorders and headache. The diagnosis of neurotic anorexia was established based on the results of examination. Intake of the solution of antibodies to cholecystokinine in homeopathic dilution C1000 in the dose of 1 tablet 2 times a day made it possible to restore the patient's appetite and sleep and eliminate headache within 3 weeks after the beginning of treatment; her body weight increased by 5 kg.

203U. Patient F. aged 57 years was taking a course of chemotherapy for III grade prostate cancer. In order to control manifestations of cachexy the patient was prescribed a composition comprising potentiated antibodies to cholecystokinine receptor in C200 homeopathic dilution and potentiated antibodies to tumor necrosis factor a (a mixture of homeopathic dilutions C12+C30+C200) in the dose of 1 tablet twice a day, which made it possible to prevent further loss of body weight.

203V. Patient R. aged 47 years suffering from III degree of obesity complained of muscle weakness and thirst. Based on the results of examination the diagnosis of decompensated II type diabetes mellitus was established. Oral administration of ultra-low doses of monoclonal antibodies to recombinant tumor necrosis factor a (a mixture of homeopathic dilutions C12+C30+C200) in the dose of 5 drops of aqueous solution 3 times a day made it possible to reduce the patient's body weight by 10% in the course of 3 weeks of treatment and achieve normoglycemia.

203W. Administration of the preparation of antibodies to TNF-α in form of the solution in homeopathic dilution C1000 to rats suffering from carbone tetrachloride-induced hepatic failure stimulated food behavior and caused increase of body weight by 10% in comparison with the control group in the course of 10 days of the experiment.

203X. Patient M. aged 51 years complained of nausea, thirst, polyuria and skin itching. Examination revealed elevated blood glucose level—up to 8.1 mmole/l fasting. The patient was prescribed the preparation of antibodies to glucose carriers (GluC) in form of aqueous solution in C200 homeopathic dilution in the dose of 10 drops 3 times a day. 1 week later blood glucose level was back to normal and the patient reported lack of thirst, polyuria and skin itching.

203Y. Patient P. aged 37 years complained of sweating, tachycardia, chills and irritability. Based on the results of examination the patient was established the diagnosis of insuloma and was suggested oral intake of potentiated solution of antibodies to insulin in homeopathic dilution C50 in the dose of 10 drops 3 times a day. Upon repeated examination 10 days later the patient reported that her irritability and hyperhydrosis subsided along with betterment of her general state of health. The course of treatment was recommended to be continued.

203Z. Patient S. aged 38 years suffering from 1 type diabetes mellitus was taken to the hospital in view of decompensation of his condition. Administration of ultra-low doses of polyclonal antibodies to receptors of glucose of Langerhans cells in homeopathic dilution C30 in the dose of 5 grains 3 times a day made it possible to enhance sensitivity to insulin therapy and to reduce the dose of administrated insulin by half 10 days after the beginning of treatment.

203AA. Patient L. aged 47 years complained of skin itching, polyuria and muscle weakness. Based on the results of the examination the patient was found to suffer from type II of diabetes mellitus. The patient was recommended intake of the preparation of antibodies to thyrosinkinase of insulin receptor in C200 homeopathic dilution in the dose of 10 drops 3 times a day. 5 days later disappearance of itching and normalization of serum glycemia level were registered.

203BB. Biological activity of activated form of ultra-low doses of antibodies to the substrate of insulin receptor 1 (SIR-1) was investigated experimentally. 1% solution of potentiated antibodies in homeopathic dilution C30 was introduced into the cell culture of human fibroblasts. 25% increase of proliferative activity of the cells was registered after 24 hours of incubation.

203CC. Biological activity of the preparation of antibodies to thyrosinkinase of insulin receptor was studied in experiments on rats suffering from alloxan diabetes. Oral administration of the solution of antibodies in homeopathic dilution C1000 in the dose of 0.2 ml every day for 3 weeks resulted in reliable 30% increase of the animals' survival rate.

203DD. Patient R. aged 46 years complained of obesity and insufficient efficacy of diet therapy. Administration of ultra-low doses of monoclonal antibodies to glycogensynthase in C200 homeopathic dilution in the dose of 1 tablet twice a day made it possible to reduce the patient's weight by 5% within 20 days of therapy.

20EE. In order to investigate experimentally the biological activity of ultra-low doses of antibodies to lipase the preparation of potentiated solution of monoclonal antibodies to lipase in C200 homeopathic dilution was administered to the mice in the dose of 0.1 ml of aqueous solution per os for 3 days. 20% increase of blood concentration of free fatty acids and glucose was registered. Conclusion on the presence of specific biological activity of the said preparation was drawn.

203FF. Patient O. aged 58 years suffering from obesity-associated ischemic heart disease complained of retrosternal pain at physical strain, palpitation and dyspnea. Intake of potentiated monoclonal antibodies to β-adrenoreceptors (a mixture of homeopathic dilutions C12+C30+C200) in the dose of 1 tablet 3 times a day made it possible to reduce the patient's body weight by 5 kg within 2 weeks and achieve subsidence of stenocardia symptoms.

203GG. Patient G. aged 64 years complained of palpitations and high blood pressure. Examination revealed hypercholesterinemia and obesity. The patient was prescribed administration of potentiated antibodies to the complex of low density and extra-low density lipoproteins (a mixture of homeopathic dilutions C12+C30+C200) in the dose of 1 tablet twice a day. After 4 weeks of treatment drop of the serum level of LDLP and ELDLP was registered along with reduction of body weight by 5 kg and disappearance of tachycardia.

203HH. Patient N. aged 65 years complained of dizziness and memory loss. Examination revealed pronounced cerebral atherosclerosis due to hypercholesterinemia. Administration of potentiated antibodies to apolipoproteide complex (a mixture of homeopathic dilutions C12+C30+C200) in the dose of 5 drops of aqueous solution twice a day made it possible to normalize cholesterol level and eliminate dizziness within 4 weeks of treatment.

203II. Patient V. aged 34 years complained of chills, weakness and hyperhydrosis. Examination revealed hypoglycemia. Administration of ultra-low doses of monoclonal antibodies to glucagon (a mixture of homeopathic dilutions C12+C30+C200) in the dose of 1 tablet twice a day made it possible to control hypoglycemia within 3 days of treatment; the patient's condition was back to normal.

203JJ. Patient Sh. aged 28 years complained of tachycardia, agitation, bulimia and loss of body weight. Examination revealed symptoms of thyrotoxicosis. The patient was prescribed combined intake of potentiated monoclonal antibodies to the fragment of triiodthyronine receptor in C200 homeopathic dilution and potentiated affinely purified polyclonal antibodies to thyroxin (a mixture of homeopathic dilutions C12+C30+C200) in the dose of 5 grains of each preparation twice a day, which made it possible to eliminate symptoms of hyperthyrosis within 20 days of treatment. Gain of 3 kg of body weight was registered.

203KK. Biological activity of ultra-low doses of potentiated antibodies to lipoprotein lipase was investigated experimentally. Rats were orally administered monoclonal antibodies to the enzyme fragment 20 amino acids long in C200 homeopathic dilution in the dose of 0.2 ml of aqueous solution for 7 days. Reliable loss of animals' body weight was registered along with decrease of their subcutaneous fat layer.

203LL. Patient R. aged 15 years was admitted to the hospital with blood pressure 100/60 and 20% body weight deficit in comparison with age standard. Administration of potentiated monoclonal antibodies to somatotropic hormone (a mixture of homeopathic dilutions C12+C30+C200) in the dose of 5 ml 3 times a day made it possible to eliminate body weight deficit within 2 weeks of treatment.

203MM. Biological activity of antibodies to somatotropic hormone receptor was investigated experimentally on cell culture of human fibroblasts. Introduction of ultra-low doses of potentiated antibodies in C200 homeopathic dilution into the incubation medium in the 1:1000 ratio resulted in increase of glucose consumption by the cells and stimulation of their proliferative activity by 30% within 24 hours of incubation.

203NN. Patient K. aged 36 years complained of excessive body weight, dyspnea and inefficacy of therapy. Administration of potentiated antibodies to somatocrinin in homeopathic dilution C30 in the dose of 10 drops of aqueous solution before meals made it possible to reduce the patient's body weight by 4 kg within 3 weeks of therapy.

203OO. It has been demonstrated in an experiment on mice that everyday oral administration of 0.2 ml of the solution of potentiated monoclonal antibodies to somatostatin receptor in C200 homeopathic dilution results in the animals gain of 5% body weight after 7 days of treatment.

203PP. Patient U. aged 54 years complained of excessive body weight and dyspnea. Examination revealed gynoid type obesity and ischemic heart disease. The patient was prescribed oral intake of potentiated monoclonal antibodies to estrogen receptor in C200 homeopathic dilution in the dose of 10 drops before meals. Within 2 weeks 4 kg loss of body weight was registered along with elimination of tachycardia.

203QQ. Patient R. aged 46 years complained of lack of appetite, weakness and dizziness. Examination revealed lowering of blood glucose level as well as that of free fatty acids. The patient was suggested intake of ultra-low doses of monoclonal antibodies to glucocorticoid receptor (a mixture of homeopathic dilutions C12+C30+C200) in the dose of 5 ml of aqueous solution twice a day. Normal blood level of glucose and fatty acids was achieved within 3 days.

EXAMPLE 204

Antibodies to Substances Involved in Regulation of Vascular Tone

204A. In order to study the effect of activated forms of ultra-low doses of antibodies (AB) angiotensin II receptor (anti-R-angiotensin-II-c) upon blood pressure (BP) in ISIAH line rats with hereditary arterial hypertension the blood pressure on their tail artery was measured 5 days after oral administration of 0.5 ml of aqueous solution of dynamized polyclonal rabbit antibodies to the C-end fragment of human angiotensin II receptor in form of homeopathic dilutions C12+C30+C200. Results of blood pressure measurements prior and after administration of the preparation are shown in the table 8. The data presented in the table 8 indicate that the preparation possesses hypotensive effect.

TABLE 8

Effect of Anti-R-angiotensin-II-c preparation upon the BP of ISIAH line hypertensive rats

| No. | No. of Rats | Initial average BP (based on three measurements) | BP after 5 days of treat | BP depression rate (3) – (4) | BP 7 days after treatment with the preparation | BP increase rate (6) – (4) | BP After the second day of treatment | BP depression rate (6) – (8) |
|---|---|---|---|---|---|---|---|---|
| 1 | 31 | 175 | 151 | 24 | 166 | 15 | 150 | 16 |
| 2 | 32 | 184 | 163 | 21 | 186 | 23 | 170 | 16 |
| 3 | 33 | 186 | 169 | 17 | 165 | –4 | 150 | 15 |
| 4 | 4 | 171 | 165 | 6 | 189 | 24 | 170 | 19 |

TABLE 8-continued

Effect of Anti-R-angiotensin-II-c preparation upon the BP of ISIAH line hypertensive rats

| No. | No. of Rats | Initial average BP (based on three measurements) | BP after 5 days of treat | BP depression rate (3) − (4) | BP 7 days after treatment with the preparation | BP increase rate (6) − (4) | BP After the second day of treatment | BP depression rate (6) − (8) |
|---|---|---|---|---|---|---|---|---|
| 5 | 34 | 187 | 172 | 15 | 190 | 18 | 175 | 15 |
| 6 | 10 | 181 | 166 | 15 | 185 | 19 | 170 | 15 |
| 7 | 11 | 171 | 162 | 9 | 169 | 7 | 155 | 14 |
| 8 | 38 | 182 | 160 | 22 | 185 | 25 | 165 | 20 |
| 9 | 16 | 180 | 169 | 11 | 183 | 14 | 165 | 18 |
| 10 | 19 | 186 | 166 | 20 | 186 | 20 | 170 | 16 |
|  | X ± m | 180 ± 1.91 | 164 ± 1.86 | 16 ± 1.88 | 180 ± 3.08 | 16.1 ± 2.81 | 164 ± 2.87 | 16.4 ± 0.62 |

204B. In order to study the effect of activated forms of ultra-low doses of antibodies (AB) angiotensin II upon blood pressure (BP) in ISIAH line rats with hereditary arterial hypertension the blood pressure on their tail artery was measured 5 days after oral administration of 0.5 ml of aqueous solution of dynamized monoclonal antibodies to angiotensin II in form of the mixture of homeopathic dilutions C12+C30+C200. Results of blood pressure measurements prior and after administration of the preparation are shown in table 9. The data presented in the table indicate that the preparation possesses marked hypotensive effect.

TABLE 9

| No. of Rats 1 | Initial BP 2 | BP taken 3 hours after a single-dose administration of the preparation 3 | BP after 5 day treatment with the preparation 4 | BP changes resulting from single-dose treatment (difference between 3 and 2) 5 | BP changes resulting from 5-day treatment (differences between 4 and 2) 6 |
|---|---|---|---|---|---|
| 11 | 200 | 167 | 161 | −33 | −39 |
| 12 | 189 | 150 | 189 | −39 | 0.0 |
| 16 | 200 | 189 | 160 | −11 | −40 |
| 19 | 167 | 178 | 144 | 11 | −23 |
| 21 | 211 | 189 | 167 | −22 | −44 |
| 22 | 178 | 167 | 205 | −11 | 27 |
| 23 | 189 | 167 | 205 | −22 | 16 |
| 27 | 178 | 194 | 200 | 16 | 22 |
| 28 | 178 | 172 | 144 | −6 | −34 |
| 30 | 189 | 178 | 178 | −11 | −11 |
| Mean ± Error in Mean | 187.9 ± 4.16 | 175.1 ± 4.21 | 175.3 ± 7.48 | −12.8* ± 5.49 (p < 0.05) | −12.6 ± 8.65 |

204C. Patient D. aged 50 years has a 10-year history of essential hypertension; based on the results of clinical and instrumental examination the patient's condition was diagnosed as 2-nd degree morbus hypertonicus with predominant affliction of the heart, left ventricle myocardial hypertrophy. The patient was prescribed administration of polyclonal rabbit antibodies to the C-end fragment of human angiotensin II receptor in form of the mixture of homeopathic dilutions C12+C3O+C200 in the dose of 1 tablet twice a day. 7 days after the beginning of treatment the patient's BP was found to stabilize on the level of 130-135/85 mm of mercury column 2 months days after the beginning of treatment the ECG findings showed regression of hypertrophy and of left ventricular overload.

204D. Patient Zh. aged 50 years has a 10-year history of morbus hypertonicus with predominant affliction of the kidneys. Prior to administration of hypotensive therapy her BP reached 180/110 mm of mercury column. During her visit to a doctor she complained of headaches, edema and excessive fatigability. As conventional anti-hypertension therapy was not efficient enough in her case she was prescribed monoclonal antibodies to angiotensin II receptor (a mixture of homeopathic dilutions C12+C30+C200) and monoclonal antibodies to angiotensin II (a mixture of homeopathic dilutions D12+C30+LM2) in the dose of 1 tablet twice a day. 7 days after the beginning of treatment the patient stated an increase in her working capacity, reduction in edema and stable drop of BP to the level of 140/95 mm of mercury column. 2 months days after the beginning of treatment her BP was found to stabilize on the level of 130/90 mm of mercury column, her proteinuria level dropped from 0.3 g/l to 0.06 g/l.

204E. Patient V. aged 42 years has a 5-year history of Cushing's disease of moderate severity. She was prescribed a complex preparation containing polyclonal rabbit antibodies to angiotensin II receptor (a mixture of homeopathic dilutions C12+C3O+C200) and monoclonal antibodies to adrenocorticotropic hormone (a mixture of homeopathic dilutions C12+C3O+C200) in the dose of 1 tablet 3 times a day for treatment of her marked arterial hypertension (up to 175/100 mm of mercury column). 2 weeks after the beginning of treatment the patient's BP dropped to 140/90 mm of mercury column along with amelioration of her general state of health. 1 month after the beginning of treatment her serum ACTH level was found to drop from 200 to 130 pg/ml and her body weight index from 37 to 35 kg/m2. The patient was recommended to continue her treatment course.

204F. Patient N. aged 52 years suffers from ischemic heart disease, exertional angina, functional class III, and obliterating atherosclerosis of the vessels of his lower extremities: He was prescribed the activated form of polyclonal rabbit antibodies to the C-end fragment of human endothelial NO synthase (nitrogen oxide synthase type III) (a mixture of homeopathic dilutions C12+C30+C200) in the dose of 1 tablet 3 times a day as monotherapy. 7 days after the beginning of treatment the patient started feeling better and stated an increase in his tolerance for physical exertion. He started feeling pain in his lower extremities after 30-40 minutes of quick walking (it used to be 10-15 minutes). 3 weeks after the beginning of treatment the patient's ECG showed regression of ischemic lesions in left ventricular myocardium and his exertional angina was henceforth attributed to the functional class II.

204G. Patient 0. aged 67 years suffers from morbus hypertonicus associated with decompensated diabetes mellitus type 2. In the course of last 2 years she developed symptoms of circulatory insufficiency (cardiac asthma and congestive lung rales) and in the course of last 2 months peripheral edema of her lower extremities was added to the clinical picture. As conventional therapy proved not efficient enough a complex preparation containing activated form of monoclonal antibodies to tumor necrosis factor-$\alpha$ (TNF-$\alpha$) (a mixture of homeopathic dilutions C12+C30+C200) and activated form of antibodies to (TNF-$\alpha$) receptor (a mixture of homeopathic dilutions D12+LM10) in the dose of 1 tablet twice a day. 10 days after the beginning of treatment regression of circulatory insufficiency symptoms was registered manifested by disappearance of peripheral edema and congestive lung symptoms along with amelioration of her general state of health. The patient managed to reduce the dose of insulin required for efficient control of her glycemia from 40 to 20 units a day.

204H. Patient D. aged 62 years suffers from discirculatory encephalopathy due to atherosclerosis with predominant affliction of cerebral arteries. He presents a history of numerous episodes of transitory cerebral ischemia (TCI). During a fresh TCI episode with right-side hemiparesis and aphasia the patient was prescribed polyclonal antibodies to nitrogen oxide endothelial synthase (a mixture of homeopathic dilutions C12+C30+C200) in the dose of (sublingual tablet every 30 minutes. 4 hours after the beginning of treatment regression of cerebral ischemic symptoms was registered (subsidence of dizziness, tinnitus, right hand weakness and aphasia). 12 hours after the beginning of treatment the TCI episode was completely arrested.

204I. Patient M. aged 32 years suffers from Raynaud syndrome associated with systemic connective tissue disease. For progressive worsening of the course of his illness the patient was prescribed monoclonal antibodies to nitrogen oxide endothelial synthase (a mixture of homeopathic dilutions C12+C30+C200) in the dose of 1 tablet 3 times a day. 7 days after the beginning of treatment the patient stated a drop in frequency, intensity and duration of paroxysms of pain after cooling of his extremities. The patient was recommended to continue the treatment course.

204J. Patient V. aged 19 years was examined for headaches and vertigo. His condition was diagnosed as hypotensive form of neuro-circulatory asthenia (BP 80/60 mm of mercury column.). the patient was prescribed monoclonal antibodies to angiotensin I (a mixture of homeopathic dilutions C12+C30+C200) in combination with activated form of angiotensin I (a mixture of homeopathic dilutions C12+C30+C200) in the dose of 1 tablet 3 times a day. 2 weeks after the beginning of treatment the patient's BP was noticed to stabilize on the level of 100/80 mm of mercury column along with drop in frequency and intensity of headache episodes.

204K. Patient O. aged 42 years was examined at the Scientific Research Institute of Labor Medicine, where he was established the diagnosis of vibratory disease, local form, 2-nd grade. As the patient suffered from angiospastic syndrome associated with vegeto-sensory polyneuropathy and trophic skin disorders resistant to conventional therapy he was prescribed administration of polyclonal rabbit antibodies to endothelin 1 (a mixture of homeopathic dilutions C12+C3O+C200) in combination with monoclonal antibodies to bradykinin (a mixture of homeopathic dilutions D6+C30+LM2) in the dose of 1 tablet 3 times a day. 10 days after the beginning of treatment reduction in intensity of the patient's angiospastic syndrome was registered and confirmed by capillaroscopic findings. 2 months after the beginning of treatment marked regression of polyneuropathy and trophic skin disorders was noticed. The patient was recommended to continue the treatment course.

204L. Patient S., aged 46, had been sent to hospital within several years because of hypertension crises. Once a crisis had been arrested the patient was put on the maintaining therapy with captopril. In order to enhance the hypotensive effect a C12 dilution of potentiated antibodies to RENIN in a dose of 1 tablet 2 times a day was added to the treatment. Combined therapy made it possible for the first time in many years to lower the patient's blood pressure to 140/100 mm Hg. The patient's condition is satisfactory.

204M. Patient H., aged 38, suffered from therapy-resistant essential hypertension. The closest to optimal drug for the patient was ENALAPRIL, which made it possible to stabilize the blood pressure at 160/110 mm Hg. The treatment protocol with an added intake of a D24 dilution of potentiated polyclonal antibodies to angiotensin-converting enzyme (in a dose of 15 drops of alcohol solution 3 times a day) made it possible to lower the patient's systolic pressure to 120-130 mm Hg. The patient had not presented any complaints for 2 months.

204N. Patient D., aged 19, had been suffering from therapy-resistant arterial hypertension for 6 months. The use of a C12 dilution of potentiated antibodies to ANGIOTENSIN II in a dose of 1 tablet 2 times a day made it possible to stabilize the patient's condition: no complaints, the blood pressure reached 120/75 mm Hg.

Antibodies to Enzymes or to Endogenous Regulators of Enzyme Activity

EXAMPLE 205

Anti-NO Synthase

205A. In order to study the effect of activated forms of ultra-low doses of antibodies to endothelial NO synthase upon sexual behavior of sexually mature male rats in condition of physiologically suppressed reproductive function 16 months-old male rats weighing 600-700 g with established degree of their sexual function suppression were orally administered dynamized antibodies to NO synthase in form of homeopathic dilutions C12+C3O+C200 for 5 days in the dose of 1.5 ml per animal. After that the males were put in the company of females (aged 4 months, weighing 300 g) in the estrus phase of their sexual cycle. Copulative activity of each male was registered for 15 minutes based on the following indices: latency time of mating (interval between the first presentation of a female and the first mating), number of courtings (sniffings and lickings), the total number of matings and the number of copulations. Reliable twofold increase in the number of courtings in comparison with the initial number was observed in all the animals after administration of 5 doses of the preparation; reliable increase of the sexual activity indices was found in 55.5% of the animals (with initial moderate and high degree of sexual activity), which on the whole is an evidence of the stimulating effect of the preparation upon sexual activity of male rats in condition of physiologically suppressed reproductive function.

205B. In order to study the effect of activated forms of ultra-low doses of antibodies to endothelial NO synthase upon sexual behavior of sexually mature male rats in condition of season suppression of their reproductive function 4 months-old male rats weighing 400-450 g were orally administered dynamized polyclonal antibodies to NO synthase in form of homeopathic dilutions C12+C30+C200 for 5 days in the dose of 1.5 ml per animal. After that the males were put in the company of females (aged 4 months, weighing 300 g) in the estrus phase of their sexual cycle. Copulative activity of each male was registered for 15 minutes based on the following indices: latency time of mating (interval between the first presentation of a female and the first mating), number of courtings (sniffings and lickings), the total number of matings and the number of copulations. Reliable reduction of the latency time of mating and of the number of courtings along with twofold increase of the total number of matings and threefold increase of the number of copulations was observed after administration of 5 doses of the preparation in animals of the experimental group in comparison with the corresponding indices in the same animals prior to administration of the preparation. Thus, administration of the preparation resulted in enhancement of copulative activity manifested by demand for repeated coituses in male rats in condition of season suppression of their reproductive function. At that enhanced copulative activity accounts for reduction of the number of courtings.

205C. Patient C. aged 51 years consulted a urologist for loss of libido, impaired erection and lack of satisfaction from sexual acts. The said symptoms had been growing in the course of the last 2 years. During the last three years the patient also had been suffering from episodes of depression, tearfulness, memory and sleeping disorders, reduced capacity for work, attacks of tachycardia and unstable blood pressure. Physical findings: moderate prostate gland enlargement. Diagnosis: erectile dysfunction due to involutional hormonal disorders. The patient was prescribed administration of monoclonal antibodies to a fragment of human endothelial NO synthase in form of a mixture of homeopathic dilutions C12, C30 and C200 in the dose of 1 tablet 3 times a day. 2 weeks after the beginning of treatment the patient noticed improved erection and enhanced libido along with betterment of his general state of health: his vital tonus went up and sleeping disorders subsided. He was recommended to take the preparation once or twice a week. Upon repeated attendance 2 months after the beginning of treatment the patient was free of previous complaints and stated restored libido, erection and satisfaction from coitus.

205D. In order to study the effect of activated forms of ultra-low doses of antibodies to endothelial NO synthase upon sexual behavior of sexually mature male rats in condition of physiologically suppressed reproductive function 16 months-old male rats weighing 600-700 g with established degree of their sexual function suppression were orally administered dynamized antibodies to the whole molecule of endothelial NO synthase in form of C200 homeopathic dilution for 5 days in the dose of 1.5 ml per animal. At that the enzyme whole molecules were isolated from bovine aortic endothelium using the method described in the article by Bredt, D. S., & 101 Snyder, S. H. Isolation of nitric oxide synthetase, a calmodulin-requiring enzyme. Proc. Natl. Acad. Sci. USA (1990), 87:682-685). After that the males were put in the company of females (aged 4 months, weighing 300 g) in the estrus phase of their sexual cycle. Copulative activity of each male was registered for 15 minutes based on the following indices: latency time of mating (interval between the first presentation of a female and the first mating), number of courtings (sniffings and lickings), the total number of matings and the number of copulations. Reliable twofold increase in the number of courtings in comparison with the initial number was observed in all the animals after administration of 5 doses of the preparation; reliable increase of the sexual activity indices was found in 55.5% of the animals (with initial moderate and high degree of sexual activity), which on the whole is an evidence of the stimulating effect of the preparation upon sexual activity of male rats in condition of physiologically suppressed reproductive function.

205E. In order to study the effect of activated forms of ultra-low doses of antibodies to endothelial NO synthase upon sexual behavior of sexually mature male rats in condition of season suppression of their reproductive function 4 months-old male rats weighing 400-450 g were orally administered dynamized natural antibodies to NO synthase in form of homeopathic dilutions C12+C30+C200 for 5 days in the dose of 1.5 ml per animal. Natural antibodies were isolated from the pool of sera of essential hypertension patients using the method of affinity chromatography (immunosorption) on columns with synthetic fragments of endothelial NO synthase adsorbed on the solid phase (sefadex) as described, for instance, in the book Immunological Methods under the editorship of G. Frimel, Moscow, Medicine Publishing House, 1987, p. 427-432. After that the males were put in the company of females (aged 4 months, weighing 300 g) in the estrus phase of their sexual cycle. Copulative activity of each male was registered for 15 minutes based on the following indices: latency time of mating (interval between the first presentation of a female and the first mating), number of courtings (sniffings and lickings), the total number of matings and the number of copulations. Reliable reduction of the latency time of mating and of the number of courtings along with twofold increase of the total number of matings and threefold increase of the number of copulations was observed after administration of 5 doses of the preparation in animals of the experimental group in comparison with the corresponding indices in the same animals prior to administration of the preparation. Thus, administration of the preparation resulted in enhancement of copulative activity manifested by demand for repeated coituses in male rats in condition of season suppression of their reproductive function. At that enhanced copulative activity accounts for reduction of the number of courtings.

EXAMPLE 206

ANTI-PSA

206A. In order to study the effect of activated forms of ultra-low doses of antibodies (AB) to prostate-specific antigen (PSA) upon the prostate condition in its acute aseptic inflammation in rats morphometric analysis of prostate sections was carried out along with evaluation of prostate density and zinc content in its tissue on the $7^{th}$ day after the operation of prostate broaching with a silk ligature. At that the animals of the experimental group were administered 1.5 ml of the preparation of polyclonal immune antibodies to bovine PSA in form of the mixture of homeopathic dilutions C12+C30+C200 by intragastric route for 3 days prior and 7 days after the operation.

TABLE 10

Effect of the AB to PSA upon the prostate state in its aseptic inflammation in rats

| Index under evaluation | Control | Experiment |
|---|---|---|
| Morphometry: share of structural elements of prostate in its aseptic inflammation (%) | | |
| Vessels | 2.98 ± 0.61 | 1.84 ± 0.25* |
| Edema | 17.3 ± 0.63 | 12.32 ± 1.29* |
| Prostate density, g/cm³ | 1.10 ± 0.03 | 1.02 ± 0.02* |
| Zinc ion content, mg % | 0.49 ± 0.11 | 2.01 ± 0.37* |

Note:
*the data differ reliably from their control counterpart, $p < 0.05$.

The results of the experiments presented in table 10 indicate that antibodies to PSA reduce manifestations of acute inflammatory reaction in the prostate gland and ameliorate its functional condition in aseptic inflammation.

206B. In order to study the prostatotropic effect of activated forms of ultra-low doses of antibodies to PSA on the model of infantile gonadectomized male rats in the condition of testosterone propionate-induced androgen deficiency gonadectomized, male rats were administered monoclonal immune antibodies to PSA in the form of the mixture of homeopathic dilutions C12+C30+C200 in the dose of 0.5 ml per 100 g of body weight by intragastric route for 7 days, starting on the following day after gonadectomy with the background administration of testosterone propionate.

TABLE 11

Effect of the AB to PSA upon the androgenic effect of testosterone propionate in gonadectomized male rats

| Group | Organ weight quotients (mg/g) | | Organ weight quotients (% of the control values) | |
|---|---|---|---|---|
| | Ventral prostate | Seminal vesicles | Ventral prostate | Seminal vesicles |
| Control 1 - intact animals | 0.21 ± 0.02 | 0.12 ± 0.01 | 100 | 100 |
| Control 2 - castrated animals | 0.09 ± 0.03* | 0.08 ± 0.01* | 42.8 | 66.6 |
| Control 3 - + Testosterone propionate + solvent | 0.17 ± 0.02* | 0.28 ± 0.01* | 188.8 | 362.5 |
| Testosterone propionate + Anti-PSA | 0.23 ± 0.01 | 0.29 ± 0.02 | 135.2 (of the control 3) | 103 (of the control 3) |

Note:
*differences in comparison with the corresponding control values are reliable, $p < 0.05$.

The results of the experiments presented in table 11 indicate that antibodies to PSA possess marked prostatotropic activity and stimulate the androgen effect of male sexual hormone upon prostate gland.

206C. Patient P. aged 31 years consulted an urologist for discomfort and nagging pain in his urethra and in the lower abdomen, bursting pain in his perineum, voiding frequency and episodic voiding difficulties. The patients had been suffering from the said symptoms for 2 years with 3-5 exacerbation episodes a year, particularly after a cold or indulgence in alcohol. Detailed history taking unearthed also such complaints as lack of satisfaction from sexual act, impaired erection and pain in the perineum after sexual act. Per rectum: prostate gland was soft and tender upon palpation. Bacteriological study of prostate secretion for pathogenic bacteria and immunofluorescent test for *Chlamydia trachomatis* were both negative. The patient's condition was diagnosed as chronic prostatitis. He was prescribed administration of the mixture of polyclonal antibodies to human prostate specific antigen in homeopathic dilution C 1000 in the dose of 1 tablet daily for a month. 10 days after the beginning of treatment the patient noticed significant reduction of pain and voiding disorders. 3 weeks after the beginning of treatment the patient stated disappearance of his problems in the sexual sphere. After the end of treatment complete clinical remission of the disease was found. The patient was recommended to take the preparation twice a week for three months. Catamnesis: a single exacerbation episode in the course of a year was quickly controlled by daily intake of the preparation for 5 days.

206D. Patient A. aged 60 years consulted a urologist for such complaints as sensation of incomplete bladder emptying frequent micturition and intermittent urine low, straining with micturition, poor stream and nicturia (4-5 voidings per night). The symptoms had been growing gradually for 5 years. There were no episodes of acute urine retention. The patient's total I—PSS score was 25. Rectal examination revealed enlarged painless prostate gland of soft-elastic consistence. Ultrasonography showed 100 ml of residual urine. The patient's condition was diagnosed as benign prostate hyperplasia. The patient refused from surgical treatment. He was prescribed administration of the mixture of polyclonal antibodies to human prostate specific antigen in form of homeopathic dilutions mixture C30+C200+C 1000 in the dose of 1 tablet daily for a month. Upon repeated attendance after a month of treatment the patient noticed that his voiding disorders subsided considerably and his total I—PSS score was reduced to 15. Ultrasonography showed 30 ml of residual urine. The patient was recommended further intake of the preparation twice a week.

EXAMPLE 207

Potentiated Antibodies to Topoisomerase II

207A. Patient T., aged 40, with an established diagnosis of lung carcinoma underwent two courses of treatment with CISPLATIN and ETOPOSIDE, after which clinical and X-ray findings revealed the tumor's primary resistance to antitumor drugs. he third course of the treatment with cytostatic drugs was combined with the administration of a C30 dilution of potentiated antibodies to topoisomerase II in a dose of 1 sublingual tablet once a day. The patient started feeling better and X-ray patterns revealed the arrest of tumor progression.

EXAMPLE 208

Potentiated Antibodies to Cytochromes aa3

208A. Patient G., aged 39, was admitted to hospital with the diagnosis of hypertensive disease, ischemic heart disease, cardiac failure due to myocardial infarction; he had been treated with intravenous infusions of SODIUM NITROPRUSSIDE (sodium nitrozylpentacyanoferrate) in a dose of 100 mg a day for 4 days. By the $5^{th}$ day the hypotensive effect of the preparation had significantly decreased as sodium cyanide accumulating as a result of SODIUM NITROPRUSSIDE metabolism played an important part in the pharmacological effect of the preparation. (Cyanides act as blockers of the mitochondria respiratory chain at the level of Cytochrome aa3). The administration of a C200 dilution of potentiated polyclonal antibodies to CYTOCHROMES aa3 in a dose of 1 tablet 3 times a day restored the efficacy of SODIUM NITROPRUSSIDE.

Antibodies to Nucleic Acids

EXAMPLE 209

Potentiated Antibodies to DNA Antigens

209A. Patient P., aged 24, with clinical diagnosis of systemic lupus erythematosus accompanied by kidney affection (nephrotic type glomerulonephritis) and heart injury (myocarditis), subacute course, III degree of activity had been taking prednisolone (50 mg daily) and curantyl (200 mg daily). Because of the lessening of the effect of prednisolone she was began to receive potentiated polyclonal antibodies to native DNA isolated from lymphocytes of the patient's peripheral blood. Antibodies were obtained by immunization of a rabbit with subsequent purification of the antiserum and its potentiation based on homeopathic technology. The intake of a C1000 dilution of potentiated antibodies to autoantigens of DNA in a dose of 1 tablet twice a day resulted in a marked inhibition of the activity of the autoimmune process within two weeks. The laboratory findings were as follows: ESR decreased from 50 to 16 mm/h, the titer of the antinuclear factor lowered. Catamnesis: 6 months of the intake of potentiated antibodies gave clinical and laboratory remission.

Antibodies to Complex Antigens

EXAMPLE 210

Potentiated Antibodies to Antigens of Fetal and Primordial Tissues and Tissue Cultures 210A. Patient A. was a newborn baby 27 days old. He was born with symptoms of perinatal encephalopathy. As immunoenzyme diagnostic methods had revealed elevated levels of embryotropic neurospecific antigens in mother before this pregnancy, it was decided to administer to the baby a C200 dilution of a potentiated polyclonal antiserum to bovine fetal brain-specific non-species-specific protein (antigen), 14-3-2 (brain-specific enolase), in an oral dose of 5 drops of an aqueous solution to be administered 3 times a day. In the course of the treatment neurological symptoms subsided gradually; the reflexes of oral and spinal automatism restored and muscle hypertonus receded. The baby became calmer and started active breast sucking A conclusion was drawn on the efficiency of potentiated antibodies to the said fetal antigen controlling normal morphogenesis of the central nervous system in the treatment of perinatal encephalopathy.

210B. Patient D., aged 4, with an established diagnosis of mental retardation had been receiving a C1000 dilution of monoclonal potentiated antibodies to primordial antigen nestin, a protein marker of neuron stem cells, in a dose of 5 drops of an aqueous solution once a day in the morning for six months with the purpose of enhancing the child's intellectual capacities. After six months of the treatment a neuropsychological examination showed that D's intellect and memory were up to the standard age level; the child's kindergarten tutor reported that the boy comprehended and learned the material well in class.

210C. Patient I., aged 8, with an established diagnosis of Down's syndrome had been receiving a C200 dilution of potentiated polyclonal antibodies to α-fetoprotein to be taken in a dose of 1 tablet a day for the first 12 months and in a dose of 1 tablet once in 3 days for subsequent 6 months. The neuropsychological examination by Bailey's method revealed a marked enhancement of the patient's intellect 1.5 years later. The patient's behavior is well ordered; he is adapted to being with other children.

210D. Patient S., aged 18, suffered from myasthenia of an unknown origin. In view of the inefficiency of conventional drugs the treatment was supplemented by the oral intake of a C30 dilution of potentiated polyclonal antibodies to the culture of neuronal stem cell of the Tera-1 line enriched with the protein extract of the embryonic tissue in a dose of 1 ml 3 times a day for 6 months. The combined treatment resulted in an increased tolerance of physical strain, receded bulbar symptoms, diplopia, and ptosis, which made it possible to reduce the daily doses of corticosteroid drugs several times.

210F. Patient M., aged 42, suffered from the astheno-neurological syndrome accompanying the remote period of vernal encephalitis. As conventional therapy proved its inefficiency, it was decided to prescribe the oral intake of a C200 dilution of potentiated polyclonal antibodies to embryonic neocortex (the antiserum was obtained by immunization of rabbits with, tissues from the occipital zone of the brain cortex of 15-day old embryos of Wistar line rats) in a dose of 1 ml twice a day, for 6 months. In the course of treatment the patient's asthenic symptoms became less pronounced, his ability to work was restored, though disseminated microsymptoms persisted in his neurological status.

210G. Patient K., aged 39, suffered from chronic alcoholism, grade II. He went to seek for narcologist's advice declaring his desire to start a sober life and asking for a new method of treatment because those he had already tried were of little effect. The prescription was: a regular intake of a C1000 dilution of polyclonal potentiated antibodies to homogenized hippocampi of embryos of Wistar line rats (hippocampi of several dozens of syngenic fetuses were used for immunization) in a dose of 1 tablet once a day. The remission had been lasting for 8 months, in the course of this period of medical observation no episodes of consuming alcoholic beverages have been registered, the patient states the absence of craving for alcohol.

210H. Patient A., aged 8, suffered from liver cirrhosis of an unknown etiology. As the conventional therapy had no significant effect, the oral intake of a C4 dilution of polyclonal potentiated antibodies to homogenized liver of the human fetus was prescribed in a dose of 1 ml 3 times a day. During four months of the therapy a clinical improvement of the patient's condition was observed, manifestations of general intoxication symptoms and liver failure subsided. The patient's emotional tone rose, the paleness of skin, the icteric hue of the scleras, and spider-like hemangiomas disappeared; the size of the liver diminished. A conclusion was drawn on high efficiency of this mode of treatment.

EXAMPLE 211

Potentiated Antibodies to Tissues or Tissue Cultures

211A. Patient O., aged 8, suffers from a malignant course of insulin-dependent diabetes mellitus. The intranasal administration of a C50 dilution of potentiated polyclonal antibodies to a culture of insular cells of the pancreata of newborn rabbits in a dose of 1 ml 3 times a day was prescribed with therapeutic purposes. After three months of the therapy the course of illness became stable, the blood glucose level went down, and the disposition to ketoacidosis receded. There were no comas or hypoglycemic episodes during the period of the treatment and the amount of insulin intake was reduced by 50%.

211B. Patient P., aged 35, suffered from insulin-dependent diabetes mellitus (mild course). As the patient was unwilling to take insulin, the recommendation was to start the oral intake of 1 ml of a C50 dilution of an aqueous solution of polyclonal potentiated antiserum to insular cells of the pancreas of a newborn calf once a day. As a result of the monotherapy with this preparation, the patient was feeling well. Her blood glucose level was within normal limits. The patient did not take insulin any more.

211C. Patient V., aged 56, suffered from obstructing atherosclerosis of coronary arteries and angina decubitus. In view the inefficiency of conventional therapy the prescription was to take intranasally a C30 dilution of potentiated polyclonal antibodies to the homogenized heart of a newborn rabbit in a dose of 3 drops of an aqueous solution 5 times a day. After six months of the therapy the intensity of pain was reduced, the patient had pain much more seldom and only after a sufficiently strong physical strain; his blood lipid formula became normal and the dose of nitrate drugs was reduced approximately by 50%.

Thus, an analysis of the examples given above shows that homeopathically potentized form of antibodies to an antigen (a substance or a pharmaceutical agent) does not produce the well-known immunological effect of binding the antigen and inhibiting its activity; on the contrary, it reproduces the antigen's activity in a modified form, which results in a partial or complete reduction of the pathological syndrome, in the regulation of whose mechanisms of development said antigen is involved. In this case such antigen-associated side effects as toxicity, addiction, and tolerance are absent.

In addition, activated antibodies in ultra-low doses potentiate (reinforce) the effect of an antigen (a pharmaceutical agent) on their combined or simultaneous administration, which makes it possible to reduce the dose of the pharmaceutical agent and to minimize its side effects.

The administration of homeopathically potentized form antibodies to a substance or a pharmaceutical agent favors the reduction of the intensity of the pathological syndromes (acute or chronic intoxication, post-intoxication disorders, dependence) caused by this substance or pharmaceutical agent.

Experimental studies of homeopathically potentized form antibodies make it possible to determine their therapeutic properties even in situations where the biological activity of the initial antigen remains unknown.

The invention claimed is:

1. A method for administering to a patient suffering from a neuropsychiatric disorder a homeopathically potentized form of at least one antibody to an antigen, which antigen is a molecule capable of treating said disorders.

2. The method of claim 1, wherein said potentised form of at least one antibody is produced by homeopathic technology.

3. The method of claim 1, wherein said antibody is a monoclonal, polyclonal, or natural.

4. The method of claim 1, wherein said antigen is an endogenous molecule.

5. The method of claim 1, wherein said antigen is an exogenous molecule.

6. The method of claim 1, wherein said neuropsychiatric disorder is attention deficit disorder.

* * * * *